US008367330B2

(12) United States Patent
Albitar

(10) Patent No.: US 8,367,330 B2
(45) Date of Patent: Feb. 5, 2013

(54) METHODS FOR DETECTING TCR-GAMMA GENE REARRANGEMENT

(75) Inventor: Maher Albitar, Coto De Caza, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 585 days.

(21) Appl. No.: 12/491,170

(22) Filed: Jun. 24, 2009

(65) Prior Publication Data

US 2010/0159456 A1    Jun. 24, 2010

Related U.S. Application Data

(60) Provisional application No. 61/140,029, filed on Dec. 22, 2008.

(51) Int. Cl.
*C12Q 1/68* (2006.01)
(52) U.S. Cl. ........................................ 435/6.1
(58) Field of Classification Search ........................ None
See application file for complete search history.

(56) References Cited

U.S. PATENT DOCUMENTS 6,720,144 B1 * 4/2004 Samoszuk et al. ........... 435/6.14

FOREIGN PATENT DOCUMENTS

WO    WO 2004/033728 A2    4/2004

OTHER PUBLICATIONS

Chang et al. (Clin Chem. Mar. 2003;49(3):513-5).*
zur Stadt et al. (J Chromatogr B Analyt Technol Biomed Life Sci. Jul. 25, 2003;792(2):287-98).*
NCBI Accession Nos. M13434 (Sep. 19, 2000).*
NCBI Accession Nos. AR493849 (May 15, 2004).*
Buck et al. (Biotechniques. 1999. 27(3): pp. 528-536).*
Taylor et al. (Blood. May 1, 1991;77(9):1989-95).*
MedicineNet.com ("Definition of Plasma." Accessed Dec. 13, 2011).*
Bagg, A., Immunoglobulin and T-Cell Receptor Gene Rearrangements: Minding Your B's and T's in Assessing Lineage and Clonality in Neoplastic Lymphoproliferative Disorders, Journal of Molecular Diagnostics, 8(4):426-429 (2006).
Chain et al., Real-time PCR method for the quantitative analysis of human T-cell receptor γ and β gene rearrangements, J. Immunol. Methods. 300 (1-2): 12-23 (2005).
Davey et al., Immunoglobulin and T-cell receptor gene rearrangement and expression in human lymphoid leukemia cells at different stages of maturation, Proc. Natl. Acad. Sci. USA, 83:8759-8763 (1986).
Diss et al., The polymerase chain reaction in the demonstration of monoclonality in T cell lymphomas, J Clin Pathol. 48:1045-1050 (1995).
Gra et al., Analysis of T-Cell Receptor-γ Gene Rearrangements Using Oligonucleotide Microchip, A Novel Approach for the Determination of T-Cell Clonality, J. Mol. Diagn. 9:249-257 (2007).
Greiner, T.C., Advances in Molecular Hematopathology, T-Cell Receptor γ and bcl-2 Genes, American journal of Pathology, 154(1):7-9 (1999).
Hara et al., Rearrangement of Variable Region T Cell Receptor γ Genes in Acute Lymphoblastic Leukemia, Vγ Gene Usage differs in Mature and Immature T Cells, J. Clin. Invest. 83:1277-1283 (1989).
Hayday, et al., Structure, Organization, and Somatic Rearrangement of T Cell Gamma Genes, Cell, 40:259-269 (1985).

(Continued)

*Primary Examiner* — Christopher M. Babic
(74) *Attorney, Agent, or Firm* — Foley & Lardner LLP

(57) ABSTRACT

The invention provides methods for detection of TCR-γ nucleic acid in acellular body fluid. The methods can be used to detect the TCR-γ gene rearrangement in acellular body fluid. The detection of TCR-γ gene rearrangement is useful in determination of clonality of T-cell population. The invention is useful in the diagnosis of lymphoproliferative disorder.

26 Claims, 45 Drawing Sheets

OTHER PUBLICATIONS

Huck, S., Dariavach, P., and Lefranc, M.-P., Variable region genes in the human T-cell rearranging gamma (TRG) locus: V-J junction and homology with the mouse genes, The EMBO Journal, 7(3):719-726 (1988).

Kuo, F.C., Hall, D., and Longtine, J.A., A Novel Method for Interpretation of T-Cell Receptor γ Gene Rearrangement Assay by Capilary Gel Electrophoresis Based on Normal Distribution, Journal of Molecular Diagnostics, 9(1):12-19 (2007).

Lawnicki et al., The Distribution of Gene Segments in T-Cell Receptor γ Gene Rearrangements Demonstrates the Need for Mulptiple Primer Sets, Journal of Molecular Diagnostics, 5(2):82-87 (2003).

Lefranc, M.-P., Forster, A., and Rabbitts, T.H., Genetic polymorphism and exon changes of the constant regions of the human T-cell rearranging gene γ, Proc. Natl. Acad. Sci. USA, 83:9596-9600 (1986).

McCarthy, S.M. and Gilar, M., UPLC Separation of DNA Duplexes, Waters Corporation, Milford, Massachusetts, p. 1-5, Jul. 2008.

Signoretti et al., Detection of Clonal T-Cell Receport γ Gene Rearrangements in Paraffin-Embedded Tissue by Polymerase Chain Reaction and Nonradioactive Single-Strand Conformational Polymorphism Analysis, Am. J. Pathol. 154:67-75 (1999).

Simon et al., Automated High-Resolution Polymerase Chain Reaction Fragment Analysis, A Method for Detecting T-Cell Receptor γ-Chain Gene Rearrangements in Lymphoproliferative Diseases, American Journal of Pathology, 152(1):29-33 (1999).

Taylor et al., Consultations in Molecular Diagnostics, T Cell Receptor γ-Chain Gene Polymerase Chain Reaction to Diagnose Central Nervous System Involvement by Cutaneous T Cell Lymphoma, Journal of Molecular Diagnostics 4(2):118-120 (2002).

Theodorou et al., Recombination pattern of the TCR γ locus in human peripheral T-cell lymphomas. J Pathol. 174:233-242 (1994).

Wood et al., Detection of clonal T-cell receptor γ gene rearrangements in early mycosis fungoides/sezary syndrome by polymerase chain reaction and denaturing gradient gel electrophoresis (PCR/DGGE). J Invest Dermatol. 103:34-41 (1994).

International Search Report for PCT Patent Application No. PCT/US2009/068537.

Stadt et al., "DHLPC based fraction collection of TCR-gamma rearrangements in childhood ALL: Direct sequencing of products amplified by a single or multiplex approach," International Journal of Onocoloqy, vol. 27, No. 2, pp. 547-552, Aug. 1, 2005.

Kuo et al., "A Novel Method for Interpretation of T-Cell Receptor gamma Gene Rearrangement Assay by Capillary Gel Electrophoresis Based on Normal Distribution," Journal of Molecular Diagnostics, vol. 9, No. 1, pp. 12-19, Feb. 1, 2007.

Shaheen et al., "Molecular immunoglobulin/T-Cell receptor clonality diagnosis by gen scan in lymphoproliferative disorders," Hematology, vol. 11, No. 2, Apr. 1, 2006.

Greiner et al., "Effectiveness of capillary electrophoresis using fluorescent-labeled primers in detecting T-cell receptor gamma gene rearrangements," Journal of Molecular Diagnostics, vol. 4, No. 3, pp. 137-143, Aug. 1, 2002.

Zhong et al., "The clinical significance of Ig heavy chain and TCR gamma gene rearrangement detected in free DNA in plasma in patients with non-Hodgkin lymphoma," Chin. J. Hematol., vol. 29, No. 4, pp. 258-262, Apr. 2008.

Tong et al., "Diagnostic developments involving cell-free (circulating) nucleic acids," Clinca Chimica Acta, vol. 363, No. 1-2, pp. 187-196, Jan. 1, 2006.

Schwarz et al., "Quantification of free total plasma DNA and minimal residual disease detection in the plasma of children with acute lymphoblastic leukemia," Annals of Hematology, vol. 88, No. 9, pp. 897-905, Jan. 23, 2009.

Yeh et al., "Plasma-based detection of clonality inlymphoid malignancies," European Journal of Haematology, vol. 82, No. 6, pp. 450-453, Feb. 10, 2009.

Supplementary European Search Report issued on Aug. 6, 2012 in application No. EP 09 83 5644.

\* cited by examiner

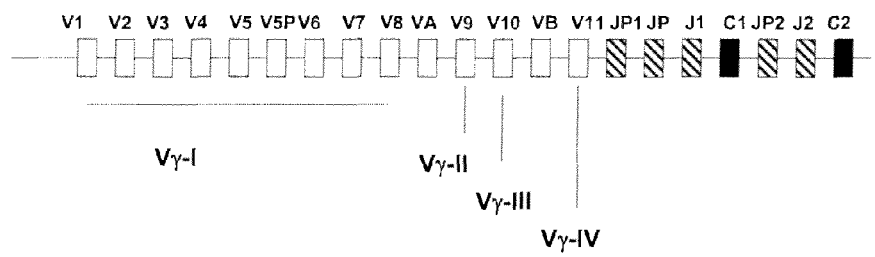
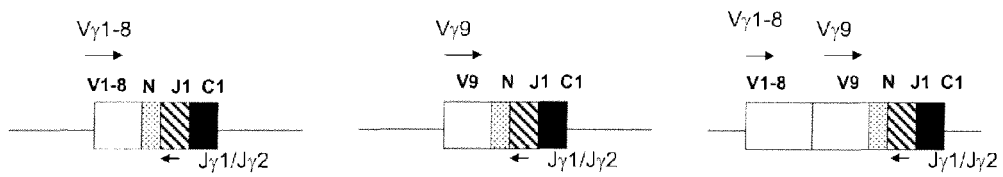
FIGURE 1

Figure 2

```
   1 ttatataatt tatatatata tatatacaca cacacacgaa tataaatggc cggtagccag
  61 gattttggaa tttgttagac ttcagttgaa atccaggctc cattatttat tcgtcaaatg
 121 acctcgaaga gtttaacctt tttaagattc caactctctc atctgtgaaa tgtggttgat
 181 tatatctcct ttggagtatt attgtaagaa ttaaactgtg gtaaagacta gcttagatat
 241 catttagttt agaaatgaac aaggtggcac aaccctggc cccaggagat gaatggtgta
 301 tccagggtaa aggttataat tgccaagtac agtgactttc caaggacat acaacctcta
 361 agtggcagtg cttggacttt tattctgtct tttccaaagc aatacattct tgaaactaaa
 421 agttctcagg ccagactctc caaagtgtcc ctatttggca gctccatctt gagaagtaac
 481 ctctcccttc cgcacactct tcgtgggatt gcattgttgg ctgctcatcc tgggctgagg
 541 cccatgaccg gaccattccc agggcaccag gcagccacag ggcctgtaag aagagcaggc
 601 aggaagtgaa gctttggctg aggtttctgg gacacactta acttccctgg aaacgatgcc
 661 tgacaccgcc tggccacagc actggcagga gatgctgctg tcttctggga acatgcagcg
 721 gccagtgagc agcacaggac acaggaacgt aaactgggga cccttcatcc atccactctg
 781 gcttcgtatc ttctccattg tccactccta ttttagcccg ggatgatcag tgatgatgtg
 841 catgagttac tcattcccat ctatgcccca gcccagactg agcatataca aaccctgttc
 901 tttgcagaat ttttcatttt tccttttaat tttctatgga aagaatatat gttatataat
 961 tcagccttat tgacacccttt ataatagcct tctaaactac acacctgatc atttatccca
1021 tccaaatata catatatttg atacagggtc tcactctgtt gcccaggctg gagtgcggtg
1081 gcacgatcac agctcactac agacttgacc tcccagactc aagggatcct cccacctcag
1141 cctcccaagt agttgggact acaggcgtgt gccatcacgt gcagctaaat ttttgtattt
1201 tttgtggaga ctgggtttca ccatgttgct caggctggtc tggaactcct gggcttaact
1261 gatctgcctg cctcggcctc ccacagtgcc gggattacag gcatgagcca ccgtgcccag
1321 cctcattgat acacattaaa tgcctactac gttccaggcc ttgtgctgtg tgctcttgat
1381 actgaggtgt gtgcccctt aagctcattg aaaacactat tgacctgcgt cactgcggtc
1441 acaaagtgat acagagagcc cagacaacca tttagaggtg aggaaattct aataattcat
1501 ggtaagcaga ttgtttccca tagtgttgct agggaacatc tcacagcaga ctgaaataga
1561 aatacaagca attgtctgcg cactagaact ttctccccaa ggcagtgcta tttttttaaa
1621 caattcttct atcatcatca tcataatgct gacctcttga tatgtaaagg tacaattacg
1681 aggagaagca gaagaacatt tacatctgtg agtttgcacc tctctcccac catagtgagc
1741 agatcacacc ctcaggaccc cagaagactg gcaaggagga cttgatagag acaaaggag
1801 agacacaaga ggggacagag tgttcatatg aagagggaga gggcatgata tagagacagt
1861 gacggcaaca gaaagtagaa agttgaagag ggacagagag cagagtggaa gtgagaagga
1921 aagaaaatga ctaggacagt ggccatacaa gcaaaaagag caagagacag agacacgtgg
1981 agaggtatag ttctctatca tggcggggga gagagagaga aaacagagaa agaaatacaa
2041 aacacagaga gagggtgaga gacaaaggga cagagagaca gcgagagagg gagggaagat
2101 ggagagagag aaaacaacag agaagagaga gaaactgtga tataaatata gcgacaggga
2161 cagggacagt gatggagaga gacagagaaa tagggaaaga tacaagaaga gagaactgga
2221 gttagggggga gagataggga gagagagaga acgatagacc tgtggagaca gaagcataca
2281 cgtggacaca cagagtgcgg cagtgttagg aagatagaga taaatataca gaaataatgg
2341 taaatattga gatagaaaaa tatatataaa gagaaaaac aaagaaatat gcatatttat
2401 atattgtaaa aatatacata aatgtattta tacatgtata atatgttata tataaaatat
2461 tatatatatt tctatacaaa aaattagccg ggtgtggtgg cggcacctg taatccctgc
2521 tactcggag gctgaggtag gagaatggca tgaaccaggg aggtggagct tgcagtgagc
2581 caagatcgcg tcactgcact ccagcctggg cgacagagcg agattccgtc tcaaaaaaaa
2641 aaaattatat gtatttctag ctttccttt ctcttcatat attctatctg tctgtctgtc
2701 tatccatact attgccacaa taacgccatg tagcaaatat cccaaactca gtggcttagc
2761 acaataatca tctacaaatt cttacaaatg cgtaggtttg ctagactgtt ctgctgatct
2821 aaaccaagct catctgatct tggctgggct tggccacatg tcaggcagct gctgggttag
2881 ctgggagggg gactgcctgg tcaaagtgcc tgggtctgaa taaatcagct ccactacaca
2941 cagggtttca tcctccaaca ggctagcctg gatttgttct aatgacaatg acagaaagca
3001 aagagctagc agaagcacat caggccactt gaagcctcaa ttcagaactg gagccctatg
3061 agttcttctt gtatttaaaa aaaaaaaag gcggggggca taaacggcgc ctcttaatcg
3121 aaggagcttt gacttatcaa gaatgagttc cacttctgga aaatttgcag tgagcccaca
3181 ctgcctgtc tggctcacaa atgcaactag gaaccctgaa tctgaggact ttgaaaaata
3241 aatgatagca agtcaactgg agaaggaaat cggaaagtga agcactatga attcccagta
3301 agtttcttat ttatttttcc tcaattatcc cctggcctgt actcagataa tcagagtata
3361 tgtacaaaga taatctgaaa tgcagaactg tacaccaggt gaggacagag agaaagggg
```

Figure 2

```
3421 actctctgtg gtcagagagc cctggttttc tgttttttgt ccttttccat tctctcgcag
3481 cccccaggca atctgagtgg cagtggcagc agctatggtg agccaggagc ctaaagctct
3541 taggaaaggg atccttctct ctgaccaggg aagctgtggc cctgagagag aatcctggtg
3601 gttttttgttc tctatcctct caccacttgg ccctggaggg agacacaatg gtgggaaatg
3661 cagtgtgcta aagccacacc tgtctggcca gacgactgga ggggcatttc ctgtgaacta
3721 gaaagtattg cagagcttgc agagagaaag aagattaagc aagaaacatc atgcaatgat
3781 gtctggactc ctgggctcac ccactagctg tgcatgcata aacgtgaccc taaacagctc
3841 caaagccaaa ggccttgcaa accgaagcag gagtaggcac tgcccaggtc ctagaatggc
3901 cactgggtgg cgcacacaca ggacaggtct gacaagacaa gtactgcaaa ggctggaaaa
3961 cggaactgac tggaactgcc caccaaacac cagtaggaag ttgtaatccc taactgcgtc
4021 agttgcctgc taacaaaaaa accccctcca cattctgtgt aatatttaaa caatgcccag
4081 agctctataa catgatattc aaagtgtaca ggatttaatc cgaaattact ccgcatgtgg
4141 aggacgagga aaatcttagc atctccaaac ggaaaagcca acaacagat gctaatcctg
4201 acacgacaca ggtgttggaa taacaaagac tttaaaggag ctatagtgac cacaggaaga
4261 aatggaaaga gaggaggaga gaaggaggta gaaagtaaat agataggaga gatacaaata
4321 gagaaataga aaaagagatg aatagagata ggcagataga gagacagaaa cataaagata
4381 tgaacagagt aagaaacagg agcactaaag caaaatagag gagactgaga gctgtaagag
4441 ggagctatag aaggaaaaat gtaaagggag gaacaaaaac gggacagaga aaaaagaaat
4501 atggacataa agacggagat ggaaggacat agtgataaga agcaatgcag gagatagaga
4561 aatagaatag tagagagaga aatagagcca gggcacgtga aagctataaa gcaattcatg
4621 gtagttgtct aaattcaaca tatcattacg gttgcataat gctaatattc tcattttaac
4681 atttctccta aatttattgg ttgtaatact tccacaaaag aactttcatt cggccaggca
4741 cagtggctca cacctgtaat cccagcacat gggaggccg aggtgggtgg atcacttgag
4801 gtcaggagtt caagaccagc ctggcccaca tggtgaaacc ccatctctat gaaaaatata
4861 aaaattagct aggtgtggtg gcgcgtgcct gtaatcccag ctacttggga ggctgaggca
4921 ggagaattgc ttgaacccccg gaggtggaga ttgcagtgag ctgagattgt gccactgcac
4981 tccagtctga gacacagagc gagactctat ctatctaaag aaaaaaaaaa agaactttca
5041 ttcttaagct ctgtggtatt ctaaaatgtt tgtacagaaa tggcaaggta aatgcttgat
5101 tattttcttt tctgttttca gaatgagatg gtgtcttagc aacctccaga ggagacttta
5161 ttttgctata ttatgttttt caagaatttg tgtaggtgtt attcttttgg tgcttaaaat
5221 gtcctaccga tggttagtga gagccactgc cgttgttttt atttgagtag agtccaaggc
5281 aaaccaacat gcctgaccct cagtcctgtt aataaagcag gctcaagcct tctcagaatg
5341 gccctgggtg gacttgcaaa tgtggacttg caatgtgaa aaggaaggtg gttcagggcc
5401 ctaatcagaa gcttcctggc aggaccaggt tctggcagct gcgttggctg ctgaaactct
5461 gaagtgcagg atgtgagcct gctgtgggac tgccctctcc caagggccat gaccagctag
5521 cgccagggtc agcttccccc acatctgcac tccctctgct gtgggcctga gcaatccatg
5581 cccctggctc tctcctgaag agggcctgct ctcagctgcc acaagagggc gatggagaac
5641 gggcctgagc agagaggcag gagctcctct gcaggtcctc ccaggaacca ccgcttctgg
5701 gaggaaggct tgggagtccc ctaagcacaca tcctcagtca cttctccctg cctgtgactc
5761 aggaagacca gctcctctta ctgtcttctg tgctagggat cacttccttg ttgagtgggg
5821 cctgagtttt aagaggatct tctgctcctc ttcatctggt ccctttcctt ccaaggcccc
5881 agagaggaag gcatgcggtg ggcctagcg gtgcttctag ctttcctgtc tcctggtgag
5941 tgcgctgcct acagagagga tcacgggttt tgttttgttt tgttattttc ttcttttgca
6001 aggagcgaca tactaagaaa tgcctcatta tattttgtgt tgttcccatt gcagccagtc
6061 agatatcttc caacttggaa gggagaacga agtcagtcac caggctgact gggtcatctg
6121 ctgaaatcac ctgtgatctt cctggagcaa gtacttata catccactgg tacctgcacc
6181 aggagggaa ggccccacag tgtcttctgt actatgaacc ctactactcc agggttgtgc
6241 tggaatcagg aatcactcca ggaagtatg acactggaag cacaaggagc aattggaatt
6301 tgagactgca aaatctaatt aaaatgatt ctgggttcta ttactgtgcc acctgggaca
6361 ggcacagtga ttcagacact gaaaatctgc ctgtggttgc ttctggtaca caagatagac
6421 cagccaactc tcatttcctg ccctgaattt actgtattct gtacaaagag aaacacagct
6481 taactcctga tctccctgc aatatcacac tccctggca gcagctgcac cctgttcccc
6541 acccctcccc aggactttcc tgaagaccaa gctgccacct ccaagcctca gctaagcagc
6601 ctggctgaga gcaagtttct ctcagctctc ctagaacatg gggaaggccc actcactctg
6661 cttcctagga cagacaggta cagctagggt ccagctgtga agcaagacat tttggacaaa
6721 aatgggaagg gtattcatac tgaatcatac atccaataat ggtccagaga tcgcagctga
6781 gagtggtgct tattccttat gtctataaca ataaagcaa tactataatg accactaaaa
```

Figure 2

```
 6841 cactaggcca atatatgcag ttgaacattc tctctctctg ccctcccttt tattctcgct
 6901 ctcctttctt acttccatgc ttgcttttat cattttctct ccctccctcc cttcctcctt
 6961 tccttccatc accccaccct cctccttttc tttccttcct tccttccttg cttttctctc
 7021 tttctctcct ttttgtgtac ataatcacaa tacttttcc acaaaatcat ttgaaatagt
 7081 ttttctctat ttgttcatgc caacattgat atagctgctt taattgttca gtttcatttt
 7141 tatattttgg aaattttgtgt attattttgt tttgtttcat atttgttttg tatacgtaaa
 7201 acatttagtt ggaactgaag tcaaaattat aaaagatgac acatttgaag attttagctt
 7261 ccattgtaga cttctcattc ctcttttctc cctgacacta taggtaacaa tattttatc
 7321 cgttttcttg aactttttca ctctgtcata gcgcagtatg tatcaattct atttcaatgc
 7381 catatttata tttttgttcc tatatttggt ttttatacat tttaatcaat cttatatttt
 7441 cccgtgtctg gattgtgtgt cttacttcta aaggtgcaca tacttcataa gtatgcataa
 7501 agacgtccat atcatttatt tgaatgtttt tatgtgttga ttatttaatg atggcatcat
 7561 tgatctatca ggaatttta tacaataatt actgtattag taataataat actggccagg
 7621 cccggtggct catgcctgta atcccagcat ttgagtagta cagtcgttag gaatacttag
 7681 gccgggagat tgcgaccagc ttagccaaca tggtgaaacc ctgtctctac taaaaataca
 7741 aaaaattagc tggctgtggc ggtgcacaca tgtaatccca gctacttgga tgctgaagca
 7801 ggagaatctc ttgagcctag aaggtggagt tttcagtgag ctaatatcac actactgcag
 7861 tccagtttgg gcaacacagt gagactctgt ctcaaaaaga ctaataataa taataatatt
 7921 gatggtaaat atgggtactg acattctggt agttaatgta ctaagcacat tgcatgcata
 7981 ttgtatttaa tctacacaga aacttcatta aggatttaaa gtactgttga atgtaacatt
 8041 agaaattggg gggttaatta acattcccta agtcatatac tttaatttga taatgattgc
 8101 aatccaagct ctgtggttca gaaaatgaga tttgttaatt cggtttgcat tcccccatcg
 8161 taggagtact agcatcattt tacaacttta cagttcattt atatttcttc ttttgagaat
 8221 tgccttgtac actcttttcc tattcttcta ttggaggatt agttttttct tattggttcg
 8281 taagaattaa tatacaccat tttagagata ctgaccctt atccaatgtg ttgaagatat
 8341 ttctcctcat ttgttattat ttacatttgg cacctttgg agaattgaac tttgaaaaaa
 8401 acaaaatcta tcaattttc tatggtgtct acttgatgt caggtttaga aaggccaatc
 8461 tcacctagaa tttctatgca attcatcatc atttagtct aatgattttc tttttattac
 8521 aactaaatca ctatttgtaa ctggtaaggt agaaatgcag caatatttgt ttccatatgg
 8581 taagtcaata tccaaaagag aacttatgaa ataattgact atttccttgt ggatattaac
 8641 atatcacttt atcacatgat aaaatattac atacatgcag cttctttct ggattttcca
 8701 ctgtgttcca tgaatcttgt cattctagtg ccagtattgc cttctcttca gcactgtagc
 8761 tttatagttc ttttcacatt ctgatgaagt ttctctcatt atcttttgt tttaagaatt
 8821 ttctgtgcat gctagtgtga tctcaatcct ctcccttccc attttaaac cgtgagactt
 8881 ctgtccagca agactttttc acgctccaag gcaggcaagc ttccctcctt cacaaggacc
 8941 tgagaattca gctttcagag ctgttcctgt ggaagcctca tgtcctgcac atatggtcca
 9001 gaggcagagg gagaccaacc ggagcccct cccttttctca ttcccagctg tgatgacagc
 9061 aaaaactgaa ctctgtgagc taggccaaca acacaattaa gagagacatt gttctacatc
 9121 tcattatgca tctttcaaac atgtgtctct atatacttct gacacaggtg gtggtaatct
 9181 gtgtatgcct tactgaattt tcacaattat attactgtac tactttgtc ccctatattt
 9241 ccatctgtga atccaggtgt actgcagatc tcagtcccct ttctgagggt agggctgaca
 9301 aataaaatat acaataccaa acaatttgga agttcagata acaacaagt ttttagttta
 9361 agtatgttcc aaatattgca tgacatggca ccctgaacta cttagaaaaa aaaaacaaaa
 9421 aaacctcaca ctcctacttc agtgaacaaa aatcctctaa taaagagatc acacccacag
 9481 gatcacacac acacaaacac acacacacac acacacccca catacaccca tttatcttag
 9541 agcagagtcc aagacccacc aacacacatg atcctcagtc ctttcatttt tattatttat
 9601 ttatttattt atatttatta tactttaagt gctagggtac atatgcacaa cgtgcaggtt
 9661 tgttacatat gtatacatgt gccatgtgg tttgttgcac ccatcaactt gtcatctaca
 9721 ttaggtatat ctcttaatgc tatccctccc ccctcccccc accccactac aggccccagt
 9781 gtgtgatgtt ccccactct gtgtccaagt gttctccttg ttcaattccc acctacgagt
 9841 gagaacatgc actgtttgga tttctgtcct tggaatagtt tgctcggaat gatggtttcc
 9901 agcttcatcc atgtccttac aaaggacatg aacgcatccc tttttatggc cgcatagtat
 9961 tccatggtgt atatgtgcca catttctta atccagtcta tcattgatgg acatttgggt
10021 tggttccaag tctctgctat cgtgaatagt gccacaataa acatatgctt tgcgtggtgc
10081 ctccaagtgt cctcgcagat gccaaagga aggtggttca gttccctaat cagagacttc
10141 ctggcaggac aaggtcctgg catcagcatt agctgctgca actctgaagg gcagggtgtg
10201 agcctgctgt gggactgccc cctcctaggg ctgggcctgc tgactccagg gtctgcttcc
```

Figure 2

```
10261 cccacctctg cactccctct gctgcaggcc tgagctctcc ttgcccctgg ctctcttctg
10321 cagagggcct gctctcagct gccacaagag ggcgccggag aacggacctg agcagagagg
10381 caggggctcc tctgcaggtc ctcccaggca ccaacccttc tgggagggag gaaggcttgg
10441 gagtcctctt agacagatcc tcagtcactt ccctctgctt gtgtctcagg aagaccacct
10501 cctcctactg tcttctgtgc tagggatcac ttccttgttg agtggaacct gagttttaag
10561 aggatcttct gctcctcttc atctggtccc tttccttcca aggcccaga gaggaaggca
10621 tgcagtgggc cctagcggtg cttctagctt tcctgtctcc tggtgagtgc gctgcctaca
10681 gagaggatca cgggttttgt tttatttct tcttttgcaa ggagtaccat actaaggaat
10741 tcctcattat atttttgtgtt gttcccattg cagccagtca gaaatcttcc aacttggaag
10801 ggagaacgaa gtcagtcatc aggcagactg ggtcatctgc tgaaatcact tgtgatcttg
10861 ctgaaggaag taacggctac atccactggt acctacacca ggaggggaag cccacagc
10921 gtcttcagta ctatgactcc tacaactcca aggttgtgtt ggaatcagga gtcagtccag
10981 ggaagtatta tacttacgca agcacaagga acaacttgag attgatactg cgaaatctaa
11041 ttgaaaatga ctttgggtc tattactgtg ccacctggga cgggcacagt gattcagatc
11101 cgccctacac cacactgaaa atctgccttg tggctgcttc tggtacacaa gatagagccg
11161 cccctctca tttcctgcca ccaaatttac cgtgtgctga acaagagaaa cattgcttaa
11221 ctcctgatct cccctgcaat attacactcc cctggcagca gctgcaccct gttccccacc
11281 ctccccagg actttcctga agaccaagcc gccatctcag ctaagcctca gagaagcagc
11341 ctggctgaga gcaaggttct cttagctctc ctaggacatg ggggaggccc actcactctg
11401 cttcctagga caaatgggta ccctagggt ccagctgtaa agcaagatat tttggacaac
11461 aaatgggaag ggaatttata ctaaattgtg tatcccatca tgatccagaa accgcagctg
11521 agactggtgc ttattcctta tgtctataac aatataagca atactataat gaccactgaa
11581 acaccaggcc taggtatgca gttgaacatt ctctccctct gccctccctt ttattctctc
11641 tctctttttt cttaattctt tgcttgcttt tattattttt ctctctccct tcctccctcg
11701 ctccatcgct ccctccgtcc ttccctccct ctctccctct ctccttccct ccttcctct
11761 cttcttttcct tccatccatt ctccttcgtt ttccttcctt ccttctttgc ttttctcttg
11821 cttttccttt tgggtacata atcagaatac ttttttccaca aaatcatttg aaataatttt
11881 tctctatgtg ttcatgtcaa cattgatata gctactttaa ttgttcagtt ttctttttta
11941 cattttggaa atttgttgta ttactttgtt ttgtttcata tctgttttgt atatataaaa
12001 catttacatg gaagtgaagt caaaattata aagatgatg catttgaaga ttttagcttc
12061 cattgtagac ttctcattct tcttttctcc ctgacactat aggtaacaat attttttggca
12121 gttcacttga gtttttcac tgtttgtcat agcggagtat gtattgtttc tatttcaatg
12181 ccatatttat attttctttc tgatattcag tttctatata ttttaatcaa tcttatattt
12241 tcctgtgtct ggactgtgtg tcttacttct aaaggtgcac atacttcata agtatgcata
12301 aagacgtcca tatcatttat ttgaatgttt ttatgcattc attattaat gatggcatca
12361 ttgatctatc aggaattttt atacaataat tactgtatta gtaataataa tactggccag
12421 gcccggtggt tcatgcctgt aatcccagca tttgggcagt ccagtcgtta ggatcactta
12481 ggccgggaga ttgcgaccag cttagccaac atggtgaaac cctgtctcta ctaaaaatac
12541 aaaaaattag ctggctatag tggcgcacac atgtaatccc agctacttga atgctgaagc
12601 aggagaatct gtagagcctg gtaggtggag ttttcagtga gctaatatca cactactgca
12661 gtccagtttg ggcaacagag tgagactctg tctcaaaaaa atgaataacg ataataataa
12721 tattgatgct acatatgggt actgacattc tggtagttaa tgtactaagc acattacatg
12781 catatttttat ttaatctaca cagaaatttc attagggttt aaagtactgt tgaatgtaac
12841 attagaaatt gaggggggtta attaacattc cctgagtcat atactttaac ttgataatga
12901 ttgcaatcca agctctgtga ttctgaaaac gagatttgta aattcagttt gcattccctc
12961 atctttggga gtactaacat tatttcacaa ctttataggt catttatagt tcttcttttg
13021 tgaattgcct tgtcatactc tttgcctatt cctctcttgg aggattaatt ttttcttatt
13081 agtttgtaag agttaatata cactatttta aagatactga cccttatcc aatgtgttga
13141 agatatttct cctcatttgt tgttatttac atttggcatc ttttggtgaa ttgaacttttg
13201 aaaaaaaag cattaaaatc tatcagtttt tctagggtgt ctagtttgat gtcaagctta
13261 gaaaggccaa tctcacctag aatttctatg caattcatca ttgtttaagt gtaatgattt
13321 tgttttttatt acaactaaat cactatctat atctggtaag aacgaaatgc aataatattt
13381 gtttccatat ggtaagtcaa tacccaaaac agaacttata aataattga ctatttcctt
13441 gtgggtatta acatatcact ttatcacatg ataaaatatt acatacgtgt ggctctcttt
13501 ctggattttc cactgtgttc catgaatctt ctcattctag tgccagtatt gccctctctt
13561 cagcactgta gctttatact tcttttcaca ttttgatgaa gtttctctca ttattttttt
13621 gttttaagaa ttttctgtgc attctagtgt gatctcaatc ctctcccttc ccatttttaa
```

Figure 2

```
13681 accatgagac ttctgtcctg caagactttt tcacgctcca aggcaggcaa gcttccctcc
13741 ttcacaagga cccgagaact cagctttcag agctgctcct acagcagcct catgtcctgc
13801 atgtgtgctc cagaggcaga gggagaccaa ccagagcccc ctcccttct cattcccagc
13861 tgtgatgaca gcagaaactg aactctctga gctagcccaa cacaacaact gagagggaca
13921 ctgttctcca tctcattatg catatttcaa acatgtgtct ctatatactt cttacagagg
13981 tggtgataat ctgtgaatgc cttactgaat tttcacaata atattactgt acttgatttg
14041 tccccttatt ttcatctgtg aagccaggtg cactgcagat attagtctgc tttctgaggg
14101 tagggatgac aaataaaata tacaataccg ggggaattgg aagttcagat aaataacaag
14161 tttttagttt aagtatgttc caaatattgc atgacatggc accagttct acttttaaaaa
14221 caaacaagca aacaaacaaa ttcacactcc tactttaatg aacaaaaatc ttctaataag
14281 gaggtcacac acacaggatt acaggcacaa cccccacaca caaacacaca cacacattta
14341 ccttagagca gagtccagga cacaccaaca cacatgatcc tcagtccttt taatttaaag
14401 cacgttcaac ccttctcaga gtggcttga gtggttgcct ccatgagtct gcagatgcga
14461 aaaggaagtt ggttccgggc cctaatcaga ggcttcctgt caggacaagg ttctggcatc
14521 agcattacct gctgcaactc tgaagggcag ggtgggagcc tgctatggga ctgcccctc
14581 caaggtgtga gcctgttaat tccagggtca gcttacccaa catctgcagt ccctcagctg
14641 gaggcctgag ctcttaatgc ccctgcctcc cttctgccct gggcctgctc tcagctgcca
14701 caagagggcg ccgaagaaag ggcctgagga gatgcaggag ctcctctgca ggtcctccca
14761 ggcaccaccc cttctgggag gaaggcttgg gagtcccta agacacatct tcagtcactt
14821 ctctctgcct gtgtctcagg aaaccagctc ctcctactgt cttctgtcgt agggatcact
14881 tccttgttga gtggggcctg agttttaaga ggatcttctg ctcctcttca tctggtccgt
14941 ttccttccaa ggcccccgag aggaaggcat gcggtgggcc ctactggtgc ttctagcttt
15001 cctgtctcct ggtgagtacg ctgcctacag agaggctcac aggttgggtt ttgttttgtt
15061 ttcttcttga aagggtgcc atacaaagga atacctcatt gtatttgtg ttgttcccat
15121 tgcagccagt cagaaatctt ccaacttgga agggagaacg aagtcagtca ccaggcagac
15181 tgggtcatct gctgaaatca cttgcgatct tactgtaaca aataccttct acatccactg
15241 gtacctacac caggagggga aggccccaca gcgtcttctg tactatgacg tctccaccgc
15301 aagggatgtg ttggaatcag gactcagtcc aggaaagtat tatactcata cacccaggag
15361 gtggagctgg atattgagac tgcaaaatct aattgaaaat gattctgggg tctattactg
15421 tgccacctgg gacaggcaca gtgattcaga cctgtcctac accacactga aaatctgcct
15481 tgtggctgcc tctggtacac aagatagagc cgcccctct catttcctgc caccaaattt
15541 cctgtattct gaacaagaga agcagctt aactcctgat ctccctccta atatcacact
15601 gtcctggcag cagctgcatc ctgttcccca ccctcccc acaactttcc tgaagatcaa
15661 gctgccatct ccaggcctca gctaagcagc ctggctgaga gcaaggttct ctcagctctc
15721 ctaggacatg gggggaggcc actcactctg cttcctatga cacacaggta caactagggt
15781 ccagctgtga agcgagatat tttggacagc aaatgggaag ggtatttata ctgaatcatg
15841 tatccactca tggtccagag atcacagctg agagtggtgc ttattcctta tgtctataac
15901 aacataagca atactataat gaccactaaa acactaggcc caggtatgca gttgaacatg
15961 gtctccctct gccctcccttt ttattctctc tctctttct tactcttg cttgttttta
16021 ttttctctc cctccctaac tcctccctc catccatcct ttcctccctt cctccttgt
16081 ttccttccat ccattctcct tccttgtttt ccttccttcc ttccttgctt ttctctctct
16141 ttctttcctt tttgggtaca taatcagaat actttttcca caaatcatt tgatataatt
16201 tttctctata tgttcatgcc aacattcata cagctagttt aattgttcag ttctcttttt
16261 cacattttgg aattttgttg tattactttg ttttgcttca tatctgtttt gtatatataa
16321 aacatttaca tgaaactgaa gccaaaatta taaaagatga tgcattgaa gatttagct
16381 tccattgtag atttctcgtt cctctttcct ccctgacact ataggtaaca atattttgg
16441 cagttcactt gagcttttc actgtttgtc atagcggagt atgtattgtt tctatttaa
16501 tgccatattt atattttcgt tctgatattt ggttttata catttaatc aatcttatat
16561 tttcccgtgt ctggactgtg tgtcttactt ctaaaggtgc acgtacttca taagtatgca
16621 taaagaagtc catatcattt atttgaatgt ttttatgcgt tgattattta atgatggcat
16681 catcgatcta tcaggaattt ttatacaata attactgtat tagtaataat aatacttgcc
16741 aggcccggtg gctcatgcct gtaatcccag catttgggca gtccagtcgt taggaacact
16801 taggccggga gattgcgacc agcttagcca acatggtgaa accctgtctc tactaaaaat
16861 acaaaaaatt agccggctgt agtggcgcac acatgtaatc ccagctactt ggatgctga
16921 ggcaggagaa actcttcaac ctggaagttg gagttttcag tgagctaaga tcacactact
16981 gcagtccagt ttgggcaaca cagcgagact ctgtctcaaa aagactaata ataataataa
17041 tattgatggt aaatatgggt actgacattc tggtagttaa cgtactaagc acattgcatg
```

Figure 2

```
17101 cacattttat ttaatctaca cagaaacttc attaaggttt taaagtactg ttgaatgtaa
17161 cattagaaat tgggggtta attaacattc cctaagtcat atactttatc ttgataatga
17221 ttgcaatgca agctctgtgg ttcctaaatg agatttgtta atttggtttg cattcccca
17281 tctttaggag tactagcatc attttacaac tttacaggtc atttatagtt cttcttttga
17341 gaattgcctt gtcatactct tttcctattc ttttttgga agattagttt tttcttatta
17401 gttcgtaaga attaatatac accattttag agatactgac cctttatcca atgtgttgaa
17461 gatatttctc ctcatttgtt attatttaca tttggcacct tttggtgaat tcaactttga
17521 aaaaaaaaca ataaaagcta tcaattttc tagggtgtct agtttgatgt caggcttaga
17581 aaggccaatc tcacctagaa tttctatgca attcatcatc gtttaagtct aatgattttc
17641 tatttattac aactaaatca ctatttgtaa ctagtaaggt agaaatgcaa caatatttgt
17701 ttccatgtgg taagtcaata ccaaaaagag aacttattta ataactgact atttccttgt
17761 gggtattaac atatcacttt atcacatgat aaaatattac atacatgcag ctctctttct
17821 ggattttcca ctgtgttcca tgaatcttgt cattctagtg ccagtattgc cctctcttca
17881 gcactgtagc tttatagttc ttttcacatt ctgatgaagt ttctctcatt atttttttgt
17941 tttaagaatt ttctgtgcat tctagtgtga tctcaatcct ctcccttccc attttaaac
18001 cgtgagactt ctgtccagca agactttttc acgctccaag gcaggcaagc ttccctcctt
18061 cacaaggacc cgagaactca gctttcagag ctgttcctgt ggaagcctca tgtcctgcac
18121 gtgtcctcca gaggcagagg gagaccaacc ggagccccct cctttctca ttcccacctg
18181 tcattcccag ctgtgaagac agcagaaacc gaactctgtg agctaggcca ataccacaac
18241 tgagaggaat attgttctac atctcattat gcatctttca aacatgtgtc tctatatact
18301 tcttacagag gtggtgataa tctgtgtatg ccttactgaa ttttcacaat tatattactg
18361 tacttccttt gtcccctata tttccatctg tgaatccagg tgtactgcag atctcagtcc
18421 cctttctgag ggtagggctg acaaataaaa tatacaatac caaacaattt ggaagttcag
18481 gtaaacaaca agttttagt ttaagtatgt tccaaatatt gcatgacatg gcaccctgaa
18541 ctacttagaa aaaaaaaac aaaaaaact cacactccta cttcaatgaa caaaaatcct
18601 ctaataaaga gatcacaacc acaggatcac acacacacaa acacacacac acacacacac
18661 ccaacacaca cacctttatc ttagagcaga gtccaagacc aaccaacaca catgatcctc
18721 agttcttta ttttattat ttctttattt atttatattt attatacttt aagtgctagg
18781 gtacatttgc acaacgtgca ggtttgttac atatgtatac atgtgccatg ttggtttgtt
18841 gcacccatca acttgtcatc tacattaggt atatcccta atgctatccc tccccctgc
18901 ccccaccccca ctacaggccc cagtgcgtga tgttccccca ctctgtgtcc aagtgttctc
18961 attgttcaat tcccacctac gagcgagaac atgcactgtt tggatttctg tccttggaat
19021 agtttgctcg gaatgatggt ttccagcttc atccatgtcc ttacaaagga catgaacgca
19081 tccctttta tggccgcata gtattccatg gtgtatatgt gtcacatttt cttaatccag
19141 tctatcactg atggacattt gggttggttc caagtctctg ctatcgtgaa tagtgccgca
19201 ataaacacac gctttgcgtg gtgcctccaa gtgtccttgc agatgccaaa aggaaggtgg
19261 ttcagttccc taatcagaga cttcctggca ggacaaggtc ctggcatcag cattagctgc
19321 tgcaactctg aaggcaggg tgtgagcctg ctgtgggact gccccctcct agggctggc
19381 ctgctgactc cagggtcagc ttccgctaca tctgcattcc ctctgctgca ggcctgagct
19441 ctcctggccc ctggctctct tctgcagagg gcctgctctc agctgccaca agagggcgcc
19501 ggagaacgga cctgagcaag agaggcagga gctcctctgc aggtcctccc aggaccaat
19561 ccttctggga gggaggaagg cttgggagtc ctcttagaca gatcctcagt cacttctctc
19621 tgcttgtgtc tcaggaagac cagctcctcc tactgtcttc tgtgctaggg atcacttcct
19681 tgttgagtgg ggcctgagtt ttaagaggat cttctgctcc tcttcatctg gtccctttcc
19741 ttccaaggcc tcagagagga aggcatgcag tgggccctag cggtgcttct agctttcctg
19801 tctcctggtg agtgcgctgc ctacagagag gatcatgggt tttgttttct ttattttctt
19861 cttttgcaag gattgccata ctaaggaatt cctcattata ttttgtgttg ttcccattgc
19921 agccagtcag aaatcttcca acttggaagg gagaacgaag tcagtcatca ggcagactgg
19981 gtcatctgct gaaatcactt gtgatcttgc tgaaggaagt accggctaca tccactggta
20041 cctacaccag gagggaagg cccacagcg tcttctgtac tatgactcct acacctccag
20101 cgttgtgttg gaatcaggaa tcagcccagg gaagtatgat acttacggaa gcacaaggaa
20161 gaacttgaga atgatactgc gaaatcttat tgaaaatgac tctgagtct attactgtgc
20221 cacctgggat gggcacagtg attcagatcc gccctacacc acactgaaaa cctgccttgt
20281 ggctgcttct ggtacacaag atagagccgc cccctctcat ttcctgccac caaatttacc
20341 gtgtgctgaa caagagaaac attgcttaac tcctgatctc ccctgcaata tcacactccc
20401 ctggcagcag ctgcaccctg ttccccaccc tccccagga cttccctgaa gaccaagcca
20461 ccatctcagc taaacctcag agaagcagcc tggctgagag caaggttctc ttagctctcc
```

Figure 2

```
20521 taggacatgg cggaagccca ctcactctgc ttcctaggac aaatgggtac ctctagggtc
20581 cagctgtgaa gcaagatatt ttggacaaca aatgagaagg gtatttatac taaattgtgt
20641 atcccatcat gatccagaaa tcgcagctga gactggtgct tattccttat atctataaca
20701 atgtaagcaa tactataatg accactgaaa caccaggcct aggtatgcag ttgaacattc
20761 tctccctctg ccctcccttt tattctctct ctcttttttt aattctttgc ttgcttttat
20821 tattttctc tctctccctt cctccttccc tccgtccttc cctccctcct tcctccctc
20881 tctccctccc tccttccctc ccttcctctc ttctttcctt ccatccattc tccttcgttt
20941 tccttccttc cttctttgct tttctcttgc tttccttttt gggtacataa tcagaatact
21001 ttttccacaa aatcatttga aataattttt ctctatgtgt tcatgtcaac attgatatag
21061 ctactttaat tgttcagttt tcttttttac attttggaaa tttgttgtat tactttgttt
21121 tgtttcatat ctgttttgca tatataaaac atttacatgg aagtgaagtc aaaatcataa
21181 aagatgatgc atttgaagat tttagcttcc attgtagact tctcattctt cttttctccc
21241 tgacactata ggtaacaata tttttggcag ttcacttgag ctgtttcact ctgttttca
21301 tagcggagta tgtattcttt ctatttgaat gccatattta tattttcttt ctgatattca
21361 gtttctatat attttaatca atcttatatt ttcctgtgtc tggactgtgt gtcttacttc
21421 taaaggtgca catacttcat aagcatgcat aaagatgtcc atatcattta tttgaatgtt
21481 tttatgcatt gattatttaa tgatggcatc actgatctat caggaattt tatacaataa
21541 ttactgtatt agtaataata atactggcca ggcccggtgg ctcatgcctg taatcccagc
21601 atttgggcag tccagtcgtt aggatcactt aggccgggag attgtgacca gctcagccaa
21661 cgtggtgaaa ccctgtctct agtaaaaata caaaaaatta gctggctgta gtggcacaca
21721 catgtaatcc cagctacttg gatgctgaag caggagaatc tgtagagcct ggtaggtgga
21781 gttttcagtg agctaatatc acactactgc agtccagttt gggcaacaga gtgagactct
21841 gtctcaaaaa aatgaataac gataataata atattgatgg tacatatggg tactgacatt
21901 ctggtagtta atgtactaag cacattacat gcatatttta tttaatctac acagaaactt
21961 cattaaggtt taaagtactg ttgaatgtaa cattagaaat tgggcggtta attaacattc
22021 cctaagtcat atgctttaat ttgataatga ttgcaatcca agctctgtgg ttccgaaaat
22081 gagatttgta aattcagttt gcattccccc atctttggga gtactagtat tatttcacaa
22141 ctttataggt tatttatagt tcttcttttg tgaattgcca tgtcatactc tttgcctatt
22201 cctctctggg aggattatt ttttcttatt atttcgtaag agttaagata cactatttta
22261 aagatactga ccctttatcg aatgtgttga agatatttcc cctcatttgt tattatttac
22321 atttggcacc ttttggtgaa ttgaactttg aaaaaaaaag cattaaaatc tatcaatttt
22381 tctagggtgt ctagtttgat gtcaagctta gaaaggccaa tctcacctag aatttctatg
22441 caattcatca ttgtttaagt gtaatgattt tgtttttatt acaactaaat cactatctat
22501 atctggtaag aacgaaatgc aataatattt gtttccatat ggtaagtcaa tacccaaaag
22561 agaacttata aaataattga ctatttcctt gtggatatta acatatcact ttatcacatg
22621 ataaaatatt acatgcatgc ggctttcttt ctggattttc tactgtgttc catgaatctt
22681 ctcattctag tgccagtatt gccctctctt cagcactgta gctttatagt tcttttcaca
22741 ttctgatgaa atttctctca ttatttttt gttttaagaa ttttctgtgc attctagtgt
22801 gatctcaatc ctctcccttc ccatttttaa accatgagac ttctgtccag caagactttt
22861 tcatgctcca aggcatggaa gctttcctcc ttcacaagga ccccgagaac tcagctttca
22921 gagctgctcc tacagcagcc tcatgtcctg cacgtgtgct ccagaggcag agggagacca
22981 accggagccc cctccctttc tcattcccag ctgtgatgac agcagaaact gaattctctg
23041 agctaggaca acacaacaac tgagagagac actgttctac atctcattat gcatctttca
23101 aacatgtgtc tctatatatt cttacagagg tggtgataat ctgcctatgc cttactgaat
23161 tttcacaata atattactat acttttttg tccctatat ttccaactgt gaatccaggt
23221 gcactgcaga tattagtctg ctttctgagg gtagggatga caaataaaat atacaatacc
23281 gggggaattg gaagtacaga aaaataacaa gtttttagtt taagtatgtt ccaaatattg
23341 catgacatgg cacccagtac tactttaaaa acaaacaagc aaacaaacaa attcacactc
23401 ctactttaat gaacaaaaat cctctaataa ggaggtcaca cacacaggat tacaggcaca
23461 acccctgccc cccaacaca cacacacaca tatttacctt agagcagact ccgggacaca
23521 ccaacacaca tgatcctcag tccttttaat aaagcacgtt caacccttct cagagtgacc
23581 ttgagtggtt gcctccatga gtctgcagat gcgaaaagga acttggttca gggccctaat
23641 cagaggcttc ctgtcaggac aaggttctgg catcagcatt acctgctgca actctgaagg
23701 gcagggtggg agcctgctat gggactgccc cctccaaggt gtgagcctgt taattccagg
23761 gtcagcttac ccaacatctg cagtccctca gctggaggcc tgagctctta atgccctgc
23821 ctcccttctg ccctgggcct gctctcaact gccacaagat ggcgcagaag aaagggcctg
23881 aggagatgcg ggagctcctc tgcaggtcct cccaggcacc accccttctg ggaggaaggc
```

Figure 2

```
23941 ttgggagtcc cctaagacac atcttcagtc acttctctct gcctgtgact caggaagacc
24001 agctcctcct actgtcttct gtgctaggga tcacttcctt gttgagtggg gccggagttt
24061 taagaggatc ttctgctcct cctcatctgg tcccttttcct tccaaggccc ccgagaggaa
24121 ggcatgcggt gggccctact ggtgcttcta gctttcctgt ctcctggtga gtacgctgcc
24181 tacagagagg ctcacaggtt gggttttgtt ttgtttactt cttttgaaag gggtgccata
24241 caaaggaata cctcattaaa ttttgtgttg ttcccattgc agccagtcag aaatcttcca
24301 acttggaagg gggaacgaag tcagtcacga ggccgactag gtcatctgct gaaatcactt
24361 gtgaccttac tgtaataaat gccttctaca tccactggta cctacaccag gaggggaagg
24421 ccccacagcg tcttctgtac tatgacgtct ccaactcaaa ggatgtgttg gaatcaggac
24481 tcagtccagg aaagtattat actcatacac ccaggaggtg gagctggata ttgatactac
24541 gaaatctaat tgaaaatgat tctgggtct attactgtgc cacctgggac aggcacagtg
24601 attcagacct gtcctacacc acactgaaaa tctgccttgt ggctgcctct ggttcacagg
24661 atagagccgc cccctctcat ttcctgtcac caaatttact gtattctgaa caagagaaag
24721 acagcttaac tcctgatctc cctcctaata tcacactgtc ctggcagcag ccgcaccctg
24781 ttccccaccc ctcccccaca actttcctga agatcaagct gccatctcca ggcctcagct
24841 aagcagcctg gctgagagca aggttctctc agctctccta ggacatgggg gaggcccact
24901 cactctgctt cctatgacac acaggtacaa ctagggtcca gctgtgaagc gagatatttt
24961 ggacagcaaa tgggaagggt atttatactg aatcatgtat ccagtcatgg tccagagatc
25021 acagctgaga gtggtgctta ttccttatgt ctataacaac ataagcaata ctataatgac
25081 cactaaaaca ctaggcccag gtatgcagtt gaacatggtc tccctctgcc ctccctttta
25141 ttctctctct cttttttctt acttctttgc ttgtttttat ttttctctcc ctccctaact
25201 ccctccctcc atccatcctt tcctccctttc ctcccttgtt tccttccatc cattctcctt
25261 ccttgttttc cttccttcct tccttgcttt tctctctctt tctttcctttt tgggtacat
25321 aatcagaata cttttttccac aaaatcattt gatataattt ttctctattt gttcatgcca
25381 acatttatac agctagttta attgttcagt tttcattttt acatttgga aatgtgttgt
25441 attactttgt tttgcttcat atctgttttg tatatataaa acgtttacat gaaactgaag
25501 ccaaaattat aaaagatgat gcatttgaag attttagctt ccattgtaga ttttttcgttc
25561 ctctttttctc cctgacacta taggtaacaa tatttttggc agttcacatg agcttttttca
25621 ctgtttgtca tagtgccgta tgtattgttt ctatttcaat gccatattta tatttttcatt
25681 ctgatattcg gttttttatac attttaatca atcttatatt ttcccgtgtc tggattgtgt
25741 gtcttacttc taaaggtgca catacttcat aagtatgcat aaagacgtcc atatcattta
25801 tttgaatgtc tttatgcatt gattatttaa tgatggcatc attgatctat caggaattttt
25861 tatacaataa ttactgtatt agtaataata atactggcca ggcccggtgg ctcatgcctg
25921 taatcccagc atttgggtgg tccagtcatt acgatcactt aggccaggag attgcgacca
25981 gcttagccaa catggtgaaa ccctgtctct actaaaaata caaaaaatta gccggctgta
26041 gtggcgcaca catgtaatcc cagctacttt ggatgctgag gcaggagaat ctctagagcc
26101 tggaaggtga aggtttcagt gagctaagat cacactacta cagtccagtt tgggcaatag
26161 agtgagactc tctctcaaaa aaatgaataa tgataataat aatattgatg gtacatatgg
26221 gtgctgacat tctggtagtt aatgtactaa gcacattaca tgcatatttt atttaatcta
26281 cacagaaact tcattaaggg tttaaagtac tgttgaatga aacataagaa aatgggggggt
26341 taattaacat tccctaagcc atatatttta atttgattat gatagcaatc caagctctgt
26401 ggttccaaaa atgagatttg ttaattcgat ttgcattccc ccatctttag gagtactagc
26461 aatatttgac aacgttatag gtcatttata attcttcttt tgagaattgc cttgtcgtac
26521 tctttgccta ttctcccttt ggaggattaa ttttttctta ttggttcgta agaattaata
26581 tgtactattt tagagatgat gacccttat ccaatgtgtt gaagatatta ctcctcattt
26641 gttattattt acatttggca ccttttagtg aattcaactt tgaaaaaaaa acaataaaac
26701 ccatcaattt ttctagggag tctagtttga tgtcagctta gaaaggccaa tctcacccag
26761 aatctgtatg caattcatca tcgtttaagt ctattgattt tcatttttatt acaactaaat
26821 cactatttgt aactggtaag gtagaaatgc gacaatattt gtttccatat ggtaagtcaa
26881 tacctaaaag agaacttatt aaataattga ctatttcctt gtgaatatta atatatcact
26941 ttatcacatg ataaaatatt acatacatgc agctctctta ctgcattttc cactgtgttc
27001 catgaatctt ctcattctag tgccagtatt gccctctctt cagcactgta gctttatagt
27061 tcttttcaca ttctgatgaa atttctctca ttatttttt gttttaagaa ttttctgtgc
27121 attctagtgt gatctcaatc ctctcccttc ccatttttaa accatgagac ttctgtccag
27181 caagactttt tcacgctcca aggcaggcaa gcttccctcc ttcacaagga cccgagaact
27241 cagctttcag agctgctcct acagcagcct cttgtcctgc atgtgtgctc cagaggcaga
27301 gggagaccaa ccagagcccc ctcccttttct cattccagc tgtgatgaca gcagaaactg
```

Figure 2

```
27361 aattctctga gctagcccaa cacaacaact gagagggaca ctgttctcca tctcattatg
27421 catatttcaa acatgtgtct ctatatactt cttacagagg tggtgataat ctgtgaatgc
27481 cttactgaat tttcacaata atattactgt acttgatttg tccccttatt ttcatctgtg
27541 aatccaggtg cactgcagat attagtctgc tttctgaggg tagggatgac aaataaaata
27601 tacaatacgc agagaattgg aagttcagat aaataacaag ttttagttt aagtatgttc
27661 caaatgttgc atgacatggc acccagtact actttaaaaa caaacaagca aacaaacaaa
27721 ctcacattcc tacttaatga acaaaaatcc tctaataagg aggtcacaca cacaggatta
27781 caggcacaac tcacccccc caacacacac acacatttac cttagagcag agtccaagac
27841 acaccaacac acatgatcct cagtccttt aatttaaagc acgttcaacc cttctcagag
27901 tggccttgag tggttgcctc catgtgtctg cagatgcgaa aaggaacttg gttcagggcc
27961 ctaatcagag gcttcctgtc aggacaaggt cctggcatca gcattagctg ctgcaactct
28021 gaagggcagg gtaggagcct gttgtgggac tgcccctcc aaggtctgag cctgttaatt
28081 ccagggtcag cttcccctaa atctgcagtc cctctgctgg aggcctgaac tctcaatgcc
28141 cctgcctccc ttctgccctg ggcctgctct cagctgccac aagagggcgc cgaagaaagg
28201 gcctgaggag acacaggagc tcctctgcag gtcctccag gaaccacccc ttctggggagg
28261 aaggcttggg agtcccctaa gacacatcct cagtcacttc tctctgcctg tgtctcagga
28321 ataccagctc ctcctactgt cttctgtgct agggatcact tccttgttga gtgggacctg
28381 agttttgaga ggatcttcta ctccttttca tctggtccct ttccttccaa ggccccagaa
28441 aggaaggcat gcggtgagcc ctagcggtgc ttctagcttt cctgtatcct ggtgagtgtg
28501 ctgcctacag agaggctcac aggttgggtt ttgtttgtt ttcttctttt gaaagggtg
28561 ccatacaaag gaatacctca ttatattta tgttttccc attgcagcca gtcagaaatc
28621 ttccaacttg gaagggagaa tgaagtcagt caccaggccg actgggtcat ctgctgaaat
28681 cacttgtgac cttactgtaa taaatgccgt ctacatccac tggtacctac agcaggaggg
28741 gaagacccca cagcatcttc tgcactatga tgtctccaac tcaagggatg tgttggaatc
28801 aggtctcagt cttggaaagt attatactca tacaccgagg aggtggagct ggaatttgag
28861 actgcaaaat ctaattgaaa atgattctgg ggtctattac tgtgccacct ggggcaggca
28921 cagtgattca gatctgccct acaccacact gaacatctgc cttgtggctg cctctggtac
28981 acaagataga gccgcccct ctcatttcct gccaccaaat ttactgtatt ctgaacaaga
29041 gaaagacagc ttaactcctg atctccctcc taatatcaca ctgtcctggc agcagctgca
29101 cctgttccc tacccctccc ccacaacttt cctgaagatc aagctgccat ctccgggcct
29161 cagttaagca gcctggctga gagtaaggtt ctctcagctc tcctaggaca tggggaggc
29221 ccactcactc tgcttcctat gacagacagg tacaactagg gtccagctgc gaatctagat
29281 attttggaca gcaaatagga aggttattta tactgaatca tttatccagt catggtccag
29341 agatcacagc tgagagtggt gcttattcct tatgtctata acaatataag caatagtata
29401 atgaccacta aaacactagg cctaggtatg cagttgaaca ttctctccct ctgccctccc
29461 ttttattctc tctctctttt ttcttacttc tttgcttgtt ttattttc tctccctccc
29521 taactccctc cctccatcca tcctttcctc cttcctccc ttgtttcctt ccatccattc
29581 tccttccttg ttttcctcct tccttccttg tttttctctc tctttctttc cttttgggt
29641 acataatgag aatactttt ccacaaaatc atttgaaata atttttctct atttgttcat
29701 gccaacattt atacagctag tttaactgtt cagttttcat ttttacattt tggaaatttg
29761 ttgtattact ttgttttgtt tcaaatctgt tttgtatata taaaatattt acatggaact
29821 gaagtcaaaa tcataaaagg tgatgcattt gaagatttta gcttccattg tagatttctt
29881 gttcctcttt tctccctgac actacaggta acaatatttt tgtcagttca cttgagctgt
29941 ttcactctgt ttgtcatagc agagtatgta ttgtttctat ttcaatgcca tatttatatt
30001 ttcattctga tatttggttt ttatacattt taataaatct tatattttcc tgtgtctgga
30061 ttgtgtgtct tacttctaaa ggtgcacata cttcataagt atgcataaag acgtccatat
30121 catttatttg aatgttttta tgtgttgatt atttaatgat ggcatcattg atccatcagg
30181 aatttttata caataattac tgtattaata acaataatac tggccacgcc cggtggctca
30241 tgcatgtaat cccagcattt ggccagtcca gtcattagga tcacttaggc cgggagattt
30301 ggaccgctc agccaacatg gtgaaaccct gtctctacta aatatacaaa aaattagccg
30361 gctgttgtgg cgcacacatg taatcccagc tactgggat gctgaggcag gagaatttct
30421 agagccagga aggtgaaggt ttcagtgagc taatatcaca ctactacagt ccagtttggg
30481 caatagagtg agactctgtc tcaaaaaaat gaataatgat aataataata ttgatggtac
30541 atatgggtgc tgacattctg gtagtaatg tactaagcac attgcatgca catttatttt
30601 aatctacaca gaaacttcat taagggttta agtaccgtt gaatgtaaca taagaaattg
30661 gggggttaat taacattccc taagtcatat actttaattt aataatgatg gcaatccaag
30721 ctctgtggtt ctgaaaatga gatttgttaa tttgatttgc attcccccat ctttaggagt
```

Figure 2

```
30781 actagcaata tttgacaacg ttataggtca tttatagttc ttcttttgag aatcgccttg
30841 tgatactctt tgcctattct ccttttggag gattaatttt ttcttattgg ttcgtaagaa
30901 ttaatatata ctattttaga gatactgacc ctttatccaa tgtgttgaag atattactcc
30961 tcatgtgtta ttatttacat ttggcaccta tggtgaattg aactttgaaa aataaaataa
31021 tatctgtcca tttttctagg gtgtctagtt tgatgccagg cttagaaagg ccaatctcac
31081 ctagaacttc tatgcaattc atcatcgttt aagtctaatg attttcattt tattacaact
31141 aaatcactat ttgtaactag taaggtagaa atgcaacaat atttgtttcc atacagtaag
31201 tcaataccaa aaagagaact tattaaataa ttgactattt ccttgtgaat attaatatat
31261 cactttatca catgataaaa tattacatac atgcagctct cttactgcat tttccactgt
31321 gttccatgaa tcttctcatt ctagtgccag tattgccctc tcttcagcac tgtagcttta
31381 tagttctttt cacattctga tgaagtttct ctcatttttt tgttttaaga attttctgtg
31441 cattctagtg tgatctcaat cctctccctt cccagtttta aacgtgaga cttctgtcca
31501 gcaagacttt ttcacgctcc aaggcaggca agcttccctc cttcacaggg acccgagaac
31561 tcagctttca gagctgttcc tgcggaagcc tcatgtcctc cacgtgtgct ccagaggcag
31621 agggagacca actggagccc cttcccttc tcattcccag ctgtgatgac agcagaaact
31681 gcaaaatttg agctaggaca acacaacaac caagagagac attgttctac atctcattat
31741 gcatatttca aacatgtgtc tctatatact tcttacagag gtggtggtaa tctgtgcatg
31801 ccctactgaa ttttcacaat tatattactg tacttgtttt gtccccttat ttccatctgt
31861 gaatccaggt gcactgcaga tattagtctg ctttctgagg gtagggatga caaataaaat
31921 atacaatacc cagggaattt ggaagttcag atatataaca agttttagt tcaagtatgt
31981 tccaaatatt tcatgacatg gcacccagta ctactttaaa aacaaacaag caaacaaaca
32041 aacttacact cctactttaa tgaacaaaaa ttgtctaata aagagatcac acccacagga
32101 ttacaggcac cccccccccc gcccccgcc acacacacac acatttacct tagagcagag
32161 tccaaggccc accaacacac atgatcctca gtccttttaa taaagaacat tcaaccctcc
32221 tcagagtggc cttgggcagt tgcctccaag tgtccttgca gatgtgaaaa ggaagttggt
32281 tcacagccct aatcagaggc ttcctggcag gacaaggtcc tggcatcagc attagctgct
32341 gcaactctga agggcaggg gtgagcctgc tgtgggactg cccctccta gggctgggcc
32401 tgctgactcc agggtcagc tttcccata tctgcactcc ctctgctgca ggcctgaact
32461 ctccatgccc ctggctctct tctgcagagg gcctgctctc agctgccaca gagggtgctg
32521 cagaactggc ctgagcagag aggcaggagc tcctctgcag gtcctcccag gcaccaccct
32581 tctggaagga aggcgtggga gtccctaag acacatcctc agtcacttct ccctgcttgt
32641 gactcaggaa gaccagcctt ccccactgcc ttctgtgcta gggatcactt ccttgttgag
32701 tgggacctga gttttgagag gatcttctgc tcctgttcat ctgggccctt tctttcaaga
32761 ccccagagac gaaggcatgt ggtgggccct agccctgctt ctagcttttcc tgtctcttgg
32821 taagtgtgct gcctacagag aggctcacag gttgggtttt gttttggatt ttcttctttt
32881 agcaagggac gccatactaa ggaataccctc attatatttt atgttgttcc cattgcagcc
32941 agtcagatat ctactaactt ggaagcgaaa ataaagtcag gcaccaggca gatgggggtca
33001 tctgctgtaa tcacctgtga tcttcctgta gaaatgcct tctacatcca ctggtaccta
33061 cgccaggagg ggaaggcccc acagcatctt ctgtactatg acatctgcaa ctccagggat
33121 atgttggaat caggagtcag tcaggaaagc atgatactta tggaagtaga aggataagct
33181 ggaaatttat acctccaaaa ctaaatgaaa atgcctctgg ggtctattac tgtgccacct
33241 aggacaggca gagtgattca gacctgctct acaccacact gaatatctgt cttgtggctg
33301 cttctggtac acaagagaga gccgtcccct ctcatttcct gccctgaatt tactgtattc
33361 tgtacaaaga gaaacagctt aactcctgat ctccccccta atattacact ctcctgtcag
33421 cagctgtacc ctgttcccca ccctccccca ggactttcct gaagactaag ctgccatctc
33481 agctaagcct cagctaagca gcctggctga gagcaaggtt ttctcagctc tcctaggaca
33541 tggggagc ccactcactc tgtttcttag ggtccagctg tgaagcgaga tattttggac
33601 agcaaatggg aagggtattt atactgaatc atgtatccaa tcatggtcca gagatcgcag
33661 ctgagagtgc tgcttactcc ttatgtctat aacaatatag gcaatattat aaataccact
33721 aaaacactag gcctagatat gcagttaaac actctctccc tctgccctcc cttttattct
33781 ctctcctttc ttacttcctt gcttgctttt attattttt cttccctccc tccctcccto
33841 cctctctccc tcccttcctt ccttccttttt ttcatttctt ccttccttgc ttttctctct
33901 ctttctttcc ttttttggta cataatccga atattttttc aacaaaatca tttgaaataa
33961 tttttcttta catgttcatg ccaacattga tatagctagt ttatttgttc agttttcatt
34021 ttaaaatttt agacatttgt tgtattattt tgttttgttt catatttgtt ttgcatatgt
34081 aaactattta catggaacta aagtcataat tttaacgaag atgcatttgg agattttaac
34141 ttacattcta gatttctttt tctctctctt tttttttttt tttttttttt gagacggatt
```

Figure 2

```
34201 ctcagtctgt cactcaggct ggagtgcagt ggagcaatct cggctcactg caacctccgc
34261 ctcctgggtt caagagattc tcctacctca gcctcccaag tagctgggat tcaggtgcc
34321 cgccagcaca tccagctaat ttttgtattt ttggtagaga cagggtttcc tcatgttggc
34381 ctggctggtc tcgaactcct gacctcagat gatcccctg cctcggcctc cctaagtgct
34441 gggattacag gcatgagcaa cctcaccagg ccccattctg gatttctctt tcctcttctc
34501 tccctgaccc tataggtaac aatatttta tcagttcagt tgaacttttt cacttttct
34561 tattcagaac aagtctttca gtattacaga aaagtctttt gtttgtcata gtgcagtata
34621 tattgtttct atttgaccgt catatttata ttttcattct gataaggttt tatacatttt
34681 aatcaatctt ttatcttcca gtgtctagat tttgtgtctt gcctctaaaa gtgcatacac
34741 ttcataagta tgaataaaga agtccatatc atttatttga atgcttttat tcatagacta
34801 tttaatgatg gcatctctga tctattggga attttaatac aataattacc gtagtaataa
34861 taatatgcta atgataaaca cgggtactga cattctggta gttactgtac taatcacatt
34921 gcatgtaagt tttatttaat cttcacagaa acccattga ggggttaaag taccattgaa
34981 tacaccagat gagaaataaa gggcttaact aacattccct aagtcatata ctttattcga
35041 tagcaattc aatccaagcg ctggggttca gaaatgaga tttgttaatt caatttgcat
35101 tttcttacct gtgtgaatgc tagcattact taacaacttt gtaggccatt tatacttctt
35161 cttttgtcaa ctgccatttc atactcttcg cctattcttc tgttggttat cattttttc
35221 ttattggttt gtaagaatta atacacctca ttttagagat attgatcctt tatcaaatgt
35281 attgaaaata tttctcgtgg tttgctatta ttttcagcac cttttggtga actgaacttt
35341 gtgtactact tttaataaaa cctatcaatt tttctaaggg gtctattttg atgttaggat
35401 cagagaggca aatctcactt acaatatgtg tgcaattcat catggttaaa gtctaatgat
35461 tttctgtttt cagttttatt acaagaaaat ctccatttgt agctggcaac atagtaactt
35521 aagaagattt gtttctggcc gggtgcagtg gctcacgcct gtaatcccag cactttggga
35581 ggctgaggtg ggtgaatcac gagatcagga gatccagact atccggggta acacggtgaa
35641 accccatctc tactaaaaat ataaaaaatt agctgggcat gttggcaggt gcctgtagtc
35701 ccagctactg agaaggctga ggcaggagaa tggcgtgaac ccaggaggcg gagcttgcag
35761 tgagccgaga ttgtgccacc gcactccagc ctggggaca gagagagact ctgtctcaaa
35821 aaaaaaaaaa aaaaaaaatt gtttccatat ggtaagtcaa ttcccaaaag agaacttatt
35881 acataatcca gtagtttctc aaggatatta acgtacaact ttatcatgtg ataaaatatt
35941 acatacacat ggctctcttt ctggactttc cagtgtgttc catgaatctt ttcattctag
36001 tgccagtatt gccgtctctt cagcactgta gctgtatagt tcttttgaca ttacagtgga
36061 gttactttcc tttattgctt ttttgtttta agggtgttct atgcattgca atgtaatggc
36121 aaatctctcc cttctaattt ttaaaccgtg agacatcggt cccagcaagg attttccagg
36181 cttcaaggca cctgagcttc cctccttcac agtgacccca agaactcagc tttcagagct
36241 gctcctgcgg cagcctcatg tcctccacgt gtgctccaga ggcagaggga gaccaaccag
36301 agccctccc tttctcattc ccagctgtga tgacagcaga aactgaattc tctgagctaa
36361 gccaatacca caaccaagag ggatgttgtt ctacatctta ttaggaatat tttaaacatg
36421 aatctaaaca tatttgttat agaggaggtg aatatctgtg tatacactac tgaatgttcc
36481 caattatttt attctacttg ttttatcacc catatcttca tctatgaatc caggtgcact
36541 gcacatatta gcctgctttc caaggataga gttgccaaat aaaatatgca atacccaggt
36601 aaattggaag ttcagataaa taacaaataa gttttgagtt caagtatgta ccacatattg
36661 catatggcac tgcaccctgt acttttttt ttcttttttt gagacggagt ctcactctgt
36721 tgtccaggct ggagtgcaat ggcacaatct ccgctcactg caagctccac ctcccgggtt
36781 cacaacattc tcctgcctca gcctcctgag tagctgggac tacaggtgcc cacccccaca
36841 accggctaat tttttgtat tttagtaga cagggtttt catcgtgtta gccaggatgg
36901 tctcaatctc ctgacctcgt gatctgccca cctcggcctc ccaaagtgct gggaatacag
36961 gcgtgagcca atctcacact cctacttgat gtggccttt tacttgagaa tgaacagaaa
37021 tcctctaaca aagaggttac aaacacaagg tcacacacac ccctcctga ccccacaca
37081 cccatttacc attgaggaga gtccatggcc gaccaacata cctgattctc actcctgttg
37141 agaggagggg ccagctgggc ttcctgggtc gagtaggggc tcagcaagct gtgaaacgca
37201 ctcatttcct gcatcacgac ttacttcggt cctggatgaa taatattgaa gatatatgct
37261 taaaatattc cgaacaccag gatttgtgca tgtgttttct tccccatgaa agctatgaac
37321 agcgaaaatt ttcctgtaag tttccctgtg ttctctctcc ctctcttcct tcccctgcc
37381 ccaaaactaa agtaaaataa cgttaactgc ccgttttct gtaaccagca gaccttatct
37441 atactcccaa ttccaattcc ttgtaaacat actttgtaaa gtcctgtaag atcctgtctc
37501 ctttgccatg acgctgcaag gtcataaagt agataaaacc taagttgcaa ttccggtttt
37561 cctcaagatc taagacatgt tacaaatggt taattgcctt tgtttctcgc tttggtaaca
```

Figure 2

```
37621 tcttcccgcc tcaggtattt cccgccttga agagtttaaa aggcaatcct ataatctaac
37681 tctggctacc cattctggac cccctccatg ctttggaagc tttgtacttt cactctgctc
37741 aataaagcct acagcttttt ctctctctcg gtccgtgttt ctatcactcg ctgcggtcag
37801 ccgccacacc aattctatgg cgtggctagg caagaacctt aggtgttaca ctgttaataa
37861 agcaggttca ggccttctca gagtggccct gggtattttg cctccaagtg tccttgcgaa
37921 tgtgaaaagg aaagcagttg aaagaccaaa tcaagcttcc tgacaggaca aggccctgga
37981 agcagcatca actgctgaaa ctctgaaggg caggtgtga gcctgctgtg gactgcccg
38041 tcctatggcc ctggccagct ggcgccaggg tcagctttcc ccacatctgc actccctctg
38101 ctggaggcct gagctctcca tgcccctggc tctcttctgc agagggcctg ctctctgctg
38161 ccacaagatg gcgctggaga aggggcctga gcagagaggc aggagctcct ctgcaggtcc
38221 tcccagacac cacccctctg ggaggaaggc tgggagtcc cctaagacag atcctccatc
38281 acttctccct gctgtgact caggaagacc agctcctcct actgccttct gtgctaggga
38341 acacttcctg tttgagtggg acctgagttt tgaaagcgtc ttctgctcct cttcatctgg
38401 tccctttcct tccaagaccc cagagaggaa ggcatgcggt gggcccagc cctgcttcta
38461 gctttcctgc ctcttggtaa gtgtgctgcc tacagagagg ctgatgggtt ttattttgtt
38521 ctgttttgtt ttctcatttt gcaaggggtg ccgttctaag gagttcctca ttatattttg
38581 tgctgttccc attgcagcca gtcagaaatc ttccaacttg caagggagaa ggaagtcagt
38641 caccaggcca gctgggtcat ctgctgtaat cacttgtgat cttactgtaa taaataccctt
38701 ctacatccac tggtacctgc accaggcggg gaaggcccca cagcatcttc catactatga
38761 cccctactac tccagggttg tgttggaatc aagaatcagt agaggaaagt attttactta
38821 tgcaagcatg aggaggagct ggaaattgat actgcaaaat ctaattgaaa atgattctgg
38881 atctattact gtgccacctg ggacaggcac agtgattcac acctgcccta caccacactg
38941 aaaatctgcc ttgtgactgc ttctggtaca caagatagac cagccccctc tcatttgttg
39001 ccaccgaatt tactgtattc tgtacaaaga gaaacacagc ataattcctg atctctcccc
39061 taatatcaca ctctcctggc agcagctgca ccttgttccc caccctcccc caggactttc
39121 ctgaagacaa gctgtcatct tcaggcctca gccaagcagc ctggctgaga gcaagactct
39181 ctcagctctc cgaggacatg ggggaggccc actcactctg cttcctcgga ccaacaggta
39241 cacctagggt ccaactgcga agcgagatat tttggacagc aaatgggaag gatatttata
39301 ctgaatcata tatctagaga tcacagctga gagtgttgct tattctttat gtctataaca
39361 atataagcaa tagtataatt accactataa cactaagcct aggtatgcag ttgaacattg
39421 tctccctctg ctttccttt tgtctctctc tctactttct tggttacttg ctatttttct
39481 acacatccct ttttctggcc tccctccct ccctccctag ctccctccct agcttgcctt
39541 cctcctccc ttcctccctt cctttcttctc cttccctccc ttacttcctt
39601 ccttcttttc ttcctccctc tctccttccc ttccttactt ccttcctttc ttcctccctc
39661 cttctcttac ttccttcttt ttttccttc ttccttttct ctctctttct ttctttttg
39721 ggcacacaat cagaatacag aatcattctc tatatgttca tgccaacttt gatacagcta
39781 gtttattcgt tcagttttca tttttatatt ttggaaatct gttgtattat tttgatttgt
39841 atatgtaaaa cctttacatg gaactgaagt caaaattata aaacaagatc aatttagaga
39901 ttttagcttc cattctagaa ttctcttttc tcttctgtgt ctcaccctat aggtaacaat
39961 atctttatta gttcagttga acttttcac ttttcttat ttattcagaa gtctatcact
40021 attacagaaa tacctctttt gcttgtcata tatgtgcagt atgcattatt tctatttgaa
40081 tggcatattt atgtttttgt tctgatattc tgtttttata catttcaatc aatcttttag
40141 ttttctgtt ctggatttga tgtcctactt ggaaaggtga acatacttca gaagtatgcc
40201 taaagaaatt catatcattt cattaatatt ttattcattt attacttgat atgatctatc
40261 tggaatttt atacaataat tactatagca ataataataa tactgatgat aaatatgggt
40321 actgactttc cggtagttac tgtactaagc acattacatg tatatttat ttaatcttca
40381 cagaaacctt atcaacgggt ttaagtaaca ttgaatatag cagatgagaa agtgaggggt
40441 taactaacat tccctaagtc atatagttta atttgatagc aattgcaatc caagctctgg
40501 ggttcagaaa atgagatttg ttcattcaat ttgcatttc ttatctttat gaatactagc
40561 attattttac aattttatag gccatttata cttcttcttt tgtgaattgc cttttcatac
40621 tgtttgccta tccttctgtt ggggtattaa ttttttctta tttgtttgta agaattaata
40681 tacaccattt tcgagatatt gatcctttat caaacgtgtt gaaaatattt ctcatcattt
40741 gctattattt attttcagca cctttttggtg aactgaactt tgtatattac ttttaataaa
40801 atctatcaat ttttctaggg tctgtattat gatgtcaggc tcagcgagac caatgtcacc
40861 tacaattagt gtgcaattca tcatcgttta agtctgattt ccttttttca gttttattac
40921 aactaaatct ctatttgtac cttttaagtt agcaacccaa ggatatttgt ttccatatgg
40981 taagtcaatt cccaaaggag aacatagtaa ataatcaagt atttccttgt ggatattaac
```

Figure 2

```
41041 atacaacttt atgacatgat aaaatattac atacacgtgg ctctctttct ggactttcca
41101 ctgtgttcca tgaatctttt cagtctagtg ccagtattgt cctctctttg ttgtatctga
41161 atgagttaga gaaaatgcca cactttgaga caaattaaga ttccgtttat ttagccggcg
41221 gccaagagac ggctaatgct caaaattctc tcggccccga agaaagggct agattttctt
41281 ttatactttg gtttggaaag gggaggggtg tctagttaaa acaattttac agaaataaag
41341 taggcaaaaa gttaaaagga taaatggtta caggaaagta aacagttcca ggtgcagggg
41401 ctttaagact attacaaggt catagacttg gggctttggg cgttatcaat cagatggatt
41461 cctgggaatt gcggatatag cttgccacag tatcttatca gttaattgca ttcttggatg
41521 tgctgggagt cagcttgcac aagttaagtc cttgaggaag gggctgccag tgaaagagcc
41581 aagatggagt ctgtctggct ctcttagcta agggagagtc aattcaggtg gaaacaaggc
41641 caggtgatta aaggaaaagg gagagtctaa aaacagggtt agtaaaaaca cggttgggca
41701 ttacatcttc agcactgtag ttttgtagtt catttatat tccagtggag attgtttctc
41761 tcattacttt tttgttttaa ggatttttctg tgcattctaa tgtgatggca gttctctccc
41821 ttctcatttt taaaccatga gagttctgtc ccaggcagga ttttcctggc tccaaggcag
41881 gtgagcttcc ctccttcaca aggaccccaa tgactcagct ttcagagctc ctccctggc
41941 agcctcaagt cctgtacgtg tggtggagag gcagagggag accaactgga gcccctgcc
42001 tttctcattc ccagctgtga tgtcagcaaa aactgaactc tctgagctag gccaaacaa
42061 caaccaagag ggacattgtt ctacgtttta tgaatatctt aaacatgtgt ccaaacttttt
42121 ttttttttt accgaagtga aatctgtgt atgcactact gaattttcac aattatttta
42181 ctatacttgt tttatcacct gtatctccat ctatgagtcc aggtccactg cagacatcag
42241 tcagctttct gaggatacgg ttgctaagta aaatatgcaa tactcaggaa atttggacgt
42301 tcagataaat aacaagtttt tagctgaagt atgtcccaaa tattgcatga catggcaccc
42361 tgtattactt taaaaaaaa actcacactt ctacttgaat gaacgaaaat cctctaataa
42421 agagatcaca cacacaggca tacactccca acacacacac acacacaaac tcacagagga
42481 tcacacaaac cccgcccca ccccacaca cccatttacc ttagaggaga gtccaagacc
42541 caccaacata cctgaccctc gatcctgtta ataaagcagg ttcaggccct ctcagagtga
42601 ccctgggtgt tgcctctagt gtccttgcag atgtgaaaag gatggtggtt tagggcccta
42661 atcagaagct tcccggcaga atgagggtct tgcagtttgcc ttacttgctg aaactctgaa
42721 gtgctgggtg tgaacctgct gtgagactac ccccttaag gtctgagcct gttaactcca
42781 gggtcagctt cccccacatc tgcactccct ctgctgcagg cctgagctct ctatgcccgg
42841 agctctcttc cttagagggc ctgctctcag ccgccacaga gggcgctgga gaactggcct
42901 gagcagagag gcagaaactc ctctgcaggt cctcctaggc accacccaga gtcccctaag
42961 acagatcctc aatcacttat ctctgcctgt gaatcaggaa gaccagctcc tcctactgtc
43021 ttctgtgtta gggatcactt ccttgttgag tggacctga gttttgagag ggtcttctgc
43081 tcctcttcgt ctggtccctt acttccaaga ccccagagag gaaggcatgc tgttggctct
43141 agctctgctt ctagcttttcc tgcctcctgg taagagtgct gcctacagag aggctcacag
43201 gttttatttt gtttcgtttt gtttattttc ttcttttgca agggatacca tactaagaaa
43261 tgcctcatta cattttgtgt tgttcccatt gcagccagtc agaaatcttc caacttggaa
43321 gggagaacaa agtcagtcac caggccaact gggtcatcag ctgtaatcac ttgtgatctt
43381 cctgtagaaa atgccgtcta caccccactgg tacctacacc aggaggggaa ggccccacag
43441 cgtcttctgt actatgactc ctacaactcc agggttgtgt tggaatcagg aatcagtcga
43501 gaaaagtatc atacttatgc aagcacaggg aagagcctta aatttatact ggaaaatcta
43561 attgaacgtg actctggggt ctattactgt gccacctggg ataggcacag tgattcagac
43621 ctgtgctaca ccacactgaa aatctgcctt gtgactactc ctggtacaca agatagacca
43681 gcctcatctc atttcctgcc catgaattca ctgtattctg tacaaagaga aacacagctt
43741 aactcctcat ctctcccta atatcacact ccctggcgg cagctgcacc ctgttctcca
43801 cccaccctc atgagttacc taaagaccaa actacaatct cccagctgtg tcagccaagc
43861 agccttgtg acagcaaagt tctttcagct cttctatggg ctggtggaga cccattccac
43921 ctgcttccta agacagacaa attcctcaag gactggtctg taaagggatt catttaggag
43981 actatatggg aagactagct tcactcaagc atttatccaa ttattgtcta taggctaaaa
44041 tagtgcttat tcattgctca ggataaatgt tggaataaca actttgcact tcagtaagac
44101 atctaacgtg tatcagatct gctatctttt ggacacactg acattttttt ctacataaca
44161 aatcatggta ctattggtct gcaggagaat gggtaaaaaa gtgatagtca taggtacgcc
44221 aacttgtggg tcatatcata ggttttcaac catttcaagc atccctgccc taatgcaagt
44281 atctgaagga tctgacccctt gcctgcagc agaattcatt ccatgtcccc tctgatatt
44341 agactgataa tttggatcag gtctcagcat gggccattga ggaacactac agccctgctg
44401 agagataaaa aggattatcc actcaaggag ttcacacctc cgggccgaca tggagaacgt
```

Figure 2

```
44461 gcctagaagc agacttggag ggtgctcagt ggtgggttgt ggaatgtaag cctgaagaag
44521 cagagtttaa ttctacgggg gtgctttcat aatttagtac cctgacaggg ctcctggtgt
44581 tggtccttag acactcctgg gatggctccc tggaaacatg gaggaaacct tggtcgcatg
44641 acatgatacg gagatgttgg agctgcctgg acacagttac agagggaggc attaaaaggc
44701 ttcgagaggt aggcatgcta gagtggactt tcccactaaa cctgagaact cactggataa
44761 ctgtattccc tgcgagagcc cagagaaccc tctgaattag gaaagaaggg catgttctga
44821 aatgggagga atcagcgttc ttgagagtct tggtggaagc tgtgccctgt ggggcagggt
44881 tgactatagg agacgctgtt aaggaattag ctcccaaggg tcaatggaga tgatgtaatt
44941 tcaaaataag agtccaaatg ggcagaatta gtgtgagaag acataaagcc agaaaagcag
45001 ccaaggagcc ctgctctaca gaaatctggg gtgacagcta ataaaccaca gtgttcctag
45061 gggtaaggaa attgggctac cacagtggta ttccacatat gtattccata tatacatata
45121 tatctctccc atatatatat atatatatat gagatatata tatgagatat atatgggaga
45181 gatatatatg atatatatga gatatatatg agatatatat gatatatata tgagatatat
45241 atgagatata gatatgtata tctctctcat atatacataa tacatatctc tctcatatat
45301 atatatatat atatatatat atatatgt aattggaacg tattaagaga agatgaatga
45361 aagaatgatg tcagctcctc ctgttctcca actcagagtc ctttgaatga aggggaaggc
45421 agattgcctt gagggagaac cttgtaatgt tctagcaagt atatatggca gtgattctcc
45481 gagccttttc ccccaaaaga tcgaagacta gttacctgag aaatttgtac acctagggaa
45541 ggggaataac taggtctttc aaggctgttg gagacggcat ctgagctaac tttgatacca
45601 agaaatgcat actgtcaacg tggtccccca ttagagtgag gacacataga agctcccoct
45661 ctaatgctag ttttaaaggc ccaagtctat ctaaaagggc agtcccatag gtggatggac
45721 tgactgtggt ctctaccctg tgtctgagga tatcagagtg gatatgatga atggacataa
45781 aataaggagg ctgcccccct acccccggat agtccaggca gccttcattc ctttatttca
45841 tttggaaccc atatggctta ttctctttca ctgactggag ctcacagtct ggctattgta
45901 acctgtctta aatcttttc tctttaaaat atcctgactt tgaggcaggt cttagaaaat
45961 gactcttcct gtctcaaaat gcagtccttc attctgattg atgaattgga agcacatggc
46021 tggtgtaaag aataagaaac taattataag ccaggaaaca gcaggagaag aaagcagaga
46081 agcaacgctt accctgaaga attaatttcc gtttagaaaa tatcacagct gatgtgtcaa
46141 aggccccggt atgcaggaat gagattaaac aaatgtggtc atgaggaaga ggtttctgaa
46201 taatgataga gaagcttgag tctacaagaa atccagagtc cagaatactg cagggagca
46261 gtgctgggtt catgtttatc tggtctcttg tctattggat cctcttcctt ccagaaccct
46321 aaaccttgaa tcagcttat agtcctggct cctagaagag tgtttctcaa agtgtactcc
46381 acggaccacc tggataagaa gcacgtgagg ctttttaatta aaaaaaaaaa aaaaagtaca
46441 ggttctggga agcatccaac acaataagac agaatcttgg aatgaagggt gaaaatgtgc
46501 attttaaaat aacctccaga gctgattctt attcaaactg acttttaaaa actgctgcac
46561 tagtggcaag agatcgaggg gctgtcctga gcctgacaca gaaaggtgtt ctagaaagct
46621 gctcacaggc tccttcgcag cccaccaaat ccgcctcact cttatctccc ccagcccctc
46681 aaagcagctg ctttgacagt ttctcacatt tttgcatgat aatccacaa ctgcaattcc
46741 ttctggcttc ctgtgacctc acgcaagaaa aagttgtgta ctaaatgaat ctgctttaac
46801 ttgctctcct tcctcgggga tcacacccttt ttaagaaagc ctgtcccttta ccttgaagca
46861 caaacatatt ctcatttta ttctcccaat accttgaagg ttttcttctg cacatgtatt
46921 tgtttgatct gccttttgtg cgtggggtgg gagttaggta ggaatcttaa agtggagagc
46981 cagtttcttc ccaaattact gacctaaccc atccttaacc cccagttcaa ggccacctt
47041 gtgatagtga agcttccaca tgctcactca gcccttctg ctctctcttc ttctctactg
47101 tgcatgtcgg cttgtacttt gccagttttc tctaaagaca caaccagagg tggggtggct
47161 gtgtgtgcac aacttcaact ttacatgtgg ggctgagtcc ctatgttgta tatccttgtg
47221 caaaagcaca atatgttaat tgctatagct tttaaaaaaaa taattaatag ttttttcataa
47281 tcaaattttc ttgcttttt gtttttcaa aaaagcatac ttttattgaa gaataaaccc
47341 cttatatatg tacacttatt tataactatg aaccatgaac taggatagaa atgcattgtg
47401 tatattacaa aacataacaa aaataatagg ggtagggagg tgcagatgtt ggtcaaagga
47461 tataaacctg cagttctatg atgaataagt tctggacatc tggaatacag catggtgact
47521 atacttagta atactatatt gtacacttga agcttactga aagagtaaat ctcaagtgtt
47581 ctcaccacac aaacccaaag gtaactatgt tctcaccaca caaacccaaa gggaactatg
47641 tattaattag cttgattgtg gtaaccattt cacaatgtat acatttgcca aaacattatg
47701 ttgtatacct ggaatatata attttattta tcaattatac ctcaataaag ctgaagagg
47761 ggattactaa ttcccacaaa atacagattt aacaaaaact tttattcaac aaacagtgct
47821 atgaagttgt aaattggaaa caaaagaaat aaaatttcat ccacagtctt ctcatcaaaa
```

Figure 2

```
47881 cccttcagtg gcattcctct ttctggtgtc ccagtcttgt caattttgct aataactgtc
47941 atcctgggaa tacccaattt atcctacatg acaaaatgac aaagtctgat tagatgagtt
48001 ctcagattct agcatggcca gaagagcact gtcctgggtc ggataaaatca cgtggaagat
48061 gcaggggatg cgtgacttta aaggtccagc ccttagtccc tggatcttca tgcaggggcc
48121 gcctcagcct ggatctgctc ttcctcacca ctgcagccct atcccacgct ggctgaggtc
48181 tgcttccacc tgggcagtga ctggatgaca tgggatgaga ggacacacct ctccctcgcc
48241 cagcatcgca tttctctttc cctggagatc tgggatcttg gtcagaatcc ttcaaacgcc
48301 acccagggct tgagagggca agccctccta caccttgact gcgttttgcc caagatttcc
48361 cccatattat tatttaaaac gtgtctaatt tagacaaata gaacctgtaa gtgctacatt
48421 gagaagagca cagggccacc gaattgggaa gacaagtaga ggaaaggaaa gcaaatgtca
48481 ccagacagaa tgtatggctg caggtttaca gcagattcta ttaaaatcta tggttgggct
48541 gggtgtggtg gttcacccct ctaatctcag cactttggga ggccaaggca gagagatcac
48601 ctgaggtcag gagttcaaga ccagccaggc caacagagca aaaccctgtc tctaccaaaa
48661 atacaaaagt tagcaaggcg tggtggcacg cgcctgtaat cccagctact ggggaggctg
48721 aggcaggaga atctctggaa cccaggaggt ggaagttgca atgagcagag atcacaccac
48781 tgcactccag cctgagctaa agagtgagac cctgtctcaa aaacaaaca aacaaaaaat
48841 ctatgattgg ctgattggct attgctaaca acttttgagt ctttaatgat cagtaattga
48901 attaaaacgg ttaaaacaac aattgagaga aacatagttt tgaacactga caacacaaaa
48961 taacttatcc atgtaaccaa aagctaccta ttcccccgaa actattgaaa taaacaaaca
49021 aaaaaattag aaagcggaaa ctttacaaaa attattctca ccaatgaggt tgtccaaatg
49081 tcaccaaatt tattatagaa tagtaataac caaatttgtg catgaatcgg tgatgacata
49141 agtatcttgt aagcattact gaagtttttt tttttttctat taaatttacc ttcaagatat
49201 gccttcagga tgaggcttc cactgcactt cattatgcaa tgccatgttg acttggtata
49261 ttacctcaga tgtgactcta atatggtttg atttgttatg acgagactaa atgaaacat
49321 atcacttttt tcatgtgcat attgcacctt ataagcacaa ggtgcaatta ataaccaat
49381 ttgaatattg aaaacatatg tagttgttat aattttttc tcctctaaaa taatattttc
49441 ttatttctaa aaaaatctag aaaatagaga aagattgaag acaaataatt tgcccatttc
49501 cattgctcac tgtctgtatt ttgcactttc tacctgtcat ttccctgcgt tgaccttttc
49561 tgaccatagc tgtcactttc tttcccatta ccctagccca cccctgggct aaaggtctat
49621 agagtgtata aatgatagcc ccagaatatc cctctgtcaa aacgttctgc tagctttgta
49681 tttgaccacc ttctcaccaa ctcagcacaa ccctaagccc tgcatgtgag aatgctgaaa
49741 actggaatca tgactttcag tttttgccat cgaagagaag ctcaggaact gggtctggtc
49801 gtgggagccc agggactcac agcttccctt cccaagccag accccttttc ttgccatgcc
49861 cacaaccttc ccctcatggc catctctttg actactcagg aggtcctggg tgtcattagc
49921 aaagctgaaa atgaaccttc atttcagtag gaactcaagg ctgggtctat ttctccaagc
49981 ctttggcagg tgtgtccttc gctggccctt cccaatgcac agtcttcacc atttccaagg
50041 acgtgccact ggcagaggat gagctggtcc tgcctccagg ccctctctgt ctgctggcct
50101 gacttagcct tcttcctttg gagacacaca cacactcaca cacacgcacg cacacacctg
50161 gttcttgaaa actgcattag tccctataat ttctactttg tgtgaacccc agagatcatt
50221 tactggaacc catccagttt ccaggtgaaa caacaacacc ccacatttct tgagcatggt
50281 ctatgcagct gggattgtgc tgcgtgctct gctcacattc tcctgtttac tgtccatgtg
50341 gccctatgac acctctcttt acagatgagg aaaagaggt gaaacaactt gcccaagact
50401 acacagctat catgttattt tagggcactg aaaatctcct tctactagga cctctggtg
50461 acacgctccg atgctggctc agacggttgg catgggtttt tttagggatt gctgttttgt
50521 gtttgtccct tcctctggag caagcagcac actcattgtt ctctgagtat aagatggtta
50581 catgaagcag aaatttgtca ccagcctggc ctggcttctc tcccaactct gattctcttt
50641 aggtattaca gccttggaaa agctacttaa aataacagcc ttactccttc atttctaaac
50701 tgaagataac atttgtccta tagagttatt ttaggattta ataaagcaat ggccctaaac
50761 caattagtgc agtgcaagag ttttgctggt gtccaaccaa tgattgctat tattgctaat
50821 tataccagca acactcttta agccttttc agcactctag ccattggtca tccctccctt
50881 caccttgtgg tcagatttct gtctctcctc tggaacttct ttcttcctcc cccatttctc
50941 tcatcagtta cctccttgca ccaccaggga aatagcagtt caggcctaa gctggtcgct
51001 accataactc aggaaagtgt ggctcaggtc catagtttga aacaggtcac tctgggctcc
51061 tctccccag tcaggatcag agatatggtg ggctgccctg ccttcctttg ggtcatcctg
51121 tttccaggtc agtctcctac ctaaggacct gtgtagaggt ggcgaggctt tggacatcc
51181 ctacctcact gctctctccc tgacagctgg ctggtggctc atcaggccgg agcagctggc
51241 ccatgtcctg gggcactagg gaagcttggt catcctgcag tgcgtggtcc gcaccaggat
```

Figure 2

```
51301 cagctacacc cactggtacc agcagaaggg ccaggtccct gaggcactcc accagctggc
51361 catgtccaag ttggatgtgc agtgggattc catcctgaaa gcagataaaa tcatagccaa
51421 ggatggcagc agctctatct tggcagtact gaagttggag acaggcatcg agggcatgaa
51481 ctactgcaca acctgggccc tgcgcagcct tgcatgctgc cccagcccta cacaaaagga
51541 ctcttcctcc cgatccaaca aggccttggg cattttcact tactcttggt cccttgggtt
51601 tccctgtggc atagaagaaa aaagtcttat ccctgtccc tcacctcccc atctatcctg
51661 gaggtccctt ccccggtccc actacagatg aggctttcag cttgtcaga ctcagtgatc
51721 tatatctcat cgaaaggggt ctgtttaaag atgctccagt tcagtgtctc tgaagccttt
51781 gcaggatgac ctgtgctcct gaatgcaggt gccactagcc acctgtggct attgagcatg
51841 ggaaacatac caagtgcaat agtccaagct gagatgggct gtgtgtctaa aatcatattt
51901 tgaagcttta gtgttaaaag tgagataact cttataatga tcaaaagttg aaatgattag
51961 gtatcttgga ctaaagccaa tagcattaaa actaatttta cctgtttctc tttacttttt
52021 ttaatgcagc aactaaaaaa attaaagtgt gtgactcaca ttggtgactc atttatttct
52081 gttggacagt gctgttagag actgatcatt taagaatctg accatctccc ctgaagaatg
52141 cacaaataaa atattttgga agagatttca agggtggagg acttgctgag atttaccaca
52201 aaatggttga aaagctgaga ctagaagcct actcctgttt ccagcttcca agctcttggc
52261 cctgggactg ttatcatttt gcaatagagt cagcaattag aagcatggga aacatgactg
52321 cccacttctc agtactttca cccgtgggcg ggctgcatag gaactgatgt gagtagacag
52381 tcgccatggc agggtgatgc agtcctccct ggatgagaca tttaccttcc acttctcctt
52441 caacagcacc ccagtgtgga acacgtgtgt atcccaagct tctctagact tttgttctcc
52501 tatctgacaa atgagggggt ttagccaaat gtctgctaag ttatatgact atgattttg
52561 tattaaagca aagccataca cataagatca ctatgcccac taccttcata taaagcagtc
52621 tttttttaaca tagaataaat gaaagaaaaa aaaagaaagc ctgtgttact gatcctccag
52681 caccaaacag gaaaccctc tgctgctcta tgtgcagaaa aaaagaaat tctttgaagt
52741 ctaagctgaa tttaaatgcc ttttcaagag aatgcttaat acactgttga tgagaatgta
52801 aattagtaca acttctctag aaaacagtat ggaaatttct caaagaacta aaaatagaac
52861 taccattcaa tccagcaatc ccataactgg atatccaccc aaagaaaaat aaatcattat
52921 attagactgc attcatatat ttatcacagc actgttcata atagcaaaaa tatggaatca
52981 acctaaatgt ccattagtgg atggctggat aaagaaaatg tggtatatat acacagtgga
53041 gtactattca tccataataa atgtggtata tacacacaat ggaatactgc ttatccatac
53101 aaaagaatga agtcctgttt tttgcagaaa catggaggaa gctggaggcc attatctaaa
53161 gtgaaacaac tcagaaatag aaagacaaat actggatgtt ctcacttata agtgggagct
53221 aaataatgtg tacaagtgga cataggggtgt ggaaccagac attggaggct tgtaagggtg
53281 gtgggggca gaaggaatac agatggaaat taagtaattt cacatcacaa tgagtattat
53341 ccaggtgtgg ggtatactaa aagccaagac tttaccactg tgcattatat gtgtgtaaca
53401 aaattgcact tgtactcctt aaatttatac aaataaaaaa caaaaggaga atcacttgga
53461 cccaggaggc aggggttgtg gtgagccgag atcgtgccat tgcactccag tctgagcaac
53521 aagaaataaa aaaaaaaaac gctacgcctt gcttctgaaa cagcccagcg tctctaacct
53581 ctactgaagg ctcagttcac ggctaaggcc ttccaacttg tgtgagaagg acagaggcca
53641 tacaggagga aactttcatt ctgttttgga gttgttcctt catttcattt ttctaattgt
53701 gctgataaaa ccaaatgggc acagagagga gatgcctcct cttctgcctg cccctctct
53761 cagtgcttta ctccaaacaa gagtaaattt ggtgaaatgg tgactatcag ggtgtggcca
53821 aatggaggcg caagctcccc agtcacctcc ttatggaaca acatctttca tttcctcaag
53881 aggagactct gccactgcag tgaaccttca ccaccacaaa cctccaccctt cactcctcac
53941 caacacctgc tgtactcttc atgaatgctg tgagcttgag cgagttctta aatttcctag
54001 ccatcagttt cctcatctcc aaaataaaga aaacagcaat gtccaaaatc aatctccctc
54061 tgaattatac tacctggttt cagcctcaac ctccagggtg atagaccagc ttagagacca
54121 agatttatc tttcctaagt gatctcacct tcagaggcat catcaccaga cttttcaagt
54181 tttgtttctt agaaatggtc ccaagttctt tccctctcat cgtctcttgc tttagggagc
54241 ctccagcta gtctgtctta gcaagacaag ggcatagctg gtgcattgct gctggtgagc
54301 agggcaagt tcacagaagg cagcatggga gagtataaca gaaatcacca tcagtttcca
54361 agggcttgct ctgtgtcagg cattgcccta aacagtctac ctgggcaaac atttattctt
54421 tgcaacatcc agtaaggtag gctgtgattt tattctcctt tggtagataa gaaacagag
54481 gcagagagaa ctactcaaag agctcaggct ttgcagcccg atagaattaa tcttaaatct
54541 gtcaccaaca agctgttaaa ccttgaccca ttacctgacc tgctttgagt agggctttgt
54601 gaagattata ctaaatttat ggtattaaac atcataatgg ctacaaactg cttgacacat
54661 taaggcattc actaagtgtc cattgcttgg taactcttta aaactgtat tttaaatggt
```

Figure 2

```
54721 gatgttttgt taacatcaga acgacaaaaa aatactacaa tggccatcca ttccctcact
54781 ccacccttte atctattcaa caaacacctg ggaatagaga gataaacagc acatgatctt
54841 actccoctgg gaactcttaa ctgtcgttta gaatgagaga gaaatgggta aacaggccaa
54901 gacttgggta ggaggtgcta ggagagagga aggcactagg tggcgtgaag agaaagcaat
54961 ttgaagcatc tccatcctgg acttactggg tgaggtaagc ttcctgggga agactgcctg
55021 gggctgagcc cagaaggata aacaggaatt agccagggaa tgtggagtag aatgcagtcc
55081 aaacacaaaa aaattcaagt caatccatag aagtgggtcg tggaattcca ggcagaaagt
55141 gactaaatga agatggaagg acaggaggg gtggccaca tcacagagaa cctcttatcc
55201 taagaactct ggacttcatc ttcagaggca aggtagagag agcaaggact ttagagcagg
55261 aaaaggacca ggtcagtcta gtggccatgg ggaaggtggg tgggaggggc cgagatggga
55321 tgtatggagg tgcgtgaggt ggaggcagtg gtgagccagg aaatgtttag gacgtagaat
55381 cctcaggaat tagagtgcgg tgaattagag gggagaattg aggctgatgc tcaagctcct
55441 ggcttgggca atgtgggtag ttatgtcata cagggaactc ggaagaagat atggtttggg
55501 ggaagggaat gagttcactc tggctatgag cagactttgt ttgagatccc atgtcagacg
55561 tacttgaaaa tgtccaagag ttagctggat atgggtacag acagctttcg atttaactga
55621 ggtccgactt aagattttt tttactttat gatggtgcaa aagtgacacg catttggtag
55681 aaaacataat ttgaccttg ctgtttcccc aggacagtga tataaggtta tgatactctc
55741 ttgcgatgct gggcagtggc agtgagctgc agctcccagt gggtaaatta agcatggaaa
55801 tctggaacac agcagctttt aagggatgca ctggggagag cagtttgtaa aaataccttg
55861 ggacggatta aatgtcttgg cttagagaaa gaacaacaga caataggaaa ctgtcattga
55921 ggagaagccg ggattcagga gatgtacatt attcaggtag ctgaggagg ggacaggaac
55981 ctgaatcttc aacagaagca aacaaactgg gatggagggc ccagcctcat gaaggtgacc
56041 agaaggaccc ggtgctgcag gctgtgtggg tagctgagca gagctaagcg gcttgacgga
56101 ccaacatctc tccagctggt tgaagacaag ctctcagaag acaatgctgc atgtcacagc
56161 cccagcaacc aacaacacca gcctgacaac ttgctggggt ggccgccttg tggtctgagg
56221 tggccgtcta aactatgtgg tctgatctca ggctgcagac cttgcaggac tgtcttcaca
56281 cagactggaa gtgctaacag gtggtgagga caccgcttta caacgatgca ggggggcccca
56341 tgtcaccctc acccatggga agtttgactt ggtggactca gccaagccac agaggtctaa
56401 cgcttctctg cggtgatttc aggctgccct ggcagaaagc acagtgcctg cagacatgct
56461 gtcactgctc cacacatcaa cgctggcagt ccttgggct cgtaagtagt tttgctcccc
56521 caatcacttt ggactgatat tctctattgt tatatatttt tataaattcc aaattcttgg
56581 tttatttact ccctcccatt ttttccccca gtgtgtgtat atggtgcagg tcacctagag
56641 caacctcaaa tttccagtac taaaacgctg tcaaaaacag cccgcctgga atgtgtggtg
56701 tctggaataa caatttctgc aacatctgta tattggtatc gagagagacc tggtgaagtc
56761 atacagttcc tggtgtccat ttcatatgac ggcactgtca gaaaggaatc cggcattccg
56821 tcaggcaaat ttgaggtgga taggatacct gaaacgtcta catccactct caccattcac
56881 aatgtagaga aacaggacat agctacctac tactgtgcct tgtgggaggt gcacagcagc
56941 agacagtttg agccatccca ttcaataaat gtttattgag tctttgttta taattacgaa
57001 ttgggaagcc acagttacca ccagtgtgct tgtaaacagt ttttaagata acattcatg
57061 tggtgactct acttggagtt gccaaattcc acatattttc tcaaagcaga agctttgcat
57121 aagtctatac aagtgaccag cctcctcttt ttcagggttg tactctctca ccaacagctt
57181 ttctaggtca cccatgctta ttttttctggt tcaacctctc ctactcatta tatatttttt
57241 ttctggtata atatatacac attttagtg tgattctttt gtactagtca atatgcatta
57301 cataagtttt ctctgacctt cctatttctc tcgattaaaa aatggatatg acattaaatg
57361 gtattcattt ttctggaggt taacatgtaa caaacgcagc atgatctaac cacgagcagg
57421 gcagactgca atgacaaatc tatcacatgc atgccttgag tggtgatgtt tgattttgta
57481 caaaatccgt aaacacttcc actaatcgaa tctaagtcaa agtccacttt ggattggggt
57541 ttgagaaaaa attcatttgc tgcaacctct gcctcccggg ttcaagcgat tcttctacct
57601 cagtttccca agtagctgag actacaggtg cgtgccacca cgcccatcta attttttgt
57661 atttttaata gagacgggt ttcgccatgt tggccaggat ggtctctatc tcctcctgac
57721 ctcgtgatct gcccacctca gccttccaaa gtgctggat tacaggcgtg agccaccgtg
57781 cctggtcatc caaccatgag cttttgatag actactctga gccaggcatt atgcacagca
57841 gaaattacaa ggcccatacg ctctgcaaag gcccgaggtt gcttctgttg aaccacattc
57901 tgctactggg ctgccattca ccactaaaat ggcagtcctc aacttgaata taactcatga
57961 ttgtaagtct cttatgaatt ttcgttactt ctagttcaac tcaggctttg caatttatta
58021 ttgttgatgg tgttgttta atttatgttt ttgccatgaa acccttctt gaaatgtgat
58081 cttacaaata taaaatagag aaaagtagat ttccactggg aaagagttca gagatgaatg
```

Figure 2

```
58141 atccttagtc tcatcttctc aaatttctct gatactttga tttttcaaca gctcaataat
58201 tatctgagta tacatataat gtacaaagtg gtcaagacct gggcctgtca tgtcagaagg
58261 acataggtcc aaatggggct ctacttacca cggataagct gtgtggcaag gccttgagct
58321 tctctagccc catttcctca cctgtgaggc aatggtcctg tggttatcat atgggtggct
58381 gtgagaactc ctgacatgat gcatttcaag gatttggcct agtgcttggc atattgtgac
58441 agcccagcgt tatctgacaa gagacaaaac tagatacaac aaaaaaataa cagcaagcac
58501 acatatatag tcatgtgtcc cttaacgaca ggaaaacatc ctgagaaatg catcctttgg
58561 caatgtcctt gttgtgcaga tattgtagag tgcccttaac acacacctac atggtacagc
58621 ctactacata cctaggatat atggtatagc ttattgctcc taagctgcaa acctgcatag
58681 catgttgctg tactgaatgc tatatgcgat tgtaacactg ataaatattt gtgtatttaa
58741 acatagcata gaaaaggtac agtaaaaata gaatataaaa aaaatgctac acatgtgtag
58801 ggcagtttca ttataatttg tccatctttg actgaaacat tattattcag cgtatgacta
58861 tatatacaag aaaacataca cacacacaca cacacacata cacacatctg gtttttttt
58921 ttttgagatg gagtttcact cttgttgccc aagctggagt gcaatggcgc gatctcggct
58981 cactgcaacc tctgcctccc aggttcaagc gattctcttg cctcagcctc caagtagctg
59041 ggattacagg cacgcactac catgcccggc taattttttg tatctttagt agagatgggg
59101 tttcgccatg ttggccaggc tggtctcgaa ctcctgagct cgtgatcacc ccacctcggc
59161 ctcccaaagt gctggatta caggcatgag ccaacacgcc tggcccatat acacatcttt
59221 atatatccag ggcttagtgc tacgtctatc atagtgtggc tattacattt tatagagaga
59281 atagctaagt atgaagaaac tcttacaaga ggttatccca gattaattta attctaagct
59341 tttggtcatg gttccctaag accttfgact cacacacagc tggacaggac agtggccttg
59401 tgcatagtgc agatgaccat tatagggaa aaacaagtcg aaattcatag tcctttactc
59461 ctcctgccct tctccttttg cttaaggtga gcttcaccag gaacattttc gccacaccaa
59521 aggaaaacta gccagaggca aaccagctct aagttaatat ttgccaatta aatggtttaa
59581 gttttggatt cacagaaaca ctgacagcat cttattagaa tatactgtac tgcatatagt
59641 agggctcaa tgaatatctg ttgaattgag attgatactt tcattattat tgatgggttc
59701 attttaccta atgggtcaac gcgttgtatg gatggatgcc ctgaatattc tgatgatttg
59761 ggttcgactt ctttfctttt ctacctgagg tgggtgagct acaatgactc tgaataatag
59821 aatcaacatt atattatcta gttaatataa aatctgaata aatctaagg aaatcttgga
59881 aagcaatatt ttcataaacc atatcatctg ttgccgaact ccccacacat acaagtacta
59941 tggaaaagt aatgtctact gcccaggagt catcttatag aaaccacaat tctagaagtt
60001 gctgtaccca cctggaaatc catgctgact gttttgtctc gggtgctttt tgctttcagt
60061 cctgtgaagg ggttcacaag aggcagactg gggtagacaa aaaaagggca cagactttga
60121 aatgcttatc tccagacatt gcgctcatga gtatttttat ctgtgtcatt tctgtacttt
60181 tgaaatggtc taatagaaaa cacattactt tttaattta ttttaaaatt gacttaaaaa
60241 aagaattcct gttttataat attaaacata tccctgcaca ttattgagca cctagagaca
60301 atatgtaaaa tgtgttggtt agaaggacct ggaagggget ctgcttgact actttttctt
60361 tcctcttctc taacaacgtt tgcttcttgt aaaaagcaaa atcttacctt ttctcctgtt
60421 tcctactgat cactgtgctg agctaaagaa aatgttagtg atttgaatgc tcaaggcagc
60481 ttattgggct tgtatgtctt cctgaacac taggattttt caagcctgta gatcaaaggt
60541 cttgggaaaa aagaaacaac ttttttcagt gagctaactg aaatagaaga gaatggcgac
60601 tcctacccac acctcttgga tcctggacat cagctctggc tgtgggcaa atgcactgc
60661 atattggcca atgtggggag gatgcagcca acttaaggcc ccttttcagg gagggaacgc
60721 tgacccacg ctcctatttc ccagctgcct gctgatgttt ccattttcta ccccсaaaaca
60781 acacctgcag gataggggaag accatccatg cagcccaggg cggtcagact ttaaggcag
60841 agttatgtgg aaaatggact tggatgagcc aaggaggaaa tcctgcagat ggcccaataa
60901 gtggattatg tttgacttca gataagtagg acaagctagg gagccagaag gttttattag
60961 ttttgtttca ctttccacaa aaccaccaag gtcccatctc caacagaaca ggatgtgtga
61021 ctgttccttg agtaaaaaaa caggaaactg gacaaatctt gagagatcat cattaattag
61081 tacttcttta gttgatttct taatatggag gagcatgtag attattaata atgcttttgt
61141 tcttgagtta agtgaaggag tcttaggtat ttgttgactc attaaataaa tcaccaacat
61201 gtagtagact caaataagaa acataaaagt gatacacatt tagataaatg attatagtgc
61261 tttatgcttg tagtgcttca tgaatcgata gtatgattaa tccaattgtg ctcgtagtgt
61321 tctttacaac aactaagttt aaaatagaga aacaatctca actctcatta gatgattgag
61381 gatagagaaa tgcctgtcac gttcatgtca agtagaattt atcccctcac ccctgttgct
61441 ataattgatg tgtctcttct gtagatccct aatttaattt cttgtcactt ttaagtcaac
61501 ttttaactag caaattagca aagtgctaag ggattcagag agattgaatc acgtgctata
```

Figure 2

```
61561 ctttactgta gtcccgttct ctttatattt tacttataaa ctaaagttac agagtaatta
61621 tcaaaactcc atatttgtgt tctgaaattg cagaatttg aatttgcagt ccataggtca
61681 gcagatttct ctgactttcc ttatttcctt tgcttagcca cagaaaaaca gaaaaatcag
61741 tgagtttaca tgcacagaat taaatgtaca gactattctc tgaaagagct cagttctatg
61801 tgaaaatgaa taatgtaata aatattctta tgagtgtagt aatagtagct attgtttatt
61861 gagtacttct tatgtgcatg gcacttata ctgcatgctt tatgtcattt gagcctaaca
61921 aaatactatc attattatta tctcattttt atagatattt tctttttta ataaactctt
61981 ttatttgcac gtttgtgtct tgggttattc gtggggtgag aaacctccac acttccaatc
62041 ccagccatct ggtacaatct ggtgttgtgg tccagctgtc ggcaaagggt agaggtgggt
62101 gcagggctgg cccccagtc tgcaccaacc tcttcagagc agggagctca gaccatggtt
62161 gtacttgcac tgcttcaggg cctcgctgaa gccttcacac agggacaggt cactctgcgt
62221 ggtcgaacag tccaggaact gccggatctc gtaggcgcag gacccatct gcagggctg
62281 gggggcagcg cgtgtggggg tctgctgggc agcaggctgg acgggctccg agctccccca
62341 tctgaaggct caggtcaggg cgctgccat gacgtgtccc acagccgagc ccacggctac
62401 ccctgcggcc atggacgcca tctaagccat gaggctcggc tggccggaag gggcggagat
62461 ggggcggctg ccggaggcgg tggctgtgtg gggcaggtg ggcagaggg gcggcgggag
62521 ggggctgggt ggtcggaccg ccgcgctgcg gcttcccaga gacatggtgg cggcggaggg
62581 acccggggcga tcttaaatga cagcgatggc ggcagcggtt ctgtcgcggg gacaaatgcc
62641 ctttatagat atttctaag tacagatttg agactttgat aaattaagat acttgatagt
62701 aagcagcgag gctgggatct gaatccaggt ctgtctgact acaaaatcta ttgccttgat
62761 ctcctacagt gatgagaaaa acaaaaccaa acacgaactt ttaaatagag acatttcagg
62821 gggaaataaa aaaatttata attcgtttta tgagttttt ttttttcatt tgcggcctta
62881 agctcctttc cccagggtca catgaagtta gttaaattga tgctaacggt gtttacttac
62941 agacaatctg cagagaattc tctacagaga attttcttat gcaatcaagt ttttctgact
63001 tctgggttct aagatttttt tcttttta acaagaaaaa aaagcgtaac caaaactgtg
63061 tttattgagc aacagaaaag cagcgagatg gaacacagag atattccccc tgattatcac
63121 ctttccgctg cactccctta ccctcagtcc gctgggagc acagaaatgt tatccaaagg
63181 tggatgggaa agggtggaaa ggctgagacc caactgcagc ctggctgag atggccacat
63241 catgttctgc ttcctgcctg gctgcccagg gagggcctgg atgggcagag ggccaagtca
63301 gtgtcaggct gggaactta catgctttc tcacttaaat attgtcatct ccttctcag
63361 aggaggaacc agagattcag agagactctg tagcctccaa gatcacgcag gcatcactag
63421 tagcagagaa gggatgtaga gcaagtgtga cggtccataa gacttactct cttcccacca
63481 caccacactc acccagcaag aactggaata aatgacaagg gagggaagag gggctcagac
63541 ttctctgtat attcacaagg atgtgaaatg tgttcctgta agcgtaccca agttgggaat
63601 ttggtccttt aaagaaaaag gttgaagcag gaagacttcc agtttgctgg atgaaacata
63661 atgcagcaat caaacagccc gactcttttg agtgaatatc aataggaata ccactatacc
63721 attcacttgt tcttcaaagg aaaaaatgaa actaatgagt ccttgattcc atgacataga
63781 taaatgttct gagaaggaag aagttaatgg atcactggga aggcttcata gagccagaag
63841 attcaagtaa aagtcttgcc aaacaagaaa aggagaaagt tcatttttgt cacagtctgg
63901 ttgcaacagt aaaaactagc ttttgtcatc atcacatttt ctaatatcga aaggacatat
63961 tttaggaaaa agcatcccaa atttataggt atgttgttat ttatagaact tcatttttt
64021 aaatcaaact cttcagtgaa ttaattttta ccactcctc aggtacagga taatgggac
64081 atttgcagcc agtttcctcc ttgcccatgt ttgctgcgag gtggggcgtg gatgtgggga
64141 acctctctg gggaagagga tgggtgcagc agcccgacga ctggtcgtga ggccccacca
64201 caaaagcct ccacttaaag gcaatgctg agagcccac cacacctcat gatgggggaat
64261 tcctctgtct agagatgtta tttattgtca ttcaagtcaa ggaactaaaa tcctaagaaa
64321 aagagcatac cccaaagcca aactaggcct cctaacagta gctctgtgct catcctgctt
64381 caacaaggag gcagagtaga gaggaaggag gtgaaagata tggaacccac tgagctccca
64441 ctttattcca ggcgtattat gcacctatct aagccaatgc tggtagatag ggatttcaat
64501 ttcattttca tagttgaggg cactggtgt cagatagcaa caagtcaagc taacagcagg
64561 ctgaactgga attaaaagca ggactgaatg attgcatgct cgcctgtata gcacactacg
64621 tggatttgct tggcattgaa gaaataggtt ttagttccag ctctaccatt tactagctga
64681 gaggccttac attaccccct cttccccatg gggaatccct tcctgcctca aaatattgtt
64741 tggattaaat aagccaatgt ttgtaaaaga gttttgaaa ttgtagacac cataacaaag
64801 taaagagtta tagttttttt taaacacatt ttcattcatt ctaatatgat ttctcatatg
64861 aattatctcc taaggatagt caatatttat ggagctccca ctataggaa ggcatccttc
64921 ttgatgaaat aagggctt aacaatccct acaacttatg actttgactt aacaaaaacg
```

Figure 2

```
64981 aaatctagca tgtgttatat gaaagtagca ggtaacaagt ggtctagcaa agctgcagtg
65041 ctatatgctg agtgatagag gtatttgttg taacatccac tccaattcct caagaaaata
65101 gatggtggca aagaagatta agtgatattg ctcattaaat gatgagaatt tttacatact
65161 ggatattcag tgggagtttc attttgtccc aatctccgct gacactctaa gctcaggaga
65221 atggtagtaa tacaaaagaa ggggacaaaa ccagagattc acagtggagg gcaagcccct
65281 ctccagcaga cattggtaat gtctgagaca ttttttactg tcacaaacag agtgagaatg
65341 ctactggtat ctagtgagta gaggccagaa gtgttactaa acatcctaca atgcacagga
65401 cagccccaca acaaagaatt atccagccca aaatgtcaat aatgcagagg ctgagaaacc
65461 ctggggtagt tggccatatt tctcaaagac ttgctaagag gtagacaaaa ctgatgactc
65521 caacctttgg ctcatgagct atatccaggc taattacagt aagagctttc ctgggactc
65581 taattttgca aagacttct ctgaaaagca ctgttgggat ttccctgaa accccctcct
65641 ctcccagtga ggaggtgatg aggtagctct tctacttcca caccaaatag gactctcagg
65701 tcctacatcc accatgggtc cagagcagag ccctgtgtgt gggtcatgga agtgttgggt
65761 ctgtgccgtg agcgtttggt ggccagataa accagtgagg actctcacct ggaaaagtgg
65821 acaggtggct tcaggtcata gcccacgtgg taacttggac caactctccc ctgaaatcag
65881 ttagataatc atgatgaaat aataataatg aaaaagaatc tttctaaaag tttctaagag
65941 ttagcaagat aacaaggtga ataacttta ccctggcaaa tggactgatt atcatggtgt
66001 catacagcta tgggtaaagt tcccatgtga tcctgaccaa tcagcaacct cagaaatgac
66061 tgatctgggc gcagggccta aggacaccca ttttctctgt gaacactctt tgaggttccc
66121 cttcctcatc ctggtgcagc ttctcctgct ccaggttccc tatttcctca gccttgtctc
66181 aggcactcag cctgagcaga cgggacgtca cagctacaga tatgcacctg ttcttcactc
66241 tgggaatgtg aacttgttct cctacttctc agattggctg agggattttt ttgaaaatga
66301 atgtctcatt tcttgataac tttggtttca ttgaaaatgc tattttgttt ctaattgaaa
66361 ttgggtaaaa acaattgaag caagtaaaaa tctttatttc attagcagaa atgaagcata
66421 tattttcact gtagggtatt tagatagaac ttttcataca cactcaggta ctgaccaaca
66481 ccaaatcagg cttttgagga tttgatattt acttggaaaa aaaccctgtt ccaggtcaat
66541 tacaggcaaa gagctgcaac catatataaa attctgtata taaattctct atataaaatt
66601 ctgtctactt ccctttagtt cttaatataa aattcctaga aaaatagaaa gacatgatga
66661 cccaatataa tggccccag gaaactagca tgacattgga gctgaggtaa tgggcacttg
66721 cccccattatc atgtctgcga ccacatcctt cccaatgtgg aagagcctcg tccagccctc
66781 tgccccagct aggcctcagc ctcagcttgc agcacttcct gtgttcctca gatgatgcct
66841 ctgtgatcac aggaaaccag aaagggagtc tgatgactat caatttcacc ccacaaatgc
66901 cagtacctat accccaagt gtctgatttg acatcatttc ctattgactt aggttcctat
66961 ttagagacta tgtttgttga aactgcatga ttatttcaga gagaaagcaa ggtccattat
67021 atcatttctt agaaacttct agtcatggtg aattgctcag ggtgaagatg ccagcaagga
67081 acaagatgga attcatatcc actcagttcc cactggctgc cagaaaatgg gatagatgtt
67141 ctacatattc agaatttcag gtgattgtca taagaacctg gtaaataaac ttattcatga
67201 aagaaataac tgatgtttag acagggcag ttatctgtcc aaacaaatag ttcatgctct
67261 ttcaagtgca ctattggggcc actttgaata cccttttgggt ttattaactt aatggaaata
67321 gggccagggg cagtggctca ggcttataat tccagcgctt tcagaggctg aggcaggcag
67381 atcatttgtc ctcaggaatt caagaccagc ctgggcaaca tggtgaaact ccatctctac
67441 aaaaacacaa aaattaacca ggtgtggtgg agcttgcctg tagtctcagc tattccggaa
67501 gctgaggtgg gaggatcact tgagcccagg aggcagaggt tgcagagaga caagattgca
67561 gcactgcact ccagcctggg atacagagca agactctgtc tcaaaaacaa acaaacaaaa
67621 ctttataggga atgaactgtg gcatttgtgg gtaattatgc gctggcccgg acttactgcc
67681 tagtcctgca gagctaggtc aagacagaat gggcagtgac tcaagacaga atgggcagtg
67741 actcaagaag ccatggctaa agggtcatgc tgaacacaca tttggaagag ttcccacccc
67801 ccaccccacc cccaccctgc tccccaccgg cattctgcct taggacccctt cttctcactg
67861 gaggggaaaa ggctaagaaa acagaaaacc ctctctgttc ttgtgaactt gctttagcag
67921 ataatatcat gggtgggata cctgagaggg gatcaaaacc tcacagccca gacttaagta
67981 aatgatcaaa atgtgtaatg aggatcatgt tttggaaatg tggccaacat attttttattc
68041 tctaaaataa atcatgtcac ctttttgtcct ttctttattg tagctaatcc atgatattta
68101 ctacccatag aaagagatgg tagttgccca gaacaaactc actttttttt tttttttttt
68161 tttttttga gatgaagtgt tactctgtcg cccaggctag agtgcagcgc acaggcgccc
68221 gccaccacgc ctggctaatt ttttttttgtt tgtttgtttt tagcagagac ggggtttcac
68281 cgtgttagcc aggatggtct caatctcctg acctcgtgat acgcccgcct cagcctccta
68341 aagtgctggg attacaggcg taagccacca cagcctgcca caaactcact ttttgaatta
```

Figure 2

```
68401 attgtgagat gttgggcttg aaaatcaggt tcaattttt tttaaagagt tttctatagt
68461 tgtgattctc tcattcatag gtcaaaaggc cacactggca aagtaacaac acagaatttt
68521 attacagctg ctagatatga agactcagca tatgatatcg gtgacgttaa taccttccca
68581 gggagaagcg ctgttccttc tggctgggaa gtgcgagccg gtgggggggag agagaggagt
68641 agagcattat gtggaggtac ttcccggttc ccttgcgtct gagggtctta tgccagaggg
68701 gatagaaagc ccaacagaaa ctcaagatag aagaaggaga atctgcgagt gtctgtctcc
68761 tgtcaagctt ccctaataca gccctggtag aacttcatca acagtggaag gcatttgcaa
68821 aggtgagccc aaaccagcac cccttccac acaggctgtc catgtagaag gcccagatgc
68881 ttctcagggt ctctgagagg atacaaagct actgaggggg ccagagggca cagcacctgg
68941 gatttggatg agaagctgca ggaagggaac tttgcacccc aagggcatgg tgtggagtca
69001 atagtggcaa gttcagtctg gttttttaca tcagccggtt cagaggaaga gtgaaatccc
69061 caagatcagc agggcaaaat gctggaagtt gtcgaggatg cagagagtag caggaagaca
69121 cctctgagaa ctcactcaca caccctgccc ctgtgtagag atgtcatcct ggggatgaga
69181 aggaggaaga cagagaaacg cagaaaagcc taagcaggca ccacaaagag accgagcccg
69241 tctgaaagag gctgctctaa cctggtggaa actattttaa gttggtaagt ttagtgcctc
69301 cccacaatat cagaacgagc aagagacgac aggtataggt tgtgtacatt tcccctctgc
69361 gttgaatgat agcgtgtgcg tgttccacca ctgtgccctg ctcaaagtta gctgggtggc
69421 tgtgccctgc tcaaagtcac ttgggtgagg ggcgcccgtg ggagccaaaa atcccatctt
69481 acacccaccc cctgcacact ctggagttgg gctgtgacat gctggagaaa ggtgtctttg
69541 tctaattatt ctgcctaagg gcatgccttt tgttaattag taaaaggaag ccttatttgt
69601 gctctgcaga gtgggggtgc tgtttggag gtaattcgtg atagaaccac acagacaaga
69661 tagattcaat ttaaataaat tgaatctatg aagcttccta accccatgga aacacaaaat
69721 tagtttacac aaaaataatc attaaagaac taatgaaaat aatgtttgaa ttcagccacc
69781 agacattaca ttccagagcc ttgagaaaaa ctgatgaaaa aaaagtcatg aaaaaaaagtc
69841 attcgcacaa gtgacaccat ggtgtgaagt caaggagcac agactctgga gtcagagggc
69901 ttgagtcaac ctgagcatct tcagctttga ctgtgaagac acagctttga ctctctgtgt
69961 tgcagagatg gtagtgccca ctccagtgac gcttgtgagg attagttgag ataataaata
70021 caaaatgctg agcatcaaac ctagagtaga gaaaggtctc aagtaagtac tcattaccag
70081 tatttgttat taatttcac ttttgtctac attcccttgt gtgaaatggt ttggataatt
70141 aattaaggaa aactttccct cagggacatt gctgatattg caatcttcac tagatacact
70201 tatctctacc tccgcctcca cctccacctt cacctccatc tcttctctgt ctctatctct
70261 atcttcctgt tgtttatcta tctaattatt tataaatgaa ctggtgggtt tgttgttgtt
70321 gcagcctggc taatgttatc cagacatatc tgaaacctca tgagtggcat ggaatggcag
70381 tccctgcttg aaccatttac ctcctttcct aacaccaaca atcacacaca cctgacactg
70441 acctgaagcc tctggcctgt cctcggaggc aaagactggg tagacaagat gcctggttac
70501 cagcaatctt ctgcaatttc ctctgagcta ttgagattgc ttttctcttt gctcaaatta
70561 tgtgagaaac ttttaaaaaa gaatttaatg tgctctttg atatttcagg tgttcattca
70621 aaagcctatg ttattctctg tctctctgtc tcttttccta gttgggtaat caaaatggca
70681 caatcagaaa tatttatatc tgcaacagaa aagaagaata aatttattca tgcacaagta
70741 cattatgtac atatatatgt ttgtgtatac atatatctgt ataattgata tatttgggag
70801 aaataaaagg tttcattaag cacacaagtt ctagagttag accctctgtc gcaaattact
70861 gtcctgtcac ttaactcctg ccagaacaaa gtgcatactt gaacaaaatg cctgctctgt
70921 aaaaatgcct tgatcttgaa taaaatgcct gctaggtcaa agcttctatt tcccaccta
70981 gaaaatggga acaataataa gaatcctcac ttaatagata atggaaaaag ttgcttgcag
71041 cacagagcct gctacagaca atgccttcaa ttaatgcaaa ctattaatat tatgaaaagt
71101 gagtatctgt tttctgacaa tgttttcaat aatataaatt ctgcctttgt tcactttatt
71161 tgtttgaaaa aacaaataaa aaaccaaaca aaaagtgtc ttaaaagtgt ccatttgtct
71221 ttcttcttga ctcctagtaa cgctttcctg tgtttaggga attttcacct catgggtttt
71281 ggtgagtgaa tgaattcatc tccctctaca gaaaagaaga atgcctgatg cattttctca
71341 gcctttattc caggtagtca ggtagatat ggactccagc aattagatac actcctcaca
71401 accctccat tacacacaca cacacacaca cacacacaca cacacacaca cacacacacg
71461 gctgctggag ttgcagggtc tggaaggaac tgtctggcag ggatggagtg tgcagggtgc
71521 ctagtgagtt ccagcgtggc cgtggctgcc ctggctgtgg cagcaccagg gctctaagcc
71581 gggccctgca gactggctca atctgcagca tgggcgctct ctcttacttc ccattcccag
71641 gacacatcct gtgcagggga agagtgagtc cttcagttg tagccacagg cccattggtc
71701 tgctgacctc cacctcctca atattcgact ccccagcatt gagtgtctca aaaacagtat
71761 ttttcagaaa agagggtgaa cagggcaact gctttaggag gagccatccg agccagctgc
```

Figure 2

```
71821 ttcctctcct gtctcctagg gaggacccaa gctgtcggag ttcatacctg tcccacaaaa
71881 cacgagccag agctggacaa aagtgacagg gacaaccact gtccaaggtt aagtgagccc
71941 tgaggcacca gaagatctcc aagaaagcca catggaaatc ataaaatgga gctgaatgga
72001 ggaaaagaga agttctgtaa tgtggaaaaa tgaagtacta acaatatttg actgttttcc
72061 cttgatttag ccaggttact acttcaaaac agtcagcaaa gcattttaac aatgaaagct
72121 gttggggaaa ttaaatggct ggaagtggag ggaaactgtg cattgtggtg catgcctgtt
72181 gtcctagcta ctcaagaggc tgaggcagga gggtggcttg agcccaggaa ttcaaggctg
72241 cagtgagcca tgatcacacc actgcactcc agcctggcca acatagcaag accctatctc
72301 tacaaaaata aaaataagaa gtggagggga gataaaaatg tagtggtagg agtagtagta
72361 ataatatcta ataattactg aaaatttact atatgtcagg aactatacta ggtgtactta
72421 gctatttagt ctgcataaaa ttttaatacc agtgttatta ttgtatccat tttcagatga
72481 gagatttgag gcacaaagag attaagaagt ttgcacaggg tcagacagcc cctatgtgat
72541 aaagatgaac agttagacat taaaacatgt tttggttggg tgcagtggct cacgcctgta
72601 atcccagcac tttgggaagc tgaggtgggt ggactgcttg agctcagaag tcggaggcca
72661 gcctgggcaa catggtgaaa ccccgtctct acaaaaaata caaaattagc caggcatggt
72721 ggtgtgcacc tgtattccca gttactcaag aggctgggga tgaaaggatt gcttgagcct
72781 cagaggttga ggctgcagtg agccatgagt gtgccactgc actccagggt gggtgacaga
72841 acaagatctt gtctcaaaaa atatatgtaa agaaaaaatt ctccaatgac atgggaagtt
72901 gctcagaata taagctgaac tgaaagaata cagaacacta tacatgtaaa tatatctata
72961 gtccataaaa tcatattaat attcatgtat ccaaaatgaa aatatctaca agtgagcata
73021 tgataatgtg aatagtagtg ggcctttgtg atatgaccgt agatgttttt attgttatct
73081 ttccccattg ctctgagttt cttcaatgag cactgttacc agcatgttct acctatcagc
73141 tgtgtgactt ctgtggagtt gatgactctg tgcctcattc cctcatccaa aaaatgaaaa
73201 ttccaagtac ccatattaag tgatcattgt gaagattaga aggtgaaaaa cgtttagaaa
73261 aaaaaaaggc tagcaaatag aaaatgctca ataagtattt gctattataa aagttaatgt
73321 ttattaaata tgcaacaatt taaaatatta tgctgaggaa aagtgttcac gaacaactcc
73381 taggcaatta gaaatccttc tcatttccac agaaattaag caaccccccat ggcccctca
73441 cattcgtgca gagaacacca tcgagattgc tagcctgatt tgagataagc agggtgagca
73501 ggaggggggc tcagtgctga gcctgcagga ggcactgaag ggcccaaaaa accatttttct
73561 ttctctcccc agttcaggcc acaccctcca gaacctgacc agagtcgtct agccaccagg
73621 tccgcacttt cctgccttct ccttgggtac accgcccga agacaggatg tcactgctgg
73681 aagcatttgc cttctcctcc tgggctcctg agttgctgtc cgaacatttc agtctagctg
73741 cgtgaccaaa atcattcttc aatgtttccc tcttctactg tcagatgttc attggaaatt
73801 ctcctctttt acttacagtt ggacttggat tatcaaaagt ggagcagttc cagctatcca
73861 tttccacgga agtcaagaaa agtattgaca taccttgcaa gatatcgagc acaaggtttg
73921 aaacagatgt cattcactgg taccggcaga aaccaaatca ggctttggag cacctgatct
73981 atattgtctc aacaaaatcc gcagctcgac gcagcatggg taagacaagc aacaaagtgg
74041 aggcaagaaa gaattctcaa actctcactt caatccttac catcaagtcc gtagagaaag
74101 aagacatggc cgtttactac tgtgctgcgt gggattacac catactagaa ctgttgaaac
74161 aacatgcaca aaatccccctc ccagggtctg tgcccaccac atccttccca acagggcaa
74221 ccacagccag tccccagctg ggctcccaga ctcaggctcg ccttctctga ggctcttccg
74281 gggctttcca ggaagctgtt atgggttata ccttcgttcc cacctgatcc caggacttgt
74341 gctccagaat cttttatttga cactgtttct taatgcatta aagacttgtc tggggactga
74401 gagaacatag gtcgtgccac tgtccatcat atcaccacct agagacttcc agtaagtagc
74461 aaggtgcagt tgagacaggg atcctattta cgtacagtca agacaacccc cctgcaatat
74521 aactatcact ggcccagttt acaatgaaag aaatgaaagc ttagagaact gaggttgcat
74581 gatctgccag acaagtcatg tctttgagct ggtctatgag accacaccga acagtttaag
74641 gattgcaatt ctctaagtaa atgctaggat atctgggata aattcgggaa ggagtaagtg
74701 ccctttttc tgggaggggt agggaggaga atttgcctgc atgagatcgt cagaatagag
74761 ctccaagtca tcccaggggc cattggatga gacccttcat gttggaataa cctttggtct
74821 tacctgtaaa ggaagagaga attgtatcgt gtgtgtgtgt gtgtgtgtgt gtgtgtgtgt
74881 gtaagttctc tacagtgttc tcaattcttt gcatatatta gctccttttaa cccacactac
74941 ctatagtgtc tgctctgttg tttctcatcaa acatatctaa ctcctgaaat aagtggagta
75001 ttagttcatg cacttgtcca aatcacagag ctgataggtg gcaggacagc ctaggggggg
75061 acccaggtaa tctggttcct cttgaatatg acactaaact gcttctgaat cacaggagta
75121 taaaagaaaa gacacattgt tcctgtcccc atggaggaga cagaactgac catcatggaa
75181 cagtaactga cacacattac taccgtgtgc tgaaacttgt gcccagggtt ccagtgatta
```

Figure 2

```
75241 ggtgtattca gagaacaagt aaaatgccaa taaagtacca aatgacttt  ctttcttttt
75301 ttttttttt  gagactgagt ctcgctctgt cgcccaggct ggagtgcagt ggcgccatct
75361 ccactcactg caagctccgc ctcccgggtt gacccattc  tcctgcctca gcctcccgag
75421 tagctgggac tactggcgcc cgccaccacg cccagctaat ttttgtatt  tttagtagag
75481 acggggttc  actgtgttag ccaggattgt ctcgatctct tgacttcgtg atccgccagc
75541 cttggcctcc caaagtgctg ggattacagg cgtgagccac tgcacccggc caccgattga
75601 cttttcaata taaaacata  agaaatttgg gttttccata tctaggtacg tgacaggtac
75661 tgttatctat acttcatgtt cattatcatt attatgtgat catgtaaatt tcttaagtct
75721 ctggaagcca tttaggcact tatagatgta gaactgagac ctaaagattt caaataactc
75781 agctgatgtt agatagggta agtagtctag aagggtgcat attgtcatag gtcattaata
75841 gtaatattca gatgagcttt tgaaggacct gatatatttt taaatataaa attaaaagat
75901 cagaatataa aactgtaaat gtaaaaccca ttaaaaaacg tttaatcatg gctgggtgca
75961 gtggttcacg cctgaaatcc cagcactttg ggaggccagg gtgggcggat cacgaggtaa
76021 ggagtttgaa accagcctgg ccaatatagt aaaacacgtt tctactaaaa atacaaaaat
76081 tagccgggtg tggtggtgca cgcctgtggt cccagctact caggaggctg aggcaggaga
76141 attgcttgaa tccgggaagt ggaggttgct gtgagccgag atcgtgccac tgtactccag
76201 tctgggtgac agagcaaagac tctgtctaaa agaaaaaaaa aatttaatcc tgtgatcctg
76261 tgtaatgatc caaacaaata tattactatc tacaaatgtg tagagaacat gcttaaaagt
76321 aaattctgat tgctcttatt ttctttattt taattaacta attaatgttc tactagagtc
76381 ttctcaaaat attttcatca ttttgcaaca tttggtcagg ttttcttcag tgaggattgg
76441 gtagttatcc aagctcccat gtttaccaac tttgtgatct gggacgtcat gcgtgccaca
76501 ctgttcttgt ctatcagaga gagataataa taccactgcc tctcaacgct ggtgagaagt
76561 gtgaaggaag taatggaaga aaacgtttag aacaatgtta gcaagtctac aatagatgtt
76621 tgatataacg ttaatttaa  aggcttatga ttacacataa aaatgaactt tatttaaaaa
76681 cacccctctc tgtgacatag tgttcatgag atagttctga agtccaaggt gagttcccac
76741 agactgccct gtcggtccct ccagcaattt caatcaagtt tcctcttgag gtgcaccctc
76801 tttataagtg aaattggatt tctctgagtt ataatctgca ttgtgacatc ccaattaatt
76861 ataaaccaaa tacttactg  tatttcaaac agaaatgact atagcttttt aaatgaggta
76921 tgaataatgc tagtgtaaaa tttcagtttg ccttttttaa aattgtaaaa tactgtccat
76981 gttttatact cctgagtcct gcatcccaa  aacattaaca gagggatcaa tttttacgtg
77041 aggtaaagaa agttatatgc ttatatatct ggaaaaatat tgtacagtct gaaaatcaag
77101 gagagaacag ctaagtttga agcagaatta gttcaactcc agagctgctc ccatcccttt
77161 ccacagacac attcttgtca ggtaatgcac cctacacccc gtcagtggtc agtgtaatgc
77221 tcctgggaac tgctcagctc ttcagtaggc catgaagtcc ccagagggca cctgacccac
77281 cacatttttc tctctcacca agtcatgcca tgctgtctcc ccactgactg gggccagcca
77341 gcaaccaggg tccttctcct ggggatatgg ctcagcagac agcaggatgt ccctgctgag
77401 aatattcata ttttctccc  tctgcagcgg tgagttgctc ctcaattatt tcaacataga
77461 tgagagatga aagtgattct ttttttcttt tattttaaga cagtctcgtt ctttcaccca
77521 ggctggagtg cagtggtgtg atctcagctc acttcaacct ctgcctcctg ggttcaagca
77581 attctctctt gtgcttcagc ctccaaagta gctaagatta caggcatgcg ccactgtgcc
77641 tagcttattt ttttatttt  agtagaggca gggttttgcc atgttggtca ggctggtctc
77701 gatctcctgg cctcatgtga tctgccctcc ttggcctccc aaagtactgt gattacagtc
77761 atgagccacc acacctggcc agatgaaagt gtttcattat catttcctct ttctatgtcc
77821 caggttcatg gggatttctc ttttttgttt gcagttgaac ttggtaagtt aaatttaaag
77881 caataaaaaa tgtcaactac atttttgtca acagagcaac agataaaagt gtctaggtat
77941 cttgtgtggt gtccactgaa gactttgtaa atatagttat acactggtac cagcagaaac
78001 tgaatctaaa ttatgagcca tctgacaaat atcacttcaa taacaagccc cagttcgagt
78061 ttgcttaggt gagaaaaaca agaaacttga ggcaagaaca aattttcaaa tgtctacttc
78121 agtcttacc  ataaacttca taggaaagga agatgaggcc atttactact gcactgctta
78181 ggacccacag catcagtgcc acactgtccc acacaacaac ctctgttggg tctctgccca
78241 accacatcct tcccatggga gcaaactcta tggactccta gctgggctcc caccctcagc
78301 cttgccttct ctgcggcact tctggatctt tctgggaagc catcttgggt taatgcttta
78361 agcaggaagc atgcctgatc atgacgttcc cagatattca ttgaacacta cttcctaatg
78421 aattaaggtt tggcctggga atgagtggac acaggctaag gtcccattcc tgtcagcatc
78481 cagataattc tattaactgc aaacggctta ggccaaggga gagaatcgtt gtgtatagga
78541 atcccatata taattatttc aacacctctg caacagaact attatttgcc catttaata
78601 aagaaattaa agcttacaag ttcaaaatga ctggtcgaag ttgagaagtg catgttttt
```

Figure 2

```
78661 gtttttaaa actggatcat gaggccacct tgaatatcta aaagtcacag ttgtacaaca
78721 gactctttga ggtgactttg gggtggagca agtgtctttt ttctgtagag aagaagatgg
78781 ttcctcactt cacactaagg ggtgtgacag tgtgatatca tcagaaaaga gccccaggca
78841 tcggactgtt aaatgagcca tactttgcat ttattaactc ctttaacctc tggcaacctc
78901 tgaggtctgt tctgttatga acagaagtgc attttactca ggtaagtgag atctatttgt
78961 cctagccact catccaggtc acacagctgg ttcatggcag tgtaggattg gacccagcta
79021 gtctggctcc agagtctgta ctcctcagtc acagaagggt aaagagaagt acattgttcc
79081 tactcccatg gagaagacaa tactgacaac ttctgtaaaa catttactgg cacaattatt
79141 attttgaact gaatcaggtg accagaattt gagcaattag gaatccttgt tgaataagtg
79201 aaataccaat aaattatcca ttttttcaaa atataaagtg atacaaattc gattattta
79261 tgatgccatc tctaaaataa ttgagaaaga aatgaagaat acctttaatc catgtacttt
79321 tcctatagca gtacatacta ggcaccccca tggaaaaata tagataccac cttgcattcg
79381 tgccacgtgt tgtcttactt attcgataat ttccaaggtc aggacaacat attcatcctc
79441 atcatcccct tttccaagga gccaggaagg ctactgaagg aaataaaggg ggttccagga
79501 aaggctgacc tggggctgga atcagacaat ccgtcatcct ttatcctccc accccgatgc
79561 actcagcctt ttgtgatcca catcctgtct gtgtaattcc tgaccatcat attccctcag
79621 ggtgggccac acttggtttc ttgaacctat atgggccttt acttgttaac tttaatatta
79681 gctaaagtag acagtaagat ctgaggaaaa acacagcgaa tctgagagga taagctgttt
79741 tcagacaggg atgcatagac aggcttgcgg aaatacttgt gtcaccctct tctcgtggtt
79801 gtctcatcta ctactcaaaa cagcctcaga gagcagcaat gaggtatcca ctgccagatc
79861 cctgtgtcca gatcatagag cagagctctc ctgcagcctt tcaggcatca gactaaatgg
79921 tgagaaacag agaagagat actagattca tagtgcattc aaatgacaga atactatgca
79981 gcctgtgaaa atgatattgt atgcatttat taataaaatt caaacatctt cacaatacaa
80041 tgtaaagaaa agttcttgaa gtgtacaaaa cctcttaaaa atataaatgt ctgtgttgat
80101 agaataattt tttaaaaaca gaaagaaatt atccaaaatt ttagaataat tattcccgag
80161 ggaataatta tttaaattat tctatgtact tttactaatt tttatatatt ttcttaagtg
80221 agatactaag gctttgttgt aagatatact taacaaagta attttctctt gtttggtagt
80281 aatactaaga cacgataacg tcattaagga ctcatgctgt gccaggtact gatatctgag
80341 tattttatgc attaccattg tgtaacacga taatataagc cccttagtac ctctagaaga
80401 tatatatgta ggcaaggtac acatgtagaa actgaggccc aagagcttaa ataactcagc
80461 ccacattcta tagggttaag tggtatagga gtgtttaatt gtattcggtc actaaaaata
80521 atgtgcacat agactcaaga cctgcagtat tgctcatgat aataaagtaa ccaaaataag
80581 agagtataaa gccaaatatg taaatcccac cgaaatatat acatatatca tatgtataaa
80641 taataccaag ccattctatt tctttttttaa aaatttttaa cttttaagtt ctgaggtaca
80701 tgtgcaggat gtgcatgttt gttacatagg taaacgtgtg ctgtgtggtt tgttgcacct
80761 atcaacccat cacctaggta ctgagccag catgcattag ctattttttcc taatgctatc
80821 cttcccaca ccctgccgc caataggccc cagtgtgtgt tgtttctctc cctgtgtcca
80881 tgtgttctca tcattaagct cccacttata aatgcggaca tgcagtgttt ggctttctgt
80941 tcctgcatta gtttgctgag gataatggct ttcagctcat ccgttttcct gtgaaggaca
81001 tgatctcctt ccattttatg gctgcatagt actccatggt atatatgtac cataatttct
81061 ttatccaatc tatcattgat gggcatttgg gttaatacca tgtctttgct accgtgaata
81121 gtgctgcaat gaacaatacc aagctattct atttccaacc ataaatatgt tgagaaaaat
81181 tcaaaggaaa agtaaatgat gggtgccttt tgttgtcaat ttttatatct cattttactc
81241 agatttcct taacggatga ctgctactca cctgagttct tatgtttacc agctctgtgt
81301 ttttgaatga gtcactcaaa ctctgtttgc cgttgtcctc atttgacaca tggagataat
81361 cataaaactt actgcacagg actgttgaga ggatcaagta aaataatata agaaaacatc
81421 tagacaagta gcaagttgta aatggatatt agatgcttgt caagtttctt actgcagttc
81481 tgaattaaca gctaattaca gaaagatagt cattgggaca gaacactgca ggtttatctt
81541 cacattttca aagccatatt tctgcaatat ggtactgctg gggaatggga gagtgggcaa
81601 gagaacatcc ctgccccacc cctagaggta cacattcata ctaggtattt ctttccagat
81661 agttaaccca cttaccogat ctgcccagca ctcatgggat gcaggaaacc ctggaactgc
81721 tcatatctgt agcagctcat gaagaaccct aaggaaccac ctcatctagt acttctgaga
81781 gacctcaaca gccccgcctt ctgccactga cttgagacct ccagtgaaca gggttacctt
81841 ctccctgggg aaccagactg gcagaaagca tgccactggt agtagctgtt atcttcttct
81901 ccctctgggt ttgtgagttg cccctaatc atttcagtct acagaagaga ttgaagtcat
81961 tctgtattat tacctcttca cgtatcgttg gcttatggga atttctcttc acttgcaatt
82021 gcacttgggc agttggaaca acctgaaata tctatttcca gaccagcaaa taagagtgcc
```

Figure 2

```
82081 cacatatctt ggaaggcatc catccaaggc tttagcagta aaatcataca ctggtactgg
82141 cagaaaccaa acaaaggctt agaatattta ttacatgtct tcttgacaat ctctgctcaa
82201 gattgctcag gtgggaagac taagaaactt gaggtaagta aaaatgctca cacttccact
82261 tccactttga aaataaagtt cttagagaaa gaagatgagg tggtgtacca ctgtgcctgc
82321 tggattaggc accacagtgt tagagttgtc aagataacct acacagaaac tatctccgag
82381 tctgtgcctg tccacatcct tctccatgtg ggcaaccaca gcggtttgct cagctgggtg
82441 cccagccgga gcctgccctc cctgcagctc ttctggaatg ttgcaggaag acatcttaga
82501 ttctgctccc ttggtgtgca gaatcacatt ggtgattcat ggtgtccaaa cgggaaaagt
82561 tttcttgttc cctctcaggg cgtgcgataa ggatgtggct cccttcttgg tgcccctctc
82621 ctcaaacctc tagggggagc atgcacacgt gcaggttgtg gggctccgac cccacagcag
82681 tgtctagggg tgaatgctta taactcctga ggccccagtg ggcctgtgtt acaaggtgtc
82741 cttttagttt ggctgtccat aggtgacttg ctttagccag ctcaattaga ccccctgcct
82801 tattgcaagg acggagggct ttctgtatcc ctgggtttct tgccttggtg tactgaaaga
82861 attggataac atgtgggctt ggagaatgag tgcaagtttt ttattttgt ttttgttttg
82921 agacggagtc tcgctttgtc gcctgggctg gagtgcagtg gcgcaatctc ggctcacgca
82981 agctccgcct cccgggttca cgccattctc ctgggcagtc tcccgagtag ctgggactac
83041 aggcgccccc caccatgcct ggctaatttt ttgtattttt agtagagacg gggtttcacc
83101 gtgttagcca ggattgtctc gaactcctga cctcgtgatc tgcccacctc ggcctcccaa
83161 agtgctggga ttacaggtgt gagccaccgc gcctggccga gtgcaaggtt ttattgagtg
83221 gaagtagctc ttagcagatg ggggagccag acgggagatg gagtgggaag gtggttttcc
83281 cctggagttg actgctcagc ggccaggctt tcctccaacc accccgccaa actctgcttt
83341 gttctgccag tcgatggcct gcagcccgcc agtctcgcca aactctgctt tgttctgcca
83401 gtcgatggcc tgcagcccgc cagtctctgt aggtgtgctt ttccacatta gtgttcctct
83461 cgatgtccag ccacttgtgt gtgtgcccac tagggtctca ggggttttat aggcacaaga
83521 tggaggcgtg gcgggccagg tggtcttgg gaaatgcaac atttgggcgt ggaggcagga
83581 gtgcctgtcc tcacctaggt ccgtgggcac aggcctggga gtggggccct cgacagggac
83641 cacgtccttc ctttccctgc acttccctcc cccaatccca tatcagtgtc agcaattagg
83701 atccaaatta gggacatttt gacactattt cctacaacat taggatatct gggaactctg
83761 aaaatacaga gtgggtggct tagagcaaaa ttcatctgtc tagtaattcg ctacgtagag
83821 atttctagta actggttcag aatgaaagta ggaagcagta tatattttac atagatattc
83881 cctgctgtta tcattatttt cccatttggt tcatgagcat tggaggtttt caaagttaga
83941 gtgatctgtc aaacatagta actgtgtgct ttttattcgc acctgaggcc atcctgaaga
84001 aatctaggga caagtaagta gatctgtaag taaacaatca cctgtttggg gtatatgaga
84061 gatgaaagta taaatcctgt gtcctagagg aagagcatgc agctcacttc acactcaggg
84121 ctcagtgctg ggacaaaaca agcactgtgc agtggaaccc agctcctagg cacagtgggg
84181 gatctcagga tgggggctat gctttggaga tcttgtcttt cagggttctg caaagaaaac
84241 taaaaatcct gagtaaaata ggattagata gttaagaaga aagataatac atgcttcctg
84301 catcggtaaa ggaaataacc ataataatac ccctcagaaa ttaataaata agaaataatg
84361 attgacaatt attttatgtt tattccatga ttaatcattg ggtggttggg aactttcaaa
84421 aaataatgaa acaaaatata aaactgtaaa actgtaaaag tcctctctca cttcttttgaa
84481 actttcaaac aacaaattaa tgatgaaaaa tccggagttt caaagatttt ctcctattta
84541 tacctttagt actatggata tctgacagca tattgccata catgcagtct acttacagtc
84601 cttgaagtaa ttgcaacgta ttttttctcc attctcccct ctgagaatca gcttgtacca
84661 tcctgatagg ataagaggag aaatgctatt gaaagcccaa tgagggaata ccaggagcct
84721 ccatggcagg tcagcccctt tccaggtgca gactcagaat ctggagtccc gcatcctgtc
84781 cgccatgatt cctgaccatg gtggtccaca gggagaatga cctgagcgcc tgagtgagtc
84841 ctcaacagac ctcacctctc acctgatgca tacataaaag caaagggaag aagattgtta
84901 aggaaataca gagcctgaga acatgaactt tcaagaaat aggtgaatga aagatggaa
84961 ttcagctttt cacaatgtca gtgttaagta ttttacatgg attattttat ttaatcctca
85021 aaagagcagt gtagagtgac tgtagtggcc acacaaggtc aggtcttaga agatgcagtc
85081 actttgactt tttaagagac tcctgggaga tttatgggga agaaaactta gagacacact
85141 agagtgagga agaggaagga aagagacacc gtatctgtgt gaatttaaag taatgaaata
85201 ctatgtagca attaagcagt gttttgaag aactataagt aaaattgaaa atattcacca
85261 tgtatttagc aggaggatat tgaacacaga actgatttaa atagtaagct ctcatgtaca
85321 tacatgtata tattgaagaa cgagcaaaag gaaaaaaatt ctccaaagtt taaagagtgg
85381 gtgtctctga aaggatgggt gattttaaca tcttcttggt acttgcacag attttacaca
85441 ttgtaacaaa aagctgctac tacttttaaa gatgtatgcc ataatggctt caatatttta
```

Figure 2

```
85501 ttgattcatg catttaataa tgaaactgtt tatataacaa cataaaatat aactatatat
85561 ggcacactta aaattatttt tatgtttttc cacttaatca tatcactact ctatagctct
85621 cagaaaaaaa aaaacaaaaa taccaaccct catgttaata ctggttacta ttgagcagaa
85681 ggtcagcaaa ctatgtctat gaccagcagt ctccagtttt gtaaataaag ttttattgaa
85741 atacaaccat gcctatttat ttatatattg tttatggctg cttttgctag ctgcttttgc
85801 acttgaatgg tagagtacat tcagtcagtc ttcactatct gtgcattaaa tacctgcgaa
85861 ttcaaccaac agtggatcaa aaatatttga aaaaaataaa aaattacaat acagcaataa
85921 aaataataca aataaaaaca atataatata gcaactacat acatagtatt tacattgtat
85981 taggtattat acataattag agatgatttg aagtgtagag gaggatgtgc atttgttata
86041 tgcaggtact atgccatttt atatcaggga cttgagcata catggatttt ggtatctgtc
86101 ggggatcctg gaacaaatcc cctgaagatt ctgagagatg actgtagcta taacagagac
86161 ccacaaagcc caaatatttt attatttggg tctttacaga aaatgatttt cagtcactgt
86221 cctagagtga tagactcatg agtgacattt attcatattt agtgtttccc aatttctcaa
86281 tttttcttta atgacccttt gttacacatc caccctcccc atattagctg tgtgacttca
86341 gataaattag ttagcatata tttgattcat tttcctaatt gtaaaatgga gaacataata
86401 atgattactc aaataaactg ttgagaaaag taacttaaat aatacaaata aagttcttgc
86461 aagtgcttgg ggcatgccta atgctcaaca aattgaagca ctacattaat catatgagtt
86521 attattgcat attagaaaat aaaattattt agactaatac tctaagtcct tggtactcaa
86581 agtttgattt gtgaaccagc agcattggct tcacttagga gcttctttta aatccagtca
86641 gtcaagcctc agcccaggcc tactgcgtca gaagctcttt tcagaaggtc cctcctacat
86701 actatggtgt ggggagtggg agtctaaggg ccaaactgtt caagatataa gctccacagt
86761 ctggtacaag tgcaagccaa tcccatttcc ataggatggt tgtgtctagt gtcctctcta
86821 atttctggag agcaatattg aactgatatt tggcctctct ggggctgaaa tagatggcat
86881 cctcccaatt aattaaacaa atatactcaa ttgtccacgt atatgtactt ttattttcat
86941 ttataaaatt tgttataaaa tcagcacaaa ttttcagtat tttatatagt gagaaataca
87001 ggtgttttat aaccttgagt tttagatcca cattcaaccc acaggaagag taattttttgc
87061 tttgagtaca aaatacatat cactgtatcc tcatatccac atatcacata tcctcatatc
87121 actaggcta ctgaaaaacg aaataggagg caacagggaa ggggagagaa attgaagtta
87181 attgccactg tcaccactca cccacacctc acccttcata ggaagagttc tcctctaacc
87241 atcaccatat tgccagatct cctgggcact ggagtattta gagggccagc catttcagat
87301 ctgacaacgc tgcactctac agaaagggtt gtcagggaat cactgtgacc cactacttct
87361 ttccctgaca cctgctcaga ccaagctacc cttgccacac actaaacatt ctaggcacag
87421 gcatcctcac tttcctgctt cttcttggga acacagcctg gcagaccaga gcatgtcagc
87481 accaggagca tgtagggatt caccttgggg tttgctccag tcatttcact ttgtatatca
87541 ggtgaagaaa ttctttatca cttcatcttt acatatcagg tgttcatgag aattaatttt
87601 ctttgcttac agttattctc agggcgttaa agttggcaca aatttaaaat acccagggca
87661 aaagataagg atgcttttat accttgtaaa atatccagcc aagactaaaa atgaagtcaa
87721 atactggtgt cagctgaaac ctaagtcggc attgatgtgt tgttgacaat cgcacctgct
87781 cagggtccat taggtgttgt ggcttacaat gatgctcatc cttccacttc aaccttgaaa
87841 gtaaatttca caaacatgaa gatgaggtca tttactgctg tgattattga gcccactggg
87901 catcaagcac acacttccct gccttctcct tgggacacag caggatgtcg ttgctggaag
87961 catcatcttt tcctctctct ggactcttac gggttcccca tcatttgac tcttgaggag
88021 agagcaagta aattatttaa tggtgcatct ttatacctca ggtcttcata tggatttctc
88081 ttctttgctt acagcttgtt ttggatacaa gaaattggag caacctgaaa tattaatttc
88141 cagagaaaaa tattaaaagt ccaaatacta tctggggtgg tatctagccg cttatactgg
88201 ctgagacata acttgatgca ttttcctcaa caacatgacc ctctcaattc acttagggc
88261 tgtagctgaa aatgatgttc ctagatctgt tttgacctac aagataaatt ctcaggaaaa
88321 aggaaatgga gatagttatg tgcttgctgg aatcacagat gagagatgtc aggacacccg
88381 cacagaatcc ctctttaggt ctgtgtgtac cagccccctt ccaacaggag cataggctta
88441 gcagggttgt cagggttgga ctgcacctcc caggacttcc ccttcaacct ctggaaactt
88501 gattatgttc acacattagg acatacagaa atcagtgtac tctgtgctca aggtccaggg
88561 attacctgaa agtttatatg atccagactc aaagagggaa tcactgagtg gcaggaaacg
88621 tgctgggtat cttacacatc ttatataacc attgcaatac tttcgcaatg tcatcttcat
88681 tttttccac tttaatatga aataatttga aagataaaat accttcttaa accccaaatg
88741 cccatgtttc ctcagctgtg tcctgtgacc ttgaagaagt tagcattcat ttgctccact
88801 catgttgggg gtgagtgtga aatgaagctc ctgccctctc ctcaggctca ttccactctg
88861 agggatcctc ctacagtcca gccagcacac ttcctttgca caggtctcag atcctcctag
```

Figure 2

```
88921 ggaagggagg gggcattaga tgatccaccg acaaggtgga tccccaccag gatggatcct
88981 cttcccggct tctgcctgtg attgcagcag ccgtttattc agggtactct gctccctctt
89041 gggcactgct ctaaatcctt tacatgtaac tcatctcatc cttgggacat cttttcacat
89101 tggtctgttg tgattctcat cttacggggg aggaaacaga ggcagagcga tgtgatttac
89161 tttgtggtca gagttcttaa ctggggggg ggaggggctg gggttctggc ttcagcgtct
89221 gtcctcgtaa ccacgctgtg tcctgactct gagagaggag gtaaaaatag catctaatat
89281 gtggtctcta cggctagaaa gaaaactgat aggaaattaa actagacatt ttagtgaaat
89341 tataaaggct gaatgcagac tagtgggaga gtgtgagccg ctggggccaa aaattttagg
89401 gaatttccca ccatcttta gacttttct ccaggaaccc tatgcaggct cttgcaggga
89461 agagcatgga gaatccagag aaagctcccc ttttggtac tggcttagaa ggggaacagt
89521 agccactgtc taaattcacc cagacctacc ccacctcttc tccactgtag aaggacttaa
89581 tctgcaagag aaggtttcta tggaatttca ttttagttga gggagggaaa aggaagccac
89641 catcaactct gcccaatact ttatccctat ctccacagag taatgagttt taatgtgcag
89701 aagggtgggt gtcaaaatca tagcccaagg cactggtgg gtgcctccta tgactggaaa
89761 tgtgccacct ctggaataag agcagcaaca gttgtgaagt tacattctca agtcccggtt
89821 tgaccctgcc tgtttaagac agaagctgaa tgaaaatagc agagaatggc tcccttcctc
89881 acctcaccac catactacct tgagcaaaag caacagtaga atgcagtgaa gagagcttca
89941 aaagacagac tgtctctggg gagcagaaca aagggatggc tcaaagccaa gaacaaggga
90001 tgattagaga aatctaaagt ctctaatgtc ctatgaagaa caaactccaa tccagacaac
90061 ttagtagcaa caacaaactt ctaacccagt ctaactccta actagattaa cacaaactcc
90121 cacactaaag gtctggcaga aagaaagatg caggcatttt tttttctt tttctttttt
90181 ctttttttt tttttttga ggcggagtct tgctctgtca cccaggctag agtgcagtgg
90241 ctgatctcag ctcactgcaa cctctacctc ccgggttcga gtgatttacc tgcctcagcc
90301 tcccgagtag ctgggactat aggcatgcgt caccatgcct ggctaatctt tctattttta
90361 gtagagacgg ggtttttacc atattggcca ggatggtctc aatctcttga cctcgtgatc
90421 tgcccacctt ggcctcccaa agtgctggga ttacaggcat gaaccagcgt gcctggccaa
90481 tgtaggcatt tttaagcatc aaatatagtt atctcagtat ctactgtgtt atacaacatc
90541 gtcccctttc aataaaaaaa tctaagtacc ttaccccaaa acaagaagga acacagtctt
90601 gaagccacaa agcaatcata cgcatcggac tctgatatga ctcagatgtt tgagctgtca
90661 ggcagggagt ttaaaataac tgatgagtat gttaaaggct ctaatggaaa aggtagacaa
90721 catgcaaggt cagacagaga atttcagcaa agagacagca attacataaa aaaattcaaa
90781 tgaaaatgca agacataaaa aaaaacaca gtaacagaaa tcaagaatgc ctttgaaggg
90841 ctcaccagta gacccatgg agataaggaa agatttggtt aacataaaga taggccacta
90901 gatatgaccc aaactgcaat gcaaggagat gagaaagaaa gaacaggaga gaaagcatat
90961 cttcatggaa gaacagaact gtggacaata tcatattttc aaacatattt gtaactagaa
91021 tccctgaaac aaaagagaca aagagcagaa caaatatttg aaaaaataat ggctgagagt
91081 attccaaatg tagtgataga taccaaacca cagaacaaaa aagctaggaa aacaccaacc
91141 aggataaata ttaaaaacag aacaaaatac ctagacatat tagatttaaa ctgttgaaaa
91201 ccaaaaataa agagaaactc ttgaaggtag ctagagggaa aaaagcagat tttccatctg
91261 aaaccacgca agcaagaaga cattggagtg aaatctacaa agtgttaaat gaaaaaactg
91321 tcacttggca taaagacagc ttcagacaaa ataaaaactg agagaattca ttgccagcag
91381 ttgcacttca caagaaatgt ctgaagttat tcaggcaaaa aaaaaaaaaa tgatatgggt
91441 caaaaacttg aattcacaca aggaaatgat aagaactgga aataaaataa atgaaggtaa
91501 aacatagtcc tttaaacctt aattgctcta aacaggagt tggcaaacta tttttgcaaa
91561 ggacccaata gtaaatatat tctacgttgg tggacaacat agtctctgtt gtaactacac
91621 aaatgggcta ttgcaacaca aaagtccttg ctactcttaa gtctggaggg acatggaact
91681 gttataacaa ccgggagggt atctgtattg aaagggacac agccaaccgg tcttagtttg
91741 agttccccca ggaagtgagc ctcaggcttt gaggacagct agttgtttg ggagacacag
91801 gaagactagt aggagagtga ggagatgatg ttaagaaaag gaaggcagat aattaaatta
91861 ctttcattaa ttagatacta aatgagcaac aggaacctca tagaagttca aaacctaaca
91921 gatcaattaa atcataattt cttgttttc tgttccttta attcgtggga ctggccatgt
91981 aaaataaata aaatctgcag accctatgt gatctgatgg ttagtgtggt agtgaaccag
92041 ggaatcttgc taagtgtcag aacgtgataa gaaagtaacc acagagcaga aaaatattcc
92101 tggtgttacc ttaagttata aagacagagc ttaaaatcga gcacacatat tatatctatg
92161 tgaagcaaat gaaaagatg agcagatatt agcctgtaag ggaatacacc aaactgttaa
92221 tagtagttgt ctctggttgg tggggacaaa aagtgactgt tttctctgca tttctttctg
92281 acccatctac ccatgttgtc ttcccatagc tatttactgc cctttgtttc tacagcttcc
```

Figure 2

```
92341 taactgttct gaaatccctt actaatcaga gcagtttccc tggtatgccc atcacacata
92401 tgggcatgtg ggacatagag attagctttt tttctgacta gattagtaaa ttcttataat
92461 agaaggacct gctgaaccaa ggctggaatt tcctactctt cactctgaaa gctggaacca
92521 atcccaaggg gctggccaca cacttggttc aaattgggta gtcctggcct gctttctgcc
92581 ttcttagagt gacctaggac ttgttcatgt ccaaggcctt accagccaca cctagaaaat
92641 agcaagaaca atagtagcaa ccatatctat accattacat ttagctcagt acctctcttt
92701 ttggatgtct gacaagtagc caaaaaaatt attgattcca attccactcc cttcccccaa
92761 tctccaagca tgtattattt tcctccccag actttcctat tgcagtaaat ggcaacagta
92821 tattgtatca tctgatggaa tggcaagggt gttttctcaa gcagatagtg ttttgttgac
92881 ttctgtgttt tttgtttctc ctagtaatga gagaagagtg cagagaccca actattactg
92941 agtttcctgt gatatgagat ctgaagggag tttacaggag ctcttgaagc tatggtttca
93001 cctgcagaaa agacacccac aaaccaggcc caaccctgtg tggtccaatc tgagactgga
93061 gtaggctgtc tcaacagagc cctgaccga aacactacag acccaatgca gggaagaccc
93121 agtcttctct ctaacttact gcaggtttag aaactctttg tgttcccct gacatgtgca
93181 gggcaatagg ccagccatga cggcaatgat tgtcattctg aagtgcatgg cccaaatggc
93241 cccatggatg tataatctcc tggtgtcact gaaagacaaa taaaagaaa gtaaattgtg
93301 agatataatt tgatattcag attcaactag ccccgctcct cacagattat tttgctaggt
93361 gttgtcactg actactcaat gcttttaga atatgcaaat caaccatttc atctgctttt
93421 tatttcgttt aatatgttct gtgattccta gaaagcaata cccagcatcc tctatatggc
93481 catttgagat acagattctc tatattatac agacctagac tatacttggg aactgcgttc
93541 cttccacaca tatctctcca actgtgaagt aattgatgaa cagggtttgg gatctggaaa
93601 acttgaactg aaatcctggc tcagtttgaa ctccctaatt ctgtttcctc acatgacttt
93661 taatggtaat aaccatttat agggtaaagc agaaagagat aaatgcatag ttagtgcctg
93721 actcatggta gacactatat ttatgagttt tcttctcttt cactatcaga aagcacaggc
93781 ccatggattg tcatcctgca gcaggggaa ggtaagtgaa aaggagattt ggggcttaga
93841 gtagcatatc aatttctcaa gacattttc cagacacgag tcttttatgc aaacatttct
93901 tgtttgccaa aaagaaacaa gtgtttcacc aggcatgttt gcctgtggga gcagtatcag
93961 ttgaaaagta tctataaatc tacaatatgc atagtggcat gttaagtacc caagtgcaa
94021 aagaaaccct aaaagactaa atcttcaggt taagaatgaa gacaggtggc acaattgcta
94081 aaaggagaa tctgattgaa agtgcagtga cccggcctct cccaaacact gccctggtgt
94141 ttttagaaac aagtgaagat ccactggact atattgtaac atatctgata ttatctaagt
94201 gatgacatat gtgaaatcaa attatgctaa tttatgaaag ttagtggtcc acagattgtc
94261 agtatgtgat tttttatct cttgtacatg tcagataatg tgttttttt tgcttcagag
94321 ggtggtctct ctcagaagtg tcttaactta ctgctgtacc tgattaatt aagatccact
94381 acaattctg aaagataaac caatgtgaaa aaaatgtgca aattattatt ttggttcatg
94441 ttggcaacca aaccctgaaa tgaaatgtga gatatatttt cgtatctttt gatggtctaa
94501 caaatttggt tgaagctgtt ctctatgaaa attattatca tcagacttga aaaagtgatg
94561 caaaacttca agcaatgcag tatcaacttg tgctttacct cacttgactt acttgttatt
94621 tatatatttg ttcattcata acccatcttc ttggaagcag gatttaagtt gcctcagttt
94681 gttaactcaa gacatgacaa atgtggcggg gaggatgtat gtgttccaaa acacagggtt
94741 agaggcgaaa ctgcttatct ttatacacat tcatttgggt ttcattttac gcctttagta
94801 aaactgaaca tcatggtctt cacatagttc ttttttttg taaacttaat aaaatatgtt
94861 ataattcatt acttactttt tacattgtat tacttaaatc tttcatggct gttgaaatgt
94921 agacagcttc taagacttct gatacttccc cacatggttc tggaataagg aaaagcagag
94981 gacaaagagg gattgaatgg gcatcatccc atctatgaca ggtgcaaagg gtaattgaca
95041 gtacgaagta acaataactt attattttca gataaaaaga cacagaaata agatctttcc
95101 attctacctt atgaagtgaa gtctctctgt ctgaattatt acataaatga taagagaaaa
95161 ttaaacagtt tttagcccct actgtgtccc atgctcgatt ataaatatcg tacaaaagtc
95221 ctgggaaata ggtctaattc tctccattta aagatgagg aaacccaggc tctgagaagt
95281 gtgtgtgccc aagggcacat caccaggagt ggaagaactg gaatctgaac ctgggttttc
95341 caattttaaa gtgtctttt cttcattccc aacttcctga gataataatt tatttcataa
95401 gaatccttta aaagctcgag taaacttgtt aatgtttatt gctgcagcca ctctgtccat
95461 ctccaccatc actgcaacaa ttcaggtcct ggttgcctct tattggatta tggcgaccac
95521 ctataaaacc atctgcttca gccaaattgc tgtcctgggg agcgcccctt cctttctgct
95581 tgcacatcta tctttctcca gtgcaaatgt gatcatgtca ctttcctctc taattttttt
95641 agcaagtcct cattgtctat tctttcaaaa acatttatt gaaaatacta taaaaataga
95701 aaatttttcca catgcttact tcctaaaaat taatgtgtta agtttctcct accccatttc
```

Figure 2

```
95761 catcccatgc cccctttactc aatggataca ataaatctcc aatatgttcc ttctggccac
95821 gtgttgcttt gtaattttaa ttttaatcta tttggaccct gtgttatctg ggatgaggta
95881 gagtggtatt tttattttct aaggtaatta ttttcctaat gcccgtttcc aaacaatcca
95941 tcatttcctt tcaatttaaa aatgctgcag cgtgttttaa atatgcacac atatttgaca
96001 catttctgg agaatttctg ttttattgt ctgtttcatt attcttacat cattatcata
96061 ttatctcagt agctttgtga taaaaattaa gatctactat gccaaatgtc tattcactgt
96121 accatttttc agaaaatctt tttcaatcat ctcatattta ttcactcctg tagaatttaa
96181 aatcaactta tctagcccaa cattaaacct cacagcctag aacaacaaca acatgtcgta
96241 gtaattctga ctggaattgc tggaaattta tagatgaatt taggatgtat tggcctcttt
96301 atgataggag ctttttattc atcaatgtat gtttctccat ttatttaggt tttattttat
96361 gcccttagga aaactaaaca ctgtgttctt catatcattc ttgtatttt ttggtaaatt
96421 taataaaaga ttttataatt cattactttt ccacatttta ttagttaaat ccttcatggc
96481 tcttgaaata ttgacagctg ctaagacttc tgatgcttcg cctcatggtc ctgaaataag
96541 gaaggccaga ggacaagaag agattgagcg ggcgtcattc catctatcac aggtgtaaag
96601 ggtcattgac agcgccacat aataattttg aattttctat taagaagaaa cctttccaa
96661 acataatttt cacccagccc cattgtcctc tccattgaat tgggggctgt gagctgctgt
96721 gtatggacag gtaccctctg tgacctcatt catatcttcc tgaatgagga ctcaggggac
96781 ttaggctgga gcagggtgga tctggagtgg acatggaggt tgtcaaggct tgtcctcctc
96841 agcccttgca agtgaacacc tcatctgtac tcaggagatc acacagctga ccccggctta
96901 agatggcaga ttttcaaca tattagataa ctggatttgt ttttttggt catgcctcag
96961 tataattaaa gaatgtatta tttcatggga gatagaattc tacaaatttc ttctattatt
97021 ccaggagaaa taataagtca ttgcagaaca cattttttca tttggcattg ccttggtaaa
97081 gcatcatgtt gccaaatgat aaaagtggct ttttgaaagt ggagaccgtt gttcaaattt
97141 ctcaagtata tctgcattga cacatttgca ttttcagtta ctaaagagct tcctccttc
97201 agaagtatct tcccaaattg ctagcagaga ggctctggtg tttgtgggaa cagaagggct
97261 tttcctttga tgtaatctca aagcagtttc aacacaattg aacccctgga aaaaaaaag
97321 acaattctct gaatactttt cctggtaatt tagaaaagca gtgggttgac ccattaaacc
97381 tgctgttttc tcttcctgct ttttttttc catttcctt ttctgttggt gcttttcaag
97441 aattactgcc ttagaagaaa acaggcaatt tatgaggaaa aattacaaac tatcacatgt
97501 cacaaacct atattcaagg acttccaaaa aagccagaag atgaaattgc tagttcaaag
97561 ttgttggatt gctagtcgtg tcccgaggat cagaaggctg agattttgt agaagcttag
97621 accggtgtga taccactggt tggttcaaga tatttgctga agggactaag ctccatagtaa
97681 cttcacctgg taagtaactt ttctttctgt ttttattcca gtaatgaaaa actgatagat
97741 gattttaga aaaaatgat caaccttatc tgaatatgtc acattcctgg cctcagtata
97801 cgaacagcaa ttttgcagat tagctgaata tggaaacaaa acgattttgt acatgatatc
97861 ttcccttccc tgtctgtaag cggattaaaa ttctacttta agaatacaca cacacacaca
97921 cacacacaca cacacacaaa agatagactc tggcaagaaa ttaaaatgtt ttgaggccca
97981 tgtctataca ccattagtgt aagtccttgg tccaagttac ttttttgttg gtcttttaag
98041 tgagagacat aaaaatggag ttttattaat tacttcttct ctgtatttg agatataaca
98101 tagtgctccc ttcttctgct agcctgccaa acccatgtta ttgattttga tctcatcctg
98161 agaaatagta tagaaaaaaa ttacttctta tagtaaatta ctatagaagg tcaatacatc
98221 ccacttatta gtgttctagt ttctttgagg gaggctgaag tcagtcaaaa tttatgcaat
98281 tgggactctt gttatatcac ctggaaatgg cccggtttaa tagaatttgt aagttcaacc
98341 agccatgtca gctccaaggt caatgaaaag agtcttcatc attttacatc ttcatttgtt
98401 cattcatcct ctcagcaaat atttatcaaa aacagttttt gttctggatg ctagagataa
98461 aagggcaaag aagacacagt ctcaacactc aaaagctgcc agtctggcag ataagtattc
98521 tagattctgg cttggttggg ccctgtccac gttctttggc ctgtggctgc cggagaagca
98581 gaaggtcttg ggttcatgag ctcattttct ttcttaattt gtgtagcagt tattgcttat
98641 aagatctatg tattgcgttt ggtgggagga tttgataaaa tgacccaata ttgtccttt
98701 aaggagaaaa ttaatattag caaagtttat tgagagccag acaccatgct aaatagtttc
98761 aatgctttat ctccttcctc atcagaccta tgcaggagat cctcttagtc ccatttcaca
98821 gatgaggaaa ctgaggccta gagaagctca gttactttct taaagtcaca tgactagtca
98881 ctgtgggaaa gtctgggatc tatctaagct tgtctactcc aaagtgcctg gtctggaccc
98941 ttatgtgata tttagaaata ttaagtcata ttttatact ttgaatattt cttcttctgt
99001 agcttgaccc tatgaatgga ctctttagtt gactatttt ctagtaacaa ctcccaattt
99061 gtattactat ttgtgtatta atacaattct tctacttcta attatggcac tgaaatgacc
99121 tctctcctcc aaaagtcat atgggatata catttattaa atactcaaaa tataatttt
```

Figure 2

```
 99181 agggtatttc tgtagaatga gtcattttga cgtcattcca ctcagctgtc tttctgtatt
 99241 ggcatcaaat ttgctagata tgttgaaact gatgtaggag ctatcgcagc tatgctatat
 99301 tgcagtgcta agtcgcataa ctcagagctg cctcagattc tctgttgagt agcacacgat
 99361 ttaatttgat gaaactgtat agatattttc aagtcaaaag tagcagtctt tcagcaatga
 99421 atcatcatta agaattcata ttttctaaca actcatcagt attctatcag tgagaactgg
 99481 attctaaaaa gaacttactt tatttttatt ttttatttt tgagatggag tctcactctg
 99541 tcgcccagct ggaatgcagt ggcatcatct ctgctcactg caacctccgc ttcccagttt
 99601 caagagattc ttctgcttcg gcctcctgag tagctaggat tacaggctcc tgccactacg
 99661 cccaactaat gttttgggtt ttttttgtat ttttagtaga gatggggttt caccatgttg
 99721 accaggctgg ttttcaactc ctgagctcaa gtgatccgct tgcctcagcc tcccaaagtg
 99781 ctaggattac agggatgagc cactgtgcct ggccaaaaag aagttatttt agaatcaatc
 99841 tagataccca tccctccata catatgaatc ccaaaatacc tataaatcat attgaatatc
 99901 tatttattaa atgtcaaaca taggaatcct attattgtct ctctttgaaa attaaggaaa
 99961 tattaactct aaattacact taagacaaag tgtatacaag aaaacttttt agggaagatt
100021 tagaagattc aggcaaaatc atgagaaaag gtaaaatcag actctctaat gtatgggata
100081 caaggagaga atgtacatag cccaaagtgc ccagggcaag gtgaggtcag ttcttaaatt
100141 cctgattaca ttcagatcca gtgtgatttt gtttgacctt tgtcttgact taacgtcagc
100201 agggccaatt tttatgtatt tatgtaaata ttgaaaaaaa tgttggcaca attttaagac
100261 aaacacaaag ggagattctt ataaaggctt ctcaggtggt gggcaagagt tgggcaaaaa
100321 aatcaaggta tttggtcccg gaacaaagct tatcattaca ggtaagtttt ctttaaattt
100381 tgcaatgtaa agaagggatg ggaggctggc aggcaggagc tggctcagaa ttctaggatt
100441 ccctccttgg tcactaatca tggtgaaatc tccagagagg tcaggtgact tggttcatgc
100501 cttaggagtc agaactttc ctgccctagc atgggagaca ttactaagga gcttagacca
100561 actgcaaatc tctaaggat ggaggcctta tgttgttcca ttggtatctc tctgttgaaa
100621 gttttgtgaa caagtttagt tttgagattt tatttcttca gttctaaaaa taaccaatgg
100681 aaaaattaa aaaaaaaaaa agtaaaatca gctaccctcc ttatttggtc accaaaagat
100741 gaaatatttg ataatttgac caaagaatgg ttaatatcaa atgttaaaat atttctcggt
100801 gtgaccatat ttagaagtaa cataagctgc atttattgtt atttaaattg gtccaatgag
100861 tttgtttatt atttgttagc ttaagtttaa agatgtaatt ttgcctggat gagagaaaac
100921 atctcataaa gatactctta gtctgttaga tccactgaaa tgaaagtttt cagagaattt
100981 tcacaaagtt gataaagcat cggaaaaaat gaaagcagtt ttacatttt aattccttag
101041 tggttgagat cttatgataa aatgaactta taagttaaaa agtgaccttc cgattctctt
101101 ttatccaatt gacttaatga gaattgtagc aatcaaattc ataatttgta attttctgag
101161 aagtgatttt tcaggaaagt gcggtgcaag aaaaggtatg gactttgttt ctcgactcct
101221 ggagctagca ctttctatgt aactcccttt taggaagtgt attttgattt accagttgtt
101281 caaattataa aaatgctggt tcattataga aaaattggaa aacacaaaaa taaacaaaaa
101341 attataattt gatattgacc ctcatcacat tatcattttg ttatatttt atttaaacat
101401 ttttctctgc ttttgtttg tttgttttac aaagttggaa tcatactaga tacacaataa
101461 tagatctggc ttttcactt cacactgctt cataaacatt cttttcaaat gtccttaata
101521 tttttcaata ccagaacaaa gttgaaactt ctgttttcac gttgatctgt acaaagaaga
101581 taatggagat tatttatcta aagtggatgt tataaagatt aaatgaaatt aaatatggaa
101641 attacctacc agaatgcctg gcacttggta ggtgatagaa atattattc ctcttctaga
101701 attcaagtta ctacccacga aaggtctta tacactcagg aatacagata aatgtatcga
101761 ctcccatcta ttcagcagct cacttcagaa caaatatcac tatttgtaaa atgctttcta
101821 tgtctaaaag actaattgta cctgcttcta aaagtaatta gaatgttta cgtattatct
101881 caaatatgat ctacctgaat acaaggtgat tttcatttt caagagaaaa tttatgttta
101941 agaaaatatg tattttcccc tcccccaact cgaatatgta aatttatagg gctacaggta
102001 aaacagtcaa atgtctacct ataacattta atttcttacc tggttcatac tttcaaagtt
102061 aaaaattata tcaatatcaa tatcagttga gaaatattgc ctttttgcc cttatatttc
102121 attaaaactt ttgttttgat gcttcacatg catgtaaagc atctatctca gaacagcttt
102181 ctaaggcatc tcaggtcaaa gcgtccactt tggaatcctc ttatgatggt gtctctgaat
102241 atttattct aagacacaat tattcactca caaaataaaa ggatatattt ttttccaatt
102301 tattctgtta ttctacagtt gtatgaagta aaaactacag agacattacc ccaagtaata
102361 atgaccaaat ccgtgataaa tttctttgcc tttttttc cttaccag tgctattccc
102421 caaactagca tcattgagtt catttcatgt cgatatctcc tccagttagt ccttctggat
102481 caaagcagag tattagaaga acattttta atatgagaag ttacacaaag actgtaccat
102541 acataaggca cctccccatg ttgtgagaga aatttggg gaaaaaagc ttcattttaa
```

Figure 2

```
102601 gttctggcac tttctatcta aatttagtat gtaggtgtcc ctatcacaga gctaggattt
102661 gcaaacatag tctccattcc ttgtgtctta tttgagcttg accttacaaa accatcaact
102721 cctggggggca aaggagaaac atgctaaatg cacaaactct ttgttattta tttaagctat
102781 ctcttttccaa aatctatttg agaagaccta aattaaaata tacaagcaca gtcagaccat
102841 taaatatata cagatgatct aaagccctaa ggaaggaga aggaaaaagg cctgtgatta
102901 cctagtgagg agcacagttt aaaattttat gctcaaaaga aggagaaaaa ggtaggggaa
102961 tacatacatc ttactaattg ataaaaagaa gcacaccaaa ttttcaaata tcatattttt
103021 ttctattact agattggaaa aagacttcaa tgcatgagtc ctttagaagg aaatggaaga
103081 gtgggcagtg ccttcaactt ccattttgga aaatgaaagg aatggtcatg aaaaacccac
103141 tgcatattac cactgcatca gtgctatggg catcctgaca tttaatgaaa tgcgcagatg
103201 gtgatgctca gcagacatgg tcaggcagat aacatgtagt gatctaaagt gacaacagag
103261 agatggattt gaggaccagg cctcttgcct tttctctacc cattctgcct tgaagggtaa
103321 agccaggtgt ttcaagctgg actttggcat gaactagaca gaagtcagtt tcaggctgaa
103381 gtttctggtg aaacttggaa ggcaaataag ttgtgctgct gattagaaaa aggctcactt
103441 gttttgaaaa acacaagtga agaattccca tacactgact gcatatatta gactttagcc
103501 aatgttccct ttgactttct taacacggta ggtaaggcaa aggataacct attaaagatt
103561 gggcgtgtga aagccatgtt tcttgtgatg atggggacga tggctttgag aatcccagag
103621 caaagtggaa tgcaaacaga ggaactgaga aattattcct cctgcttaat tgctatggat
103681 ttaactgcca ctccaaaatg ctgaattttt tttagtaagg gcaatgcttg gtcctatagg
103741 gttaaaatgt catgtcaagg cacacaatca tagcaaacag attgctaatc ataacaatga
103801 catcatcatc atcataatct cttatatttc catagcattt attttgagg cagggtcttc
103861 ccctgttgcc caggcaggag tgcagtggtg tgatcaattc tcactgcagc ctcgaactcc
103921 taggctcaag tgaccctcct gcctcagctt ctcgagtagc tgggcctaca gtcgtgcaca
103981 tcatgctcag ctaatgcttt ttgtattttt agtgaatatg gggtctcact gtgttgccca
104041 ggctggcctc aaaattctga gctcaagcaa tcctccacc tcagcctccc aaagtgctgg
104101 aattataggc acaaaccact gcactgggac ctataacatt ttaatcaaat tgctttttta
104161 tatcttgttt cattttggtc tcacttcagt gctggtagcg atgttgaact gattttgaaa
104221 catcactgtt tttagacaaa taaacacca aaagctttaa gttatttgat ttgtggagca
104281 acagaacttg ttatgagcaa aatgaaccag gactggaacc ctggtctttt gagaatccca
104341 gaccaccaga atttgaagaa ctcaggggaaa ctgaattaga gttttttgata tggactgaat
104401 cactgtggaa ttattataag aaactctttg gcagtggaac aacacttgtt gtcacaggta
104461 agtatcggaa gaatacaaca tttccaaggt aatagaggga aagcaggaaa ttattaaact
104521 ggaataatgt aataatgttt agaaaaaaga ggaattggat ggggatttga tgtagaaaac
104581 ttaggagaga cttttaaaaca aacgctcata ctaaaagaga acatagataa cattgcacag
104641 atatcataat aagatttggc tttgtgcata tacggacttc cataaaggggc tcatatgtaa
104701 tgtatgaaat gatctcatta aaatgtctgg ccctgagacc aaatgtatta tgacaggtaa
104761 gtttgtgata gactctacag agtggacaca tattcatctc tgatggtcaa agacatgttt
104821 actcttgttg tgaaggagcc cgggtgttgg agtcaggtcc acctggaact ctggctccac
104881 cactcactgc ttagtgaaat tgagtgatta ttctctggcc tcagttttct aatccataaa
104941 atgggataac agtatgaatt cagcagggtt gtataagaat tgcacaacat agtgtgaatt
105001 aagtacttgg cacattgtcc aacccaaaat aggtgcccaa caaatgtttt ctggattcac
105061 atgtaaagag acaatgggat ctactatgga gagttgctct cagtccatct aatttacaga
105121 gcagcaattc tccagaggat tcagctgtac ttctaactgc tcaaatggaa ggttatcaac
105181 atcagctcac acacgcaaaa attgaactta tggattcgtt tcttgttagc aggcttttta
105241 atcacgtggc aaaaacattg tattaagatg tctgtttttt attttgttg ttctatgtgc
105301 tttacttaat cctttatctt aattgatatc atttctaaca ccaacatatt ggtcctaaga
105361 tttatagcca attagtttag ggttctgttc atatgtctca ggaaaaaaag gttaaaatct
105421 taccaaaaat ggtcaagata tcaaatcaat taaatccagt tggaaacatc ataaatctga
105481 aatacatatt taaacataaa atggctataa ctatttagct aatgaaaaaa taagaaatag
105541 agaacactta aataaatatc catatgtaga tttaatatat cataccgtct ctaaaaactg
105601 tagttgatat ttggtaaatt tacaatgctg cattttaata aactacaaac aacttaggca
105661 atttaactca aatatactat ttgattttgc aaataaatgt acataaatga atccaacaat
105721 aaaataaatt ttatttatta ttttaaataa aatatgtaaa ttctatttgt tattgaagta
105781 agtaaaaatg taccatactt ggccataaaa aactcttaat atgtacattt taaagtagt
105841 attttaaaaa tcatgtgaga ggatgatcca caatatcggc ccttaccatg tgtaatcaag
105901 tatgctattt aatgattcgt taactactac gttgagaaag ttttggaagt tccagattca
105961 ttttgtcctg aaaagaatga aacttaaaga atctagctaa agaaggggga caagagcaa
```

Figure 2

```
106021 tgaatgctgt ggtaccgtac agaaaatgtc caagtttatc atttgatttt taatttcttt
106081 agtacaatga attagaagta tttcaatgaa gagacactag ttcttaggat gaaaattaga
106141 ttggaaaata tattgactag agactacaat tatataaata taatgtacaa ttgaaaaatt
106201 actcatattt tataacatgc ttttaaaatt agaagcaaac tatatggtgg agaaatatac
106261 actgtctcac aagtataaca agtaaaatac tatttgcact aaaagcaaag agtatgaaat
106321 taagatgagc acattatgcc taattaaatt tatagcatgc tcacaaatta atatttctgt
106381 atatgtttac taattttgta tgaaaatcag aagctttgct acacagacag aaattatcaa
106441 gactgttttc ttttcttctg aaatgagaaa tttaattctt attttcttag aaattgttca
106501 attattaaat tcacttcaaa ccagccaaag cattggagtt tcaattggaa atcaaaatag
106561 aaagaattgt aacatttata atttcagtta ttagattaaa aatacgtgta taacccatta
106621 acattccaga ttcaagtgat atgcctttgt aaacatatga tgctttgtta tgtatcttga
106681 ccctatccct ataagaagct ctgaaatcat gacttttaat agagcaatta tatgtacatt
106741 ttattcagca ggctaagatg aagagaataa tggagcttta aaacagttaa gcagcatata
106801 ggacagatac aaattctggg agagacataa agagtcaaaa tatagataca ctgatttaca
106861 cagaccttct cattaatggg gtaaatttat ataaaaccca gtataaaaaa tacacccctg
106921 gtgcattctt agtcattctt aaacttcaaa tgaaattcca aaataaaatg tgcttttggt
106981 gaatattttc tgaagcaaaa tgaaattttg ataagtgcgt tactgcagaa gattaacaca
107041 agagtatttc tgaaaataat caagaaaaaa tttaaataag agttttggaa agttgccatt
107101 ttgtttctaa attcaggaga tggtgaataa tctggaggta cagctgtaaa tactgctgca
107161 tcccaaaact tggagggtgc agatgtgaaa ttgagatgtt atataaagtt agatattaac
107221 taggggggact gctcatggta tacacattga agctacatgg tcaacttgat agacagtatg
107281 tacatgcgga agtagattct ctttaaaaca agtgactgtg tatgttaaaa ataaaagtga
107341 acaaaatggc taggcatggt ggctcacacc tataatccca ggatttggga ggctgaggca
107401 ggcagatcac ttgagcgcag gagttttaaa ccagcctggt caatatggtg aaacatgttc
107461 ctagaaaaaa aatattagcc aggcatggtg atgcatacct gtagtcccag ctacttggga
107521 ggctgaggtg ggaggatcac ttgagcctgg gaagtcgaga ctgcagtgag ctatgatctt
107581 gccgctgcat tccaacctgg acgacagagc aagcccagt ctcaacaaca acaaaaattt
107641 tgacattgat tcatatggga aataagataa ataataagat aaatatggtg catcgcagaa
107701 tcagttaaat gaagagtggg agtacacgaa attgcagaac atgagaatgt gtcatatttg
107761 gccaaagaac ataagttaca aaggatggaa aagggaagtg ggaaaaggac caaagagtct
107821 catctgtaga gagatcatta aggttttctg accttccact ttccctgcc atccaccttg
107881 aaaacctgct tcactatgat gaaacaaaag agattaaaaa ataaaataaa tatgctcatg
107941 aactttggaa gccctggtag gaggcagtta aaaatcacac tcatcacagc atgtgcagaa
108001 taaacaaagg ccaggttttc gtccagcatc tgacatttga gagctgtgac ttttggcaag
108061 ttatttaatg tcttgattct cttttcaaca tctgtaaaat aagcacaata ataagtactg
108121 tgcagcctat cctggatgaa aggccgcagt ggacaccagc tcaatggcat cttctctttt
108181 tatggttatg tactaggcca ctccaaactg tgcaatgtgt gtgtttctct aatgattctt
108241 ttaaactcat atttcatttc tccccataga taaacaactt gatgcagatg tttcccccaa
108301 gcccactatt tttcttcctt caattgctga acaaagctc cagaaggctg aacatacct
108361 ttgtcttctt gagaaatttt tccctgatgt tattaagata cattggcaag aaaagaagag
108421 caacacgatt ctgggatccc aggagggaa caccatgaag actaacgaca catacatgaa
108481 atttagctgg ttaacggtgc cagaaaagtc actggacaaa gaacacagat gtatcgtcag
108541 acatgagaat aataaaaacg gagttgatca agaaattatc tttcctccaa taaagacagg
108601 tatgtgttta cgcatatcat ctgtcagaac acttctttga agtgaatgc tgcatttttt
108661 cctttcagta ttaatgaaaa acaaacataa atctttctta aatattgtta catttaatgg
108721 tagcataaat gccctgctac ttttctatag aattaaaatg gtataggttt tggagaaaac
108781 aaaattgaaa agttactga aggtttgtca gcctcagctc cattatccaa aataagaaag
108841 tcacgtgctg gttttaggg ttgttagatg gattaaagaa acaacataca cagaagcatc
108901 tagcaacgtg acacgtggta aacgctcaaa aagtgttctc ccttcttttg atgactttac
108961 ttgatcagga aataacatat atatgtcttt caggaatgtt ctgcccaagc aggagagtca
109021 ctcacctcaa tcttgctacc cacaaagttt aacctaaaaa caacgggttc attgttgaca
109081 aaatgatgtt tatctgttgt tgacagaatg atgtttatct aaaaacagtt ccaatttct
109141 atttcctttg ctgagacaca aaggggaggc aaatgtgcaa agcttgaggg tagtcttacc
109201 actgtgctta agtgttctga tttttctagt gatcagggca aaataaaaag tatagtaagt
109261 tccaaggcag tgaatattat acaggagaga agttacagtt ttataatgtg ttttccttta
109321 cactaaattc taaaagtaaa aagtcttttt ttttttttga cagagtttca ctcttgttgc
109381 ccaagcaggt gtgctatggt atgatctcag ctcactgcaa cctccacctc ccgggttcaa
```

Figure 2

```
109441 gtgattctct tacttcagcc tcccgacagg ctgggattgc aggcgcctgc caccacacct
109501 ggctaatttt tgtgttttta gtagagatgg ggtttcacca tgttggccag gctggtctca
109561 aattcctgac ctcaagtgat ccatccacct cggcctccaa gtgctgggat tatgggcgtc
109621 agccactgtg cccagcctaa aagtaaaatg tctttcatga gcttcccaag gcagctacgt
109681 taaggaggac acttctctta atgtcattct acagtagatt tctaatgctc tttcttggaa
109741 gtttgttttt ctgagaaaag ctaaaaatat aacatggaag tgatcatatt atataatcaa
109801 tgaagtgctt ttcaaggaga taaaactaat ctggtccaca cttgcaacca accttgattg
109861 agagagagag agaactcagg atacacttga agattttatt atggggaaca gttactttat
109921 tcttttacc tcaatcaatg catggaaata agtgatagtc attttcattt atcttttaat
109981 aaatgaagtc accatgagga aaataaaaag acattgaaaa cccattaaag tcagcccttta
110041 aagatatttg gacatgcaga cttgataact aacgtttgca ttcttgagac ttacccaaaa
110101 cccatacctc aagtccaagt ttttagaatt catgaaataa agatctcagt gagtgcataa
110161 aattgcgcac cagaatcata tccgtataga caagaacaca tctactagaa aaataataaa
110221 ccaacacacc aatgcaactg tgttttcttc tgttttaaag tatgttgtct ttgtatgcat
110281 gtttgcttct tccttttttt ttttaacatc acagataaat tcaactctca cctcaggttt
110341 tattgagaga actgtcaatg tgacttggcc tctgtctttc tagtcccaga aagaattgca
110401 ctgaaatctg agctcctgta ataaaaacaa ccatttgctg agagtaatta acatactgaa
110461 agagattttc ttagagtaca caatggtgac attatattgc ctctttataa ataactttct
110521 atctatttct gtggattatt cctacaaagt acttttcata tgtccaattt cttttcttcc
110581 cctacaacta ctgtctgaat actggctctg ctatttgctg atatgattct cggcaagttg
110641 cctgcacttt ttaaacttta tttcctcatt cagaacatgg ggccatacat aatacaactc
110701 acttcagtgt tattggggaa ttaaacaaaa aatgcatggg aagcatttaa catagtgcct
110761 gacacaataa tgagtactca gtagatgtta gcttttatta atattgttgt tgttatgtcc
110821 agaaacacta tacctccaga aaatcatggg tacttgctgg ggacattggg gatatgcatg
110881 atttggaaaa gaatgactgc ttttttgct tagatgagaa attttctaa gccagactcc
110941 ttcaaatatg taagattctg ttgtggattc aaggactgaa agaattcttg gccgagtgtg
111001 gtggcttatc cctgtaatcc cagcattttg tgaggacaag gcaggaagat tgcttgagtc
111061 caggagtttg aaaccagcct gcgcaacatg gcgaaaccct gtctctacaa aaaatacaaa
111121 cattagctcg gagtgagtgc tgacatgtgc ctgtactccc agctactcag aaggctgaga
111181 tgggaggatc tcatgagcct ggggagtttg aggcttcagt gagccgtgat gacaccgtac
111241 tatactccac tccagcctgg gtgacagtga gaccctgcct caaaaaacaa acaaacaaac
111301 aaacaaaaca aaattaatct ttttgctgat gtcatgtcag cagtgtgtgt tgaaggctgt
111361 aaagcagcca tttgttcagt ttattttcc attgaacaag tatttatcaa aaacatactt
111421 tgtggcagtc actatgctag gagctatgaa tacagaagga aaagtaaatg ctcttggata
111481 ctacactcca gttgtgataa aaagaaaaa atgtattctt caccaacttc aacatcttga
111541 tgtgcaaaaa cataatacat gaattagatc tacctaatta cacagaatta gaccaattgt
111601 ttctggaatt gtgggctcat attttaata actgtcctcc tgcctctctg tcgacaggtt
111661 ttataaatat tcatttaatt acacacacac acacgaacaa ttgactagta cttgctctca
111721 ttcttctaga tgtcatcaca atggatccca aagacaattg ttcaaaagat gcaaatggta
111781 agctttttgtg ttttttcccttcctcctgatc attttgtttt gaacttctct ggcttgaaaa
111841 atcagggaat ggatttgct aggttggatg ctgcagaatg gacctagtga tattttaaat
111901 tagtccctca ttttctagga gttgtattaa caaacctaac tactgctttg gggtatgaga
111961 tgactgtaaa ttagagaggg tacagtggta tagtgatatg cttttaatta tttcaaaaaa
112021 aagatttat tcattcatgt gtcttttc ttttcttt cttttttt tttttttgga
112081 cagagtcttg ctctgtcacc caggctgag tgcggtggca gtatctcagc tcaccacaac
112141 ctccgcctcc cggcttcaag tgattctcct gcctcagctt ctcgagtagc tgggactaca
112201 ggcgcgtgcc accatgcccg gctaattttt gtatttttag tagagttggg gtttcaccat
112261 gttggccagg atggcctcga atttgtgacc tcgtgatctg cccctcgcc ctcccgaact
112321 gttgggatta caggcgtgag tcactgtgcc cggcctcctg tcctgtcttt tgtttaatga
112381 ctggaaaaa catgatacca tgttgcttct cgagttgttt tgtttagtc tttggtcttt
112441 gctagtagct aataacacga actagtgttt atcaagtgct tttacacag aagggcttgg
112501 gctgtgttct gcattttctt gtttaaccct cttaaaactc ctataaaatg gtacatattt
112561 ttctcccaat ttacagtccc tttaaagcaa ataattataa aaatcccctat acatgtcaca
112621 cagctagatc tgggatttca aatcaggcca tcaaacaaag agtttatgta cttagtaagt
112681 tttctgttct ttttctacaa tagagtcaga tagcaagaaa ttaccaagcc aggaacctga
112741 aacaaaacgg acatcatgtg gggctgggtg ggtgcatggg ctttgcagac tggactttca
112801 ctccagctct tttaatgatt aggtgtaagt gacctacatt ttgtgagcaa cagttttctc
```

Figure 2

```
112861 atcagccaac aaagaataat tacaccagat tcacagttat tgaagagata aaggcatgaa
112921 tgtgagatgt ctggcatagg gcatctcatt tagcagacac agaatgagta cttgtttctg
112981 gctttttctc tctacatatg cacaaagaat gcgactagaa gcatgggctc tagccctgct
113041 caactttcct ctatttccaa taccaagggg ctctgactta ggctgccaca ccaggcaagg
113101 agggcagtac cacctcactt gaccaagggc agggagtcac ggacacatca cttcttgaga
113161 tccttttcca caccaaggac tgatgtttct ggaattctca ctttatgaag acaaaacata
113221 taaatggaaa ttttctcagg tagagactca ctcttgtagc tcattgagta ggcactagtg
113281 gtccaccccc actgtcttta cttattcctt gacatcacat atctcttgca aaacctcaaa
113341 taatattaaa tgcaatcacc caataatagc atagccataa ttagaggcat ttaggaaaga
113401 caggtgagtg tgccacaact acctaacaca tcagcaaatc tggattaacc actttctttg
113461 attttccaca atgcaacctt acttttcaat agttgggaat gttctaagtg aatttagcag
113521 aggttgttaa tcaacttgaa agctgaattc tgacttgtct gactcttggt ggtgctggta
113581 gcagtagatg tttactttta ggttttggtg gtggtggaat atcacttcaa cgtaaatcat
113641 cagaaataag tatttgtgaa ccctctcgc attaatgtat cttattctgt aaaagaaca
113701 tgtgcaattt ctcttagata cactactgct gcagctcaca aacacctctg catattacat
113761 gtacctcctc ctgctcctca agagtgtggt ctatttgcc atcatcacct gctgtctgct
113821 tagaagaacg gctttctgct gcaatggaga gaaatcataa cagacggtgg cacaaggagg
113881 ccatcttttc ctcatcggtt attgtcccta gaagcgtctt ctgaggatct agttgggctt
113941 tctttctggg tttgggccat ttcagttctc atgtgtgtac tattctatca ttattgtata
114001 acggttttca aaccagtggg cacacagaga acctcactct gtaataacaa tgaggaatag
114061 ccacggcgat ctccagcacc aatctctcca tgttttccac agctcctcca gccaacccaa
114121 atagcgcctg ctatagtgta gacatcctgc ggcttctagc cttgtccctc tcttagtgtt
114181 ctttaatcag ataactgcct ggaagccttt catttacac gccctgaagc agtcttcttt
114241 gctagttgaa ttatgtggtg tgttttccg taataagcaa aataaattta aaaaatgaa
114301 aagttgactt ttgtccatgg tattttaatt ggatgacatc aaattgaaca tccaaggtaa
114361 gaaacagcat ggcaattggg ctgtggaatt ctgtattggt tgtaagaatg gtccaacacc
114421 ccatttctaa ttctttccct gagatcgtgg ttatcacacc ttctaagaag aactacaacc
114481 aaatgaagga gctcatgtga cttctgtttg aaaggtcacc agagtcagat tcattcggtt
114541 taggacattc cagtggctat aggacactat ctactgtgac gcgtaccgtg tgagctcagc
114601 tctagagtgt ttcacagaca ctgtgttttcc tgatcctcac gatacccca tgagagctgc
114661 cctaaaagca gagaggcagc gtgatggaga ggttcagcac atgctctctg atcccaggaa
114721 tcctgggtat ggtgtttcgt atctgtgtga cctcaggtga gttccaggaa ctctatgtgc
114781 cataatctcc tcatgtaaaa tgaagttata atgccccgtt tcctggagtt atgtggatta
114841 gatgagttaa tgacacctgg cacatgcaag tcctccacag tgtcggcacg cactgttggt
114901 agctctactc tagagacagt aataaaccaa aaagtatctg acacaggcct caatcaactt
114961 agaagtttat tttgcctatg ttaagggcat gcccaacttc ctgagataat aatttattc
115021 ataagaatat tttaaaaact cgagtaaact tgttaatgtt tattgctgca gccactctgt
115081 ccatctccac catcactgca acaacgcagg tccttgttgc ctcttattgg cttatggtga
115141 ccacctataa aaccatctgc ttcacccaaa ttgctgtcct ggggagtgcc ccttcctttc
115201 tgcttgcaca tttatcttcc tcaagtgcaa atgtgatcat gtgactttcc tccctaaatc
115261 ttttagcaag tcctcattgt ctattcttct ttcaaaaaca tttatttgaa aatactatta
115321 aaatagaaaa ttttccacat tcttacttct taaaaattaa tgtgttttaa gtttctccta
115381 ctccatttcc atcccatgcc ctttactca atggatgcaa ttattcttct acatgttcct
115441 tctggccatg tgtagctttg tcatttaat tttaatctat ttggaccctg tgttatctgg
115501 gatgaggtag agtgatattt ttattttctc aggtaattat ttgcctaatg cctgtttcca
115561 aataatccac catttcctta caatttaaaa atgctccagc atgtttttaa tagctacaca
115621 tatttgacac attttctgga gaatttctgt ttatttgtc tatttcatta ttcttgtatc
115681 attatcatat tatctcagta gctttgtggc aagtattaag atctactatg ccaaatgtct
115741 attcactgta ccattttca gaaaattctt tttcaatcat ctcatattta ttcactcctg
115801 tagaatttaa aatcaactta tctagcctaa cattaaacct cacaccctag aacaacaaca
115861 tgtcgtagta attctgacta aaattgctgg aaatttatag atgaatttag ggtgtattgg
115921 cctctttatg atagaagctt tttattcatc aatgtatgtt tctccattta tttaggtttt
115981 attttatgcc cttaggaaaa ctaaatactg tgttcttcat atcattcttg tatttttttg
116041 gtaaatttaa taaagattt tataattcat tacttcttca cattttatta gttaaatcct
116101 tcatggctct tgaaatattg acagctgcta agacttctga tgcttcccct catgtcctg
116161 aaataaggaa ggccagagga caaaagaga ttgagtgggc gtcattccat ctatcacagg
116221 tgtaaagggt cattgacagc gccacataat aatttttgaat tttctattaa gaagaaaccc
```

Figure 2

```
116281 tttccaaaca taattttcac ccagccccat tgtcttctcc attgttgtgg gggctgtggc
116341 ctgccgtgta tggataggtg ccctctgtga cctcactcat accttcctga atgaagactc
116401 aggagactta ggctggagca gggtggatct ggagtggaca tggaggttgt caaggcttgt
116461 cctcctcagt ccttgcaact gaacacctca tctgtacaca ggagatcaca cagccgacac
116521 cagcttaaga tggcagattt ttcaacatat cagataacta aattttttt tttggttatg
116581 ccatagttta aataaagaat gtattacttc atgggacata gaattctaca aatttcttct
116641 gctattccag gaaaaatgat aagtcattgt ggaaaacatt tcctcatttg gcattgcctt
116701 ggtaaagcat cgtgttgcca aatgatacaa gtggcttttt gaaagtggag acctttgttc
116761 aaatttctca agtatatctg tgttgacaca tttgcatttt cagttactaa agagcttcct
116821 cctttcagaa gtatcttccc aaattactaa caggccctgg tgtttgtggg aacagaaggg
116881 cttttccttt gatgtaatct caaagcagtt tcaacacaat tgaaccctg gaaattaaaa
116941 aagaaaaaaa acgacaattc tctgaatact ttcctggta atttagaaaa gtagtgcatt
117001 gacccactga gcctgctctt ttttctctct atcgcccagg ctggagtgca atggcacgat
117061 ctcggctcac tgcaacctct gcctccctgg ttcaagcaat tctcctgcct cagcctcccg
117121 agtagctgtg actacaggca cacgccacca cgcccggata atattttttt gtatgttagt
117181 agagacgggg tttcactgtg ttgccaaagc tggtcttgaa ctcctgagtt caggcaatcc
117241 acctgactca gcctctgaaa gtgctaggat tacaggcgtg acccactgcg cccggccttt
117301 cttttttgt tgttgttggt ttttatctt aacatttctt ttttctgttg atgcttttca
117361 agaattactg ccttagaaga aagcaggcaa tttatgagga aaaattacaa actatcacat
117421 gtcacaaaac ctatattcaa ggacttccaa aaaagccaga agatgaaatt gctagttcaa
117481 agttgttgga ttgctagtca tgtcatgagg atcagaaggt tgagatttt gtagaagctt
117541 agaccagtgt gatagtagtg attggatcaa gacgtttgca aaagggacta ggctcatagt
117601 aacttcgcct ggtaagtaat tttttttctg ttttattcc agtaatgaaa aactgataga
117661 tgttttag aaaaaatga tcaaccttac ctgaatatgt cacattcctg gcctcagtat
117721 acgaacagca attttcagg gtagctgaat gcctggcact tggtaggtga tagaaatatt
117781 atttcctctt ccagaattca agttactacc caagagaggt ctttatacac tcaggaatac
117841 agataaatgt atcaatcccc atctattcaa cagctcactt cagaagaaat gtcactattc
117901 ataaaatgct ttttatttct aaaagcctaa ttgtacctgc ttctaaaagc aattagaatg
117961 ttttacgtat tatctcaaat atgatctgcc tgaatacaag gtgatttttc attttccaga
118021 gaaatttat acaagtttaa gaaaatatgt attttcccct ccccccaactt gaatatgtaa
118081 atttataggg atacaagtaa aaaagtgaaa tgtctaatta taacattcaa tttcttaact
118141 ggatcatacc tcaaagttaa agattatatc aataccaata tcagttgaga atatattgcct
118201 tttttgcct tatatttcat taaaattttt gtttatgct tcacatgcat gtaaagcatc
118261 tatctcagag caactttcta aggcatctca ggtctcagtg tccattttgg attcctcaaa
118321 tgatgatgtc cctgaatatt ttactctaag aaacaatgat ccactcacaa aataaaagga
118381 aattattttt tccgatttat tctgttattc tacacttgta tgaagtaagt aagaactaca
118441 gggactttag ctccaagtaa taatgaccaa atccatgata aatttctttg ctttttttcc
118501 ttttaccagt gctatcccca aaactagcat tcattgagtt catttcatgt cggtatctcc
118561 tccagttagt cccttctggat caaagcagag tattagaaga acatttttta atatgagagt
118621 ttacacaaag actgtaccat acataaggca cctccccatg ttgtgagaga aaaatttgg
118681 aaaaaaagcc tcattttagg ttctggcact ttctatctaa atttagtatg taggtgtccc
118741 tatcacagag ctaggatttg caaacatatt ctccattcct tgtgtcttat ttgagcttga
118801 ccttacaaaa ccatcaactc ctgggacaa aagagaaaca tgctaaatgc acaaactctt
118861 tgttatttat ttaagctatc tgtttctaaa atctatttga gaagacctaa attaaaatac
118921 acaagcacag tcagaccatt aatatatac agatgatcta agccctaag gaaaggagaa
118981 ggaaaaaggc ctgtgattac ctagtgagga gcacagttta aatttatg ctcaaaagaa
119041 ggagaaaaag gtagggaat acatacatct tactaattga taaaagaag cacaccaaat
119101 tttcaaatat catattttt ctattactaa attggaaaaa gacttcaatg catgagtcct
119161 ttagaaggaa atggaagagt gggcagtgcc ttcaacttcc attttggaaa atgaaaggaa
119221 tgtcatgaa aaacccactg catattacca ctgcatcagt gctatggca tcctgacatt
119281 taatgaaatg cgcagatggt gatgctcagc agacatggtc aggcagataa catgtagtga
119341 tctaaagtga caacagagag atggatttga ggaccaggcc tcttgccttt tctctaccca
119401 ttctcccttg aagggtcaag ccaggtgttt cgagcgggac tttggcataa actagacaga
119461 agtcagtttg aggctgaagt ttctggtgaa acttggaagg caaataagtt gtgctgctga
119521 ttagaaaaag gctcacttgt tttgaaaaac acaagtgaag aatttccata cactgacact
119581 gactgcatat attagacttt agccaatatt ccctttgatt ttcttaacac ggcaggtaag
119641 gcaaaggata acctattaaa gattgggtgt gtggaaggca tgtttcttgt gatgatgggg
```

Figure 2

```
119701 acgatggctt tgagaatccc agagcaaagt ggaatgcaaa cagaggaact gagaaattat
119761 tcttcctgct taattgctat ggatttaact gccactccaa aatgctgaat ttttttagt
119821 aaggcaatg cttggtccta tagggttaaa atgtcatgtc aaggcacaca atcatagcaa
119881 acagattgcc aatcataaca atgacaccat attcatcata atctcttata tttccacagc
119941 atttttttt gaggcagggt cttcccctgt tgcccagtcg ggagtgcagt ggtgtgatca
120001 aggctcactg cagcctcgaa ctcctaggct caagtgaccc tcctgcctca gcctctcgag
120061 tagctgggcg tacagtcgtg cacatcatgc tcagctaatg cttttgtat ttttagtaaa
120121 tatgggtct cactagatac tgggttgccc aggctggctt caaaattctg agctcaagca
120181 atcctcccac ctcagcctcc caaagtgctg ggattatagg cacgagccac tgcactggga
120241 cctataacat tttaatcaaa ttgcttttt atatcttgtt tcatttggt ctcacttcag
120301 tgttggtagc gatgttgaac tgattttgaa acatcactgt ttttagacaa ataaaacacc
120361 aaaagcttta agttatttga tttgtggagc aacagaactt gttatgagca aatgaacca
120421 ggactggaac cctggtcttt tgagaatccc agaccaccag aatttgaaga actcaggaa
120481 actgaattag agttttgat atggactgaa tcactgtgga attattataa gaaactcttt
120541 ggcagtggaa caacacttgt tgtcacaggt aagtatcgga agaatacaac atttccaagg
120601 taatagaggg aaggcaggaa atgattaaac tggaataatg taataatgtt tagaaaaaag
120661 aggaattgga tggggattg atgtagaaat cctaggagag actttaaaac aaatgctcat
120721 actaaaagag aacatagata acatggcaca gatatcataa taggatttgg ctttgtgcat
120781 atacggactt ccataaaggg ctcatatgta atgtatgaaa tgatctcatt aaaatgtctg
120841 gccctgagac caaatgtatt atgacaggtt agtttgtgat agactctata aagcggacac
120901 atgttcatct ctgatggtca aagagatgtt gactcttgtt gtgaaggagc ccgggtgttg
120961 gagtcaggtc cacctggaac tctggctcca ctactcactg cttagtgaaa ttgagtgatt
121021 attctctggc ctcagttttc taatccataa aatgggataa cagtatgaat tcagcagggt
121081 tgtataagaa ttgcacaaca tagtgtgaat taagtacttg gcacattgtc aacccaaaa
121141 taggtgccca acaaatgttt tctggattca catgtaaaga gacaatggga tctactatgg
121201 agagttgctc tcagtccatc taatttacag agcagcaatt ctccagagga ttcagctgta
121261 cttctaactg ctcaaatgga aggttatctt aacatcagct cacagacaaa aattgaactt
121321 atggattcgt ttcttgttag cagactttt aatcacgtgg caaaaacatt gtattaagat
121381 gtctgttttt tattttgtt gttctatgtg ctttacttaa tcctttatct taattgatat
121441 catttctaac accaacatat tggtcctaag atttatagcc aattagttta gggttctgtt
121501 catatgtctc aggaaaaaaa ggttaaaatc ttaccaaaaa tagtcaagat atcaaatcaa
121561 ttaaatccag ttggaaacat cataaatctg aaatacatat ttaaacataa aatggctata
121621 actatttagc tagtgaaaaa ataagaaata gagaactctt aaataaatat ccacatgtag
121681 atttaatata tcataccgtc tataaaactg tagttgatac ttggtaaatt tacaacgctg
121741 cattttaata aactacaaac aacttaggca atttaactca aatatactat ttgattatgc
121801 aaataaatgt atataaatga atccaacagg tttatttaaa taaataaaat atatatattc
121861 tatttgttac tgaagtaagt aaaaatgtac catacttgac cataaaaaac actcttaata
121921 tgtacatttt aaaagtagta ttttaaaaat catgtgagag gatgatccag aatatcggcc
121981 cttaccatgt ataatcgagt atgctattta atgattcgtt aactattacc ttgagaaagt
122041 tatggaagtt ccagattcat tttgtcctga aaagaatgaa acttaaagaa tctagctaaa
122101 gaaaggggca agagacaatg aatgctgtgg taccgtacag aaaatgtcca agtttatcat
122161 ttgatttta attctttag tacaatgaat tagaagtatt tcaatgaaga gacactagtt
122221 cttaggatga aaattagatt ggaaaataca ttgactagag actaaaatta tataaatata
122281 atgtacaatt gaaaaattac tcatatttta taacatgctt ttaaaattag aagcaaacta
122341 tatggtggag aaatatacac tgtctcacaa gtaacaag taaaatacta tttgcactaa
122401 aagcaaagag tatgaaatta agatgagcac attatgccta attaaattta tagcatgctc
122461 acaaattaat atttctgtat atgtttacta attttgtatg aaaatcagaa gctttgctac
122521 acagacagaa attatcaaga ttgttttctt ttcttctgaa atgagaaatt taattcttat
122581 tttcttaaga aattgttcaa ttattaaact cacttcaaac cagccaaagc attggagttt
122641 caatgggaaa tcaaataga aagaattgta acatttataa tttcagttat tagattaaaa
122701 atacgtgtat aacccattaa catcccagat tcaagtgata tgcctttgta aacatatgat
122761 gctttgttat gtatcttgac cctatcccta taagaagctc tgaaatcatg acttttaata
122821 gagcaattac atactcattt tattcagcag gctaagacaa agagaataat ggagatttaa
122881 aacagttaaa tagcatatta ggacagatac aaattctggg agagacataa agagtcaaaa
122941 tatagataca ctgatttaca tagaccttct cattaatggg gtaaatttat ataaaaacca
123001 gtataaaaat tacaccccctg gtgcattctt agtcattctt aaacttcaaa tgaaattcca
123061 aataaaaatg tgcttttggt gaatattttc taaagcaaaa tgaaattttg ataagtgcat
```

Figure 2

```
123121 tactggagaa gattaacaca agagtatttc tgaaaataat caagaaaaaa tttaaataag
123181 aattttggaa atgttgccat tttgtttcta aagtcaagag atggtgaata atctggaggt
123241 acagctgtaa gtactgctgc atcccaaaac ttggagggtg cagatgtgaa attgagatgt
123301 tatataaagt tagatattaa ctaggggac tgctcatggt atacacattg aagctacatg
123361 gtcaacttga tagacagtat gtacatgcgg aagtagattc tctttaaaac aagtgactgt
123421 gtatgttaaa aataaaagtg aacaaaatgg ctaggcatgg tggctcacac ctataatccc
123481 aggatttggg aggctgaggc aggcagatca cttgagcgca ggagttttaa accagctgg
123541 tcaatatggt gaaatatgtc tctagaaaaa acaaatatta gccaggcatg gtgatgcata
123601 cctgtagtcc cagctacttg ggaggctgag gtgggaggat cacttgagcc tgggaagtcg
123661 agactgcagt gagctatgat cttgccgctg cattccaacc tggacgacag agcaagcccc
123721 agtctcaaca acaacaacaa aaatttgac attgattcat atgggaaata agataaataa
123781 caagataaat atggtgcatc gcagaatcag ttaaatgaag agtggaagta cacgaaattg
123841 cagaacatga gaatgtgtca tatttggcca aagaacataa gttacaaagg atggaaaagg
123901 gaagtgagaa aaggaccaaa gagtctcatc tgtagagaga tcattaaggt tttctgacct
123961 tccactttcc cctgccatcc accttgaaaa cctgcttcac tgtgatgaaa caaaagagat
124021 ttaaaaataa aataaatatg ctcatgaact ttggaagccc tggtaggagg cagttaaaaa
124081 tcacactcat cacagcatgt gcagaataaa caaggccag gttttcgtcc agcatctgac
124141 acttgagagc tgtgactttt ggcaagttat ttaatgtctt gattctcttt tcaacatctg
124201 taaaataagc acaataataa gtactgtgca gcctatcctg gatgaaaggc cgcggtggac
124261 accagctcaa tggcatcttc tcttttatg gttatgtact aggccactcc aaaccgtgca
124321 atgtgtgtgt tctctaatg attctttaa actcatattt catttctccc catagataaa
124381 caacttgatg cagatgtttc ccccaagccc actattttc ttccttcgat tgctgaaaca
124441 aaactccaga aggctggaac atacctttgt cttcttgaga aatttttccc agatattatt
124501 aagatacatt ggcaagaaaa gaagagcaac acgattctgg gatcccagga ggggaacacc
124561 atgaagacta acgacacata catgaaattt agctggttaa cggtgccaga agagtcactg
124621 gacaaagaac acagatgtat cgtcagacat gagaataata aaaacggaat tgatcaagaa
124681 attatctttc ctccaataaa gacaggtatg tgtttacaca tatcatctgt cagaacactt
124741 ctttgaaagt gaatgctgca ttttttcctt tcagtattaa tgaaaaacat aaatctttct
124801 taaaaattgt tacatttaat ggtagcgtaa atgccctgct actttctat agaattaaaa
124861 tggtataggt tttggagaaa acaaaattga aaagttgct gaaggtttgt cagcctcagc
124921 tccattatcc aaaataagaa agtcacgtgc tggttttag ggttgttaga tggattaaag
124981 aaacaacata cacagaagca tctagcaacg tgacacgtgg taaacgctca aaaagtgttc
125041 tcccttcttt tgatgacttt acttgatcag gaaataacat atatatgtct ttcaggaatg
125101 ttctgcccaa gcaggagagt cactcacctc aatcttgcta cccacaaagt ttaacctaaa
125161 aacaacgggt tcattgttga caaaataatg tttatctgaa gataactgta gatcatattt
125221 atctgtagat aatgtttatc tgtggagtgt ggctctacaa aacatagaat agtcttggtc
125281 actgcagttt tatagaggcc ttgggttttt cagagtttca ttttatatat caccataaag
125341 taacatttca taattacagg ttggtaaggc ttacatgtac aaacattctt ccattttcca
125401 taataaatgc atttcctgcc attggtgaat gcagctcaat aaacatttat tgtacaatta
125461 tgacacgcca ggcttagtgg aaatgtggat gaacagacaa ggatgagtta ctgtcctaag
125521 gatgatgcat gacagtgcag agaatatact ctcttcctga tcactcaggg tcactcatga
125581 ttcatgcgcg aggtcccaaa acagtgcctt tgatgcagat tctgtacatc tctagacgat
125641 tggtccaagg gctgaatgtg ctctggccca gtggtccagt ctgtcactat atgtcaacat
125701 cctgaatatg aacataacag tccaacatct caagagtggg catgaaaagg actcattttg
125761 tgcttttcc tgtggttaac aagtcctttt tagcctgggg gaacaagcat taacaaaatg
125821 tttgaagatc tttgccacgt accattccaa atttctaggg taagtcttta gcttttcaga
125881 tcctgagttt ctgcaatgat caaatgtgat ttggacagtt gcgttgactt tctcctgggg
125941 ctataatgga gtgcaaagga acaatggca gggaaaatgc ttgctttcaa aatggtagca
126001 tggatgtgtt cattcgtgta gttactgtat taggtatagc ctttcctgaa actaactgaa
126061 gtggggttat aaaaacagtc ccaattttct atttcctttg ctgagacaca aagaggagac
126121 aaaagagcaa agcttgaggg tagttttacc actgtgctta agtgttctga tttttccagt
126181 gatcagggtg aaataaaaag catagtaagt tccaggcag tgaataccat acaggagaca
126241 agttacagtt ttataatgtg ttttacttta cactaaattc taaaagtaaa atgtcttttt
126301 ttttttccga gacagagttt cactcttgta gcccaggcag gagtgctatg gtgtgatctc
126361 ggctcacagc aacctccacc tccagtttc aagcgattct tctgcctcag cctcccgaga
126421 agttgaaatt acaggtgcct ggcaccatat ctcgctaatt attctatttt tagtagagat
126481 cgggttttac catgttggcc aggctggtct cgaactcctg acttcaagtg atccacccgc
```

Figure 2

```
126541  ctcagcctcc  caaagtgctg  ggattacagg  tgtgagtcac  tgtgccggac  ctaacagtaa
126601  aatgtctttc  atgtgcttct  caaggcaact  acattaagga  ggacacatct  cttaatgtca
126661  ttctacagta  gatttctaat  gctctttctt  ggaagtttgt  ttttctgaga  agagctaaaa
126721  atataataac  atggaagtga  tcatattata  taatcaatga  agtgctttca  aaggagataa
126781  aactaacctg  gtctgcattt  gcaaccagcc  ttgattgaga  gagagagaac  tcaggataca
126841  cttagagatt  ttattatggg  gaatagttac  tttattcatt  ttacctcaat  caatgcatgg
126901  aaataagtga  cagtcatttt  catttatctt  ttaataaata  aagtcaccat  gaggaaaatg
126961  aaaacccatt  aaagtcagtc  cttaaagata  tttggacatg  cagacatgat  aactaacatt
127021  tccattcgtg  agacttaccc  aaaacctata  cctcaagtcc  atttcttaga  atacatgaaa
127081  taaagatctc  agtgagtgta  taaaactgca  caccagaatc  atatccgtat  agacaagaat
127141  acatctacta  gaaaaatata  aaccaaaaca  ccaaggtgac  tctgtttttt  tctgttttaa
127201  aatatgttgt  ctttgtatgc  atgtttgctt  cttccttttt  tttttaaac   atcgcagata
127261  aattcaactc  tcacctcagt  tgagagagaa  ctgtcaatgt  gacttggcct  ctctctttct
127321  agtcccagaa  agaattgcac  tgaaatgctg  agctcctgta  ataaaaatga  ccatttgctg
127381  agagtaatta  acatactgaa  agagatttc   ttagaatagt  gcacaatggc  ccaatggtga
127441  cattatattg  tctctttata  aattatttc   tatctatttc  tgtggattat  ttctacaaag
127501  cacttttcat  atgtccaatt  ccttttattc  ccctacaagt  actgactgac  tactggctct
127561  gctgttcact  gatatgactt  tcggcaagtt  gcctgcactt  tttaaacgtt  atttcctcat
127621  tcagaacatg  gggccataca  aaatacaact  cacttcagtg  ttattgggga  attaaacaaa
127681  taaatgcatg  ggaagcattt  aacatagtgc  ctgacacaat  aatgagcact  cagtagatgt
127741  tagcttttat  taatattgtt  gttgctatgt  ccagaaacac  tatacctcca  gaaaatcatg
127801  ggtacttgct  ggggacgttg  gggatatgca  tgattttgaa  aggagtgact  gctctttact
127861  gctcagatga  gaaattttc   taagccagac  tccttcaaac  atgtaagatt  ctgttgtgga
127921  ttctaggact  gaaagaattc  ttggccgagt  gtggtggctt  atcctggtaa  tctcatcatt
127981  tgggaggaca  aggcaggaag  attgcttgag  cccaggagtt  ggaaacaagc  ctggacaaca
128041  tggcgaaacc  ctgtctctac  aaaaaatacaa aacattagct ggtcatggga  gtgagtgcct
128101  gtactcccag  ctactcagga  ggctaagata  ggaggatcac  ctgagcctgg  gcagtttgag
128161  gtttcagtga  gccgtgatga  caccatacta  tactccactc  cagcctgggt  gacagtgaca
128221  tcctgcctca  aaaaaccccc  caaaattatt  cttttttgctg atttcatgtc  agcagtgtgt
128281  gctgaaggct  gtaaagtagc  cacttgttct  gtttatttt   ccattgaaca  agtatttatc
128341  aaaaacgtac  tttgtggaag  gcactgtgct  aggaactatg  catacagaag  gaaaaccaaa
128401  tgttcttgga  tactacactc  cagttgtgat  aaaaaagaaa  aagtattct   tcacaaactt
128461  caacattttg  atgtgcaaaa  acataatata  tgaattagat  ctacctaact  acacagaatt
128521  agaccaatta  tttctgggat  tatgggctca  tatttaat    aactgtcctc  ctacctctct
128581  gttgacaggt  tttataaata  ttcatttaat  tacacacagt  cacagacaca  ctcagacaca
128641  cacacataca  cacacacaca  caccttgaca  aataatgggc  atgaacaatt  gactggtact
128701  tgctctcatt  cttctagatg  tcaccacagt  ggatcccaaa  tacaattatt  caaaggatgc
128761  aaatggtaag  tttttgtgtt  tttatttcc   tcctgatcat  tttaagtttt  gaacttctct
128821  ggcttgaaaa  atcagggaat  ggatttgct   aggttggatg  ctgcagaatg  gacctaatca
128881  tatttttaaat tagtccctct ttttctagga  gttgtattaa  caaacctaac  tactgcttca
128941  tgtaagagat  gactgtaaat  tgaagggtac  agtgatatgc  tttcagttat  ttcaaaaaac
129001  agactttact  catccatgtg  tcttttttct  tttcttttt   ttctttttg   agacggagtc
129061  tcgctctgtt  gaacaggctg  gattgcagtg  acgcgatctc  acctcactac  aacctccgcc
129121  tctggagttc  aagcgattct  ccagcctcag  cttctcaagt  agctgggact  acaggcacat
129181  gccaccatgt  ccgggtcatc  tttgtatttt  tagcagagac  cgggtttcac  tatgttggcc
129241  aggctggtct  agaattcctg  acttcgtgat  ctgccccctc  agccctccga  agtgctggga
129301  ttacagacgt  gagtcactgt  gcccgccta   acagtaaaat  gtctttcatg  cgcttctcaa
129361  ggcaactacg  ttaaggagga  cacttctctt  aatgtcattc  tacagtagat  ttctaatgct
129421  ctttcttgga  agtttgtttt  tctgagaaaa  gctaaaaata  taacatggaa  gtgatcatat
129481  tgtataatca  atgaagtgct  tttcaaggag  ataaaactaa  tctggtccac  gtttgcaacc
129541  aaccttgatt  gagagagaga  gagaactcag  gatacacttg  gagatttat   tatggggaat
129601  agttacttta  ttcttttc    ctcaatcaat  tcatgaaat   aagtgatagt  catattcatt
129661  tatctttaa   taaatgaagt  caccatgagg  aaaataaaaa  gacattgaaa  acccattaaa
129721  gttagcccct  aaagatattt  ggacatgcag  acttgataac  taacgtttgc  attcttgaga
129781  cttacccaaa  acccatacct  caagtccatg  ttttagaat   tcatgaaata  aagatctcag
129841  tgagtgcata  aaattgcgca  ccagaatcat  atccgtatag  acaagaacac  atctactaga
129901  aaataataa   accaacacac  caatgcaact  gtgttttctt  ctgttttaaa  atatgttgtc
```

Figure 2

```
129961 tttgtatgca tgtttgcttc ttcctttttt tttttaaca tcacagataa attcaactct
130021 cacctcaggt tttattgaga gaactgtcaa tgtgacttgg cctctgtctt tctagtccca
130081 gaaagaatcg cactgaaatg ctgagctcct gtaataaaaa tgaccatttg ctgagagtaa
130141 ttaacatact gaaagagatt ttcttagagt acacaatggt gacattatat tgtctcttta
130201 taaataactt tctatctatt tctgtggatt attcctacaa agtacttttc atatgtccag
130261 tttcttttct tcccctacaa ctaccgtctg aatactggct ctgctatttg ctgatatgat
130321 tctcggcaag ttgcctgcac tttttaaact ttatttcctc attcagaaca tggggccatg
130381 taatactcat gtacgtgagt attacgtaat aatgctcact taagtgttac tggggaatta
130441 aacaaaaaaa tgcatggcaa gcatttaaca tagtgcctga cacaataatg agcactcagt
130501 agatgttaga ttttattaat attgttgttg ttatgtccgg aaacactata cctccagaaa
130561 atcatgggta cttgcttggg atgttgggga tatgcatgat ttggaaaggt atgactgctt
130621 ttttctgctt agatgagaaa tttttctaag ccagactcct tcaaatatgt aagattctgt
130681 tgtggattct aggacggaaa gaattcttgg tcaggtgtgg tttcttatcc ctgtaatccc
130741 agaatttgg gaggacaagg caggaagatt gcttgagccc aggagtttga aaccagcctg
130801 ggcaacaaga cgaaaccctg tctctacaaa agtacataaa ttagcttggc ttggtggtgt
130861 gtgcctgtat taccagctat tcgggagact gagatgggag gatctcctga acctgtgaag
130921 tttgaggctt cagtgagccg tgatgacacc atactatact cgactccagc ctgtgcgaca
130981 gtgagactct gcgtcaaaaa aaaaacccca aaattattgt ttttgctgat ttcaggtcag
131041 cagtgtgtgc tgaagggtgt aaagtagcca cttgatcagt ttatttttcc actgaacaag
131101 tatttatcaa aaacatactt tgtggtctgt ttttgataaa taaaaaggca ctgtgctagg
131161 agccatgaat acagaaggaa aaccaaatgt tcttggatac tacactccag ttgtgataaa
131221 aaagaaaaat gtattcttca cgaacttcaa cattttgata tgcaaaaaca tagtatataa
131281 attagatcta cctgattacg tagaatcaga ccaattattt ctggaattga gggctcatat
131341 ttttaataac tgtcctcctg cctctctgtt gacaggtttt ataaatattc atttaattac
131401 acacacacac acacacacct tgacaaataa tggacatgaa caattgacta gtacttgctc
131461 tcattcttct agatgtcatc acaatggatc ccaaagacaa ttggtcaaaa gatgcaaatg
131521 gtaagctttt gtgttttttcc tttcctcctg atcattttaa gttttgaact tctctggctt
131581 gaaaaatcag ggaatgggcc gggtgcggtg gctcacgcct gtaatcccag cactttggga
131641 ggccgaggcg gcggatcac gaggtcagga gatcgagacc atcccggcta aaacggtgaa
131701 accccgtctc tactaaaaat acaaaaaatt agccgggctt agtggcgggc gcctgtagtc
131761 ccagctactt gggaggctga ggcaggagaa tggcgtgaac ccggaggcg gagcttgcag
131821 tgagccgaga ttgcgccact gcactccact ccagcctggg cgacagagcg agactccgtc
131881 tcaaaaaaaa aaaaaaaaaa aaaaaagaa aaatcaggga atggattttg ctaggttgga
131941 tgctgcagaa tggacctagt gatattttaa attagtccct ctttttctag gagttgtatt
132001 aacaaaccta actactgctt cgggtatgag atgactgtaa attagagggt acagtgatat
132061 gctttcagtt atttcaaaaa acagacttta ttcatccgtc tgtctttttt tttttttttt
132121 ttttttttt ttgagacgga ggagtctcac tctatcaccc aggctggagt gcagtggcgc
132181 gatctcggct caccataacc tccgccttac tggttcaagc gattctccag cctcagcttc
132241 tcaagtagct gggactacag gtgcacacca ccatacctgg ctaattttg tatttttaat
132301 agagatgggg tttcaccacg ctggccagga tggtcttgaa ttcttgacct cgtgatctgc
132361 cccctcgggc tcccaaactt ctgggattat aggcgtgagc cactgtgccc ggccttctgt
132421 cttttgttat aatgactggg gaaaacatga taccatgttg cttcttgagt tgttttgttt
132481 tagtctttgg tctttgctag tagctaataa cacgaactag tgtttatcaa gtgcttttta
132541 cacagaaggg cttgttctgc attttctagt ttaatcatct taatactcct ataaagtagt
132601 acaatatatt ttctcccatt ttacagtccc tttaaagtaa ataactataa aaatcccttta
132661 tacatgtcac acagctaggt ctggcatttc aaatcaggac atcaaacaaa gaattcgtgc
132721 agttactaag tcctctattt tttctacaat agaaaaaata gcaagaatta cagatagcaa
132781 gacattacaa ggcaggaatc tgaaacgaaa gggacataat gtggggctgg gtgggtgcat
132841 gagctttgca gactagactt tcattccagc tcttttaatg attaggtgta agtgacctac
132901 attttgtgag taacagtttt ctcatcagcc aactaagaat aattacacca gattcacagt
132961 tattgaagag ataagggcat gaatgtgaga tgtctggcgt agggtatctc atttagcaga
133021 cacagaatga atacttgttt ctggcttttt ctctctacat atgcacaaag aatgtgacta
133081 gaagcattgg ctctagccct gctcaacttt cctctatttc aataccaag gggctctgac
133141 ttaggctgcc acaccaggca aggaggggca gtaccacctc acttgaccaa gggcagggag
133201 tcacggacac atcacttcct gagatccttt tccacaccaa ggactgatgt ttctgaatt
133261 ctcactttat gaagacaaaa catataaatg gaaatttctg caggaagaga ctcactcttg
133321 tagctcattg agtaggcact agtggtccac ccccactgtc tttacttatt ccttgacatc
```

Figure 2

```
133381 acatatctct tgtaaaacct caaataatgt taaatgcaat cacccaataa tagcatagcc
133441 ataattagag gcatttagga aagacaggtg agtgtgccac aactacctaa cacatcagca
133501 aatctggatt aaccactttc tttgattttc cacaatgcaa ccttactttt taatagttgg
133561 gaatgttcta agtgaattta gcagaggttg ttaatcaact tgaaagctga attctgactt
133621 gtctgactct tggtggtgct ggtagcagta gatgtttact tttaggtttt ggtggtggtg
133681 gaatatcact tcaacgtaaa tcatcagaaa taagtatttg tgaaccctc tcgcattaat
133741 atatcttatt ctgtaaaaag aacatgtgca atttctctta gatacactac tgctgcagct
133801 cacaaacacc tctgcatatt acacgtacct cctcctgctc ctcaagagtg tggtctattt
133861 tgccatcatc acctgctgtc tgcttagaag aacggctttc tgctgcaatg gagagaaatc
133921 ataacagacg gtggcacaag gaggccatct tttcctcatc ggttattgtc cctagaagcg
133981 tcttctgagg atctagttgg gctttctttc tgggtttggg ccatttcagt tctcatgtgt
134041 gtactattct atcattattg tataatggtt ttcaaaccag tgggcacaca gagaacctca
134101 ctctgtaata acaatgagga atagccatgg cgatctccag caccaatctc tccatgtttt
134161 ccacagctcc tccagccaac ccaaatagcg cctgctatag tgtagacagc ctgcggcttc
134221 tagccttgtc cctctcttag tgttcttaa tcagataact gcctggaagc ctttcatttt
134281 acacgccctg aagcagtctt ctttgctagt tgaattatgt ggtgtgtttt tccgtaataa
134341 gcaaaataaa tttaaaaaaa tgaaaagttg actttttgtcc atggtatttt aattggatga
134401 catcaaattg aacatccaag gtaagaaaca acatggcaat tgggctgtgg aattctgtat
134461 tggttgtaag aatggtccaa cacccattt ctaattcttt ccctgagatc gtggttatca
134521 caccttctaa gaggaactac aaccaaacga aggagcccat gtggcttctg tttgaaaggt
134581 caccagagtc agattcatct ggtttaggac attccagtgg ctataggaca ctatctactg
134641 tgacgcgtac cgtgtgagct cagctgtaga gtgtttcgca gacactgtgt ttcctgatcc
134701 tcacgatacc cccgtgagag ctgccctaaa agcagagagg cagcgtgatg gagaggttca
134761 gcacatgctc tctgatccca ggaatcctgg gtatggtgtt tcgtatctgt gtgacctcag
134821 gtgagttcca ggaaatctat gtgccataat ctcctcatgt aaaatgaagt tataatgccc
134881 catttcctga agttatgtgg attagatgag ttaatgacac ctggcacatg caagtcctcc
134941 acagtatcgg cacgcactgt tggtgctcta gagacagtaa taaaccaaaa agtgtctgac
135001 acaggcctca atcaacttag aagtttattt tgcctagtct aagggcatga tcagaagaaa
135061 ataacatgga atcacagaaa cagtctatgg tctacacctt tctccaaaga tgaaattgag
135121 ggcctcaatg tttaaaaaag gaaagtgggc tggaggggag agagggaggg tataattatc
135181 cacatgttgc aagagcaagg gagcaggtag gggaactgcc aattatgtat tcatgttgcg
135241 ctcaataaat cagcacttta cataagatat ggttaacata gagtagctac ctctggagct
135301 atttcacctt tcatctgtag ctctctgttt aggcacaaaa ggaaaggcag cttctcacat
135361 gacccagctt ttggcttatt tttttctaaa acatagcatg atgaattggg atccagagtt
135421 tttctttttcc tttcacatag tagattccac acatatgcaa aagcactaac agttatctct
135481 actctcacct ctccgcagag aggttaggtg gtgggaatag ggacccagtg agtgtctact
135541 atgcactagg catccgaaat ccttgatgag ccagttgagg tcagtacaat taaggctcac
135601 agttcacaga tgagaaagat taaattacct actcaaggtc actattttta aagtaatagt
135661 cgtaatttaa agctaggtcc ctctgaaccc agagcccata tatttaaaca cacacacaca
135721 cacacacaca catttatcca acatcacgac tttcctttca ccgactttca actggggaaa
135781 acaaaacaaa acatgcgttg tttctttact aaaggcatcc tcaccagagt caatgagaat
135841 tttcttaagg aaataatggt gcacctgtgt tttctcctta tctacactcc aggccactgg
135901 tttgtcacta atttcccatt tgttttttct ctttgggtaa aattggccta ctctggaatt
135961 accattattg cttccttggc tgtaaagagt atagaaattc taccctgtg agtgtgtgtc
136021 ctagatctgc agctgctctt tttgggggtg ctaatggact gtaaatttca gacacagcag
136081 gacggttcat ggtgctctct gggtatgtat aacattctga caccccagct ccttccagag
136141 actaaacagg ctcagagctc tgcagaatca ccttggagga gattctggaa cacccacgtg
136201 catttctgag gtaggagtta gaagaaggtt atgcattgtt cttggtccag tacgtttcca
136261 ccatggcaca gctaccacat atcgggagct cacatggtgt gggaggaata ctagtcacac
136321 ttcacagcta gttagagccc tgccacttg gtctggctct aacaagctgt accatttgtt
136381 cttttctttt ccttttttg agaaggagtc tcattctgtt gcctaggccg gagtgcagtg
136441 acatgatctt ggctcactgc aatctccacc tccaggttca agtgattctc tgcctcagc
136501 ttcccaagta gctgggatta taggtgccca ccaccacact cagctaacct cagtcctgcc
136561 ttcaggcgat ccgcccaact cggcctccca aagtgctggg attacaggct tcagccacca
136621 tgaccggcca catttgttc ttaaccatcc cacattgcct aagttcatct gtctttagaa
136681 gaatgtgttt agattaaata atttcagatt tctacctaaa gttacaaatt cagtgattac
136741 caccctgagg aagtaatgat agcaatcaca aatacagtgc ccaccatgta cccggtcctg
```

Figure 2

```
136801 gcttaaggac gtgttcactc atttaattct cacaaaaatt ctatatgtac aattatctct
136861 gttctatgga tggggaaact gaggcagagg gggctaaaga actttcgcat aatcaaacag
136921 ctactaagaa acagggctgg aatttgaact caagcagcca ggctccagga cctccgctct
136981 taccttctat gttatttcct cttagagtga aaacaggtta cttgtagttt caattaacac
137041 atgaaaatgt ccttccttat taggctatga agtaggaagg aaattgcctc tttggctgtt
137101 cacatttccc ctccttgctc caatgctgtt cagataatta gagggttata agccaacctg
137161 ccaatttgtc aatgctggga agacttttat atgctgagct cccatccatc atataggact
137221 tctgtgatta aagaccgaag cacatggttg gacaaaataa gtaccagaac aggcagtgcc
137281 cacaggtgtg caatggaaaa attaggcaaa gatttataca gttctacaca aaaacacgta
137341 tctcaatagt cactacagag ttagcatact ccacacgctt gtcaaataaa aagaaaaaa
137401 actccaatat ggtgacaccc tgtctctact aaaaatacaa aaattagcca ggtgtagtgg
137461 cttgtgcctg taatcccagc tacttgggag gctgaggcag gagaaccact tgaacccggg
137521 aggcggaggt tgcagtgagc cgagatcgcg caactgcatt ccagcctagg cgacagagcg
137581 agactctgtc tcaaaaaaga aaagaaaga aaaaaaaaaa ggaaaaacta tatataaaaa
137641 aactccatat atttctcaac tataaaaaag taaaacttca gttcaacagt tctcaaaata
137701 tttctaatta tttattcttt ctactgtttt ggaattcctt tcctcataga ttttattttt
137761 gaaggttttt ggtcttttcaa gaaggtcacg attaatgttt tccccattat actaatcaaa
137821 gtcctatata actgccagtg agaaattctg agtaataaga gataaccaga gacactacac
137881 ccatataatt cagccaaaca gctagaaatt caagattttc attagccatg aaaagttatt
137941 tgagtagatg cgtagcttgc accatgattt gttaggttct ttttcattta tttgcttttt
138001 ctgttgtgtt tgaggaatag tgagtaccaa ccacttactg agcagcagaa atatggcttg
138061 gcagcttgcg tcctctctct ctaatgctct caactgcatc accttacagc cattatgctc
138121 atttcactga taagaaaacc agatctcgag gttaaaaaat atgcccaatt aaccactgag
138181 tgagtcccag agttcacatg attccaggac tgtctgactt aagacctgct gccttatcca
138241 tcctaccagg ggctctcctt atgggagcct ttatcacggg ccaggcatca ggaccttgga
138301 aaatcctctt ttcataattc taatatgcag ccagggtgga ggccagcaag tgactgaaat
138361 agtgcctgaa ctccagctgt gctccacaca agccgtaagg aaacatctca gagctcacta
138421 cacacgggtg gaacacacgc cacctggaag gtgttcttat catgggaccc atttatttcc
138481 caaggaaacg aaagggggtgt accaagattt atgtgcaagg atgttcattc acgatagtgt
138541 tatttcaaac agccccaaat taacccaggt gaacaatcag aaattcataa atagacaaat
138601 acgcatcttc caaaagtat agattcttta acccatttcc catttagaaa aaagtgcagc
138661 tcgctgtttt tacataaaca cactcttttg aggctgaagc aaatatgact gattttcaac
138721 gtgaatataa aatgtcaaat ctgttcctgg gctgggtgca gtggctcacg cctgtaatac
138781 tagcatttg ggaggctgag gcgggtggac tgcctgagct caggagttcg agaccagcct
138841 gggcaacacg gtgaaacccc gtctctatta aaatacaaaa aattagccgg gagtggcagc
138901 gtgcacctgt agtcccagct actcaggagg ctgagtcagg accatcactt gaacccggag
138961 gcggaacgga ggttgcagtg agctgagatc acgccactgc actccagcct gggcgacaca
139021 gtgagactct ctctctctta aaacaaaac aaaacaaaaa ctgttcttgg agttatttct
139081 aaacagaact tctctctaat cctaatgtaa catcatgtac atttctgttg cattaggatt
139141 agaaatgagt attcttgggg caaaaggaa atgggttaaa aactggaaaa taaatagata
139201 tggagttgaa aaataatatt catagcataa atcctattgt gagataaata catttgaaca
139261 cttacatggt tcgaaaacac tccattttt atttagttaa atatggatgt acatatataa
139321 gtatccatgt acatgtatat atgttctcat ttccccttt tacacaggga gtatatagca
139381 tatattaatc tgcacatctc tttccattta taaatcttaa agctcttttt atgtttatat
139441 acagggcac ttcactacag gtatttttt tttcttttt ttgttttga gacagagtct
139501 tgctctgtgg cccaggctgg agtgcagtgg ctgatctcgg ctcactgcaa cctctgcctc
139561 ctggttcaa acgattctcc tgcctcagct cccgagtag ctgggattac aggctcccac
139621 caccatgccc aactaatttt tgtgttttta gtagagacag ggtttcacca ggttggccag
139681 gctggtcccg aacttctgac ctcaagtgat tcgcccacct cagcctccca aagtgctggg
139741 attacaagtg tgagccactg tgcccagcta aatacagata ttttcactg gtgaacatac
139801 tttcaatcgg tgccttggtt tagtaccagt cttttgctat tataaaaaat gctgaaatga
139861 atgatagtgt tttatgtcat ttgaacatat gcactggtaa ttttgatggg tactgccaaa
139921 ctgccctcca tagaaatggc cctaacccct tctcccacaa tgtgtgtgag tgctgacagc
139981 ctactgctta atgttgggtt ttgctaattt gacaggtaaa aatagtactg cattgtggtt
140041 ttaatttgct ttttttctta ctgtgagtga agataaacat ctttttatgt ttaaggtcta
140101 ttttatatta ttctgtgcca tatttgttca tgtcctttgg ccattttttc tactgagtaa
140161 taacacaaat aggcatgcca ttcatttata tgtgtgtctg tgtatttctg cagacaaaga
```

Figure 2

```
140221 taaaacaatg ttcattgttg gtatgtgggt gaaaaaataa gtgattgtgt gttttctgtt
140281 ttctccggtg aatcctttta aagtaaacat ttttatatat tagaattaaa acaatgtgtt
140341 actgaacatt gggaaggttt tctggtttgc ctacaatcag cttgtttctg tgaaacatgt
140401 tcttttggaa accaagtaga gaatcctact tgtaaacaaa gcaagaccaa ccagacttaa
140461 gaaagatcaa atttaattta gatctactcc ttgattctca tgaattgatt gaatctcttt
140521 agggcaaata cctggcctct atagagaaat ctggaatgat ttctgcactg ggagaggaaa
140581 ctttcagatc actaagggct ttgtggggct gatatcacca gccgaggtac tgggcaatgt
140641 ctcctgtggt ttcacacttc ttagcgattt ccttccccaa cgcaagctgg gctgccccga
140701 acttcagcaa tgtagagaga gaatgcag  (SEQ ID NO: 1)
```

METHODS FOR DETECTING TCR-GAMMA GENE REARRANGEMENT

CROSS-REFERENCE TO RELATED APPLICATIONS

This application claims the benefit of U.S. Provisional Applications 61/140,029, filed Dec. 22, 2008 which is hereby incorporated by reference in its entirety.

FIELD OF THE INVENTION

This invention relates to the field of cancer diagnosis. In particular, the invention relates to the determination of clonality of T-cell, diagnosis and prognosis of patients having lymphoproliferative disease associated with T-cell receptor gamma (TCR-γ) gene rearrangement.

BACKGROUND OF THE INVENTION

The following discussion of the background of the invention is merely provided to aid the reader in understanding the invention and is not admitted to describe or constitute prior art to the invention.

T cell receptors recognize foreign antigens which have been processed as small peptides and bound to major histocompatibility complex (MHC) molecules at the surface of antigen presenting cells (APC). Each T cell receptor is a dimer consisting of one alpha and one beta chain or one delta and one gamma chain. The human T-cell receptor gamma (TCR-γ) locus is located on chromosome 7 (7p14) and includes V (variable), J (joining), and C (constant) segments (Lefranc et al. Curr. Top. Microbiol. Immunol. 1991; 173: 3-9).

To date 14 V gene (V γ) segments (TRGV1, TRGV2, TRGV3, TRGV4, TRGV5, TRGV5P, TRGV6, TRGV7, TRGV8, TRGVA, TRGV9, TRGV10, TRGVB, TRGV11), including 6 pseudogenes have been identified upstream to five J gene (J γ) segments (TRGJP1, TRGJP, TRGJ1, TRGJP2, and TRGJ2), and two C gene (C γ) segments (TRGC1 and TRGC2) in the TCR-γ locus (Lefranc et al. Nature. 1985; 316: 464-466; Lefranc et al. Cell. 1986; 45: 237-246; Quertermous et al. Science. 1986; 231: 252-255; Forster et al. EMBO J. 1987; 6: 1945-1950; Huck et al. EMBO J. 1988; 7(3): 719-726). Several V segments of the gamma locus are known to be incapable of encoding a protein and are considered pseudogenes.

Rearrangement of TCR-γ genes is an important part of thymocyte development. During T cell development, the gamma chain is synthesized by a recombination event at the DNA level joining a V segment with a J segment; the C segment is later joined by splicing at the RNA level. Recombination of many different V segments with several J segments provides a wide range of antigen recognition. The status of TCR-γ gene rearrangements helps define developmental stages. Analysis of TCR-γ gene rearrangement can be used to detect clonality in a T-cell population (Signoretti et al. Am. J. Pathol. 1999; 154: 67-75; Chain et al. J. Immunol. Methods. 2005; 300(1-2): 12-23).

Clonality is not synonymous with malignancy because it can be detected in non-neoplastic lymphocytic infiltrates (Wood et al. J Invest Dermatol. 1994; 103: 34-41). Nevertheless, it is generally accepted that most neoplasms are clonal in origin. Thus, detection of clonal cells with identical rearrangement favors a diagnosis of malignancy. Peripheral T-cell lymphomas arise from T cells that undergo malignant transformation after most rearrangements of TCR loci are completed. T-cell clonality estimation is important for the differential diagnosis between malignant and nonmalignant T-cell proliferation (Diss et al. J Clin Pathol. 1995; 48: 1045-1050; Signoretti et al. Am. J. Pathol. 1999; 154: 67-75; Gra et al. J. Mol. Diagn. 2007; 9: 249-257).

SUMMARY OF THE INVENTION

This invention relates to detection of TCR-γ nucleic acid in acellular body fluid. The invention is useful for detecting TCR-γ gene rearrangements in such fluid and for diagnosis relating to lymphoproliferative disorder.

In one aspect, the invention provides a method for diagnosing an individual as having a lymphoproliferative disorder, the method comprising: a) providing an acellular bodily fluid sample from the individual, wherein the sample comprises TCR-γ nucleic acid; b) determining the relative abundance of a plurality of V-γ/J-γ gene rearrangements in the TCR-γ nucleic acid; and d) identifying the individual as having a lymphoproliferative disorder when the TCR-γ nucleic acid comprises at least one major arrangement.

In one aspect, the invention provides a method for identifying the rearrangement of the TCR-γ gene in an individual. The method includes a) providing an acellular bodily fluid sample of the individual comprising TCR-γ nucleic acid b) identifying the arrangement of V γ gene segments joined with J γ gene segments on a single polynucleotide. The arrangement of V γ joined with J γ gene segments on a single polynucleotide in the acellular body fluid is indicative of rearrangement of the TCR-γ gene.

In another aspect, the invention provides a method of determining the clonality of a T-cell population of an individual comprising: evaluating nucleic acid from an acellular bodily fluid sample of the individual to determine the relative abundance of a plurality of V-γ/J-γ gene rearrangements in the TCR-γ nucleic acid, and identifying the individual as having a monoclonal T-cell population when at least one major arrangement is identified. The presence of a multiple rearrangements of the V γ and J γ gene segments in TCR-γ gene is indicative of polyclonality.

In some embodiments of the above aspects of the invention, the relative abundance of a plurality of V-γ/J-γ gene rearrangements in the TCR-γ nucleic acid in the sample may be compared with the relative abundance of a plurality of V-γ/J-γ gene rearrangements of a reference TCR γ nucleic acid. In some embodiments, the reference TCR γ nucleic acid may be derived from polyclonal T-cells. In another embodiment, the reference TCR γ nucleic acid may be derived from monoclonal T-cells. In one embodiment of the above aspects of the invention, the method further includes identifying at least one major arrangement and comparing the identity of at least one major arrangement to known V-γ/J-γ gene rearrangements.

In some embodiments of the above aspects of the invention, major V-γ/J-γ gene rearrangements comprise at least 10%, at least 25%, at least 50% or at least 80% of the TCR-γ nucleic acid present in the acellular body fluid sample.

In certain embodiments of these methods, the TCR-γ gene arrangement is determined by amplifying at least a portion of the TCR-γ nucleic acid, for example, using one or more oligonucleotide primers directed to any one or more (e.g., two, three, four, five, six, or more) of the V-γ gene segments and/or any one or more (e.g., two, three, four, five, six, or more) of the J-γ gene segments. In other embodiments, the TCR-γ gene arrangement is any one or more of those identified in Table 1. Suitable amplification primers include, for example, oligonucleotide primers containing the sequence of SEQ ID No's: 2 and/or 3, or complements thereof. In some embodiments, the amplification method may also include a third and/or a fourth primer (e.g., nested PCR or semi-nested PCR). The TCR-γ gene arrangement, including the identity of the V-γ and J-γ gene segments, may be determined using any suitable method including, for example, by determining the nucleotide sequence of all or a portion (e.g., the V-γ and J-γ gene segment junction) of the TCR-γ nucleic acid, by oligonucleotide probe hybridization. In one embodiment, the identity of at least one major arrangement is determined using a nucleic acid probe specific for the junction of a portion of V-γ gene segments and a portion of J-γ gene segment. Optionally, amplified TCR-γ nucleic acid or portion thereof comprising one or more V-γ/J-γ gene rearrangements may be separated by size. The size of the amplified TCR-γ nucleic acid may be determined by various techniques known in the art such as, gel electrophoresis, chromatography (e.g., capillary electrophoresis, HPLC, size exclusion chromatography).

In some embodiments, the TCR-γ gene rearrangement may be detected by Southern blot. In another embodiment, the TCR-γ gene rearrangement may be detected by fluorescent in situ hybridization, by flow cytometry, by hybridization of a probe to genomic DNA comprising the rearrangement.

In one embodiment, the TCR-γ gene rearrangement may be detected by real time PCR using TaqMan® probes. In one embodiment, the primers used to detect the TCR-γ gene rearrangement in a real time PCR reaction may be SEQ ID NO: 2 and SEQ ID NO: 3. In other embodiments, the forward primers may be any of SEQ ID NO: 4-6, and 10-13 and reverse primers may be any of SEQ ID NO: 7-9, 14-16. In one embodiment, the TaqMan® probe used to detect the TCR-γ gene rearrangement in a real time PCR reaction may contain SEQ ID NO: 17-29.

In some embodiments, the nucleic acid of a second gene is amplified from the acellular body fluid as an internal control. The second gene is preferably one which is unrelated to TCR-γ either structurally or functionally and is not associated with a lymphoproliferative disorder.

In other embodiments, the identity of the TCR-γ gene arrangement is used to identify a specific lymphoproliferative disorder such as, for example, T-cell acute lymphoblastic leukemia, large granular lymphocytic leukemia, mycosis fungoides, peripheral T-cell lymphoma, T-lymphoblastic lymphoma, T-cell prolymphocytic leukemia, Sezary syndrome, and γδ-hepatosplenic lymphoma. In other embodiments, the lymphoproliferative disorder is diagnosed by identifying the presence of a clonal T cell population expressing any one of the TCR-γ gene arrangement identified in Table 1.

"Individual" as used herein means a human or any other animal which contains a TCR-γ nucleic acid that can be amplified using the primers and methods described herein. An individual can be a patient, which refers to a human presenting to a medical provider for diagnosis or treatment of a disease. A human includes pre and post natal forms.

"Sample" or "patient sample" as used herein includes biological samples such as tissues and body fluids. "Body fluids" may include, but are not limited to, blood, serum, plasma, saliva, cerebral spinal fluid, pleural fluid, tears, lactal duct fluid, lymph, sputum, urine, amniotic fluid, and semen. A sample may include a body fluid that is "acellular." An "acellular body fluid" includes less than about 1% (w/w) whole cellular material. Plasma or serums are examples of acellular bodily fluids. An acellular sample can be derived from a sample comprising cells by removing more than 99% (w/w) of the cells from sample. A sample may include a specimen of natural or synthetic origin.

"Plasma" as used herein refers to acellular body fluid derived from blood by removing whole cellular material from blood by methods known in the art (e.g., centrifugation, filtration, and the like).

"Serum" is an acellular body fluid obtained from clotted blood after the clotted fraction is removed.

"Nucleic acid" or "nucleic acid sequence" as used herein refers to an oligonucleotide, nucleotide or polynucleotide, and fragments or portions thereof, which may be single or double stranded, and represent the sense or antisense strand. A nucleic acid may include DNA or RNA, and may be of natural or synthetic origin and may contain deoxyribonucleotides, ribonucleotides, or nucleotide analogs in any combination.

Non-limiting examples of polynucleotides include a gene or gene fragment, genomic DNA, exons, introns, mRNA, tRNA, rRNA, ribozymes, cDNA, recombinant polynucleotides, branched polynucleotides, plasmids, vectors, isolated DNA of any sequence, isolated RNA of any sequence, synthetic nucleic acid, nucleic acid probes and primers. Polynucleotides may be natural or synthetic. Polynucleotide may comprise modified nucleotides, such as methylated nucleotides and nucleotide analogs, uracyl, other sugars and linking groups such as fluororibose and thiolate, and nucleotide branches. A nucleic acid may be modified such as by conjugation, with a labeling component. Other types of modifications included in this definition are caps, substitution of one or more of the naturally occurring nucleotides with an analog, and introduction of chemical entities for attaching the polynucleotide to other molecules such as proteins, metal ions, labeling components, other polynucleotides or a solid support. Nucleic acid may include nucleic acid that has been amplified (e.g., using polymerase chain reaction).

"Genomic nucleic acid" as used herein refers to the nucleic acid in a cell that is present in the cell chromosome(s) of an organism which contains the genes that encode the various proteins of the cells of that organism. A preferred type of genomic nucleic acid is that present in the nucleus of a eukaryotic cell. In a preferred embodiment a genomic nucleic acid is DNA. Genomic nucleic acid can be double stranded or single stranded, or partially double stranded, or partially single stranded or a hairpin molecule. Genomic nucleic acid may be intact or fragmented (e.g., digested with restriction endonucleases or by sonication or by applying shearing force by methods known in the art). In some cases, genomic nucleic acid may include sequence from all or a portion of a single gene or from multiple genes, sequence from one or more chromosomes, or sequence from all chromosomes of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA. Genomic nucleic acid representing the total nucleic acid of the genome is referred to as "total genomic nucleic acid."

Genomic nucleic acid may be obtained by methods of extraction/purification from acellular body fluids as is well known in the art. The ultimate source of genomic nucleic acid can be normal cells or may be cells that contain one or more mutations in the genomic nucleic acid, e.g., duplication, deletion, translocation, and transversion. Included in the meaning of genomic nucleic acid is genomic nucleic acid that has undergone recombination and may comprise rearranged genes. Also included in the meaning of genomic nucleic acid is genomic nucleic acid that has been subjected to an amplification step that increases the amount of the target sequence of interest sought to be detected relative to other nucleic acid sequences in the genomic nucleic acid.

"Gene" as used herein refers to a DNA sequence that comprises control and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Included in the meaning of genes that do not encode a functional protein. Such genes are often referred to as pseudogenes.

The term "reference TCR-γ nucleic acid" as used herein means TCR-γ nucleic acid where the arrangement of variable (V) and joining (J) gene segments are known or the source of TCR-γ nucleic acid is known. A reference TCR-γ nucleic acid can be derived from monoclonal T-cells. A reference TCR-γ nucleic acid can be derived from polyclonal T-cells. A reference TCR-γ nucleic acid may be a TCR-γ nucleic acid with known rearranged variable (V) and joining (J) gene segments. A reference TCR-γ nucleic acid can be TCR-γ genomic nucleic acid where variable (V) and joining (J) gene segments have not been rearranged such as the nucleic acid sequence of SEQ ID NO: 1.

The term "rearranged" or "rearrangement" as used herein in the context of TCR-γ gene means a nucleic acid sequence or an event where V and J gene segments of TCR-γ have been rearranged with respect to the reference TCR-γ nucleic acid sequence such as SEQ ID NO: 1. A V-J rearrangement may result from genetic recombination.

The term "major arrangement" as used herein in the context of the arrangement of V-γ and J-γ gene segment of TCR-γ gene means that the arrangement is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 99% or 100% of total possible arrangements of V-γ and J-γ gene segments of TCR-γ gene present in a acellular body fluid sample.

The term "relative abundance" as used herein in the context of the arrangement of V-γ and J-γ gene segment of TCR-γ gene means the proportion of an arrangement of V-γ and J-γ gene segment relative to the total arrangements of V-γ and J-γ gene segments in TCR-γgene present in a nucleic acid sample.

The term "V-γ/J-γ gene rearrangements" as used herein means the arrangements of V-γ gene segments joined with J-γ gene segments in single TCR-γ nucleic acid.

The term "clonality" or "clonal" as used herein in the context of T-cell means how the T-cells are derived from a source. For example, monoclonal T-cells were derived from one cell type having one specific arrangement of V and J gene segments. On the other hand, polyclonal T-cells were derived from more than one cell type having more than one arrangement of V and J gene segments.

"Identity" and "identical" as used herein refer to a degree of identity between sequences. There may be partial identity or complete identity. A partially identical sequence is one that is less than 100% identical to another sequence. Preferably, partially identical sequences have an overall identity of at least 70% or at least 75%, more preferably at least 80% or at least 85%, most preferably at least 90% or at least 95% or at least 99%. Sequence identity determinations may be made for sequences which are not fully aligned. In such instances, the most related segments may be aligned for optimal sequence identity by and the overall sequence identity reduced by a penalty for gaps in the alignment.

"Substantially all" as used herein means at least about 60%, 70%, 80%, 90%, or 95-100%.

"Substantially pure" as used herein means a nucleic acid, represents more than 50%, 60%, 75%, 90%, 95% or more of the nucleic acid in a sample. The nucleic acid sample may exist in solution or as a dry preparation.

"Isolated" as used herein when referring to a nucleic acid (e.g., an oligonucleotide such as RNA, DNA, or a mixed polymer) means a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised from a genome are also considered to be isolated.

"A portion of" in the context of a nucleic acid refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides, at least about 5,000 nucleotides, at least about 10,000 nucleotides, at least about 20,000 nucleotides, at least about 50,000 nucleotides, at least about 100,000 nucleotides, at least about 500,000 nucleotides, at least about 1,000,000 nucleotides or more.

"Specific hybridization" as used herein is an indication that two nucleic acid sequences hybridize to each other but not to other related sequences under chosen hybridization conditions. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

"High stringency hybridization conditions" as used herein refers to hybridization under conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C.

"Complement" as used herein refers to the complementary sequence to a nucleic acid according to standard Watson/Crick pairing rules. A complement sequence can also be a sequence of RNA complementary to the DNA sequence or its complement sequence, and can also be a cDNA. The complement of a nucleic acid sequence as used herein refers to an polynucleotide which, when aligned with the nucleic acid sequence such that the 5' end of one sequence is paired with the 3' end of the other, is in "antiparallel association". For example, for the sequence "5"-A-G-T-3'" is complementary to the sequence "3'-T-C-A-5". Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

"Substantially complementary" as used herein means that two sequences hybridize under highly stringent hybridization conditions. The skilled artisan will understand that substantially complementary sequences need not hybridize along their entire length.

"Oligonucleotide" as used herein refers to a molecule that has a sequence of nucleic acid bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group in this position. Oligonucleotides also may include derivatives, in which the hydrogen of the hydroxyl group is replaced with organic groups, e.g., an allyl group. Oligonucleotides may comprise modified nucleobases, modified sugar moieties, and modified internucleotide linkages.

Oligonucleotides can be used as primers or probes for specifically amplifying (i.e., amplifying a particular target nucleic acid sequence) or specifically detecting (i.e., detecting a particular target nucleic acid sequence) a target nucleic acid and generally are capable of specifically hybridizing to the target nucleic acid. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, reverse transcription, PCR, or a combination thereof. The oligonucleotide may be modified. For example, the oligonucleotide may be labeled with an agent that produces a detectable signal (e.g., a fluorophore).

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" may occur naturally, as in a purified restriction digest or may be produced synthetically. The term "primer" as used herein includes all forms of primers that may be synthesized including peptide nucleic acid primers, locked nucleic acid primers, phosphorothioate modified primers, labeled primers, and the like. Primers may comprise modified nucleobases, modified sugar moieties, and modified internucleotide linkages.

Primers are typically between about 10 and about 100 nucleotides in length, and preferably at least about 10, 15, 20, 25, 30, 35, 40, 50, 60, 75, 100 nucleotides or more in length. An optimal length for a particular primer application may be readily determined in the manner described in H. Erlich, PCR Technology, Principles and Application for DNA Amplification (1989).

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid.

Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be fully complementary to a target nucleic acid sequence or partially complementary. A probe may be used to detect the presence or absence of a target nucleic acid. Probes are typically at least about 10, 15, 20, 25, 30, 35, 40, 50, 60, 75, 100 nucleotides or more in length. However, longer probes are possible. Longer probes can be from few hundred bases to few million bases in length (e.g. BAC, YACs, genomic DNA fragments etc.).

The term "detectable label" as used herein refers to a molecule or a compound or a group of molecules or a group of compounds associated with a nucleic acid and is used to identify the nucleic acid.

In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluorescence, chemiluminescence, or any other appropriate means.

"Target nucleic acid" as used herein refers to a nucleic acid molecule (e.g., DNA or RNA) containing a sequence that has at least partial complementarity with a primer oligonucleotide and/or a probe oligonucleotide. A probe may specifically hybridize to a target nucleic acid.

"Detecting" as used herein in context of detecting a signal from a detectable label to indicate the presence of a nucleic acid of interest in the sample (or the presence or absence of a protein of interest in the sample) does not require the method to provide 100% sensitivity and/or 100% specificity. As is well known, "sensitivity" is the probability that a test is positive, given that the person has a genomic nucleic acid sequence, while "specificity" is the probability that a test is negative, given that the person does not have the genomic nucleic acid sequence. A sensitivity of at least 50% is preferred, although sensitivities of at least 60%, at least 70%, at least 80%, at least 90% and at least 99% are clearly more preferred. A specificity of at least 50% is preferred, although specificity of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

"About" as used herein means in quantitative terms, plus or minus 10%.

The phrase "lymphoproliferative disorders" refer to several disorders or several conditions in which lymphocytes are produced in excessive quantities. Lymphoproliferative disorders may be malignant or non-malignant. Non-limiting examples of such disorders include chronic lymphocytic leukemia, acute lymphoblastic leukemia, hairy cell leukemia, lymphomas, multiple myeloma, Wiskott-Aldrich syndrome, post-transplant lymphoproliferative disorder, Autoimmune lymphoproliferative syndrome (ALPS), lymphoid interstitial pneumonia, T-cell acute lymphoblastic leukemia (ALL), large granular lymphocytic leukemia, peripheral T-cell lymphoma, T-lymphoblastic lymphoma, T-cell prolymphocytic leukemia, γδ-hepatosplenic lymphoma, Sezary syndrome, mycosis fungoides.

"Diagnose" or "diagnosis" or "diagnosing" as used herein refer to distinguishing or identifying a disease, syndrome or condition or distinguishing or identifying a person having a particular disease, syndrome or condition. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

"Treatment," "treating," or "treat" as used herein refers to care by procedures or application that are intended to relieve illness or injury. Although it is preferred that treating a condition or disease will result in an improvement of the condition, the term treating as used herein does not indicate, imply, or require that the procedures or applications are at all successful in ameliorating symptoms associated with any particular condition. Treating a patient may result in adverse side effects or even a worsening of the condition which the treatment was intended to improve.

"Determining a prognosis" as used herein refers to the process in which the course or outcome of a condition in a patient is predicted. The term "prognosis" does not refer to the ability to predict the course or outcome of a condition with 100% accuracy. Instead, the term refers to identifying an increased or decreased probability that a certain course or outcome will occur in a patient exhibiting a given condition/marker, when compared to those individuals not exhibiting the condition. The nature of the prognosis is dependent upon the specific disease and the condition/marker being assessed. For example, a prognosis may be expressed as the amount of time a patient can be expected to survive, the likelihood that the disease goes into remission, or to the amount of time the disease can be expected to remain in remission.

BRIEF DESCRIPTION OF THE FIGURES

FIG. 1 shows a schematic representation of reference TCR-γ genomic nucleic acid. FIG. 1A shows the organization of the different gene segments in the reference TCR-γ genomic nucleic acid. Variable gene segments V1-V11, V5P, VA, VB are shown as open boxes. The variable region subgroups Vγ-I, Vγ-II, Vγ-III, and Vγ-IV are indicated. Joining gene segments JP1, JP, J1, JP2, and J2 are shown as shaded boxes. Constant gene segments C1 and C2 are shown as solid boxes. FIG. 1B shows exemplary rearrangements of TCR-γ genes. The positions of the primer that allow the amplification of the rearranged genes are indicated as arrows above the variable (V) and joining (J) gene segments. "N" represents variable diversity region at the junction of V-J segments.

FIG. 2 shows an exemplary reference TCR-γ genomic nucleic acid sequence (SEQ ID NO: 1)

DETAILED DESCRIPTION OF THE INVENTION

Figure 3A:
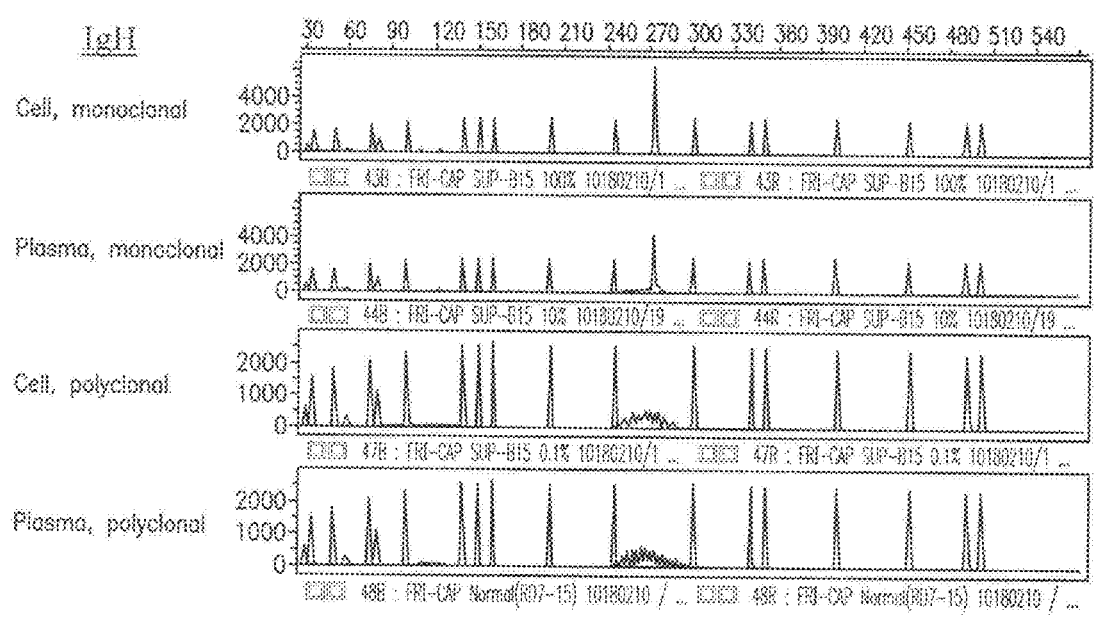
FIG. 3 shows the results of the analysis of the PCR amplified fragments of IgH (FIG. 3A) and TCR-γ gene (FIG. 3B) by capillary gel electrophoresis (CGE). Representative CGE profiles of matched peripheral blood and plasma samples are shown. The expected product sizes ranged from 220-310 bp for IgH and 140-180 bp for TCR-γ.

The present invention provides methods for detection of TCR-γ nucleic acid in acellular body fluid. Exemplary TCR-γ nucleic acid includes but is not limited to genomic DNA, mRNA, and cDNA derived from mRNA. The methods can be used to detect the rearrangement of TCR-γ genes. The status of TCR-γ gene rearrangements can help define the developmental stages and determine the clonality of T-cells. The methods of the present invention is useful in diagnosis of lymphoproliferative disorder. The methods are specially useful when it is difficult to diagnose a T-cell lymphoproliferative disorder based only on clinical, histological and immunohistochemical criteria.

TCR-γ Nucleic Acid

TCR-γ nucleic acid detected by the methods of the invention may be intact or fragmented and also may be double or single stranded. In some cases, TCR-γ nucleic acid is partially double stranded. In other cases, TCR-γ nucleic acid comprises a translated region. In yet other cases, TCR-γ nucleic acid may include an untranslated region. Non-limiting examples of untranslated region include introns and pseudogenes.

In some instances, TCR-γ nucleic acid may comprise TCR-γ reference nucleic acid, Reference TCR-γ nucleic acid may comprise variable gene V γ segments, joining gene (J γ) segments, and constant gene (C γ) segments. In some cases, the TCR-γ reference nucleic acid may be TCR-γ reference genomic nucleic acid nucleic acid such as SEQ ID NO: 1. A schematic representation of the organization of the V γ; J γ, and C γ gene segments in a reference TCR-γ genomic nucleic acid is shown in FIG. 1. In some cases, TCR-γ nucleic acid may comprise rearranged TCR-γ genes. In some cases, TCR-γ nucleic acid includes both reference TCR-γ nucleic acid and TCR-γ nucleic acid with rearranged TCR-γ genes.

Human TCR-γ locus (also known as TRG@, TRG, TCRG) is located in human chromosome 7p14. Exemplary sequences of human chromosome 7 include but are not limited to GenBank Accession numbers: NW_001839003, NT_079596, NT_079592, NW_923240, NT_007819, NT_007914. Exemplary TCR-γ genomic nucleic acid includes but is not limited to GenBank Accession numbers NG_001336. Sequence of reference TCR-γ genomic nucleic acid is shown in FIG. 2 and listed as SEQ ID NO: 1. These sequences are incorporated herein by reference.

Variable gene segments of TCR-γ locus As of date, 14 variable gene (V γ) segments in TCR-γ genomic nucleic acid are known and they include TRGV1, TRGV2, TRGV3, TRGV4, TRGV5, TRGV5P, TRGV6, TRGV7, TRGV8, TRGVA, TRGV9, TRGV10, TRGVB, TRGV11 (Forster et al. EMBO J. 1987; 6: 1945-1950; Hara et al. J. Clin. Invest. 1989; 83: 1277-1283). Of these 14 variable genes, several V segments of the gamma locus are known to be incapable of encoding a protein and are considered pseudogenes. These pseudogenes include TRGV1, TRGV5P, TRGV6, TRGV7, TRGVA, TRGV10, TRGVB.

Non-limiting exemplary sequences of variable gene (V γ) segments in TCR-γlocus are provided below. For TRGV1: nucleotides 5893-6362 of SEQ ID NO: 1, GenBank Accession numbers AH003002, M12949; for TRGV2: nucleotides 10620-11084 of SEQ ID NO: 1, GenBank Accession number M13429; for TRGV3: nucleotides 14969-15436 of SEQ ID NO: 1, GenBank Accession number M13430; for TRGV4: nucleotides 19765-120233 of SEQ ID NO: 1, GenBank Accession numbers M13584, X 13354; for TRGV5: nucleotides 24124-24593 of SEQ ID NO: 1, GenBank Accession number X13355; for TRGV5P: nucleotides 28449-28918 of SEQ ID NO: 1, GenBank Accession numbers M30893, M13431; for TRGV6: nucleotides 32777-33248 of SEQ ID NO: 1, GenBank Accession number M13432; for TRGV7: nucleotides 38434-38907 of SEQ ID NO: 1, GenBank Accession number M13433; for TRGV8: nucleotides 43127-43605 of SEQ ID NO: 1, GenBank Accession number M13434; for TRGVA: nucleotides 51085-51502 of SEQ ID NO: 1; for TRGV9: nucleotides 56456-56931 of SEQ ID NO: 1, GenBank Accession number X15274; for TRGV10: nucleotides 73668-74138 of SEQ ID NO: 1, GenBank Accession number X07206, for TRGVB: nucleotides 77715-78185 of SEQ ID NO: 1; for TRGV11: nucleotides 81870-82332 of SEQ ID NO: 1, GenBank Accession number X07207. Sequences of the V γ segments listed in the GenBank Accession numbers indicated above are incorporated herein by reference.

Based on the sequence homology the V γ segments are categorized into 4 families V γ -I (TRGV1, TRGV2, TRGV3, TRGV4, TRGV5, TRGV5P, TRGV6, TRGV7, TRGV8); V γ -II (TRGV9); V γ -III (TRGV10) and V γ -IV (TRGV11) (LeFranc et al. Cell. 1986; 45: 237-246; Huck et al. FEBS Lett. 1987; 224: 291-296; Theodorou et al. J. Pathol. 1994; 174: 233-242). Members of V γ -I family of genes have closely related sequences.

Joining gene segments of TCR-γ locus Non-limiting exemplary sequences of the joining gene (J γ) segments are provided below. For TRGJP1: nucleotides 97630-97689 of SEQ ID NO: 1, GenBank Accession number X08084; for TRGJP: nucleotides 100300-100361 of SEQ ID NO: 1, GenBank Accession number X58182, M12950; for TRGJ1: nucleotides 104408-104457 of SEQ ID NO: 1, GenBank Accession number M12960; for TRGJP2: nucleotides 117552-117611 of SEQ ID NO: 1, GenBank Accession number M16016; for TRGJ2: nucleotides 120519-120568 of SEQ ID NO: 1, GenBank Accession number M12961. Sequences of the J γ segments listed in the GenBank Accession numbers indicated above are incorporated herein by reference.

Constant gene segments of TCR-γ locus Two constant gene (C γ) segments TRGC1 and TRGC2 for TCR-γ locus are known. Non-limiting exemplary sequences of the constant gene (C γ) segments are provided below. For TRGC1: nucleotides 108270-113860 of SEQ ID NO: 1 and for TRGC2: nucleotides 120519-120568 of SEQ ID NO: 1.

Diversity regions En some embodiments, nucleic acid comprising the junction of V γ-J γ segments may further comprise a diversity region (N) with sequences of variable length and are described in for example, Huck et al. EMBO J. 1988; 7(3): 719-726. Sequences of these diversity regions (N) are incorporated herein by reference.

Rearrangement of TCR-γ Genes

Rearrangement of TCR-γ genes is an important part of thymocyte development. During T cell development, the gamma chain is synthesized by a recombination event at the DNA level joining a V segment with a J segment; the C segment is later joined by splicing at the RNA level. Recombination of many different V segments with several J segments provides a wide range of antigen recognition.

Analysis of TCR-γ gene rearrangement can be used to detect clonality in a T-cell population (Signoretti et al. Am. J. Pathol. 1999; 154: 67-75; Chain et al. J. Immunol. Methods. 2005; 300(1-2): 12-23). Clonality is not synonymous with malignancy because it can be detected in nonneoplastic lymphocytic infiltrates (Wood et al. J Invest Dermatol. 1994; 103: 34-41). Nevertheless, it is generally accepted that most neoplasms are clonal in origin. Thus, detection of clonal cells with identical rearrangement favors a diagnosis of malignancy. Peripheral T-cell lymphomas arise from T cells that undergo malignant transformation after most rearrangements of TCR loci are completed. T-cell clonality estimation is important for the differential diagnosis between malignant and nonmalignant T-cell proliferation (Diss et al. J Clin Pathol. 1995; 48: 1045-1050; Signoretti et al. Am. J. Pathol. 1999; 154: 67-75; Gra et al. J. Mol. Diagn. 2007; 9: 249-257).

Regarding the variable genes in the TCR-γ-rearranged alleles, members of the V γ -I subgroup were the most frequently used, followed by V γ -II, V γ -III, and V γ -IV. Joining segment usage was as follows: J1 or J2 are used more often than JP1 or JP2 (Theodorou et al. J. Pathol. 1994: 174: 233-242).

The analysis of TCR-γ gene rearrangement is informative about the T-cell clonality. TCR-γ gene rearrangement is often associated lymphoproliferative disorder. Thus determination of T-cell clonality by assessing the TCR-γ gene rearrangement is useful in the diagnosis of lymphoproliferative disorder. The determination of T-cell clonality by assessing the TCR-γ gene rearrangement is specially useful when diagnosis is difficult based on clinical, histological and immunohistochemical criteria.

Exemplary TCR-γ gene rearrangements associated with several lymphoproliferative disorders are listed in Table 1 below. Although the listed TCR-γ gene rearrangements are commonly associated with lymphoproliferative disorder, other TCR-γ gene rearrangements are possible. Any of such rearrangements can be detected by the methods of the present invention.

TABLE 1

Exemplary TCR-γ gene rearrangements associated with several lymphoproliferative disorders

| Diagnosis | Rearrangement |
|---|---|
| LGL | (TRGV2, TRGV9, TRGJ1/TRGJ2); (TRGV2, TRGV8, TRGJP2); (TRGV8, TRGV10, TRGJ1/TRGJ2); (TRGV3, TRGV5, TRGJ1/TRGJ2); (TRGV7, TRGV8, TRGJ1/TRGJ2); (TRGV4, TRGV8, TRGJ1/TRGJ2); (TRGV10, TRGJ1/TRGT2); (TRGV4, TRGV5, TRGJ1/TRGJ2); (TRGV9, TRGJ1/TRGJ2); (TRGV8, TRGJ1/TRGJ2); (TRGV9, TRGJ1/TRGJ2); (TRGV4, TRGV5, TRGJ1/TRGJ2); (TRGV2, TRGV10, TRGJ1/TRGJ2); (TRGV9, TRGV11, TRGJ1/TRGJ2); (TRGV4, TRGV5, TRGJ1/TRGJ2); (TRGV10, TRGJ1/TRGJ2); (TRGV2, TRGJP2); and (TRGV8, TRGJ1/TRGJ2) |
| MF | (TRGV9, TRGJP2); (TRGV10, TRGJ1/TRGJ2); (TRGV7, TRGJ1/TRGJ2); |

TABLE 1-continued

Exemplary TCR-γ gene rearrangements associated
with several lymphoproliferative disorders

| Diagnosis | Rearrangement |
|---|---|
| | and<br>(TRGV8, TRGV10, TRGJ1/TRGJ2) |
| PTCL | (TRGV2, TRGV10, TRGJP1); (TRGV7, TRGV8, TRGJ1/TRGJ2); (TRGV7, TRGV8, TRGJ1/TRGJ2); (TRGV2, TRGV3, TRGJ1/TRGJ2); (TRGV2, TRGJP1); (TRGV3, TRGV10, TRGJ1/TRGJ2); (TRGV4, TRGV9, TRGJP1); (TRGV4, TRGV5, TRGJ1/TRGJ2); (TRGV3, TRGJ1/TRGJ2); (TRGV2, TRGV10, TRGJ1/TRGJ2); (TRGV10, TRGJP);<br>and<br>(TRGV2, TRGJ1/TRGJ2) |
| TLL | (TRGV4, TRGV8, TRGJ1/TRGJ2); (TRGV3, TRGV10, TRGJ1/TRGJ2); (TRGV8, TRGV10, TRGJ1/TRGJ2);<br>and<br>(TRGV9, TRGV11, TRGJ1/TRGJ2) |
| TPLL | (TRGV2, TRGJ1/TRGJ2); (TRGV2, TRGV3, TRGJ1/TRGJ2);<br>and<br>(TRGV2, TRGV8, TRGJ1/TRGJ2) |
| SS | (TRGV4, TRGV10, TRGJP1); (TRGV5, TRGV9, TRGJ1/TRGJ2); (TRGV4, TRGV9, TRGJ1/TRGJ2); (TRGV7, TRGV10, TRGJ1/TRGJ2); (TRGV9, TRGV11, TRGJP1); (TRGV9, TRGV10, TRGJ1/TRGJ2);<br>and<br>(TRGV2, TRGV3, TRGJ1/TRGJ2) |
| HSL | (TRGV9, TRGJ1/TRGJ2) |

LGL: large granular lymphocytic leukemia, MF mycosis fungoides: PTCL: peripheral T-cell lymphoma, TLL: T-lymphoblastic lymphoma, TPLL: T-cell prolymphocytic leukemia, SS: Sezary syndrome, HSL: γδ-hepatosplenic lymphoma. Exemplary rearrangement indicated as (TRGV4, TRGV9, TRGJ1/TRGJ2) means gene segments TRGV4 (Vγ4) is joined to TRGV9 (Vγ9), and TRGV9 is joined to TRGJ1 (Jγ1) or TRGJ2 (Jγ2) by recombination resulting in a nucleic acid sequence Vγ4-Vγ9-Jγ1 or Vγ4-Vγ9-Jγ1 on a single polynucleotide.

TCR-γ mRNA Full length and partial sequences of rearranged TCR-γ mRNA sequences are known. Exemplary sequences includes GenBank accession numbers: M30892, M30891, M16804, M16768, S73842, BC030554, BC017861, BC105589, S72525, S60175, S73838, S73835, S74779, Z22689, Z22687, Z22686, Z22685, Z22683, Z22682, Z22680, Z22679, Z22678, Z22677, Z22701, Z22676, X72500, Z22690, M89834, M89856, M89830, M89854, M89841, M89828, AJ132840, AJ132839, AJ132838, AJ132837, AJ132836, AJ132835, AJ132834, AJ132833, AJ132832, AJ132831, AJ132790, AJ132789, AJ132738, AJ132787, AJ132786, AJ132785, AJ132784. AJ132783, AJ132783. Sequences of these are incorporated herein by reference.

Detection of TCR-γ gene rearrangement. The TCR-γ gene rearrangement may be detected by amplification. In one example, the amplification method is by PCR. The PCR method may include a primer pair where one primer of the primer pair hybridizes to a portion of Vγ region and the other primer of the primer pair hybridizes to a portion of Jγ region.

In one example, a consensus primer may be used for the members of the Vγ-I subgroup due to high degree of sequence homology between its member of variable gene segments. In another example, a consensus primer may be used for Jγ 1 and Jγ 2 gene segments due to high degree of sequence homology between the two joining gene segments. In one specific example, the consensus primer Vγ-I subgroup is SEQ ID NO: 2 and the consensus primer for Jγ 1/Jγ 2 subgroup is SEQ ID NO: 3. Sequences of SEQ ID NO: 2 and 3 are shown below:

5'-CAGGGTTGTGTTGGAATCAGG-3'    (SEQ ID NO: 2)

5'-TGTTCCACTGCCAAAGAGTTTCTT-3'    (SEQ ID NO: 3)

Since many TCR-γ gene rearrangements involve Vγ-I subgroup of variable genes and Jγ 1 and Jγ 2 joining gene segments, SEQ ID NO: 2 and 3 may be used as a primer pair to amplify portions of TCR-γ gene comprising Vγ-Jγ junctions in many cases.

Individual primers directed to each the variable regions subgroups Vγ-I, Vγ-II, Vγ-III, and Vγ-IV may be used along with primers directed to each of the joining gene segment subgroups Jγ 1/Jγ 2; Jγ P1/Jγ P2 and Jγ P to amplify portions of TCR-γ gene comprising the appropriate Vγ-Jγ junctions. In some cases, portions of TCR-γ rearranged gene comprising Vγ-Jγ junctions may be amplified by multiplexed PCR. Alternatively, the multiplexed PCR reaction may use nested PCR primers. Exemplary sequences of the primers that may be used in the PCR reactions including multiplexed PCR and nested multiplexed PCR are shown in Table 2 below. The primers listed below are provided as examples. Other primers may be designed to hybridize to portions of variable and joining gene segments using the sequence of TCR-γ gene locus provided in SEQ ID NO: 1 as a guide.

TABLE 2

Nucleic acid sequences of primers for PCR reaction

| Gene | Description | Sequence | SEQ ID NO |
|---|---|---|---|
| V γ1-8 | V γ1-8<br>(forward) | 5'-TCTTCCAACTTGGAAGGGAGA-3'<br>5'-GAAGGCCCCACAGCGTCTTC-3' | 4<br>10 |
| V γ9 | V γ9<br>(forward) | 5'-TCTGCAACATCTGTATATTGGTATC-3'<br>5'-AAGGAATCTGGCATTCCGTCAG-3' | 5<br>11 |
| V γ10-11 | V γ10-11<br>(forward) | 5'-CTGGTACCGGCAGAAACCAAA-3' | 6 |
| J γ1/<br>J γ2 | J γ1/J γ2<br>(reverse) | 5'-TAAACATTATTACATTATTCCAGTT-3'<br>5'-TCTTCCGATACTTACCTGTGACAAC-3' | 7<br>14 |
| J γP1/<br>J γP2 | J γP1/<br>J γP2<br>(reverse) | 5'-TCTATCAGTTTTTCATTACTGGAAT-3'<br>5'-GAAGTTACTATGAGCCTAGTCCCTT-3' | 8<br>15 |
| J γP | J γP<br>(reverse) | 5'-CTCCCATCCCTTCTTTACATTGCA-3'<br>5'-AAGCTTTGTTCCGGGACCAAATAC-3' | 9<br>16 |
| V γ10 | V γ10<br>(forward) | 5'-TGTCTCAACAAAATCCGCAGCT-3' | 12 |
| V γ11 | V γ11<br>(forward) | 5'-GGAAGACTAAGAAACTTGAGGT-3' | 13 |

Amplifying portions of TCR-γ rearranged gene comprising Vγ-Jγ junctions is possible by nested PCR or hemi-nested PCR using combinations of primers listed above. For example, SEQ ID NO:4 and SEQ ID NO: 7 may be used as outer primer pair and SEQ ID NO: 10 and SEQ ID NO: 14 may used as an inner primer pair in a nested PCR reaction to amplify portions of TCR-γ rearranged gene where any of the gene segments of V γ -I subgroup is joined to J γ 1 or J γ 2 gene segments. Similarly, SEQ ID NO: 5 and SEQ ID NO: 8 may be used as outer primer pair and SEQ ID NO: 11 and SEQ ID NO: 15 may used as an inner primer pair in a nested PCR reaction to amplify portions of TCR-γ rearranged gene where any of the gene segment of V γ 9 is joined to J γ P1 or J γ P2.

Portions of TCR-γ gene comprising the Vγ-Jγ junctions may be detected using nucleic acid probes comprising a detectable label. In some instances, the probes may used to detect the amplicons generated during amplification reactions to amplify portions of TCR-γ gene comprising the Vγ-Jγ junctions. In other instances, the probes may be used in nucleic acid arrays to detect portions of TCR-γ gene. Exemplary sequences of probes are listed in Table 3.

TABLE 3

Sequence of Probes

| Gene | Probe sequence | SEQ ID NO: |
|---|---|---|
| V γ2 | 5'-CAACACAACCTTGGAGTTGTA-3' | 17 |
| V γ3 | 5'-ACATCCCTTGCGGTGGAGA-3' | 18 |
| V γ4 | 5'-ACAACGCTGGAGGTGTA-3' | 19 |
| V γ5 | 5'-ACACATCCTTTGAGTTGGAGA-3' | 20 |
| V γ7 | 5'-ACCCTGGAGTAGTAGGGGT-3' | 21 |
| V γ8 | 5'-AACACAACCCTGGAGTTGTA-3' | 22 |
| V γ9 | 5'-GTCCTGTTTCTCTACATTGTG | 23 |
| V γ10 | 5'-CTTGATGGTAAGGATTGAAGT-3' | 24 |
| V γ11 | 5'-GAAGTGGAAGTGTGAGCATTT-3' | 25 |
| J γ1/J γ2 | 5'-GTTGTTCCACTGCCAAAGAGTT-3' | 26 |
| J γP | 5'-GCAAATATCTTGAACCAACCAGT-3' | 27 |
| J γP1 | 5'-CTTGATTTTTTTGCCCAACTCTTG-3' | 28 |
| J γP2 | 5'-TGCAAACGTCTTGATCCAATCAC-3' | 29 |

In one embodiment, the amplification reaction may include an internal control such as, for example, wild-type K-ras nucleic acid sequence. Full length and partial genomic sequences of human K-ras gene have been reported. Exemplary sequences include but are not limited to NCBI GenBank accession numbers: EU332849, EF685662, EF685661, EF471957, EF471953, CH471094, AC022509, NT_009714, NW_925328, NW_001838052, and NG_007524. These sequences are incorporated herein by reference. Exemplary sequence of human K-ras genomic DNA sequence is described by GenBank accession number NG_007524. Portion of human K-ras gene may be amplified using the primers SEQ ID NO: 33 and SEQ ID NO: 34. The oligonucleotide probe to detect a portion of human K-ras gene may be SEQ ID NO: 31. In another example, the oligonucleotide probe to detect a portion of human K-ras gene may be SEQ ID NO; 32.

Detection of TCR-γ gene rearrangement in an acellular body fluid can be used for the diagnosis of lymphoproliferative disorder particularly when it is difficult to diagnose a lymphoproliferative disorder based only on clinical, histological and immunohistochemical criteria. Exemplary lymphoproliferative disorder includes but not limited to T-cell acute lymphoblastic leukemia (ALL), large granular lymphocytic leukemia, peripheral T-cell lymphoma, T-lymphoblastic lymphoma, T-cell prolymphocytic leukemia, γδ-hepatosplenic lymphoma, Sezary syndrome, mycosis fungoides (Gra et al. J Mol. Diagn. 2007; 9: 249-257).

Sample

Sample may be of human or non-human origin. Sample may be obtained from an individual who is suspected of having a disease, or a genetic abnormality. In other cases, sample may be obtained from a healthy individual who is assumed of having no disease, or a genetic abnormality. In some examples, the sample may be obtained from an individual suspected of having lymphoproliferative disorder. In one example, the sample may be obtained from an individual suspected of having T-cell acute lymphoblastic leukemia (T-ALL). In some embodiments, the sample may be obtained from an individual diagnosed with lymphoma. In other embodiments, the sample may be obtained from an individual diagnosed with precursor B-leukemia.

An individual's plasma or serum may be used efficiently to detect TCR-γ nucleic acid and rearrangement of TCR-γ genes by the methods of the present invention. Detection of the rearrangement of TCR-γ genes in plasma of an individual has been found be at least as sensitive if not more so than detecting the same translocation from paired peripheral blood cells of the same individual.

Plasma or Serum Preparation Methods

Methods of plasma and serum preparation are well known in the art. Either "fresh" blood plasma or serum, or frozen (stored) and subsequently thawed plasma or serum may be used. Frozen (stored) plasma or serum should optimally be maintained at storage conditions of −20 to −70 degrees centigrade until thawed and used. "Fresh" plasma or serum should be refrigerated or maintained on ice until used, with nucleic acid (e.g., RNA, DNA or total nucleic acid) extraction being performed as soon as possible. Exemplary methods are described below.

Blood can be drawn by standard methods into a collection tube, preferably siliconized glass, either without anticoagulant for preparation of serum, or with EDTA, sodium citrate, heparin, or similar anticoagulants for preparation of plasma. Blood may be collected using commercially available kits and tubes such as BD Vacutainer® Push Button Blood Collection Set (BD, NJ, USA). Since heparin may interfere with RT-PCR, EDTA is the preferred anticoagulant for blood specimens in which PCR amplification is planned.

Nucleic Acid Extraction and Amplification

The nucleic acid (DNA or RNA) may be isolated from the sample according to any methods well known to those of skill in the art. If necessary the sample may be collected or concentrated by centrifugation and the like. In some embodiments, nucleic acid may be intact. Nucleic acid may be fragmented (e.g., digested with restriction endonucleases, or by sonication or by applying shearing force by methods known in the art).

Various methods of extraction are suitable for isolating the DNA or RNA. Suitable methods include phenol and chloroform extraction. See, Maniatis et al., Molecular Cloning, A Laboratory Manual, 2d, Cold Spring Harbor Laboratory Press, page 16.54 (1989). Numerous commercial kits also yield suitable DNA and RNA including, but not limited to, QIAamp™ mini blood kit, Agencourt Genfind™, Roche Cobas® Roche MagNA Pure® or phenol:chloroform extraction using Eppendorf Phase Lock Gels®, and the NucliSens extraction kit (Biomerieux, Marcy l'Etoile, France), Wizard Genomic DNA Kit (Cat.# A1620, Promega Corp. Madison, Wis.), Wizard SV Genomic DNA Kit (Cat.# A2360, Promega Corp. Madison, Wis.), the SV Total RNA Kit (Cat.# X3100, Promega Corp. Madison, Wis.), PolyATract System (Cat.# Z5420, Promega Corp. Madison, Wis.), or the PurYield RNA System (Cat.# Z3740, Promega Corp. Madison, Wis.). In other methods, mRNA may be extracted from patient blood/bone marrow samples using MagNA Pure LC mRNA HS kit and MagNA Pure LC Instrument (Roche Diagnostics Corporation, Roche Applied Science, Indianapolis, Ind.).

Extraction of DNA from acellular body fluids. DNA may be extracted from acellular body fluids, such as serum and plasma, using any appropriate method. Many suitable methods are known in the art including, for. In one such example, using the Qiamp Blood Kit (Qiagen, Hilden, Germany) according to the manufacturer's protocol for blood and body fluids, with the following modifications. First, heat about 7.5 to 12 ml of plasma at 99° C. for 5 min on a heat block. Centrifuge the heated sample at 14,000 rpm for 30 min and collect the clear supernatant (about 1 ml). Incubate the collected supernatant with Proteinase K (20 mg/ml; Boehringer Mannheim, Mannheim, Germany) and buffer AL (Qiagen) at a 1:10 ratio overnight at 55° C. Finally, use a single column repeatedly to process a single sample, and quantify the purified DNA spectrophotometrically. Total DNA from plasma may be isolated using BioRobot® EZ1 automated nucleic acid purification workstation (QiaGen, CA, USA).

Extraction of RNA from acellular body fluids. RNA may be extracted from plasma or serum using silica particles, glass beads, or diatoms, as in the method or adaptations of Boom et al. J. Clin. Micro. 1990; 28: 495-503 and Cheung et al. J. Clin Micro. 1994; 32: 2593-2597. As an alternative method, RNA may be extracted from plasma or serum using the Acid Guanidinium Thiocyanate-Phenol-chloroform extraction method described by Chomczynski, P. and Sacchi, N., Anal. Biochem. 1987; 162: 156-159. Trace amounts of contaminating DNA may be removed from RNA prior to proceeding to further RNA analysis. This may be accomplished using DNase, for example by the method as described by Rashtchian, A. PCR Methods Applic. 1994; 4: S83-S91. These methods are incorporated herein by reference.

Detection of Target Nucleic Acid

Detection of nucleic acid by size. Methods for detecting the presence or amount of polynucleotides are well known in the art and any of them can be used in the methods described herein so long as they are capable of separating individual polynucleotides by the difference in size of the nucleic acid. The separation technique used should permit resolution of nucleic acid as long as they differ from one another by at least one nucleotide. The separation can be performed under denaturing or under non-denaturing or native conditions—i.e., separation can be performed on single- or double-stranded nucleic acids. Useful methods for the separation and analysis of the amplified products include, but are not limited to, electrophoresis (e.g., agarose gel electrophoresis, capillary electrophoresis (CE)), chromatography (HPLC), and mass spectrometry.

CE provides exceptional separation of the polynucleotides in the range of at least 10-1,000 base pairs with a resolution of a single base pair. CE can be performed by methods well known in the art, for example, as disclosed in U.S. Pat. Nos. 6,217,731; 6,001,230; and 5,963,456, which are incorporated herein by reference. High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3100 genetic analyzer (Applied Biosystems, Foster City, Calif.). Near the end of the CE column, in these devices the amplified DNA fragments pass a fluorescent detector which measures signals of fluorescent labels. These apparatuses provide automated high throughput for the detection of fluorescence-labeled PCR products.

HPLC may used to analyze nucleic acids such as single and double stranded DNA based on their size. Methods for separation of single and double stranded DNA by HPLC are known in the art. Nucleic acid may be purified by HPLC using either anion exchange or reverse phase columns. Typically reverse phase HPLC columns include C8, C14, C18 columns (Waters, Mass., USA, Agilent, CA, USA), or poly (styrene-divinylbenzene) columns such as PRP-1 and PRP-3 (Hamilton Company, NV, USA) may be used. When reverse phase columns are used, the nucleic acid bound to the column may be eluted with a gradient of increasing concentration of hydrophobic solvent such as acetonitrile. Several variations of mobile phases are possible to elute the bound nucleic acid from reverse phase columns such as: Buffer A) 50 mM Sodium Hydroxide pH 12.7, Buffer B) 1:1 50 mM Sodium Hydroxide: Acetonitrile (Germann et al. Anal Biochem. 1987; 156: 399); Buffer A) 10 mM Potassium Phosphate pH 7, Buffer B) 7:1:2 V:V:V Acetonitrile: Methanol: 10 mM Potassium Phosphate pH 7 (Arghavani et al. Anal Biochem. 1995; 231: 201). An exemplary method is described by Glfar et al. (Waters Application note 2007; 720002376en). The method of Glfar et al. separates 50-600 bases of double stranded DNA using a solvent system with two mobile phases. Mobile phase A comprise 0.1M triethylammonium acetate and Mobile phase B comprise 20% acetonitrile in 0.1M triethylammonium acetate. A C18 column (2.1×50 mm, 1.7 µM) column with a pore size of 300 A° was used for this purpose. The gradient used for separation is 57.5-84.5>© B in 20 minutes. The separation of DNA was monitored at 260 nm. This method is incorporated herein by reference. Other HPLC based methods for analysis of nucleic acids (both DNA and RNA) are described by Wang et al. (J Mol. Diagn. 2007; 9(4): 441-451); Chen et al. (Chem Res Toxicol. 2008); Kim et al. (RNA. 2007; 13(2): 289-294), Reddy et al. American Lab. 1995; 15: 15. All of these methods are incorporated herein by reference.

Exemplary anion exchange HPLC column for analysis of nucleic acid include PRP-X600 (Hamilton Company, NV, USA). Exemplary purification condition include Conditions: Mobile phase A) 20 mM TRIS, 1 mM EDTA pH 9.0; B) 1N Sodium Chloride in 20 mM TRIS, 1 mM EDTA; linear gradient: 60-67.5% B (0-15 min), 67.5-75% B (15-45 min) at 1.0 mL/min, Ambient. UV at 260 nm. Another exemplary purification condition include mobile phase: A) 85:15 100 mM TRIS pH 8.0:Acetonitrile; B) 85:15 100 mM TRIS pH 4.0, 2.5 M Lithium Chloride:Acetonitrile; linear gradient 0-100% B for 10 min at 2.0 mL/min; 85° C., UV at 260 nm.

Nucleic acid may be also be analyzed and detected by size using agarose gel electrophoresis. Methods of performing agarose gel electrophoresis are well known in the art. See Sambrook et al., Molecular Cloning: A Laboratory Manual (2nd Ed.) (1989), Cold Spring Harbor Press, N.Y.

DNA sequencing. Detection of nucleic acid is possible by DNA sequencing. Sequencing may be carried out by the dideoxy chain termination method of Sanger et al. (Proc. Natl. Acad. Sci. USA 1977; 74: 5463-5467) with modifications by Zimmermann et al. Nucleic Acids Res. 1990; 18: 1067. Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit"

from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373A DNA or in the presence of dye terminators CEQ™ Dye Terminator Cycle Sequencing Kit, (Beckman 608000).

Alternatively, sequencing can be performed by a method known as Pyrosequencing (Pyrosequencing, Westborough, Mass.). Detailed protocols for Pyrosequencing can be found in: Alderborn et al. Genome Res. 2000; 10: 1249-1265.

Detection of target nucleic acid by probes. Probes are capable of hybridizing to at least a portion of the target nucleic acid for example, a portion of TCR-γ nucleic acid, a portion of K-ras nucleic acid, or to any other target sequence of interest. In some cases, the probe can hybridize to a portion of Vγ region and to a portion of Jγ region.

Probes can be about 10 bases, about 20 bases, about 30 bases, about 40 bases, about 50 bases, about 60 bases, about 75 bases, about 100 bases, about 150 bases, about 200 bases. However, probes can be longer. Longer probes can be from few hundred bases to few million bases. In one embodiment, the nucleic acid probes are derived from one, several or all of the human genomic nucleic acid segments provided in a compendium of bacterial artificial chromosomes (BACs) compiled by The BAC Resource Consortium. (see McPherson et al., Nature 409:934-41, 2001).

Probes consist of a detectable label or a plurality of detectable labels. The detectable label associated with the probe can generate a detectable signal directly. Alternatively, the detectable label associated with the probe can be detected indirectly using a reagent, in which the reagent includes a detectable label, and binds to the label associated with the probe. In one example, the reagent includes a detectable label is a labeled antibody. In another example, the reagent including a detectable label is a primary antibody/secondary antibody pair, in which the detectable label may be in the primary antibody, or in the secondary antibody or in both.

Probes can be TaqMan® probes, molecular beacons, and Scorpions (e.g., Scorpion™ probes). These types of probes are based on the principle of fluorescence quenching and involve a donor fluorophore and a quenching moiety. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes. Suitable quenchers are selected based on the fluorescence spectrum of the particular fluorophore. Useful quenchers include, for example, the Black Hole™ quenchers BHQ-1, BHQ-2, and BHQ-3 (Biosearch Technologies, Inc.), and the ATTO-series of quenchers (ATTO 540Q, ATTO 580Q, and ATTO 612Q; Atto-Tec GmbH).

With Scorpion primers, sequence-specific priming and PCR product detection is achieved using a single molecule. The Scorpion primer maintains a stem-loop configuration in the unhybridized state. The fluorophore is attached to the 5' end and is quenched by a moiety coupled to the 3' end, although in suitable embodiments, this arrangement may be switched The 3' portion of the stem also contains sequence that is complementary to the extension product of the primer. This sequence is linked to the 5' end of a specific primer via a non-amplifiable monomer. After extension of the primer moiety, the specific probe sequence is able to hind to its complement within the extended amplicon thus opening up the hairpin loop. This prevents the fluorescence from being quenched and a signal is observed. A specific target is amplified by the reverse primer and the primer portion of the Scorpion primer, resulting in an extension product. A fluorescent signal is generated due to the separation of the fluorophore from the quencher resulting from the binding of the probe element of the Scorpion primer to the extension product.

TaqMan® probes (Heid, et al., Genome Res. 1996; 6: 986-994) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al. Nature Biotech. 1998; 16: 49-53. When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

Detection by Hybridization. Nucleic acid such as TCR-γ can be detected by hybridization to a nucleic probe. The methods of the present invention can incorporate all known methods and means and variations thereof for carrying out DNA hybridization, see, e.g., Sambrook, et al., 1989, Molecular Cloning: A Laboratory Manual, Second Edition, Cold Spring Harbor Press, Plainview, N.Y.

The nucleic acid of interest may form a complex on a solid support prior to being detected. The complex may comprise a capture probe anchored to a solid support, the nucleic acid of interest hybridized to the capture probe, and a detectably labeled probe hybridized to the nucleic acid of interest. In some cases, the solid support may comprise a first member of a binding pair and the capture probe may comprise a second member of the binding pair. The binding of the first member of the binding pair to the second member of the binding pair may anchor the capture probe to the solid support. Examples of solid support include but are not limited to beads, microparticles, microarray plates, microwells. Examples of binding pair include but are not limited to biotin/streptavidin, ligand-receptor, hormone-receptor, and antigen-antibody.

TCR-γ gene rearrangement can be detected by performing an array-based comparative genomic hybridization (CGH) to detect the rearrangement of the TCR-γ genes in a sample, or to diagnose a genetic abnormality in an individual. The resolution of array-based CGH is primarily dependent upon the number, size and map positions of the nucleic acid elements within the array, which are capable of spanning the entire genome. Bacterial artificial chromosomes, or BACs, which can each accommodate on average about 150 kilobases (kb) of cloned genomic DNA, may be used in the production of the array. Alternatively, smaller oligonucleotide probes capable of hybridizing to the rearranged TCR-γ genes may be utilized.

The hybridized complexes can also be detected using flow cytometry. Flow cytometry is a technique well-known in the art. Flow cytometers hydrodynamically focus a liquid suspension of particles (e.g., cells or synthetic microparticles or beads) into an essentially single-file stream of particles such that each particle can be analyzed individually. Flow cytometers are capable of measuring forward and side light scattering which correlates with the size of the particle. Thus, particles of differing sizes may be used in invention methods simultaneously to detect distinct nucleic acid segments. In addition fluorescence at one or more wavelengths can be measured simultaneously. Consequently, particles can be sorted by size and the fluorescence of one or more fluorescent labels probes can be analyzed for each particle. Exemplary flow cytometers include the Becton-Dickenson Immunocytometry Systems FACSCAN. Equivalent flow cytometers can also be used in the invention methods.

Detection is possible by Southern blotting and hybridization with a labeled probe. The techniques involved in Southern blotting are well known to those of skill in the art and may be found in many standard books on molecular protocols. See, Sambrook et al., Molecular Cloning: A Laboratory Manual (2nd Ed.) (1989), Cold Spring Harbor Press, N.Y.

Detectable Label

The term "detectable label" as used herein refers to a molecule or a compound or a group of molecules or a group of compounds associated with a probe and is used to identify the probe hybridized to a genomic nucleic acid or reference nucleic acid.

Detectable labels include but are not limited to fluorophores, isotopes (e.g. 32P, 33P, 35S, 3H, 14C, 125I, 131I), electron-dense reagents (e.g., gold, silver), nanoparticles, enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

In some embodiments, the detectable label is a fluorophore. Suitable fluorescent moieties include but are not limited to the following fluorophores working individually or in combination:
4-acetamido-4'-isothiocyanatostilbene-2,2' disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3® Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®, propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (TEXAS RED®); terbium chelate derivatives; N,N,N',N'-tetramethyl-6-carboxyrhodamine (TAMRA); tetramethyl rhodamine; tetramethyl rhodamine isothiocyanate (TRITC).

Kits

The present inventions also contemplate diagnostic systems in kit form. A diagnostic system of the present inventions may include a kit which contains, in an amount sufficient for at least one assay, any of the hybridization assay probes, amplification primers, for detecting TCR-γ nucleic acid and TCR-γ gene rearrangement in a packaging material. Typically, the kits will also include instructions recorded in a tangible form (e.g., contained on paper or an electronic medium) for using the packaged probes, primers, and/or antibodies in a detection assay for determining the presence or amount of TCR-γ nucleic acid and TCR-γ gene rearrangement in a test sample.

The various components of the diagnostic systems may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present inventions may contain a reconstitution reagent for reconstituting the lyophilized reagents of the kit. In preferred kits for amplifying target nucleic acid derived from an individual, the enzymes, nucleotide triphosphates and required cofactors for the enzymes are provided as a single lyophilized reagent that, when reconstituted, forms a proper reagent for use in the present amplification methods.

In one embodiment, the kit may comprise at least three lyophilized oligonucleotides: a primer pair to amplify a portion of TCR-γ nucleic acid and a portion of nucleic acid comprising TCR-γ gene rearrangement and a detectably labeled probe capable of hybridizing to the amplicon generated. In some preferred kits, at least two lyophilized oligonucleotides: the primer pair for amplification of at least a portion of nucleic acid comprising TCR-γ gene rearrangement may have sequences of SEQ ID NO: 2, 3, or complements and fragments thereof respectively. In some embodiments, the kit may comprise primers and probes for internal control. In one embodiment, the kit may comprise primers and probes for amplification and detection of human K-ras gene. In one embodiment, the kit may comprise oligonucleotide probes SEQ ID NO: 31 and SEQ ID NO: 32. In another embodiment, the kit may comprise primers for amplifying a portion of K-ras gene: SEQ ID NO: 33 and SEQ ID NO: 34.

Some preferred kits may further comprise to a solid support for anchoring the nucleic acid of interest on the solid support. The target nucleic acid may be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

The versatility of the invention is illustrated by the following Examples which illustrate preferred embodiments of the invention and are not limiting of the claims or specification in any way.

Example 1

Sample Collection

Blood was collected in EDTA-containing tubes (Becton Dickinson, NJ) from 215 individuals suspected with lymphoid malignancies (based on tissue biopsies and typical lymphoid infiltrate diagnosis) and 195 individuals without lymphoid malignancies. Plasma was separated from blood cells by differential centrifugation at 1000×g for 15 min. Respective blood cells were separated from RBC by differential centrifugation using Puregene® RBC lysis solution (Gentra Systems, MN, USA). The cell pellet was washed with phosphate-buffered saline. Both plasma and cell samples were cryopreserved at −80° C. for future use.

Total DNA from plasma and cell samples were isolated using BioRobot® EZ1 automated nucleic acid purification workstation (QiaGen, CA, USA).

Example 2

PCR Amplification of Isolated DNA

PCR amplification was performed in triplicate for K-ras gene, IgH gene, IgH/Bcl-1 translocation, TCR-γ, and IgH/Bcl-2 translocation using the primers listed in Table 4. PCR was performed using ABI 7900 detection system and the PCR conditions discussed below. For detection of TCR-γ gene rearrangement, PCR primers SEQ ID NO: 2 and 3 were used. In each experiment, amplification of the K-ras gene served as an internal positive control and sterile water served as negative control and used as base line.

TABLE 4

Sequences of primers and probes used in PCR analysis

| Primer | |
| --- | --- |
| Internal reference gene | |
| K-ras-F probe | 5'-FAM-ATGACTGAATATAAACTTGT-3' (SEQ ID NO: 31) |
| K-ras-R probe | 5'-FAM-TGGTAGTTGGAGCTGGTGGCGTA-TAMRA-3' (SEQ ID NO: 32) |
| K-ras-F | 5'-GCCTGCTGAAAATGACTGAAT-3' (SEQ ID NO: 33) |
| K-ras-R | 5'-GGTCCTGCACCAGTAATATGC-3' (SEQ ID NO: 34) |
| IgH chain gene | |
| J$_H$-FAM | 5'-FAM-ACCTGAGGAGACGGTGACC-3' (SEQ ID NO: 35) |
| FR2a | 5'-TGGRTCCGMCAGGCYCNGG-3' (SEQ ID NO: 36) |
| FR3a | 5'-TGTCGACACGGCYSTGTATTACTG-3' (SEQ ID NO: 37) |
| V$_H$-FR3a-FAM | 5'-FAM-ACACGGCCGTGTATTACTG-3' (SEQ ID NO: 38) |
| J$_H$-CDR3 | 5'-GTGACCAGGGTNCCTTGGCCCCAG-3' (SEQ ID NO: 39) |
| TCR-γ chain gene | |
| TceIIV-F-FAM | 5'-FAM-CAGGGTTGTGTTGGAATCAGG-3' (SEQ ID NO: 2) |
| TceIIJ-R | 5'-TGTTCCACTGCCAAAGAGTTTCTT-3' (SEQ ID NO: 3) |
| BCL-1 gene | |
| BCL-1 MTC-F | 5'-TGGATAAAGGCGAGGAGCATAA-3' (SEQ ID NO: 40) |
| BCL-1 MTC-F probe | 5'-FAM-ACTGCATATTCGGTTAGACTGTGATTAGCTTT-TAMRA-3' (SEQ ID NO: 41) |
| J$_H$-BCL-1-R | 5'-ACCTGAGGAGACGGTGACC-3' (SEQ ID NO: 42) |
| BCL-2 gene | |
| BCL-2 MBR-F | 5'-TTAGAGAGTTGCTTTACGTGGCC-3' (SEQ ID NO: 43) |
| BCL-2 MCR-F | 5'-CCTGGCTTCCTTCCCTCTGT-3' (SEQ ID NO: 44) |
| BCL-2 MBR probe | 5'-FAM-CAGGAGGGCTCTGGGTGGGTCTGT-TAMRA-3' (SEQ ID NO: 45) |
| BCL-1 MCR probe | 5'-FAM-TGTCCTTCCTTTCCACTCCTCCCCAGA-TAMRA-3' (SEQ ID NO: 46) |
| J$_H$-BCL-2-R | 5'-ACCTGAGGAGACGGTGACC-3' (SEQ ID NO: 30) |

PCR Conditions

For IgH gene: 94° C. for 8 min, 52° C. for 20 sec, and 72° C. for 5 min. Cycle repeated for 35 times. For TCR-γ gene: 94° C. for 8 min, 60° C. for 90 sec, 72° C. for 10 min. Cycle repeated for 35 times. For IgH/Bcl-1 translocation: 95° C. for 10 min (1$^{st}$ cycle); 95° C. for 15 see, 60° C. for 1 min. Cycle repeated 44 times. For IgH/Bcl-2 translocation: 95° C. for 10 min (1$^{st}$ cycle); 95° C. for 15 sec, 60° C. for 1.5 min. Cycle repeated 44 times. For K-ras, the PCR condition was same as the individual genes indicated above.

Example 3

Analysis of the PCR Amplified Fragments

PCR amplified fragments were analyzed by capillary electrophoresis using ABI PRISM® 3100 genetic analyzer (Applied Biosystems, CA, USA). The results of the separation by capillary electrophoresis of the amplified products from plasma and cell samples are shown in FIG. 3, The sizes of the products are indicated in the top of the spectrum (ranging from 30 bases to over 540 bases). The relative number/amount of each product size is indicated on the y-axis. The size of the K-ras amplified product was 108-bp.

Clonal rearrangement of the IgH gene resulted in predominant products with a size range of 220-310 by for FR2a/J$_H$ primer pair, 70-150 by for FR3/Jh primer pair and 50-140 by for FR3a/CDR3 primer pair for monoclonal population in both cell and plasma samples (FIG. 3A). For polyclonal IgH cell and plasma samples, multiple peaks were observed between the product sizes 220-310 by indicating the presence of multiple rearranged IgH genes.

Figure 3B:
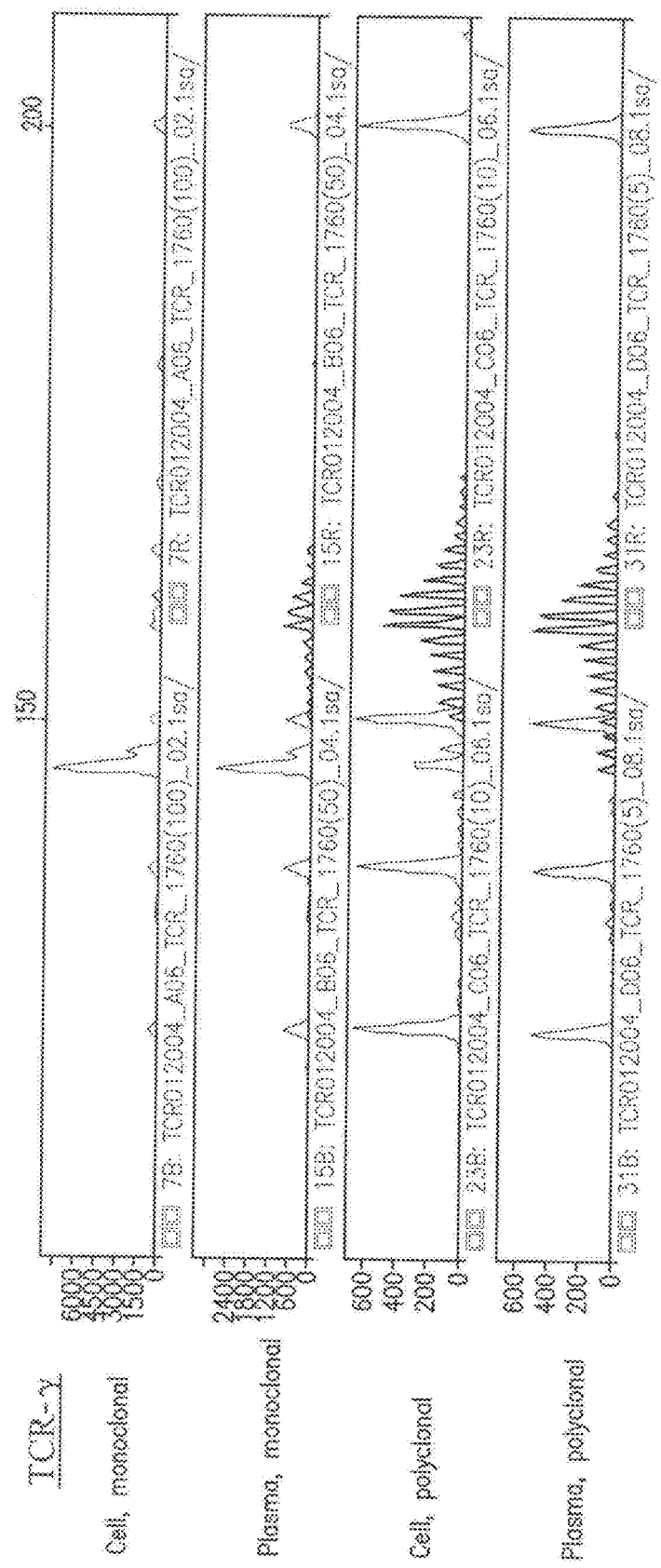

Clonal rearrangement of the TCR-γ gene resulted in predominant products with a size range of 140-180 by using primer pairs SEQ ID NO: 2 and 3 with one major peak and one minor peak were observed for monoclonal population in both cell and plasma samples (FIG. 3B). For polyclonal TCR-γ cell and plasma samples, multiple peaks were observed between the 140-180 by product sizes indicating the presence of multiple rearranged TCR-γgenes.

Example 4

Sensitivity of Detection of Nucleic Acids Comprising IgH, TCR-γ, IgH/Bcl-1 Translocation and IgH/Bcl-2 Translocation in Acellular Body Fluid To analyze the sensitivity of detection of nucleic acids in plasma, PCR amplification followed by capillary electrophoresis was performed on nucleic acids isolated from paired plasma and peripheral blood cells (PB) and tested for IgH gene rearrangement (B-cell clonality) and TCR-γ gene rearrangement (T-cell clonality), IgH/Bcl-1 translocation and IgH/Bcl-2 translocation. Clonal rearrangement of the IgH gene resulted in predominant products with a size range of 220-310 by for FR2a/J$_H$ primer pair, 70-150 hp for FR3/Jh primer pair and 50-140 by for FR3a/CDR3 primer pair. Clonal rearrangement of the TCR-γgene resulted in predominant products with a size range of 140-180 hp using primer pairs SEQ ID NO: 2 and 3 and shown in FIG. 3. Results from paired plasma and peripheral blood cells were compared. The results are shown in Table 5 below.

TABLE 5. Correlation between matched plasma and peripheral blood (PB) cell samples for 4 lymphoid malignancy-specific gene rearrangements

| PB cells | Plasma, n (%) | | Total samples | Concordance, P* |
|---|---|---|---|---|
| | Positive in Plasma | Negative in Plasma | | |
| IgH | | | | |
| Positive in PB | 17 (100) | 0 (0) | 17 | |
| Negative in PB | 0 (0) | 40 (100) | 40 | 100% |
| TCR-γ | | | | |
| Positive in PB | 17 (100) | 0 (0) | 17 | |
| Negative in PB | 0 (0) | 40 (100) | 40 | 100% |
| IgH/Bcl-1 | | | | |
| Positive in PB | 7 (100) | 0 (0) | 7 | |
| Negative in PB | 0 (0) | 30 (100) | 30 | 100% |

*All comparisons used Fisher's exact test.
The numbers of healthy subjects included as the control group in IgH, TCR-γ, BCL-1, and BCL-2 studies are 54, 35, 52 and 54, respectively.

A 100% concordance was observed for B-cell clonality between results from PB cells and plasma. 17 of 57 cases were identified as monoclonal and rest were identified as polyclonal population.

Plasma and PB cell analysis yielded 100% concordance for determination of T-cell clonality in 57 patients. 17 of the 57 patients (30%) were monoclonal population.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for diagnosing an individual as having a lymphoproliferative disorder, said method comprising:
   a) providing an acellular bodily fluid sample containing less than 1% cells from said individual, wherein said sample comprises TCR-γ nucleic acid;
   b) determining the relative abundance of a plurality of V-γ/J-γ gene rearrangements in said TCR-γ nucleic acid by HPLC or capillary electrophoresis to determine the presence or absence of at least one major arrangement; and
   c) identifying said individual as having a lymphoproliferative disorder when said TCR-γ nucleic acid comprises at least one major arrangement.

2. The method of claim 1, wherein major arrangements comprise at least 10% of said TCR-γ nucleic acid present in said acellular body fluid sample.

3. The method of claim 1, wherein major arrangements comprise at least 25% of said TCR-γ nucleic acid present in said acellular body fluid sample.

4. The method of claim 1, wherein major arrangements comprise at least 50% of said TCR-γ nucleic acid present in said acellular body fluid sample.

5. The method of claim 1, wherein major arrangements comprise at least 80% of said TCR-γ nucleic acid present in said acellular body fluid sample.

6. The method of claim 1, further comprises comparing the relative abundance of a plurality of V-γ/J-γ gene rearrangements in said TCR-γ nucleic acid in said sample with the relative abundance of a plurality of V-γ/J-γ gene rearrangements of reference TCR-γ nucleic acid.

7. The method of claim 6, wherein said reference TCR-γ nucleic acid is derived from polyclonal T-cells.

8. The method of claim 6, wherein said reference TCR-γ nucleic acid is derived from monoclonal T-cells.

9. The method of claim 1, wherein said lymphoproliferative disorder is selected from the group consisting of: T-cell acute lymphoblastic leukemia (ALL), large granular lymphocytic leukemia, peripheral T-cell lymphoma, T-lymphoblastic lymphoma, T-cell prolymphocytic leukemia, γδ-hepatosplenic lymphoma, Sezary syndrome, and mycosis fungoides.

10. The method of claim 9, wherein said lymphoproliferative disorder is T-cell acute lymphoblastic leukemia.

11. The method of claim 1, wherein said acellular body fluid is plasma or serum.

12. The method of claim 1, wherein said TCR-γ nucleic acid is genomic DNA or mRNA.

13. The method of claim 1, wherein said method comprises amplifying said TCR-γ nucleic acid using at least one primer comprising the sequence of SEQ ID NO: 2, 3, or complements thereof.

14. The method of claim 1, further comprising determining the size of nucleic acid comprising V-γ/J-γ gene rearrangements.

15. The method of claim 14, wherein said determining the size comprises HPLC.

16. The method of claim 14, wherein said determining the size comprises capillary electrophoresis.

17. The method of claim 1, further comprising identifying said at least one major arrangement and comparing the identity of said major arrangement to known V-γ/J-γ gene rearrangements.

18. The method of claim 17, wherein the identity of said at least one major arrangement is determined using a nucleic acid probe specific for the junction of a portion of V-γ gene segments and a portion of J-γ gene segment.

19. A method of determining the clonality of a T-cell population of an individual comprising:
   a) providing an acellular bodily fluid sample containing less than 1% cells from said individual, wherein said sample comprises TCR-y nucleic acid;
   b) evaluating the nucleic acid from the acellular bodily fluid sample of said individual by HPLC or capillary electrophoresis to determine the relative abundance of a plurality of V-γ/J-γ gene rearrangements in said TCR-γ nucleic acid, and
   c) identifying the individual as having a monoclonal T-cell population when at least one major arrangement is identified.

20. The method of claim 19, wherein major arrangements comprise at least 10% of said TCR-γ nucleic acid in said acellular body fluid sample.

21. The method of claim 19, wherein major arrangements comprise at least 25% of said TCR-γ nucleic acid in said acellular body fluid sample.

22. The method of claim 19, wherein major arrangements comprises at least 50% of said TCR-γ nucleic acid in said acellular body fluid sample.

23. The method of claim 19, wherein said major arrangement comprises at least 80% of said TCR-γ nucleic acid in said acellular body fluid sample.

24. The method of claim 19, wherein said acellular body fluid is plasma or serum.

25. The method of claim 19, wherein said TCR-γ nucleic acid is genomic DNA or mRNA.

26. The method of claim 19, further comprising identifying at least one major arrangement and comparing the identity of at least one major arrangement to known V-γ/J-γ gene rearrangements.

* * * * *

SEQUENCE LISTING

<160> NUMBER OF SEQ ID NOS: 46

<210> SEQ ID NO 1
<211> LENGTH: 140728
<212> TYPE: DNA
<213> ORGANISM: Homo sapiens

<400> SEQUENCE: 1

```
ttatataatt tatatatata tatatacaca cacacacgaa tataaatggc cggtagccag      60
gattttggaa tttgttagac ttcagttgaa atccaggctc cattatttat tcgtcaaatg     120
acctcgaaga gtttaacctt tttaagattc caactctctc atctgtgaaa tgtggttgat     180
tatatctcct ttggagtatt attgtaagaa ttaaactgtg gtaaagacta gcttagatat     240
catttagttt agaaatgaac aaggtggcac aaccccctggc cccaggagat gaatggtgta     300
tccagggtaa aggttataat tgccaagtac agtgactttc caaggacat acaacctcta      360
agtggcagtg cttggacttt tattctgtct tttccaaagc aatacattct tgaaactaaa     420
agttctcagg ccagactctc caaagtgtcc ctatttggca gctccatctt gagaagtaac     480
ctctcccttc cgcacactct tcgtgggatt gcattgttgg ctgctcatcc tgggctgagg     540
cccatgaccg gaccattccc agggcaccag gcagccacag ggcctgtaag aagagcaggc     600
aggaagtgaa gctttggctg aggtttctgg gacacactta acttccctgg aaacgatgcc     660
tgacaccgcc tggccacagc actggcagga gatgctgctg tcttctggga acatgcagcg     720
gccagtgagc agcacaggac acaggaacgt aaactgggga cccttcatcc atccactctg     780
gcttcgtatc ttctccattg tccactccta ttttagcccg ggatgatcag tgatgatgtg     840
catgagttac tcattcccat ctatgcccca gcccagactg agcatataca aaccctgttc     900
tttgcagaat ttttcatttt tccttttaat tttctatgga aagaatatat gttatataat     960
tcagccttat tgacaccctt ataatagcct tctaaactac acacctgatc atttatccca    1020
tccaaatata catatatttg atacagggtc tcactctgtt gcccaggctg gagtgcggtg    1080
gcacgatcac agctcactac agacttgacc tcccagactc aagggatcct cccacctcag    1140
cctcccaagt agttgggact acaggcgtgt gccatcacgt gcagctaaat ttttgtattt    1200
tttgtggaga ctgggtttca ccatgttgct caggctggtc tggaactcct gggcttaact    1260
gatctgcctg cctcggcctc ccacagtgcc gggattacag gcatgagcca ccgtgcccag    1320
cctcattgat acacattaaa tgcctactac gttccaggcc ttgtgctgtg tgctcttgat    1380
actgaggtgt gtgccccctt aagctcattg aaaacactat tgacctgcgt cactgcggtc    1440
acaaagtgat acagagagcc cagacaacca tttagaggtg aggaaattct aataattcat    1500
ggtaagcaga ttgtttccca tagtgttgct agggaacatc tcacagcaga ctgaaataga    1560
aatacaagca attgtctgcg cactagaact ttctccccaa ggcagtgcta ttttttttaaa   1620
caattcttct atcatcatca tcataatgct gacctcttga tatgtaaagg tacaattacg    1680
aggagaagca gaagaacatt tacatctgtg agtttgcacc tctctcccac catagtgagc    1740
agatcacacc ctcaggaccc cagaagactg gcaaggagga cttgatagag acaaaaggag    1800
agacacaaga ggggacagag tgttcatatg aagaggggaga gggcatgata tagagacagt    1860
gacggcaaca gaaagtagaa agttgaagag ggacagagag cagagtggaa gtgagaagga    1920
aagaaaatga ctaggacagt ggccatacaa gcaaaaagag caagagacag agacacgtgg    1980
agaggtatag ttctctatca tggcgggga gagagagaga aaacagagaa agaaatacaa     2040
```

-continued

```
aacacagaga gagggtgaga gacaaaggga cagagagaca gcgagagagg gagggaagat    2100
ggagagagag aaaacaacag agaagagaga gaaactgtga tataaatata gcgacaggga    2160
cagggacagt gatggagaga gacagagaaa tagggaaaga tacaagaaga gagaactgga    2220
gttaggggga gagataggga gagagagaga acgatagacc tgtggagaca gaagcataca    2280
cgtggacaca cagagtgcgg cagtgttagg aagatagaga taaatataca gaaataatgg    2340
taaatattga gatagaaaaa tatatataaa gagaaaaaac aaagaaatat gcatatttat    2400
atattgtaaa aatatacata aatgtattta tacatgtata atatgttata tataaaatat    2460
tatatatatt tctatacaaa aaattagccg ggtgtggtgg cgggcacctg taatccctgc    2520
tactcgggag gctgaggtag gagaatggca tgaaccaggg aggtggagct tgcagtgagc    2580
caagatcgcg tcactgcact ccagcctggg cgacagagcg agattccgtc tcaaaaaaaa    2640
aaaattatat gtatttctag cttteetttt ctcttcatat attctatctg tctgtctgtc    2700
tatccatact attgccacaa taacgccatg tagcaaatat cccaaactca gtggcttagc    2760
acaataatca tctacaaatt cttacaaatg cgtaggtttg ctagactgtt ctgctgatct    2820
aaaccaagct catctgatct tggctgggct tggccacatg tcaggcagct gctgggttag    2880
ctgggagggg gactgcctgg tcaaagtgcc tgggtctgaa taaatcagct ccactacaca    2940
cagggtttca tcctccaaca ggctagcctg gatttgttct aatgacaatg acagaaagca    3000
aagagctagc agaagcacat caggccactt gaagcctcaa ttcagaactg gagccctatg    3060
agttcttctt gtatttaaaa aaaaaaaaag gcgggggggca taaacggcgc ctcttaatcg    3120
aaggagcttt gacttatcaa gaatgagttc cacttctgga aaatttgcag tgagcccaca    3180
ctgccttgtc tggctcacaa atgcaactat gaaccctgaa tctgaggact ttgaaaaata    3240
aatgatagca agtcaactgg agaaggaaat cggaaagtga agcactatga attcccagta    3300
agtttcttat ttatttttcc tcaattatcc cctggcctgt actcagataa tcagagtata    3360
tgtacaaaga taatctgaaa tgcagaactg tacaccaggt gaggacagag agaaagggggg   3420 actctctgtg gtcagagagc cctggttttc tgttttttgt ccttttccat tctctcgcag    3480
cccccaggca atctgagtgg cagtggcagc agctatggtg agccaggagc ctaaagctct    3540
taggaaaggg atccttctct ctgaccaggg aagctgtggc cctgagagag aatcctggtg    3600 gttttttgttc tctatcctct caccacttgg ccctggaggg agacacaatg gtgggaaatg    3660
cagtgtgcta aagccacacc tgtctggcca gacgactgga ggggcatttc ctgtgaacta    3720
gaaagtattg cagagcttgc agagagaaag aagattaagc aagaaacatc atgcaatgat    3780
gtctggactc ctgggctcac ccactagctg tgcatgcata aacgtgaccc taaacagctc    3840
caaagccaaa ggccttgcaa accgaagcag gagtaggcac tgcccaggtc ctagaatggc    3900
cactgggtgg cgcacacaca ggacaggtct gacaagacaa gtactgcaaa ggctggaaaa    3960
cggaactgac tggaactgcc caccaaacac cagtaggaag ttgtaatccc taactgcgtc    4020
agttgcctgc taacaaaaaa accccctcca cattctgtgt aatatttaaa caatgcccag    4080
agctctataa catgatattc aaagtgtaca ggatttaatc cgaaattact ccgcatgtgg    4140
aggacgagga aaatcttagc atctccaaac ggaaaagcca acaacagat gctaatcctg     4200 acacgacaca ggtgttggaa taacaaagac tttaaaggag ctatagtgac cacaggaaga    4260
aatggaaaga gaggaggaga aaggaggta gaaagtaaat agataggaga gatacaaata     4320
gagaaataga aaagagatg aatagagata ggcagataga gagacagaaa cataaagata     4380
tgaacagagt aagaaacagg agcactaaag caaaatagag gagactgaga gctgtaagag    4440
```

```
ggagctatag aaggaaaaat gtaaagggag gaacaaaaac gggacagaga aaaaagaaat    4500
atggacataa agacggagat ggaaggacat agtgatagaa agcaatgcag gagatagaga    4560
aatagaatag tagagagaga aatagagcca gggcacgtga aagctataaa gcaattcatg    4620
gtagttgtct aaattcaaca tatcattacg gttgcataat gctaatattc tcattttaac    4680
atttctccta aatttattgg ttgtaatact tccacaaaag aactttcatt cggccaggca    4740
cagtggctca cacctgtaat cccagcacat tgggaggccg aggtgggtgg atcacttgag    4800
gtcaggagtt caagaccagc ctggcccaca tggtgaaacc ccatctctat gaaaaatata    4860
aaaattagct aggtgtggtg gcgcgtgcct gtaatcccag ctacttggga ggctgaggca    4920
ggagaattgc ttgaaccccg gaggtggaga ttgcagtgag ctgagattgt gccactgcac    4980
tccagtctga gacacagagc gagactctat ctatctaaag aaaaaaaaaa agaactttca    5040
ttcttaagct ctgtggtatt ctaaaatgtt tgtacagaaa tggcaaggta aatgcttgat    5100
tattttcttt tctgttttca gaatgagatg gtgtcttagc aacctccaga ggagacttta    5160
ttttgctata ttatgttttt caagaatttg tgtaggtgtt attcttttgg tgcttaaaat    5220
gtcctaccga tggttagtga gagccactgc cgttgttttt atttgagtag agtccaaggc    5280
aaaccaacat gcctgaccct cagtcctgtt aataaagcag gctcaagcct tctcagaatg    5340
gccctgggtg gacttgcaaa tgtggacttg caaatgtgaa aaggaaggtg gttcagggcc    5400
ctaatcagaa gcttcctggc aggaccaggt tctggcagct gcgttggctg ctgaaactct    5460
gaagtgcagg atgtgagcct gctgtgggac tgccctctcc caagggccat gaccagctag    5520
cgccagggtc agcttccccc acatctgcac tccctctgct gtgggcctga gcaatccatg    5580
cccctggctc tctcctgaag agggcctgct ctcagctgcc acaagagggc gatggagaac    5640
gggcctgagc agagaggcag gagctcctct gcaggtcctc ccaggaacca ccgcttctgg    5700
gaggaaggct tgggagtccc ctaagacaca tcctcagtca cttctccctg cctgtgactc    5760
aggaagacca gctcctctta ctgtcttctg tgctagggat cacttccttg ttgagtgggg    5820
cctgagtttt aagaggatct tctgctcctc ttcatctggt cccttccctt ccaaggcccc    5880
agagaggaag catgcggtg ggccctagcg gtgcttctag cttcctgtc tcctggtgag    5940 tgcgctgcct acagagagga tcacgggttt tgttttgttt tgttattttc ttcttttgca    6000
aggagcgaca tactaagaaa tgcctcatta tattttgtgt tgttcccatt gcagccagtc    6060
agatatcttc caacttggaa gggagaacga agtcagtcac caggctgact gggtcatctg    6120
ctgaaatcac ctgtgatctt cctggagcaa gtaccttata catccactgg tacctgcacc    6180
aggaggggaa ggccccacag tgtcttctgt actatgaacc ctactactcc agggttgtgc    6240
tggaatcagg aatcactcca ggaaagtatg acactggaag cacaaggagc aattggaatt    6300
tgagactgca aaatctaatt aaaaatgatt ctgggttcta ttactgtgcc acctgggaca    6360
ggcacagtga ttcagacact gaaaatctgc ctgtggttgc ttctggtaca caagatagac    6420
cagccaactc tcatttcctg ccctgaattt actgtattct gtacaaagag aaacacagct    6480
taactcctga tctcccctgc aatatcacac tccctggca gcagctgcac cctgttcccc    6540
accctccccc aggactttcc tgaagaccaa gctgccacct ccaagcctca gctaagcagc    6600
ctggctgaga gcaagtttct ctcagctctc ctagaacatg gggaaggccc actcactctg    6660
cttcctagga cagacaggta cagctagggt ccagctgtga agcaagacat tttggacaaa    6720
aatgggaagg gtattcatac tgaatcatac atccaataat ggtccagaga tcgcagctga    6780
gagtggtgct tattccttat gtctataaca atataagcaa tactataatg accactaaaa    6840
```

```
cactaggcca atatatgcag ttgaacattc tctctctctg ccctcccttt tattctcgct    6900
ctcctttctt acttccatgc ttgcttttat cattttctct ccctccctcc cttcctcctt    6960
tccttccatc accccaccct ccttcctttc tttccttcct tccttccttg cttttctctc    7020
tttctctcct ttttgtgtac ataatcacaa tacttttcc acaaaatcat ttgaaatagt     7080
ttttctctat ttgttcatgc caacattgat atagctgctt taattgttca gtttcatttt    7140
tatattttgg aaatttgtgt attattttgt tttgtttcat atttgttttg tatacgtaaa    7200
acatttagtt ggaactgaag tcaaaattat aaaagatgac acatttgaag attttagctt    7260
ccattgtaga cttctcattc ctcttttctc cctgacacta taggtaacaa tattttatc     7320 cgttttcttg aacttttca ctctgtcata gcgcagtatg tatcaattct atttcaatgc     7380
catatttata tttttgttcc tatatttggt tttatacat tttaatcaat cttatatttt     7440
cccgtgtctg gattgtgtgt cttacttcta aaggtgcaca tacttcataa gtatgcataa    7500
agacgtccat atcatttatt tgaatgtttt tatgtgttga ttatttaatg atggcatcat    7560
tgatctatca ggaattttta tacaataatt actgtattag taataataat actggccagg    7620
cccggtggct catgcctgta atcccagcat ttgagtagta cagtcgttag gaatacttag    7680
gccgggagat tgcgaccagc ttagccaaca tggtgaaacc ctgtctctac taaaaataca    7740
aaaaattagc tggctgtggc ggtgcacaca tgtaatccca gctacttgga tgctgaagca    7800
ggagaatctc ttgagcctag aaggtggagt tttcagtgag ctaatatcac actactgcag    7860
tccagttggg gcaacacagt gagactctgt ctcaaaaaga ctaataataa taataatatt    7920
gatggtaaat atgggtactg acattctggt agttaatgta ctaagcacat tgcatgcata    7980
ttgtatttaa tctacacaga aacttcatta aggatttaaa gtactgttga atgtaacatt    8040
agaaattggg gggttaatta acattcccta agtcatatac tttaatttga taatgattgc    8100
aatccaagct ctgtggttca gaaaatgaga tttgttaatt cggtttgcat tcccccatcg    8160
taggagtact agcatcattt tacaacttta cagttcattt atatttcttc ttttgagaat    8220
tgccttgtac actcttttcc tattcttcta ttggaggatt agtttttct tattggttcg     8280 taagaattaa tatacaccat tttagagata ctgacccttt atccaatgtg ttgaagatat    8340
ttctcctcat ttgttattat ttacatttgg caccttttgg agaattgaac tttgaaaaaa    8400
acaaaatcta tcaatttttc tatggtgtct actttgatgt caggtttaga aaggccaatc    8460
tcacctagaa tttctatgca attcatcatc atttaagtct aatgattttc tttttattac    8520
aactaaatca ctatttgtaa ctggtaaggt agaaatgcag caatatttgt ttccatatgg    8580
taagtcaata tccaaaagag aacttatgaa ataattgact atttccttgt ggatattaac    8640
atatcacttt atcacatgat aaaatattac atacatgcag cttctctttct ggattttcca    8700 ctgtgttcca tgaatcttgt cattctagtg ccagtattgc cttctcttca gcactgtagc    8760
tttatagttc ttttcacatt ctgatgaagt ttctctcatt atctttttgt tttaagaatt    8820
ttctgtgcat gctagtgtga tctcaatcct ctcccttccc attttttaaac cgtgagactt    8880 ctgtccagca agacttttc acgctccaag gcaggcaagc ttccctcctt cacaaggacc      8940
tgagaattca gctttcagag ctgttcctgt ggaagcctca tgtcctgcac atatggtcca    9000
gaggcagagg gagaccaacc ggagcccct ccctttctca ttcccagctg tgatgacagc     9060
aaaaactgaa ctctgtgagc taggccaaca acacaattaa gagagacatt gttctacatc    9120
tcattatgca tctttcaaac atgtgtctct atatacttct gacacaggtg gtggtaatct    9180
gtgtatgcct tactgaattt tcacaattat attactgtac tactttgtc ccctatattt      9240
```

```
ccatctgtga atccaggtgt actgcagatc tcagtcccct ttctgagggt agggctgaca    9300
aataaaatat acaataccaa acaatttgga agttcagata acaacaagt ttttagttta    9360 agtatgttcc aaatattgca tgacatggca ccctgaacta cttagaaaaa aaaaacaaaa    9420
aaacctcaca ctcctacttc agtgaacaaa atcctctaa taaagagatc acacccacag    9480
gatcacacac acacaaacac acacacacac acaccccca catacaccca tttatcttag    9540
agcagagtcc aagacccacc aacacacatg atcctcagtc cttcatttt tattatttat    9600 ttatttattt atatttatta tactttaagt gctagggtac atatgcacaa cgtgcaggtt    9660
tgttacatat gtatacatgt gccatgttgg tttgttgcac ccatcaactt gtcatctaca    9720
ttaggtatat ctcttaatgc tatccctccc ccctccccc accccactac aggcccagt     9780 gtgtgatgtt cccccactct gtgtccaagt gttctccttg ttcaattccc acctacgagt    9840
gagaacatgc actgtttgga tttctgtcct tggaatagtt tgctcggaat gatggtttcc    9900
agcttcatcc atgtccttac aaaggacatg aacgcatccc ttttatggc cgcatagtat     9960 tccatggtgt atatgtgcca catttcctta atccagtcta tcattgatgg acatttgggt    10020
tggttccaag tctctgctat cgtgaatagt gccacaataa acatatgctt tgcgtggtgc    10080
ctccaagtgt cctcgcagat gccaaaagga aggtggttca gttccctaat cagagacttc    10140
ctggcaggac aaggtcctgg catcagcatt agctgctgca actctgaagg gcagggtgtg    10200
agcctgctgt gggactgccc cctcctaggg ctgggcctgc tgactccagg gtctgcttcc    10260
cccacctctg cactccctct gctgcaggcc tgagctctcc ttgcccctgg ctctcttctg    10320
cagagggcct gctctcagct gccacaagag ggcgccggag aacggacctg agcagagagg    10380
caggggctcc tctgcaggtc ctcccaggca ccaacccttc tgggagggag aaggcttgg     10440 gagtcctctt agacagatcc tcagtcactt ccctctgctt gtgtctcagg aagaccacct    10500
cctcctactg tcttctgtgc tagggatcac ttccttgttg agtggaacct gagttttaag    10560
aggatcttct gctcctcttc atctggtccc tttccttcca aggccccaga gaggaaggca    10620
tgcagtgggc cctagcggtg cttctagctt tcctgtctcc tggtgagtgc gctgcctaca    10680
gagaggatca cgggttttgt tttattttct tcttttgcaa ggagtaccat actaaggaat    10740
tcctcattat attttgtgtt gttcccattg cagccagtca gaaatcttcc aacttggaag    10800
ggagaacgaa gtcagtcatc aggcagactg ggtcatctgc tgaaatcact tgtgatcttg    10860
ctgaaggaag taacggctac atccactggt acctacacca ggaggggaag gccccacagc    10920
gtcttcagta ctatgactcc tacaactcca aggttgtgtt ggaatcagga gtcagtccag    10980
ggaagtatta tacttacgca agcacaagga acaacttgag attgatactg cgaaatctaa    11040
ttgaaaatga ctttggggtc tattactgtg ccacctggga cgggcacagt gattcagatc    11100
cgccctacac cacactgaaa atctgccttg tggctgcttc tggtacacaa gatagagccg    11160 cccccctctca tttcctgcca ccaaatttac cgtgtgctga acaagagaaa cattgcttaa    11220
ctcctgatct cccctgcaat attacactcc cctggcagca gctgcaccct gttccccacc    11280
ctcccccagg actttcctga agaccaagcc gccatctcag ctaagcctca gagaagcagc    11340
ctggctgaga gcaaggttct cttagctctc ctaggacatg ggggaggccc actcactctg    11400
cttcctagga caaatgggta ccccctagggt ccagctgtaa agcaagatat tttgacaac     11460 aaatgggaag ggaatttata ctaaattgtg tatcccatca tgatccagaa accgcagctg    11520
agactggtgc ttattcctta tgtctataac aaatataagca atactataat gaccactgaa    11580
acaccaggcc taggtatgca gttgaacatt ctctcccctct gccctccctt ttattctctc    11640
```

```
tctctttttt cttaattctt tgcttgcttt tattattttt ctctctccct tcctccctcg    11700
ctccatcgct ccctccgtcc ttccctccct ctctccctct ctccttccct ccttcctctt    11760
cttctttcct tccatccatt ctccttcgtt ttccttcctt ccttctttgc ttttctcttg    11820
ctttcctttt tgggtacata atcagaatac ttttccaca aaatcatttg aaataatttt    11880
tctctatgtg ttcatgtcaa cattgatata gctactttaa ttgttcagtt ttctttttta    11940
cattttggaa atttgttgta ttactttgtt ttgtttcata tctgttttgt atatataaaa    12000
catttacatg gaagtgaagt caaaattata aaagatgatg catttgaaga ttttagcttc    12060
cattgtagac ttctcattct tcttttctcc ctgacactat aggtaacaat attttttggca   12120 gttcacttga gttttttcac tgtttgtcat agcggagtat gtattgtttc tatttcaatg    12180
ccatatttat attttctttc tgatattcag tttctatata ttttaatcaa tcttatattt    12240
tcctgtgtct ggactgtgtg tcttacttct aaaggtgcac atacttcata agtatgcata    12300
aagacgtcca tatcatttat ttgaatgttt ttatgcattc attatttaat gatggcatca    12360
ttgatctatc aggaattttt atacaataat tactgtatta gtaataataa tactggccag    12420
gcccggtggt tcatgcctgt aatcccagca tttgggcagt ccagtcgtta ggatcactta    12480
ggccgggaga ttgcgaccag cttagccaac atggtgaaac cctgtctcta ctaaaaatac    12540
aaaaaattag ctggctatag tggcgcacac atgtaatccc agctacttga atgctgaagc    12600
aggagaatct gtagagcctg gtaggtggag ttttcagtga gctaatatca cactactgca    12660
gtccagtttg ggcaacagag tgagactctg tctcaaaaaa atgaataacg ataataataa    12720
tattgatgct acatatgggt actgacattc tggtagttaa tgtactaagc acattacatg    12780 catatttat ttaatctaca cagaaatttc attagggttt aaagtactgt tgaatgtaac     12840
attagaaatt gagggggtta attaacattc cctgagtcat atactttaac ttgataatga    12900
ttgcaatcca agctctgtga ttctgaaaac gagatttgta aattcagttt gcattccctc    12960
atctttggga gtactaacat tatttcacaa ctttataggt catttatagt tcttcttttg    13020
tgaattgcct tgtcatactc tttgccaatt cctctcttgg aggattaatt ttttcttatt    13080
agtttgtaag agttaatata cactattta aagatactga cccttatcc aatgtgttga      13140 agatatttct cctcatttgt tgttatttac atttggcatc ttttggtgaa ttgaactttg    13200
aaaaaaaaag cattaaaatc tatcagtttt tctagggtgt ctagtttgat gtcaagctta    13260
gaaaggccaa tctcacctag aatttctatg caattcatca ttgtttaagt gtaatgattt    13320 tgttttatt acaactaaat cactatctat atctggtaag aacgaaatgc aataatattt      13380
gtttccatat ggtaagtcaa tacccaaaac agaacttata aaataattga ctatttcctt    13440
gtgggtatta acatatcact ttatcacatg ataaaatatt acatacgtgt ggctctcttt    13500
ctggattttc cactgtgttc catgaatctt ctcattctag tgccagtatt gccctctctt    13560
cagcactgta gctttatact tcttttcaca ttttgatgaa gttctctca ttattttttt     13620 gttttaagaa ttttctgtgc attctagtgt gatctcaatc ctctcccttc ccattttaa     13680 accatgagac ttctgtcctg caagactttt tcacgctcca aggcaggcaa gcttccctcc    13740
ttcacaagga ccgagaact cagctttcag agctgctcct acagcagcct catgtcctgc      13800
atgtgtgctc cagaggcaga gggagaccaa ccagagcccc ctccctttct cattcccagc    13860
tgtgatgaca gcagaaactg aactctctga gctagcccaa cacaacaact gagagggaca    13920
ctgttctcca tctcattatg catatttcaa acatgtgtct ctatatactt cttacagagg    13980
tggtgataat ctgtgaatgc cttactgaat tttcacaata atattactgt acttgatttg    14040
```

```
tcccccttatt ttcatctgtg aagccaggtg cactgcagat attagtctgc tttctgaggg    14100
tagggatgac aaataaaata tacaataccg ggggaattgg aagttcagat aaataacaag    14160 ttttttagttt aagtatgttc caaatattgc atgacatggc acccagttct actttaaaaa    14220
caaacaagca aacaaacaaa ttcacactcc tactttaatg aacaaaaatc ttctaataag    14280
gaggtcacac acacaggatt acaggcacaa ccccacaca caaacacaca cacacattta    14340
ccttagagca gagtccagga cacaccaaca cacatgatcc tcagtccttt taatttaaag    14400
cacgttcaac ccttctcaga gtggccttga gtggttgcct ccatgagtct gcagatgcga    14460
aaaggaagtt ggttccgggc cctaatcaga ggcttcctgt caggacaagg ttctggcatc    14520
agcattacct gctgcaactc tgaagggcag ggtgggagcc tgctatggga ctgcccccctc   14580 caaggtgtga gcctgttaat tccagggtca gcttacccaa catctgcagt ccctcagctg    14640
gaggcctgag ctcttaatgc ccctgcctcc cttctgccct gggcctgctc tcagctgcca    14700
caagagggcg ccgaagaaag ggcctgagga gatgcaggag ctcctctgca ggtcctccca    14760
ggcaccaccc cttctgggag gaaggcttgg gagtccccta agacacatct tcagtcactt    14820
ctctctgcct gtgtctcagg aaaccagctc ctcctactgt cttctgtgct agggatcact    14880
tccttgttga gtggggcctg agttttaaga ggatcttctg ctcctcttca tctggtccgt    14940
ttccttccaa ggcccccgag aggaaggcat gcggtgggcc ctactggtgc ttctagcttt    15000
cctgtctcct ggtgagtacg ctgcctacag agaggctcac aggttgggtt ttgttttgtt    15060
ttcttcttga aaggggtgcc atacaaagga atacctcatt gtattttgtg ttgttcccat    15120
tgcagccagt cagaaatctt ccaacttgga agggagaacg aagtcagtca ccaggcagac    15180
tgggtcatct gctgaaatca cttgcgatct tactgtaaca aataccttct acatccactg    15240
gtacctacac caggagggga aggccccaca gcgtcttctg tactatgacg tctccaccgc    15300
aagggatgtg ttggaatcag gactcagtcc aggaaagtat tatactcata cacccaggag    15360
gtggagctgg atattgagac tgcaaaatct aattgaaaat gattctgggg tctattactg    15420
tgccacctgg gacaggcaca gtgattcaga cctgtcctac accacactga aaatctgcct    15480
tgtggctgcc tctggtacac aagatagagc cgccccctct catttcctgc caccaaattt    15540
cctgtattct gaacaagaga aagacagctt aactcctgat ctccctccta atatcacact    15600
gtcctggcag cagctgcatc ctgttcccca ccctccccc acaactttcc tgaagatcaa    15660
gctgccatct ccaggcctca gctaagcagc ctggctgaga gcaaggttct ctcagctctc    15720
ctaggacatg ggggaggccc actcactctg cttcctatga cacacaggta caactagggt    15780
ccagctgtga agcgagatat tttggacagc aaatgggaag ggtatttata ctgaatcatg    15840
tatccactca tggtccagag atcacagctg agagtggtgc ttattcctta tgtctataac    15900
aacataagca atactataat gaccactaaa acactaggcc caggtatgca gttgaacatg    15960
gtctccctct gccctccctt ttattctctc tctcttttct tacttctttg cttgtttta    16020 tttttctctc cctccctaac tccctccctc catccatcct ttcctcccct cctcccttgt    16080
ttccttccat ccattctcct tccttgtttt ccttccttcc ttccttgctt ttctctctct    16140
ttctttcctt tttgggtaca taatcagaat acttttttcca caaaatcatt tgatataatt    16200
tttctctata tgttcatgcc aacattcata cagctagttt aattgttcag ttctcttttt    16260
cacattttgg aatttttgttg tattacttttg ttttgcttca tatctgtttt gtatatataa    16320
aacatttaca tgaaactgaa gccaaaatta taaaagatga tgcatttgaa gattttagct    16380
tccattgtag atttctcgtt cctctttttct ccctgacact ataggtaaca atatttttgg    16440
```

```
cagttcactt gagcttttc  actgtttgtc atagcggagt atgtattgtt tctatttaa   16500
tgccatattt atatttcgt  tctgatattt ggttttata  cattttaatc aatcttatat  16560
tttcccgtgt ctggactgtg tgtcttactt ctaaaggtgc acgtacttca taagtatgca  16620
taaagaagtc catatcattt atttgaatgt ttttatgcgt tgattattta atgatggcat  16680
catcgatcta tcaggaattt ttatacaata attactgtat tagtaataat aatacttgcc  16740
aggcccggtg gctcatgcct gtaatcccag catttgggca gtccagtcgt taggaacact  16800
taggccggga gattgcgacc agcttagcca acatggtgaa accctgtctc tactaaaaat  16860
acaaaaaatt agccggctgt agtggcgcac acatgtaatc ccagctactt ggatgctga   16920
ggcaggagaa actcttcaac ctggaagttg gagttttcag tgagctaaga tcacactact  16980
gcagtccagt ttgggcaaca cagcgagact ctgtctcaaa aagactaata ataataataa  17040
tattgatggt aaatatgggt actgacattc tggtagttaa cgtactaagc acattgcatg  17100
cacatttat  ttaatctaca cagaaacttc attaaggttt taaagtactg ttgaatgtaa  17160
cattagaaat tgggggtta  attaacattc cctaagtcat atactttatc ttgataatga  17220
ttgcaatgca agctctgtgg ttcctaaatg agatttgtta atttggtttg cattccccca  17280
tctttaggag tactagcatc attttacaac tttacaggtc atttatagtt cttcttttga  17340
gaattgcctt gtcatactct tttcctattc ttttttgga  agattagttt tttcttatta  17400
gttcgtaaga attaatatac accatttag  agatactgac cctttatcca atgtgttgaa  17460
gatatttctc ctcatttgtt attatttaca tttggcacct tttggtgaat tcaactttga  17520
aaaaaaaaca ataaaagcta tcaattttc  tagggtgtct agtttgatgt caggcttaga  17580
aaggccaatc tcacctagaa tttctatgca attcatcatc gtttaagtct aatgattttc  17640
tatttattac aactaaatca ctatttgtaa ctagtaaggt agaaatgcaa caatatttgt  17700
ttccatgtgg taagtcaata ccaaaaagag aacttattta ataactgact atttccttgt  17760
gggtattaac atatcacttt atcacatgat aaaatattac atacatgcag ctctctttct  17820
ggattttcca ctgtgttcca tgaatcttgt cattctagtg ccagtattgc cctctcttca  17880
gcactgtagc tttatagttc ttttcacatt ctgatgaagt ttctctcatt attttttgt   17940
tttaagaatt ttctgtgcat tctagtgtga tctcaatcct ctcccttccc atttttaaac  18000
cgtgagactt ctgtccagca agactttttc acgctccaag gcaggcaagc ttccctcctt  18060
cacaaggacc cgagaactca gctttcagag ctgttcctgt ggaagcctca tgtcctgcac  18120
gtgtgctcca gaggcagagg gagaccaacc ggagccccct cccttctca  ttcccacctg  18180
tcattcccag ctgtgaagac agcagaaacc gaactctgtg agctaggcca ataccacaac  18240
tgagaggaat attgttctac atctcattat gcatctttca aacatgtgtc tctatatact  18300
tcttacagag gtggtgataa tctgtgtatg ccttactgaa ttttcacaat tatattactg  18360
tacttccttt gtcccctata tttccatctg tgaatccagg tgtactgcag atctcagtcc  18420
cctttctgag ggtagggctg acaaataaaa tatacaatac caaacaattt ggaagttcag  18480
gtaaacaaca agttttagt  ttaagtatgt tccaaatatt gcatgacatg caccctgaa   18540
ctacttagaa aaaaaaaac  aaaaaaaact cacactccta cttcaatgaa caaaaatcct  18600
ctaataaaga gatcacaacc acaggatcac acacacacaa acacacacac acacacacac  18660
ccaacacaca cacctttatc ttagagcaga gtccaagacc aaccaacaca catgatcctc  18720
agttcttta  ttttattat  ttctttattt atttatattt attatacttt aagtgctagg  18780
gtacatttgc acaacgtgca ggtttgttac atatgtatac atgtgccatg ttggtttgtt  18840
```

```
gcacccatca acttgtcatc tacattaggt atatctccta atgctatccc tccccctgc    18900
ccccacccca ctacaggccc cagtgcgtga tgttccccca ctctgtgtcc aagtgttctc   18960
attgttcaat tcccacctac gagcgagaac atgcactgtt tggatttctg tccttggaat   19020
agtttgctcg gaatgatggt ttccagcttc atccatgtcc ttacaaagga catgaacgca   19080
tccctttta  tggccgcata gtattccatg tgtatatgt  gtcacatttt cttaatccag   19140
tctatcactg atggacattt gggttggttc caagtctctg ctatcgtgaa tagtgccgca   19200
ataaacacac gctttgcgtg gtgcctccaa gtgtccttgc agatgccaaa aggaaggtgg   19260
ttcagttccc taatcagaga cttcctggca ggacaaggtc ctggcatcag cattagctgc   19320
tgcaactctg aagggcaggg tgtgagcctg ctgtgggact gcccctcct  agggctgggc   19380
ctgctgactc cagggtcagc ttccgctaca tctgcattcc ctctgctgca ggcctgagct   19440
ctcctggccc ctggctctct tctgcagagg gcctgctctc agctgccaca agagggcgcc   19500
ggagaacgga cctgagcaag agaggcagga gctcctctgc aggtcctccc aggcaccaat   19560
ccttctggga gggaggaagg cttgggagtc ctcttagaca gatcctcagt cacttctctc   19620
tgcttgtgtc tcaggaagac cagctcctcc tactgtcttc tgtgctaggg atcacttcct   19680
tgttgagtgg ggcctgagtt ttaagaggat cttctgctcc tcttcatctg gtcccttcc   19740
ttccaaggcc tcagagagga aggcatgcag tgggccctag cggtgcttct agcttttctg   19800
tctcctggtg agtgcgctgc ctacagagag gatcatgggt tttgttttct ttatttctt   19860
cttttgcaag gattgccata ctaaggaatt cctcattata ttttgtgttg ttcccattgc   19920
agccagtcag aaatcttcca acttggaagg gagaacgaag tcagtcatca ggcagactgg   19980
gtcatctgct gaaatcactt tgtgatcttgc tgaaggaagt accggctaca tccactggta   20040
cctacaccag gagggaagg  ccccacagcg tcttctgtac tatgactcct acacctccag   20100
cgttgtgttg gaatcaggaa tcagcccagg gaagtatgat acttacgaa  gcacaaggaa   20160
gaacttgaga atgatactgc gaaatcttat tgaaaatgac tctggagtct attactgtgc   20220
cacctgggat gggcacagtg attcagatcc gccctacacc acactgaaaa cctgccttgt   20280
ggctgcttct ggtacacaag atagagccgc ccctctcat  ttcctgccac caaatttacc   20340
gtgtgctgaa caagagaaac attgcttaac tcctgatctc ccctgcaata tcacactccc   20400
ctggcagcag ctgcaccctg ttcccacacc tcccccagga cttccctgaa gaccaagcca   20460
ccatctcagc taaacctcag agaagcagcc tggctgagag caaggttctc ttagctctcc   20520
taggacatgc cggaagccca ctcactctgc ttcctaggac aaatgggtac ctctagggtc   20580
cagctgtgaa gcaagatatt ttggacaaca aatgagaagg gtatttatac taaattgtgt   20640
atcccatcat gatccagaaa tcgcagctga gactggtgct tattccttat atctataaca   20700
atgtaagcaa tactataatg accactgaaa caccaggcct aggtatgcag ttgaacattc   20760
tctccctctg ccctcccttt tattctctct ctctttttt  aattctttgc ttgctttat   20820
tattttctc  tctctcccctt cctccttccc tccgtccttc cctccctcct tccctccctc   20880
tctccctccc tccttccctc ccttcctctc ttctttcctt ccatccattc tccttcgttt   20940
tccttccttc cttctttgct tttctcttgc tttccttttt gggtacataa tcagaatact   21000
ttttccacaa aatcatttga ataattttt  ctctatgtgt tcatgtcaac attgatatag   21060
ctactttaat tgttcagttt tcttttttac attttggaaa tttgttgtat tactttgttt   21120
tgtttcatat ctgtttttgca tatataaaac atttacatgg aagtgaagtc aaaatcataa   21180
aagatgatgc atttgaagat tttagcttcc attgtagact tctcattctt cttttctccc   21240
```

```
tgacactata ggtaacaata tttttggcag ttcacttgag ctgtttcact ctgttttca    21300 tagcggagta tgtattcttt ctatttgaat gccatattta tattttcttt ctgatattca    21360
gtttctatat attttaatca atcttatatt ttcctgtgtc tggactgtgt gtcttacttc    21420
taaaggtgca catacttcat aagcatgcat aaagatgtcc atatcattta tttgaatgtt    21480
tttatgcatt gattatttaa tgatggcatc actgatctat caggaatttt tatacaataa    21540
ttactgtatt agtaataata atactggcca ggcccggtgg ctcatgcctg taatcccagc    21600
atttgggcag tccagtcgtt aggatcactt aggccgggag attgtgacca gctcagccaa    21660
cgtggtgaaa ccctgtctct agtaaaaata caaaaaatta gctggctgta gtggcacaca    21720
catgtaatcc cagctacttg gatgctgaag caggagaatc tgtagagcct ggtaggtgga    21780
gttttcagtg agctaatatc acactactgc agtccagttt gggcaacaga gtgagactct    21840
gtctcaaaaa aatgaataac gataataata atattgatgg tacatatggg tactgacatt    21900
ctggtagtta atgtactaag cacattacat gcatatttta tttaatctac acagaaactt    21960
cattaaggtt taaagtactg ttgaatgtaa cattagaaat tgggcggtta attaacattc    22020
cctaagtcat atgctttaat ttgataatga ttgcaatcca agctctgtgg ttccgaaaat    22080
gagatttgta aattcagttt gcattccccc atctttggga gtactagtat tatttcacaa    22140
ctttataggt tatttatagt tcttcttttg tgaattgcca tgtcatactc tttgcctatt    22200
cctctcttgg aggattaatt ttttcttatt atttcgtaag agttaagata cactatttta    22260
aagatactga cccttatcg aatgtgttga agatatttcc cctcatttgt tattatttac    22320
atttggcacc ttttggtgaa ttgaactttg aaaaaaaaag cattaaaatc tatcaatttt    22380
tctagggtgt ctagtttgat gtcaagctta gaaaggccaa tctcacctag aatttctatg    22440
caattcatca ttgtttaagt gtaatgattt tgtttttatt acaactaaat cactatctat    22500
atctggtaag aacgaaatgc aataatattt gtttccatat ggtaagtcaa tacccaaaag    22560
agaacttata aaataattga ctatttcctt gtggatatta acatatcact ttatcacatg    22620
ataaaatatt acatgcatgc ggctttcttt ctggattttc tactgtgttc catgaatctt    22680
ctcattctag tgccagtatt gccctctctt cagcactgta gctttatagt tcttttcaca    22740
ttctgatgaa atttctctca ttattttttt gttttaagaa ttttctgtgc attctagtgt    22800
gatctcaatc ctctcccttc ccatttttaa accatgagac ttctgtccag caagactttt    22860
tcatgctcca aggcatggaa gctttcctcc ttcacaagga ccccgagaac tcagcttttca   22920 gagctgctcc tacagcagcc tcatgtcctg cacgtgtgct ccagaggcag agggagacca    22980
accggagccc cctccctttc tcattccag ctgtgatgac agcagaaact gaattctctg     23040
agctaggaca acacaacaac tgagagagac actgttctac atctcattat gcatctttca    23100
aacatgtgtc tctatatatt cttacagagg tggtgataat ctgcctatgc cttactgaat    23160
tttcacaata atattactat actttttttg tcccctatat ttccaactgt gaatccaggt    23220
gcactgcaga tattagtctg ctttctgagg gtagggatga caaataaaat atacaatacc    23280
gggggaattg gaagtacaga aaaataacaa gtttttagtt taagtatgtt ccaaatattg    23340
catgacatgg cacccagtac tactttaaaa acaaacaagc aaacaaacaa attcacactc    23400
ctactttaat gaacaaaaat cctctaataa ggaggtcaca cacacaggat tacaggcaca    23460 accccctgccc ccccaacaca cacacacaca tatttacctt agagcagact ccgggacaca   23520
ccaacacaca tgatcctcag tccttttaat aaagcacgtt caacccttct cagagtgacc    23580
ttgagtggtt gcctccatga gtctgcagat gcgaaaagga acttggttca gggccctaat    23640
```

```
cagaggcttc ctgtcaggac aaggttctgg catcagcatt acctgctgca actctgaagg    23700
gcagggtggg agcctgctat gggactgccc cctccaaggt gtgagcctgt taattccagg    23760
gtcagcttac ccaacatctg cagtccctca gctggaggcc tgagctctta atgcccctgc    23820
ctcccttctg ccctgggcct gctctcaact gccacaagat ggcgcagaag aaagggcctg    23880
aggagatgcg ggagctcctc tgcaggtcct cccaggcacc accccttctg ggaggaaggc    23940
ttgggagtcc cctaagacac atcttcagtc acttctctct gcctgtgact caggaagacc    24000
agctcctcct actgtcttct gtgctaggga tcacttcctt gttgagtggg gccggagttt    24060
taagaggatc ttctgctcct cctcatctgg tccctttcct tccaaggccc ccgagaggaa    24120
ggcatgcggt gggccctact ggtgcttcta gctttcctgt ctcctggtga gtacgctgcc    24180
tacagagagg ctcacaggtt gggttttgtt ttgtttactt cttttgaaag gggtgccata    24240
caaaggaata cctcattaaa ttttgtgttg ttcccattgc agccagtcag aaatcttcca    24300
acttggaagg gggaacgaag tcagtcacga ggccgactag gtcatctgct gaaatcactt    24360
gtgaccttac tgtaataaat gccttctaca tccactggta cctacaccag gaggggaagg    24420
ccccacagcg tcttctgtac tatgacgtct ccaactcaaa ggatgtgttg gaatcaggac    24480
tcagtccagg aaagtattat actcatacac ccaggaggtg gagctggata ttgatactac    24540
gaaatctaat tgaaaatgat tctggggtct attactgtgc cacctgggac aggcacagtg    24600
attcagacct gtcctacacc acactgaaaa tctgccttgt ggctgcctct ggttcacagg    24660
atagagccgc cccctctcat ttcctgtcac caaatttact gtattctgaa caagagaaag    24720
acagcttaac tcctgatctc cctcctaata tcacactgtc ctggcagcag ccgcaccctg    24780
ttccccaccc ctcccccaca actttcctga agatcaagct gccatctcca ggcctcagct    24840
aagcagcctg gctgagagca aggttctctc agctctccta ggacatgggg gaggcccact    24900
cactctgctt cctatgacac acaggtacaa ctagggtcca gctgtgaagc gagatatttt    24960
ggacagcaaa tgggaagggt atttatactg aatcatgtat ccagtcatgg tccagagatc    25020
acagctgaga gtggtgctta ttccttatgt ctataacaac ataagcaata ctataatgac    25080
cactaaaaca ctaggcccag gtatgcagtt gaacatggtc tccctctgcc ctcccttttta   25140 ttctctctct cttttttctt acttctttgc ttgtttttat ttttctctcc ctccctaact    25200
ccctccctcc atccatcctt tcctcccttc ctcccttgtt tccttccatc cattctcctt    25260
ccttgttttc cttccttcct tccttgcttt tctctctctt tctttccttt tgggtacat     25320 aatcagaata cttttttccac aaaatcattt gatataattt ttctctatttt gttcatgcca   25380 acatttatac agctagttta attgttcagt tttcattttt acattttgga aatgtgttgt    25440
attactttgt tttgcttcat atctgttttg tatatataaa acgtttacat gaaactgaag    25500
ccaaaattat aaaagatgat gcatttgaag attttagctt ccattgtaga tttttcgttc    25560
ctcttttctc cctgacacta taggtaacaa tattttttggc agttcacatg agcttttttca   25620 ctgtttgtca tagtgccgta tgtattgttt ctatttcaat gccatattta tattttcatt    25680
ctgatattcg gttttatac atttaatca atcttatatt ttcccgtgtc tggattgtgt     25740
gtcttacttc taaaggtgca catacttcat aagtatgcat aaagacgtcc atatcattta    25800
tttgaatgtc tttatgcatt gattatttaa tgatggcatc attgatctat caggaatttt    25860
tatacaataa ttactgtatt agtaataata atactggcca ggcccggtgg ctcatgcctg    25920
taatcccagc atttgggtgg tccagtcatt acgatcactt aggccaggag attgcgacca    25980
gcttagccaa catggtgaaa ccctgtctct actaaaaata caaaaaatta gccggctgta    26040
```

-continued

```
gtggcgcaca catgtaatcc cagctacttt ggatgctgag gcaggagaat ctctagagcc   26100
tggaaggtga aggtttcagt gagctaagat cacactacta cagtccagtt tgggcaatag   26160
agtgagactc tctctcaaaa aaatgaataa tgataataat aatattgatg gtacatatgg   26220
gtgctgacat tctggtagtt aatgtactaa gcacattaca tgcatatttt atttaatcta   26280
cacagaaact tcattaaggg tttaaagtac tgttgaatga acataagaa atgggggt     26340 taattaacat tccctaagcc atatatttta atttgattat gatagcaatc caagctctgt   26400
ggttccaaaa atgagatttg ttaattcgat ttgcattccc ccatctttag gagtactagc   26460
aatatttgac aacgttatag gtcatttata attcttcttt tgagaattgc cttgtcgtac   26520
tctttgccta ttctcccttt ggaggattaa ttttttctta ttggttcgta agaattaata   26580
tgtactattt tagagatgat gacccttat ccaatgtgtt gaagatatta ctcctcattt     26640
gttattattt acatttggca ccttttagtg aattcaactt tgaaaaaaaa acaataaaac   26700
ccatcaattt ttctagggag tctagtttga tgtcagctta gaaaggccaa tctcacccag   26760
aatctgtatg caattcatca tcgtttaagt ctattgattt tcattttatt acaactaaat   26820
cactatttgt aactggtaag gtagaaatgc gacaatattt gtttccatat ggtaagtcaa   26880
tacctaaaag agaacttatt aaataattga ctatttcctt gtgaatatta atatatcact   26940
ttatcacatg ataaaatatt acatacatgc agctctctta ctgcattttc cactgtgttc   27000
catgaatctt ctcattctag tgccagtatt gccctctctt cagcactgta gctttatagt   27060
tcttttcaca ttctgatgaa atttctctca ttatttttt gttttaagaa ttttctgtgc   27120
attctagtgt gatctcaatc ctctcccttc ccattttaa accatgagac ttctgtccag   27180
caagactttt tcacgctcca aggcaggcaa gcttccctcc ttcacaagga cccgagaact   27240
cagctttcag agctgctcct acagcagcct cttgtcctgc atgtgtgctc cagaggcaga   27300
gggagaccaa ccagagcccc ctcccttct cattcccagc tgtgatgaca gcagaaactg    27360
aattctctga gctagcccaa cacaacaact gagagggaca ctgttctcca tctcattatg   27420
catatttcaa acatgtgtct ctatatactt cttacagagg tggtgataat ctgtgaatgc   27480
cttactgaat tttcacaata atattactgt acttgatttg tccccttatt ttcatctgtg   27540
aatccaggtg cactgcagat attagtctgc tttctgaggg tagggatgac aaataaaata   27600
tacaatacgc agagaattgg aagttcagat aaataacaag ttttagttt aagtatgttc     27660 caaatgttgc atgacatggc acccagtact actttaaaaa caaacaagca aacaaacaaa   27720
ctcacattcc tacttaatga acaaaaatcc tctaataagg aggtcacaca cacaggatta   27780
caggcacaac tcacccccc caacacacac acacatttac cttagagcag agtccaagac   27840
acaccaacac acatgatcct cagtcctttt aatttaaagc acgttcaacc cttctcagag   27900
tggccttgag tggttgcctc catgtgtctg cagatgcgaa aaggaacttg gttcagggcc   27960
ctaatcagag gcttcctgtc aggacaaggt cctggcatca gcattagctg ctgcaactct   28020
gaagggcagg gtaggagcct gttgtgggac tgccccctcc aaggtctgag cctgttaatt   28080
ccagggtcag cttcccctaa atctgcagtc cctctgctgg aggcctgaac tctcaatgcc   28140
cctgcctccc ttctgccctg ggcctgctct cagctgccac aagagggcgc cgaagaaagg   28200
gcctgaggag acacaggagc tcctctgcag gtcctcccag gaaccacccc ttctgggagg   28260
aaggcttggg agtcccctaa gacacatcct cagtcacttc tctctgcctg tgtctcagga   28320
ataccagctc ctcctactgt cttctgtgct agggatcact tccttgttga gtgggacctg   28380
agttttgaga ggatcttcta ctccttttca tctggtccct ttccttccaa ggccccagaa   28440
```

```
aggaaggcat gcggtgagcc ctagcggtgc ttctagctttt cctgtatcct ggtgagtgtg   28500
ctgcctacag agaggctcac aggttgggtt ttgtttttgtt ttcttcttttt gaaaggggtg   28560 ccatacaaag gaatacctca ttatatttta tgttttttccc attgcagcca gtcagaaatc   28620
ttccaacttg gaagggagaa tgaagtcagt caccaggccg actgggtcat ctgctgaaat   28680
cacttgtgac cttactgtaa taaatgccgt ctacatccac tggtacctac agcaggaggg   28740
gaagacccca cagcatcttc tgcactatga tgtctccaac tcaagggatg tgttggaatc   28800
aggtctcagt cttggaaagt attatactca tacaccgagg aggtggagct ggaatttgag   28860
actgcaaaat ctaattgaaa atgattctgg ggtctattac tgtgccacct ggggcaggca   28920
cagtgattca gatctgccct acaccacact gaacatctgc cttgtggctg cctctggtac   28980
acaagataga gccgcccct ctcatttcct gccaccaaat ttactgtatt ctgaacaaga   29040
gaaagacagc ttaactcctg atctccctcc taatatcaca ctgtcctggc agcagctgca   29100
ccctgttccc tacccctccc ccacaacttt cctgaagatc aagctgccat ctccgggcct   29160
cagttaagca gcctggctga gagtaaggtt ctctcagctc tcctaggaca tggggaggc   29220 ccactcactc tgcttcctat gacagacagg tacaactagg gtccagctgc gaatctagat   29280
attttggaca gcaaatagga aggttattta tactgaatca tttatccagt catggtccag   29340
agatcacagc tgagagtggt gcttattcct tatgtctata acaatataag caatagtata   29400
atgaccacta aaacactagg cctaggtatg cagttgaaca ttctctccct ctgccctccc   29460
ttttattctc tctctctttt ttcttacttc tttgcttgtt tttatttttc tctccctccc   29520
taactccctc cctccatcca tcctttcctc ccttcctccc ttgtttcctt ccatccattc   29580
tccttccttg ttttcctcct tccttccttg tttttctctc tctttctttc cttttttgggt   29640 acataatgag aatactttt ccacaaaatc atttgaaata attttctct atttgttcat   29700 gccaacattt atacagctag tttaactgtt cagttttcat ttttacattt tggaaatttg   29760
ttgtattact ttgttttgtt tcaaatctgt tttgtatata taaaatattt acatggaact   29820
gaagtcaaaa tcataaaagg tgatgcattt gaagattta gcttccattg tagatttctt   29880
gttcctcttt tctccctgac actacaggta acaatatttt tgtcagttca cttgagctgt   29940
ttcactctgt ttgtcatagc agagtatgta ttgtttctat ttcaatgcca tatttatatt   30000
ttcattctga tatttggttt ttatacattt taataaatct tatattttcc tgtgtctgga   30060
ttgtgtgtct tacttctaaa ggtgcacata cttcataagt atgcataaag acgtccatat   30120
catttatttg aatgttttta tgtgttgatt atttaatgat ggcatcattg atccatcagg   30180
aatttttata caataattac tgtattaata acaataatac tggccacgcc cggtggctca   30240
tgcatgtaat cccagcattt ggccagtcca gtcattagga tcacttaggc cgggagtttt   30300
ggacccgctc agccaacatg gtgaaaccct gtctctacta aatatacaaa aaattagccg   30360
gctgttgtgg cgcacacatg taatcccagc tactttggat gctgaggcag gagaatttct   30420
agagccagga aggtgaaggt ttcagtgagc taatatcaca ctactacagt ccagtttggg   30480
caatagagtg agactctgtc tcaaaaaaat gaataatgat aataataata ttgatggtac   30540
atatgggtgc tgacattctg gtagttaatg tactaagcac attgcatgca catttttattt   30600 aatctacaca gaaacttcat taagggttta agtaccgtt gaatgtaaca taagaaattg   30660
gggggttaat taacattccc taagtcatat actttaattt aataatgatg gcaatccaag   30720
ctctgtggtt ctgaaaatga gatttgttaa tttgatttgc attcccccat ctttaggagt   30780
actagcaata tttgacaacg ttataggtca tttatagttc ttcttttgag aatcgccttg   30840
```

```
tgatactctt tgcctattct ccttttggag gattaatttt ttcttattgg ttcgtaagaa  30900
ttaatatata ctattttaga gatactgacc ctttatccaa tgtgttgaag atattactcc  30960
tcatgtgtta ttatttacat ttggcaccta tggtgaattg aactttgaaa aataaaataa  31020
tatctgtcca tttttctagg gtgtctagtt tgatgccagg cttagaaagg ccaatctcac  31080
ctagaacttc tatgcaattc atcatcgttt aagtctaatg attttcattt tattacaact  31140
aaatcactat ttgtaactag taaggtagaa atgcaacaat atttgtttcc atacagtaag  31200
tcaataccaa aaagagaact tattaaataa ttgactattt ccttgtgaat attaatatat  31260
cactttatca catgataaaa tattacatac atgcagctct cttactgcat tttccactgt  31320
gttccatgaa tcttctcatt ctagtgccag tattgccctc tcttcagcac tgtagcttta  31380
tagttctttt cacattctga tgaagtttct ctcattttt tgttttaaga attttctgtg  31440
cattctagtg tgatctcaat cctctccctt cccagtttta aaccgtgaga cttctgtcca  31500
gcaagacttt ttcacgctcc aaggcaggca agcttccctc cttcacaggg acccgagaac  31560
tcagctttca gagctgttcc tgcggaagcc tcatgtcctc cacgtgtgct ccagaggcag  31620
agggagacca actggagccc cttccctttc tcattcccag ctgtgatgac agcagaaact  31680
gcaaaatttg agctaggaca acacaacaac caagagagac attgttctac atctcattat  31740
gcatatttca aacatgtgtc tctatatact tcttacagag gtggtggtaa tctgtgcatg  31800
ccctactgaa ttttcacaat tatattactg tacttgtttt gtcccttat ttccatctgt  31860
gaatccaggt gcactgcaga tattagtctg ctttctgagg gtagggatga caaataaaat  31920
atacaatacc cagggaattt ggaagttcag atatataaca agttttagt tcaagtatgt  31980
tccaaatatt tcatgacatg gcacccagta ctacttaaa aacaaacaag caaacaaaca  32040
aacttacact cctactttaa tgaacaaaaa ttgtctaata aagagatcac acccacagga  32100
ttacaggcac cccccccccc gccccccgcc acacacacac acatttaccct tagagcagag  32160
tccaaggccc accaacacac atgatcctca gtccttttaa taaagaacat tcaaccctcc  32220
tcagagtggc cttgggcagt tgcctccaag tgtccttgca gatgtgaaaa ggaagttggt  32280
tcacagccct aatcagaggc ttcctggcag gacaaggtcc tggcatcagc attagctgct  32340
gcaactctga agggcagggt gtgagcctgc tgtgggactg ccccctccta gggctgggcc  32400
tgctgactcc agggtcagc tttccccata tctgcactcc ctctgctgga ggcctgaact  32460
ctccatgccc ctggctctct tctgcagagg gcctgctctc agctgccaca gagggtgctg  32520
cagaactggc ctgagcagag aggcaggagc tcctctgcag gtcctcccag gcaccaccct  32580
tctggaagga aggcgtggga gtcccctaag acacatcctc agtcacttct ccctgcttgt  32640
gactcaggaa gaccagcctt ccccactgcc ttctgtgcta gggatcactt ccttgttgag  32700
tgggacctga gttttgagag gatcttctgc tcctgttcat ctgggccctt tctttcaaga  32760
ccccagagac gaaggcatgt ggtgggccct agccctgctt ctagctttcc tgtctcttgg  32820
taagtgtgct gcctacagag aggctcacag gttgggtttt gttttggatt tttcttcttt  32880
agcaagggac gccatactaa ggaataccte attatatttt atgttgttcc cattgcagcc  32940
agtcagatat ctactaactt ggaagcgaaa ataaagtcag gcaccaggca gatggggtca  33000
tctgctgtaa tcacctgtga tcttcctgta gaaaatgcct tctacatcca ctggtaccta  33060
cgccaggagg ggaaggcccc acagcatctt ctgtactatg acatctgcaa ctccagggat  33120
atgttggaat caggagtcag tcaggaaagc atgatactta tggaagtaga aggataagct  33180
ggaaatttat acctccaaaa ctaaatgaaa atgcctctgg ggtctattac tgtgccacct  33240
```

```
aggacaggca gagtgattca gacctgctct acaccacact gaatatctgt cttgtggctg   33300
cttctggtac acaagagaga gccgtcccct ctcattcct gccctgaatt tactgtattc   33360
tgtacaaaga gaaacagctt aactcctgat ctcccccta atattacact ctcctgtcag   33420
cagctgtacc ctgttcccca ccctccccca ggactttcct gaagactaag ctgccatctc   33480
agctaagcct cagctaagca gcctggctga gagcaaggtt ttctcagctc tcctaggaca   33540
tgggggaggc ccactcactc tgtttcttag ggtccagctg tgaagcgaga tattttggac   33600
agcaaatggg aagggtattt atactgaatc atgtatccaa tcatggtcca gagatcgcag   33660
ctgagagtgc tgcttactcc ttatgtctat aacaatatag gcaatattat aaataccact   33720
aaaacactag gcctagatat gcagttaaac actctctccc tctgccctcc cttttattct   33780
ctctcctttc ttacttcctt gcttgctttt attattttt cttccctccc tccctccctc   33840
cctctctccc tcccttcctt cctccttt ttcatttctt ccttccttgc ttttctctct   33900
ctttctttcc tttttgggta cataatccga atattttc aacaaaatca tttgaaataa   33960
ttttctttta catgttcatg ccaacattga tatagctagt ttatttgttc agttttcatt   34020
ttaaaatttt agacatttgt tgtattattt tgttttgttt catatttgtt ttgcatatgt   34080
aaactattta catggaacta aagtcataat tttaacgaag atgcatttgg agattttaac   34140
ttacattcta gatttctttt tctctctctt ttttttttt tttttttttt gagacggatt   34200
ctcagtctgt cactcaggct ggagtgcagt ggagcaatct cggctcactg caacctccgc   34260
ctcctgggtt caagagattc tcctacctca gcctcccaag tagctgggat ttcaggtgcc   34320
cgccagcaca tccagctaat ttttgtattt ttggtagaga cagggtttcc tcatgttggc   34380
ctggctggtc tcgaactcct gacctcagat gatccccctg cctcggcctc cctaagtgct   34440
gggattacag gcatgagcaa cctcaccagg ccccattctg gatttctctt tcctcttctc   34500
tccctgaccc tataggtaac aatatttta tcagttcagt tgaacttttt cacttttct   34560 tattcagaac aagtctttca gtattacaga aaagtctttt gtttgtcata gtgcagtata   34620
tattgtttct atttgaccgt catatttata ttttcattct gataaggttt tatacatttt   34680
aatcaatctt ttatcttcca gtgtctagat tttgtgtctt gcctctaaaa gtgcatacac   34740
ttcataagta tgaataaaga agtccatatc atttatttga atgctttat tcatagacta   34800 tttaatgatg gcatctctga tctattggga attttaatac aataattacc gtagtaataa   34860
taatatgcta atgataaaca cgggtactga cattctggta gttactgtac taatcacatt   34920
gcatgtaagt tttatttaat cttcacagaa accccattga ggggttaaag taccattgaa   34980
tacaccagat gagaaataaa gggcttaact aacattccct aagtcatata ctttattcga   35040
tagcaatttc aatccaagcg ctggggttca gaaaatgaga tttgttaatt caatttgcat   35100
tttcttacct gtgtgaatgc tagcattact taacaacttt gtaggccatt tatacttctt   35160
cttttgtcaa ctgccatttc atactcttcg cctattcttc tgttggttat catttttttc   35220
ttattggttt gtaagaatta atacacctca ttttagagat attgatcctt tatcaaatgt   35280
attgaaaata tttctcgtgg tttgctatta ttttcagcac cttttggtga actgaacttt   35340
gtgtactact tttaataaaa cctatcaatt tttctaaggg gtctattttg atgttaggat   35400
cagagaggca aatctcactt acaatatgtg tgcaattcat catggttaaa gtctaatgat   35460
tttctgtttt cagttttatt acaagaaaat ctccatttgt agctggcaac atagtaactt   35520
aagaagattt gtttctggcc gggtgcagtg gctcacgcct gtaatcccag cactttggga   35580
ggctgaggtg ggtgaatcac gagatcagga gatccagact atccggggta acacggtgaa   35640
```

| | | | | | |
|---|---|---|---|---|---|
| acccatctc | tactaaaaat | ataaaaaatt | agctgggcat | gttggcaggt | gcctgtagtc | 35700
| ccagctactg | agaaggctga | ggcaggagaa | tggcgtgaac | ccaggaggcg | gagcttgcag | 35760
| tgagccgaga | ttgtgccacc | gcactccagc | ctggggaca | gagagagact | ctgtctcaaa | 35820
| aaaaaaaaaa | aaaaaaaatt | gtttccatat | ggtaagtcaa | ttcccaaaag | agaacttat | 35880
| acataatcca | gtagtttctc | aaggatatta | acgtacaact | ttatcatgtg | ataaaatatt | 35940
| acatacacat | ggctctcttt | ctggactttc | cagtgtgttc | catgaatctt | ttcattctag | 36000
| tgccagtatt | gccgtctctt | cagcactgta | gctgtatagt | tcttttgaca | ttacagtgga | 36060
| gttactttcc | tttattgctt | ttttgtttta | agggtgttct | atgcattgca | atgtaatggc | 36120
| aaatctctcc | cttctaattt | ttaaaccgtg | agacatcggt | cccagcaagg | attttccagg | 36180
| cttcaaggca | cctgagcttc | cctccttcac | agtgacccca | agaactcagc | tttcagagct | 36240
| gctcctgcgg | cagcctcatg | tcctccacgt | gtgctccaga | ggcagaggga | gaccaaccag | 36300
| agcccctccc | tttctcattc | ccagctgtga | tgacagcaga | aactgaattc | tctgagctaa | 36360
| gccaatacca | caaccaagag | ggatgttgtt | ctacatctta | ttaggaatat | tttaaacatg | 36420
| aatctaaaca | tatttgttat | agaggaggtg | aatatctgtg | tatacactac | tgaatgttcc | 36480
| caattatttt | attctacttg | ttttatcacc | catatcttca | tctatgaatc | caggtgcact | 36540
| gcacatatta | gcctgctttc | caaggataga | gttgccaaat | aaaatatgca | atacccaggt | 36600
| aaattggaag | ttcagataaa | taacaaataa | gttttgagtt | caagtatgta | ccacatattg | 36660
| catatggcac | tgcaccctgt | acttttttt | ttcttttttt | gagacggagt | ctcactctgt | 36720
| tgtccaggct | ggagtgcaat | ggcacaatct | ccgctcactg | caagctccac | ctcccgggtt | 36780
| cacaacattc | tcctgcctca | gcctcctgag | tagctgggac | tacaggtgcc | cacccccaca | 36840
| accggctaat | ttttttgtat | ttttagtaga | gacagggttt | catcgtgtta | gccaggatgg | 36900
| tctcaatctc | ctgacctcgt | gatctgccca | cctcggcctc | ccaaagtgct | gggaatacag | 36960
| gcgtgagcca | atctcacact | cctacttgat | gtggcctttt | tacttgagaa | tgaacagaaa | 37020
| tcctctaaca | aagaggttac | aaacacaagg | tcacacacac | ccctcctga | ccccacaca | 37080
| cccatttacc | attgaggaga | gtccatggcc | gaccaacata | cctgattctc | actcctgttg | 37140
| agaggagggg | ccagctgggc | ttcctgggtc | gagtagggc | tcagcaagct | gtgaaacgca | 37200
| ctcatttcct | gcatcacgac | ttacttcggt | cctggatgaa | taatattgaa | gatatatgct | 37260
| taaaatattc | cgaacaccag | gatttgtgca | tgtgttttct | tccccatgaa | agctatgaac | 37320
| agcgaaaatt | ttcctgtaag | tttccctgtg | ttctctctcc | ctctcttcct | tccccctgcc | 37380
| ccaaaactaa | agtaaaataa | cgttaactgc | ccgttttct | gtaaccagca | gaccttatct | 37440
| atactcccaa | ttccaattcc | ttgtaaacat | actttgtaaa | gtcctgtaag | atcctgtctc | 37500
| ctttgccatg | acgctgcaag | gtcataaagt | agataaaacc | taagttgcaa | ttccggtttt | 37560
| cctcaagatc | taagacatgt | tacaaatggt | taattgcctt | tgtttctcgc | tttggtaaca | 37620
| tcttcccgcc | tcaggtattt | cccgccttga | agagtttaaa | aggcaatcct | ataatctaac | 37680
| tctggctacc | cattctggac | cccctccatg | ctttggaagc | tttgtacttt | cactctgctc | 37740
| aataaagcct | acagctttt | ctctctctcg | gtccgtgttt | ctatcactcg | ctgcggtcag | 37800
| ccgccacacc | aattctatgg | cgtggctagg | caagaacctt | aggtgttaca | ctgttaataa | 37860
| agcaggttca | ggccttctca | gagtggccct | gggtattttg | cctccaagtg | tccttgcgaa | 37920
| tgtgaaaagg | aaagcagttg | aaagaccaaa | tcaagcttcc | tgacaggaca | aggccctgga | 37980
| agcagcatca | actgctgaaa | ctctgaaggg | cagggtgtga | gcctgctgtg | gactgccccg | 38040

```
tcctatggcc ctggccagct ggcgccaggg tcagctttcc ccacatctgc actccctctg   38100
ctggaggcct gagctctcca tgcccctggc tctcttctgc agagggcctg ctctctgctg   38160
ccacaagatg gcgctggaga aggggcctga gcagagaggc aggagctcct ctgcaggtcc   38220
tcccagacac caccccctctg ggaggaaggc tggggagtcc cctaagacag atcctccatc   38280
acttctccct gcctgtgact caggaagacc agctcctcct actgccttct gtgctaggga   38340
acacttcctg tttgagtggg acctgagttt tgaaagcgtc ttctgctcct cttcatctgg   38400
tccctttcct tccaagaccc cagagaggaa ggcatgcggt gggccccagc cctgcttcta   38460
gctttcctgc ctcttggtaa gtgtgctgcc tacagagagg ctgatgggtt ttattttgtt   38520
ctgttttgtt ttctcatttt gcaaggggtg ccgttctaag gagttcctca ttatattttg   38580
tgctgttccc attgcagcca gtcagaaatc ttccaacttg caagggagaa ggaagtcagt   38640
caccaggcca gctgggtcat ctgctgtaat cacttgtgat cttactgtaa taaataccct   38700
ctacatccac tggtacctgc accaggcggg aaggcccca cagcatcttc catactatga   38760
cccctactac tccagggttg tgttggaatc aagaatcagt agaggaaagt attttactta   38820
tgcaagcatg aggaggagct ggaaattgat actgcaaaat ctaattgaaa atgattctgg   38880
atctattact gtgccacctg ggacaggcac agtgattcac acctgcccta caccacactg   38940
aaaatctgcc ttgtgactgc ttctggtaca aagatagac cagcccctc tcatttgttg   39000 ccaccgaatt tactgtattc tgtacaaaga gaaacacagc ataattcctg atctctcccc   39060
taatatcaca ctctcctggc agcagctgca ccttgttccc cacctcccc caggactttc   39120 ctgaagacaa gctgtcatct tcaggcctca gccaagcagc ctggctgaga gcaagactct   39180
ctcagctctc cgaggacatg ggggaggccc actcactctg cttcctcgga ccaacaggta   39240
cacctagggt ccaactgcga agcgagatat tttggacagc aaatgggaag gatatttata   39300
ctgaatcata tatctagaga tcacagctga gagtgttgct tattctttat gtctataaca   39360
atataagcaa tagtataatt accactataa cactaagcct aggtatgcag ttgaacattg   39420
tctccctctg cttttccttt tgtctctctc tctactttct tggttacttg ctattttcct   39480
acacatccct tttctggcc tccctccct ccctccctag ctccctccct agcttgcctt   39540
ccttccttcc ttccttcctt cctttcttcc tccctctctc cttcccttcc ttacttcctt   39600
cctttctttc ttcctcccctc tctccttccc ttccttactt ccttccttc ttcctccctc   39660 cttctcttac ttccttcttt ttttcctttc ttccttttct ctctctttct ttcttttttg   39720
ggcacacaat cagaatacag aatcattctc tatatgttca tgccaacttt gatacagcta   39780
gtttattcgt tcagttttca ttttatatt ttggaaatct gttgtattat tttgatttgt   39840
atatgtaaaa ccttttacatg gaactgaagt caaaattata aaacaagatc aatttagaga   39900
ttttagcttc cattctagaa ttctcttttc tcttctgtgt ctcaccctat aggtaacaat   39960
atctttatta gttcagttga acttttcac ttttcttat ttattcagaa gtctatcact   40020
attacagaaa tacctctttt gcttgtcata tatgtgcagt atgcattatt tctatttgaa   40080
tggcatattt atgtttttgt tctgatattc tgttttata catttcaatc aatctttag   40140 tttctggtgt ctggattttg tgtcctactt ggaaaggtga acatacttca gaagtatgcc   40200
taaagaaatt catatcattt cattaatatt ttattcattt attacttgat atgatctatc   40260
tggaattttt atacaataat tactatagca ataataataa tactgatgat aaatatgggt   40320
actgactttc cggtagttac tgtactaagc acattacatg tatatttat ttaatcttca   40380 cagaaacctt atcaacgggt ttaagtaaca ttgaatatag cagatgagaa agtgaggggt   40440
```

```
taactaacat tccctaagtc atatagttta atttgatagc aattgcaatc caagctctgg    40500
ggttcagaaa atgagatttg ttcattcaat ttgcattttc ttatctttat gaatactagc    40560
attattttac aattttatag gccatttata cttcttcttt tgtgaattgc cttttcatac    40620
tgtttgccta tccttctgtt ggggtattaa ttttttctta tttgtttgta agaattaata    40680
tacaccattt tcgagatatt gatcctttat caaacgtgtt gaaaatattt ctcatcattt    40740
gctattattt attttcagca ccttttggtg aactgaactt tgtatattac ttttaataaa    40800
atctatcaat ttttctaggg tctgtattat gatgtcaggc tcagcgagac caatgtcacc    40860
tacaattagt gtgcaattca tcatcgttta agtctgattt ccttttttca gttttattac    40920
aactaaatct ctatttgtac cttttaagtt agcaacccaa ggatatttgt ttccatatgg    40980
taagtcaatt cccaaaggag aacatagtaa ataatcaagt atttccttgt ggatattaac    41040
atacaacttt atgacatgat aaaatattac atacacgtgg ctctctttct ggactttcca    41100
ctgtgttcca tgaatctttt cagtctagtg ccagtattgt cctctctttg ttgtatctga    41160
atgagttaga gaaaatgcca cactttgaga caaattaaga ttccgtttat ttagccggcg    41220
gccaagagac ggctaatgct caaaattctc tcggccccga agaaagggct agattttctt    41280
ttatactttg gtttggaaag gggaggggtg tctagttaaa acaattttac agaaataaag    41340
taggcaaaaa gttaaaagga taaatggtta caggaaagta aacagttcca ggtgcagggg    41400
ctttaagact attacaaggt catagacttg gggctttggg cgttatcaat cagatggatt    41460
cctgggaatt gcggatatag cttgccacag tatcttatca gttaattgca ttcttggatg    41520
tgctgggagt cagcttgcac aagttaagtc cttgaggaag gggctgccag tgaaagagcc    41580
aagatggagt ctgtctggct ctcttagcta agggagagtc aattcaggtg gaaacaaggc    41640
caggtgatta aaggaaaagg gagagtctaa aaacagggtt agtaaaaaca cggttgggca    41700
ttacatcttc agcactgtag ttttgtagtt cattttatat tccagtggag attgtttctc    41760
tcattacttt tttgtttaa ggattttctg tgcattctaa tgtgatggca gttctctccc    41820
ttctcatttt taaaccatga gagttctgtc ccaggcagga ttttcctggc tccaaggcag    41880
gtgagcttcc ctccttcaca aggaccccaa tgactcagct ttcagagctc ctcccctggc    41940
agcctcaagt cctgtacgtg tggtggagag gcagagggag accaactgga gcccctgcc    42000
tttctcattc ccagctgtga tgtcagcaaa aactgaactc tctgagctag ccaaaacaa    42060
caaccaagag ggacattgtt ctacgtttta tgaatatctt aaacatgtgt ccaaactttt    42120
tttttttttt accgaagtga aaatctgtgt atgcactact gaattttcac aattatttta    42180
ctatacttgt tttatcacct gtatctccat ctatgagtcc aggtccactg cagacatcag    42240
tcagcttttct gaggatacgg ttgctaagta aaatatgcaa tactcaggaa atttggacgt    42300
tcagataaat aacaagtttt tagctgaagt atgtcccaaa tattgcatga catggcaccc    42360
tgtattactt taaaaaaaaa actcacactt ctacttgaat gaacggaaat cctctaataa    42420
agagatcaca cacacaggca tacactccca acacacacac acacacaaac tcacagagga    42480
tcacacaaac acccgcccca cccccacaca cccatttacc ttagaggaga gtccaagacc    42540
caccaacata cctgacctc gatcctgtta ataaagcagg ttcaggccct ctcagagtga    42600
ccctgggtgt tgcctctagt gtccttgcag atgtgaaaag gatggtggtt tagggcccta    42660
atcagaagct tcccggcaga atgagggtct tgcagttgcc ttacttgctg aaactctgaa    42720
gtgctgggtg tgaacctgct gtgagactac ccccttaag gtctgagcct gttaactcca    42780
gggtcagctt ccccacatc tgcactccct ctgctgcagg cctgagctct ctatgcccgg    42840
```

```
agctctcttc cttagagggc ctgctctcag ccgccacaga gggcgctgga gaactggcct    42900
gagcagagag gcagaaactc ctctgcaggt cctcctaggc accacccaga gtcccctaag    42960
acagatcctc aatcacttat ctctgcctgt gaatcaggaa gaccagctcc tcctactgtc    43020
ttctgtgtta gggatcactt ccttgttgag tgggacctga gttttgagag gtcttctgc    43080 tcctcttcgt ctggtcccct acttccaaga ccccagagag gaaggcatgc tgttggctct    43140
agctctgctt ctagctttcc tgcctcctgg taagagtgct gcctacagag aggctcacag    43200
gttttatttt gtttcgtttt gtttattttc ttcttttgca agggatacca tactaagaaa    43260
tgcctcatta cattttgtgt tgttcccatt gcagccagtc agaaatcttc aacttggaa    43320 gggagaacaa agtcagtcac caggccaact gggtcatcag ctgtaatcac ttgtgatctt    43380
cctgtagaaa atgccgtcta cacccactgg tacctacacc aggaggggaa ggccccacag    43440
cgtcttctgt actatgactc ctacaactcc agggttgtgt tggaatcagg aatcagtcga    43500
gaaaagtatc atacttatgc aagcacaggg aagagcctta aatttatact ggaaaatcta    43560
attgaacgtg actctggggt ctattactgt gccacctggg ataggcacag tgattcagac    43620
ctgtgctaca ccacactgaa aatctgcctt gtgactactc ctggtacaca agatagacca    43680
gcctcatctc atttcctgcc catgaattca ctgtattctg tacaaagaga aacacagctt    43740
aactcctcat ctctcccta atatcacact ccctggcgg cagctgcacc ctgttctcca    43800 ccccacctc atgagttacc taaagaccaa actacaatct cccagctgtg tcagccaagc    43860
agccttgctg acagcaaagt tctttcagct cttctatggg ctggtggaga cccattccac    43920
ctgcttccta agacagacaa attcctcaag gactggtctg taagggatt catttaggag    43980 actatatggg aagactagct tcactcaagc atttatccaa ttattgtcta taggctaaaa    44040
tagtgcttat tcattgctca ggataaatgt tggaataaca actttgcact tcagtaagac    44100
atctaacgtg tatcagatct gctatctttt ggacacactg acatttttt ctacataaca    44160 aatcatggta ctattggtct gcaggagaat gggtaaaaaa gtgatagtca taggtacgcc    44220
aacttgtggg tcatatcata ggttttcaac catttcaagc atccctgccc taatgcaagt    44280
atctgaagga tctgaccctt gccctgcagc agaattcatt ccatgtcccc tctggatatt    44340
agactgataa tttggatcag gtctcagcat gggccattga ggaacactac agccctgctg    44400
agagataaaa aggattatcc actcaaggag ttcacacctc cgggccgaca tggagaacgt    44460
gcctagaagc agacttggag ggtgctcagt ggtgggttgt ggaatgtaag cctgaagaag    44520
cagagtttaa ttctacgggg gtgctttcat aatttagtac cctgacaggg ctcctggtgt    44580
tggtccttag acactcctgg gatggctccc tggaaacatg gaggaaacct tggtcgcatg    44640
acatgatacg gagatgttgg agctgcctgg acacagttac agagggaggc attaaaaggc    44700
ttcgagaggt aggcatgcta gagtggactt tcccactaaa cctgagaact cactggataa    44760
ctgtattccc tgcgagagcc cagagaaccc tctgaattag gaaagaaggg catgttctga    44820
aatgggagga atcagcgttc ttgagagtct tggtggaagc tgtgccctgt ggggcagggt    44880
tgactatagg agacgctgtt aaggaattag ctcccaaggg tcaatggaga tgatgtaatt    44940
tcaaaataag agtccaaatg gcagaatta gtgtgagaag acataaagcc agaaaagcag    45000
ccaaggagcc ctgctctaca gaaatctggg gtgacagcta ataaaccaca gtgttcctag    45060
gggtaaggaa attgggctac cacagtggta ttccacatat gtattccata tatacatata    45120
tatctctccc atatatatat atatatatat gagatatata tatgagatat atatgggaga    45180
gatatatatg atatatatga gatatatatg agatatatat gatatatata tgagatatat    45240
```

```
atgagatata gatatgtata tctctctcat atatacataa tacatatctc tctcatatat   45300
atatatatat atatatatat atatatatgt aattggaacg tattaagaga agatgaatga   45360
aagaatgatg tcagctcctc ctgttctcca actcagagtc ctttgaatga aggggaaggc   45420
agattgcctt gagggagaac cttgtaatgt tctagcaagt atatatggca gtgattctcc   45480
gagcctttc ccccaaaaga tcgaagacta gttacctgag aaatttgtac acctagggaa    45540
ggggaataac taggtctttc aaggctgttg gagacggcat ctgagctaac tttgatacca   45600
agaaatgcat actgtcaacg tggtccccca ttagagtgag gacacataga agctcccct    45660
ctaatgctag ttttaaaggc ccaagtctat ctaaaagggc agtcccatag gtggatggac   45720
tgactgtggt ctctaccctg tgtctgagga tatcagagtg gatatgatga atggacataa   45780
aataaggagg ctgccccct accccggat agtccaggca gccttcattc ctttatttca     45840
tttggaaccc atatggctta ttctctttca ctgactggag ctcacagtct ggctattgta   45900
acctgtctta aatcttttc tctttaaaat atcttgactt tgaggcaggt cttagaaaat    45960
gactcttcct gtctcaaaat gcagtccttc attctgattg atgaattgga agcacatggc   46020
tggtgtaaag aataagaaac taattataag ccaggaaaca gcaggagaag aaagcagaga   46080
agcaacgctt accctgaaga attaatttcc gtttagaaaa tatcacagct gatgtgtcaa   46140
aggcccccggt atgcaggaat gagattaaac aaatgtggtc atgaggaaga ggtttctgaa  46200
taatgataga gaagcttgag tctacaagaa atccagagtc cagaatactg caggggagca   46260
gtgctgggtt catgtttatc tggtctcttg tctattggat cctctttctt ccagaaccct   46320
aaaccttgaa tcagccttat agtcctggct cctagaagag tgtttctcaa agtgtactcc   46380
acggaccacc tggataagaa gcacgtgagg cttttaatta aaaaaaaaaa aaaagtaca    46440
ggttctggga agcatccaac acaataagac agaatcttgg aatgaagggt gaaaatgtgc   46500
attttaaaat aacctccaga gctgattctt attcaaactg acttttaaaa actgctgcac   46560
tagtggcaag agatcgaggg gctgtcctga gcctgacaca gaaaggtgtt ctagaaagct   46620
gctcacaggc tccttcgcag cccaccaaat ccgcctcact cttatctccc ccagcccctc   46680
aaagcagctg ctttgacagt ttctcacatt tttgcatgat aatcccacaa ctgcaattcc   46740
ttctggcttc ctgtgacctc acgcaagaaa aagttgtgta ctaaatgaat ctgctttaac   46800
ttgctctcct cctcggggga tcacaccttt ttaagaaagc ctgtccctta ccttgaagca   46860
caaacatatt ctcatttta ttctcccaat accttgaagg ttttcttctg cacatgtatt    46920
tgtttgatct gccttttgtg cgtggggtgg gagttaggta ggaatcttaa agtggagagc   46980
cagtttcttc ccaaattact gacctaaccc atccttaacc cccagttcaa ggccaccttt   47040
gtgatagtga agcttccaca tgctcactca gcccttctg ctctctcttc ttctctactg    47100
tgcatgtcgg cttgtacttt tgccagtttc tctaaagaca caaccagagg tggggtggct   47160
gtgtgtgcac aacttcaact ttacatgtgg ggctgagtcc ctatgttgta tatccttgtg   47220
caaaagcaca atatgttaat tgctatagct tttaaaaaaa taattaatag ttttttcataa  47280
tcaaattttc ttgctttttt gttttttcaa aaaagcatac ttttattgaa gaataaaccc   47340
cttatatatg tacacttatt tataactatg aaccatgaac taggatagaa atgcattgtg   47400
tatattacaa aacataacaa aaataatagg ggtagggagg tgcagatgtt ggtcaaagga   47460
tataaacctg cagttctatg atgaataagt tctggacatc tggaatacag catggtgact   47520
atacttagta atactatatt gtacacttga agcttactga aagagtaaat ctcaagtgtt   47580
ctcaccacac aaacccaaag gtaactatgt tctcaccaca caaacccaaa gggaactatg   47640
```

```
tattaattag cttgattgtg gtaaccattt cacaatgtat acatttgcca aaacattatg    47700
ttgtatacct ggaatatata attttattta tcaattatac ctcaataaag ctgaaagagg    47760
ggattactaa ttcccacaaa atacagattt aacaaaaact tttattcaac aaacagtgct    47820
atgaagttgt aaattggaaa caaaagaaat aaaatttcat ccacagtctt ctcatcaaaa    47880
cccttcagtg gcattcctct ttctggtgtc ccagtcttgt caattttgct ataactgtc     47940
atcctgggaa tacccaattt atcctacatg acaaaatgac aaagtctgat tagatgagtt    48000
ctcagattct agcatggcca gaagagcact gtcctgggtc ggataaatca cgtggaagat    48060
gcaggggatg cgtgacttta aaggtccagc ccttagtccc tggatcttca tgcaggggcc    48120
gcctcagcct ggatctgctc ttcctcacca ctgcagccct atcccacgct ggctgaggtc    48180
tgcttccacc tgggcagtga ctggatgaca tgggatgaga ggacacacct ctccctcgcc    48240
cagcatcgca tttctctttc cctggagatc tgggatcttg gtcagaatcc ttcaaacgcc    48300
acccagggct tgagagggca agccctccta caccttgact gcgttttgcc caagatttcc    48360
cccatattat tattttaaac gtgtctaatt tagacaaata gaacctgtaa gtgctacatt    48420
gagaagagca cagggccacc gaattgggaa gacaagtaga ggaaaggaaa gcaaatgtca    48480
ccagacagaa tgtatggctg caggtttaca gcagattcta ttaaaatcta tggttgggct    48540
gggtgtggtg gttcacccct ctaatctcag cactttggga ggccaaggca gagagatcac    48600
ctgaggtcag gagttcaaga ccagccaggc caacagagca aaaccctgtc tctaccaaaa    48660
atacaaaagt tagcaaggcg tggtggcacg cgcctgtaat cccagctact ggggaggctg    48720
aggcaggaga atctctggaa cccaggaggt ggaagttgca atgagcagag atcacaccac    48780
tgcactccag cctgagctaa agagtgagac cctgtctcaa aaaacaaaca aacaaaaaat    48840
ctatgattgg ctgattggct attgctaaca acttttgagt ctttaatgat cagtaattga    48900
attaaaacgg ttaaaacaac aattgagaga aacatagttt tgaacactga caacacaaaa    48960
taacttatcc atgtaaccaa aagctaccta ttcccccgaa actattgaaa taaacaaaca    49020
aaaaaattag aaagcggaaa ctttacaaaa attattctca ccaatgaggt tgtcccaaatg   49080
tcaccaaatt tattatagaa tagtaataac caaatttgtg catgaatcgg tgatgacata    49140
agtatcttgt aagcattact gaagtttttt tttttctat taaatttacc ttcaagatat     49200
gccttcagga tgaggctttc cactgcactt cattatgcaa tgccatgttg acttggtata    49260
ttacctcaga tgtgactcta atatggtttg atttgttatg acgagactaa aatgaaacat    49320
atcacttttt tcatgtgcat attgcacctt ataagcacaa ggtgcaatta aataaccaat    49380
ttgaatattg aaaacatatg tagttgttat aattttttc tcctctaaaa taatattttc      49440
ttatttctaa aaaatctag aaaatagaga aagattgaag acaaataatt tgcccatttc      49500
cattgctcac tgtctgtatt ttgcactttc tacctgtcat ttccctgcgt tgaccttttc    49560
tgaccatagc tgtcactttc tttcccatta ccctagccca ccctgggct aaaggtctat      49620
agagtgtata aatgatagcc ccagaatatc cctctgtcaa aacgttctgc tagctttgta    49680
tttgaccacc ttctcaccaa ctcagcacaa ccctaagccc tgcatgtgag aatgctgaaa    49740
actggaatca tgactttcag tttttgccat cgaagagaag ctcaggaact gggtctggtc    49800
gtgggagccc agggactcac agcttccctt cccaagccag acccctttc ttgccatgcc      49860
cacaaccttc ccctcatggc catctcttg actactcagg aggtcctggg tgtcattagc      49920
aaagctgaaa atgaaccttc atttcagtag gaactcaagg ctgggtctat ttctccaagc    49980
cttggcagg tgtgtccttc gctggccctt cccaatgcac agtcttcacc atttccaagg    50040
```

-continued

| | | | | | |
|---|---|---|---|---|---|
| acgtgccact | ggcagaggat | gagctggtcc | tgcctccagg | ccctctctgt | ctgctggcct | 50100 |
| gacttagcct | tcttcctttg | gagacacaca | cacactcaca | cacacgcacg | cacacacctg | 50160 |
| gttcttgaaa | actgcattag | tccctataat | ttctactttg | tgtgaacccc | agagatcatt | 50220 |
| tactggaacc | catccagttt | ccaggtgaaa | caacaacacc | ccacatttct | tgagcatggt | 50280 |
| ctatgcagct | gggattgtgc | tgcgtgctct | gctcacattc | tcctgtttac | tgtccatgtg | 50340 |
| gccctatgac | acctctcttt | acagatgagg | aaaagaggt | gaaacaactt | gcccaagact | 50400 |
| acacagctat | catgttattt | tagggcactg | aaaatctcct | tctactagga | cctctgggtg | 50460 |
| acacgctccg | atgctggctc | agacggttgg | catgggtttt | tttagggatt | gctgttttgt | 50520 |
| gtttgtccct | tcctctggag | caagcagcac | actcattgtt | ctctgagtat | aagatggtta | 50580 |
| catgaagcag | aaatttgtca | ccagcctggc | ctggcttctc | tcccaactct | gattctcttt | 50640 |
| aggtattaca | gccttggaaa | agctacttaa | aataacagcc | ttactccttc | atttctaaac | 50700 |
| tgaagataac | atttgtccta | tagagttatt | ttaggattta | ataaagcaat | ggccctaaac | 50760 |
| caattagtgc | agtgcaagag | ttttgctggt | gtccaaccaa | tgattgctat | tattgctaat | 50820 |
| tataccagca | acactctta | agccttttc | agcactctag | ccattggtca | tccctccctt | 50880 |
| caccttgtgg | tcagatttct | gtctctcctc | tggaacttct | ttcttcctcc | cccatttctc | 50940 |
| tcatcagtta | cctccttgca | ccaccaggga | aatagcagtt | caggccctaa | gctggtcgct | 51000 |
| accataactc | aggaaagtgt | ggctcaggtc | catagtttga | acaggtcac | tctgggctcc | 51060 |
| tctcccccag | tcaggatcag | agatatggtg | ggctgccctg | ccttcctttg | ggtcatcctg | 51120 |
| tttccaggtc | agtctcctac | ctaaggacct | gtgtagaggt | ggcgaggctt | tgggacatcc | 51180 |
| ctacctcact | gctctctccc | tgacagctgg | ctggtggctc | atcaggccgg | agcagctggc | 51240 |
| ccatgtcctg | gggcactagg | gaagcttggt | catcctgcag | tgcgtggtcc | gcaccaggat | 51300 |
| cagctacacc | cactggtacc | agcagaaggg | ccaggtccct | gaggcactcc | accagctggc | 51360 |
| catgtccaag | ttggatgtgc | agtgggattc | catcctgaaa | gcagataaaa | tcatagccaa | 51420 |
| ggatggcagc | agctctatct | tggcagtact | gaagttggag | acaggcatcg | agggcatgaa | 51480 |
| ctactgcaca | acctgggccc | tgcgcagcct | tgcatgctgc | cccagcccta | cacaaaagga | 51540 |
| ctcttcctcc | cgatccaaca | aggccttggg | cattttcact | tactcttggt | cccttgggtt | 51600 |
| tccctgtggc | atagaagaaa | aaagtcttat | ccctgtccc | tcacctcccc | atctatcctg | 51660 |
| gaggtccctt | ccccggtccc | actacagatg | aggctttcag | cttgtgcaga | ctcagtgatc | 51720 |
| tatatctcat | cgaaaggggt | ctgtttaaag | atgctccagt | tcagtgtctc | tgaagccttt | 51780 |
| gcaggatgac | ctgtgctcct | gaatgcaggt | gccactagcc | acctgtggct | attgagcatg | 51840 |
| ggaaacatac | caagtgcaat | agtccaagct | gagatgggct | gtgtgtctaa | aatcatattt | 51900 |
| tgaagcttta | gtgttaaaag | tgagataact | cttataatga | tcaaaagttg | aaatgattag | 51960 |
| gtatcttgga | ctaaagccaa | tagcattaaa | actaattta | cctgtttctc | tttacttttt | 52020 |
| ttaatgcagc | aactaaaaaa | attaaagtgt | gtgactcaca | ttggtgactc | atttatttct | 52080 |
| gttggacagt | gctgttagag | actgatcatt | taagaatctg | accatctccc | ctgaagaatg | 52140 |
| cacaaataaa | atattttgga | agagatttca | agggtggagg | acttgctgag | atttaccaca | 52200 |
| aaatggttga | aaagctgaga | ctagaagcct | actcctgttt | ccagcttcca | agctcttggc | 52260 |
| cctgggactg | ttatcatttt | gcaatagagt | cagcaattag | aagcatggga | aacatgactg | 52320 |
| cccacttctc | agtactttca | cccgtgggcg | ggctgcatag | gaactgatgt | gagtagacag | 52380 |
| tcgccatggc | agggtgatgc | agtcctccct | ggatgagaca | tttaccttcc | acttctcctt | 52440 |

```
caacagcacc ccagtgtgga acacgtgtgt atcccaagct tctctagact tttgttctcc   52500
tatctgacaa atgagggggt ttagccaaat gtctgctaag ttatatgact atgattttg    52560
tattaaagca aagccataca cataagatca ctatgcccac taccttcata taaagcagtc   52620
ttttttaaca tagaataaat gaaagaaaaa aaagaaagc ctgtgttact gatcctccag    52680
caccaaacag gaaacccctc tgctgctcta tgtgcagaaa aaaagaaat tctttgaagt    52740
ctaagctgaa tttaaatgcc ttttcaagag aatgcttaat acactgttga tgagaatgta   52800
aattagtaca acttctctag aaaacagtat ggaaatttct caagaacta aaaatagaac    52860
taccattcaa tccagcaatc ccataactgg atatccaccc aaagaaaaat aaatcattat   52920
attagactgc attcatatat ttatcacagc actgttcata atagcaaaaa tatggaatca   52980
acctaaatgt ccattagtgg atggctggat aaagaaaatg tggtatatat acacagtgga   53040
gtactattca tccataataa atgtggtata tacacacaat ggaatactgc ttatccatac   53100
aaaagaatga agtcctgttt tttgcagaaa catggaggaa gctggaggcc attatctaaa   53160
gtgaaacaac tcagaaatag aaagacaaat actggatgtt ctcacttata agtgggagct   53220
aaataatgtg tacaagtgga catagggtgt ggaaccagac attggaggct tgtaagggtg   53280
gtgggggca gaaggaatac agatggaaat taagtaattt cacatcacaa tgagtattat    53340
ccaggtgtgg ggtatactaa aagccaagac tttaccactg tgcattatat gtgtgtaaca   53400
aaattgcact tgtactcctt aaatttatac aaataaaaa caaaggaga atcacttgga    53460
cccaggaggc agggggttgtg gtgagccgag atcgtgccat tgcactccag tctgagcaac   53520
aagaaataaa aaaaaaaac gctacgcctt gcttctgaaa cagcccagcg tctctaacct   53580
ctactgaagg ctcagttcac ggctaaggcc ttccaacttg tgtgagaagg acagaggcca   53640
tacaggagga aactttcatt ctgttttgga gttgttcctt catttcattt ttctaattgt   53700
gctgataaaa ccaaatgggc acagagagga gatgcctcct cttctgcctg cccctctct    53760
cagtgcttta ctccaaacaa gagtaaattt ggtgaaatgg tgactatcag ggtgtggcca   53820
aatggaggcg caagctcccc agtcacctcc ttatggaaca acatctttca tttcctcaag   53880
aggagactct gccactgcag tgaaccttca ccaccacaaa cctccacctt cactcctcac   53940
caacacctgc tgtactcttc atgaatgctg tgagcttgag cgagttctta aatttcctag   54000
ccatcagttt cctcatctcc aaaataaaga aaacagcaat gtccaaaatc aatctccctc   54060
tgaattatac tacctggttt cagcctcaac ctccagggtg atagaccagc ttagagacca   54120
agattttatc tttcctaagt gatctcacct tcagaggcat catcaccaga cttttcaagt   54180
tttgttctct agaaatggtc ccaagttctt tccctctcat cgtctcttgc tttagggagc   54240
ctcccagcta gtctgtctta gcaagacaag ggcatagctg gtgcattgct gctggtgagc   54300
aggggcaagt tcacagaagg cagcatggga gagtataaca gaaatcacca tcagtttcca   54360
agggcttgct ctgtgtcagg cattgcccta aacagtctac ctgggcaaac atttattctt   54420
tgcaacatcc agtaaggtag gctgtgattt tattctcctt tggtagataa gaaaacagag   54480
gcagagagaa ctactcaaag agctcaggct ttgcagcccg atagaattaa tcttaaatct   54540
gtcaccaaca agctgttaaa ccttgaccca ttacctgacc tgctttgagt agggctttgt   54600
gaagattata ctaaatttat ggtattaaac atcataatgg ctacaaactg cttgacacat   54660
taaggcattc actaagtgtc cattgcttgg taactcttta aaaactgtat tttaaatggt   54720
gatgttttgt taacatcaga acgacaaaaa aatactacaa tggccatcca ttccctcact   54780
ccacccttc atctattcaa caaacacctg ggaatagaga gataaacagc acatgatctt    54840
```

```
actcccctgg gaactcttaa ctgtcgttta gaatgagaga gaaatgggta aacaggccaa   54900
gacttgggta ggaggtgcta ggagagagga aggcactagg tggcgtgaag agaaagcaat   54960
ttgaagcatc tccatcctgg acttactggg tgaggtaagc ttcctgggga agactgcctg   55020
gggctgagcc cagaaggata aacaggaatt agccagggaa tgtggagtag aatgcagtcc   55080
aaacacaaaa aaattcaagt caatccatag aagtgggtcg tggaattcca ggcagaaagt   55140
gactaaatga agatgaagg acagggaggg ggtggccaca tcacagagaa cctcttatcc   55200
taagaactct ggacttcatc ttcagaggca aggtagagag agcaaggact ttagagcagg   55260
aaaaggacca ggtcagtcta gtggccatgg ggaaggtggg tgggaggggc cgagatggga   55320
tgtatggagg tgcgtgaggt ggaggcagtg gtgagccagg aaatgtttag gacgtagaat   55380
cctcaggaat tagagtgcgg tgaattagag gggagaattg aggctgatgc tcaagctcct   55440
ggcttgggca atgtgggtag ttatgtcata cagggaactc ggaagaagat atggtttggg   55500
ggaagggaat gagttcactc tggctatgag cagactttgt ttgagatccc atgtcagacg   55560
tacttgaaaa tgtccaagag ttagctggat atgggtacag acagctttcg atttaactga   55620
ggtccgactt aagattttt tttactttat gatggtgcaa aagtgacacg catttggtag   55680
aaaacataat ttgacctttg ctgtttcccc aggacagtga tataaggtta tgatactctc   55740
ttgcgatgct gggcagtggc agtgagctgc agctcccagt gggtaaatta agcatggaaa   55800 tctgaacac agcagctttt aagggatgca ctggggagag cagtttgtaa aaataccttg   55860
ggacggatta aatgtcttgg cttagagaaa gaacaacaga caataggaaa ctgtcattga   55920
ggagaagccg ggattcagga gatgtacatt attcaggtag ctgagggagg ggacaggaac   55980
ctgaatcttc aacagaagca aacaaactgg gatggagggc ccagcctcat gaaggtgacc   56040
agaaggaccc ggtgctgcag gctgtgtggg tagctgagca gagctaagcg gcttgacgga   56100
ccaacatctc tccagctggt tgaagacaag ctctcagaag acaatgctgc atgtcacagc   56160
cccagcaacc aacaacacca gcctgacaac ttgctggggt ggccgccttg tggtctgagg   56220
tggccgtcta aactatgtgg tctgatctca ggctgcagac cttgcaggac tgtcttcaca   56280
cagactggaa gtgctaacag gtggtgagga caccgcttta caacgatgca gggggcccca   56340
tgtcaccctc acccatggga agtttgactt ggtggactca gccaagccac agaggtctaa   56400
cgcttctctg cggtgatttc aggctgccct ggcagaaagc acagtgcctg cagacatgct   56460
gtcactgctc cacacatcaa cgctggcagt ccttggggct cgtaagtagt tttgctcccc   56520
caatcacttt ggactgatat tctctattgt tatatatttt tataaattcc aaattcttgg   56580
tttatttact ccctcccatt tttttcccca gtgtgtgtat atggtgcagg tcacctagag   56640
caacctcaaa tttccagtac taaaacgctg tcaaaaacag cccgcctgga atgtgtggtg   56700
tctggaataa caatttctgc aacatctgta tattggtatc gagagagacc tggtgaagtc   56760
atacagttcc tggtgtccat ttcatatgac ggcactgtca gaaaggaatc cggcattccg   56820
tcaggcaaat ttgaggtgga taggatacct gaaacgtcta catccactct caccattcac   56880
aatgtagaga aacaggacat agctacctac tactgtgcct tgtgggaggt gcacagcagc   56940
agacagtttg agccatccca ttcaataaat gtttattgag tctttgttta taattacgaa   57000
ttgggaagcc acagttacca ccagtgtgct tgtaaacagt ttttaagata aacattcatg   57060
tggtgactct acttggagtt gccaaattcc acatattttc tcaaagcaga agctttgcat   57120
aagtctatac aagtgaccag cctcctcttt ttcagggttg tactctctca ccaacagctt   57180
ttctaggtca cccatgctta ttttttctggt tcaacctctc ctactcatta tatattttt   57240
```

```
ttctggtata atatatacac attttttagtg tgattctttt gtactagtca atatgcatta    57300
cataagttttt ctctgacctt cctatttctc tcgattaaaa aatggatatg acattaaatg    57360
gtattcattt ttctggaggt taacatgtaa caaacgcagc atgatctaac cacgagcagg    57420
gcagactgca atgacaaatc tatcacatgc atgccttgag tggtgatgtt tgattttgta    57480
caaaatccgt aaacacttcc actaatcgaa tctaagtcaa agtccacttt ggattggggt    57540
tgagaaaaa attcatttgc tgcaacctct gcctcccggg ttcaagcgat tcttctacct    57600
cagtttccca agtagctgag actacaggtg cgtgccacca cgcccatcta attttttttgt    57660
attttttaata gagacggggt ttcgccatgt tggccaggat ggtctctatc tcctcctgac    57720
ctcgtgatct gcccacctca gccttccaaa gtgctgggat tacaggcgtg agccaccgtg    57780
cctggtcatc caaccatgag cttttgatag actactctga gccaggcatt atgcacagca    57840
gaaattacaa ggcccatacg ctctgcaaag gcccgaggtt gcttctgttg aaccacattc    57900
tgctactggg ctgccattca ccactaaaat ggcagtcctc aacttgaata taactcatga    57960
ttgtaagtct cttatgaatt ttcgttactt ctagttcaac tcaggctttg caatttatta    58020
ttgttgatgg tgttgtttta atttatgttt ttgccatgaa acccttctctt gaaatgtgat    58080
cttacaaata taaaatagag aaaagtagat ttccactggg aaagagttca gagatgaatg    58140
atccttagtc tcatcttctc aaatttctct gatactttga ttttttcaaca gctcaataat    58200
tatctgagta tacatataat gtacaaagtg gtcaagacct gggcctgtca tgtcagaagg    58260
acataggtcc aaatggggct ctacttacca cggataagct gtgtggcaag gccttgagct    58320
tctctagccc catttcctca cctgtgaggc aatggtcctg tggttatcat atgggtggct    58380
gtgagaactc ctgacatgat gcatttcaag gatttggcct agtgcttggc atattgtgac    58440
agcccagcgt tatctgacaa gagacaaaac tagatacaac aaaaaaataa cagcaagcac    58500
acatatatag tcatgtgtcc cttaacgaca ggaaaacatc ctgagaaatg catcctttgg    58560
caatgtcctt gttgtgcaga tattgtagag tgcccttaac acacacctac atggtacagc    58620
ctactacata cctaggatat atggtatagc ttattgctcc taagctgcaa acctgcatag    58680
catgttgctg tactgaatgc tatatgcgat tgtaacactg ataaatattt gtgtatttaa    58740
acatagcata gaaaaggtac agtaaaaata gaatataaaa aaaatgctac acatgtgtag    58800
ggcagtttca ttataatttg tccatctttg actgaaacat tattattcag cgtatgacta    58860
tatatacaag aaaacataca cacacacaca cacacacata cacacatctg gttttttttt    58920
ttttgagatg gagtttcact cttgttgccc aagctggagt gcaatggcgc gatctcggct    58980
cactgcaacc tctgcctccc aggttcaagc gattctcttg cctcagcctc caagtagctg    59040
ggattacagg cacgcactac catgcccggc taatttttgtg tatctttagt agagatgggg    59100
tttcgccatg ttggccaggc tggtctcgaa ctcctgagct cgtgatcacc ccacctcggc    59160
ctcccaaagt gctgggatta caggcatgag ccaacgcgcc tggcccatat acacatcttt    59220
atatatccag ggcttagtgc tacgtctatc atagtgtggc tattacattt tatagagaga    59280
atagctaagt atgaagaaac tcttacaaga ggttatccca gattaatttta attctaagct    59340
tttggtcatg gttccctaag acctttgact cacacacagc tggacaggac agtggccttg    59400
tgcatagtgc agatgaccat tataggggaa aaacaagtcg aaattcatag tccttttactc   59460
ctcctgccct tctccttttg cttaaggtga gcttcaccag gaacattttc gccacaccaa    59520
aggaaaacta gccagaggca aaccagctct aagttaatat ttgccaatta aatggtttaa    59580
gttttggatt cacagaaaca ctgacagcat cttattagaa tatactgtac tgcatatagt    59640
```

```
agggctcaa tgaatatctg ttgaattgag attgatactt tcattattat tgatgggttc    59700
atttaccta atgggtcaac gcgttgtatg gatggatgcc ctgaatattc tgatgatttg    59760
ggttcgactt ctttctcttt ctacctgagg tgggtgagct acaatgactc tgaataatag   59820
aatcaacatt atattatcta gttaatataa aatctgaata aaatctaagg aaatcttgga   59880
aagcaatatt ttcataaacc atatcatctg ttgccgaact ccccacacat acaagtacta   59940
tggaaaaagt aatgtctact gcccaggagt catcttatag aaaccacaat tctagaagtt   60000
gctgtaccca cctggaaatc catgctgact gttttgtctc gggtgctttt tgctttcagt   60060
cctgtgaagg ggttcacaag aggcagactg gggtagacaa aaaagggca cagactttga    60120
aatgcttatc tccagacatt gcgctcatga gtattttat ctgtgtcatt tctgtacttt    60180
tgaaatggtc aatagaaaaa cacattactt tttaatttta ttttaaaatt gacttaaaaa    60240
aagaattcct gttttataat attaaacata tccctgcaca ttattgagca cctagagaca    60300
atatgtaaaa tgtgttggtt agaaggacct ggaagggggct ctgcttgact acttttttctt  60360
tcctcttctc taacaacgtt tgcttcttgt aaaaagcaaa atcttacctt ttctcctgtt    60420
tcctactgat cactgtgctg agctaaagaa aatgttagtg atttgaatgc tcaaggcagc    60480
ttattgggct tgtatgtctt cctggaacac taggattttt caagcctgta gatcaaaggt    60540
cttgggaaaa aagaaacaac ttttttcagt gagctaactg aaatagaaga gaatggcgac    60600
tcctacccac acctcttgga tcctggacat cagctctggc tgtggggcaa atggcactgc    60660
atattggcca atgtggggag gatgcagcca acttaaggcc cctttttcagg gagggaacgc   60720
tgaccccacg ctcctatttc ccagctgcct gctgatgttt ccattttcta cccccaaaca    60780
acacctgcag gatagggaag accatccatg cagcccaggg cggtcagact tttaaggcag    60840
agttatgtgg aaaatggact tggatgagcc aaggaggaaa tcctgcagat ggcccaataa    60900
gtggattatg tttgacttca gataagtagg acaagctagg gagccagaag gttttattag    60960
ttttgtttca ctttccacaa aaccaccaag gtcccatctc caacagaaca ggatgtgtga    61020
ctgttccttg agtaaaaaaa caggaaactg gacaaatctt gagagatcat cattaattag    61080
tacttctttta gttgatttct taatatggag gagcatgtag attattaata atgcttttgt   61140
tcttgagtta agtgaaggag tcttaggtat ttgttgactc attaaataaa tcaccaacat    61200
gtagtagact caaataagaa acataaaagt gatacacatt tagataaatg attatagtgc    61260
tttatgcttg tagtgcttca tgaatcgata gtatgattaa tccaattgtg ctcgtagtgt    61320
tctttacaac aactaagttt aaaatagaga aacaatctca actctcatta gatgattgag    61380
gatagagaaa tgcctgtcac gttcatgtca agtagaattt atcccctcac ccctgttgct    61440
ataattgatg tgtctcttct gtagatccct aatttaattt cttgtcactt ttaagtcaac    61500
ttttaactag caaattagca aagtgctaag ggattcagag agattgaatc acgtgctata    61560
ctttactgta gtcccgttct ctttatattt tacttataaa ctaaagttac agagtaatta    61620
tcaaaactcc atatttgtgt tctgaaattg gcagaatttg aatttgcagt ccataggtca    61680
gcagatttct ctgactttcc ttattttctt tgcttagcca cagaaaaaca gaaaaatcag    61740
tgagtttaca tgcacagaat taaatgtaca gactattctc tgaaagagct cagttctatg    61800
tgaaaatgaa taatgtaata aatattctta tgagtgtagt aatagtagct attgtttatt    61860
gagtacttct tatgtgcatg gcactttata ctgcatgctt tatgtcattt gagcctaaca    61920
aaatactatc attattatta tctcattttt atagatattt tcttttttta ataaactctt    61980
ttatttgcac gtttgtgtct tgggttattc gtggggtgag aaacctccac acttccaatc    62040
```

```
ccagccatct ggtacaatct ggtgttgtgg tccagctgtc ggcaaagggt agaggtgggt    62100
gcagggctgg ccccccagtc tgcaccaacc tcttcagagc agggagctca gaccatggtt    62160
gtacttgcac tgcttcaggg cctcgctgaa gccttcacac agggacaggt cactctgcgt    62220
ggtcgaacag tccaggaact gccggatctc gtaggcgcag acccatct gcaggggctg     62280 gggggcagcg cgtgtggggg tctgctgggc agcaggctgg acgggctccg agctccccca    62340
tctgaaggct caggtcaggg cgctgcccat gacgtgtccc acagccgagc ccacggctac    62400
ccctgcggcc atggacgcca tctaagccat gaggctcggc tggccggaag gggcggagat    62460
ggggcggctg ccgaggcgg tggctgtgtg ggggcaggtg ggcagagggc gcggcggag    62520 ggggctgggt ggtcggaccg ccgcgctgcg gcttcccaga gacatggtgg cggcggaggg    62580
acccgggcga tcttaaatga cagcgatggc ggcagcggtt ctgtcgcggg acaaatgcc    62640 ctttatagat attttctaag tacagatttg agactttgat aaattaagat acttgatagt    62700
aagcagcgag gctgggatct gaatccaggt ctgtctgact acaaaatcta ttgccttgat    62760
ctcctacagt gatgagaaaa acaaaaccaa acacgaactt ttaaatagag acatttcagg    62820
gggaaataaa aaaatttata attcgtttta tgagttttt ttttttcatt tgcggcctta    62880
agctcctttc cccagggtca catgaagtta gttaaattga tgctaacggt gtttacttac    62940
agacaatctg cagagaattc tctacagaga attttcttat gcaatcaagt ttttctgact    63000
tctgggttct aagatttttt tcttttttta acaagaaaaa aaagcgtaac caaaactgtg    63060
tttattgagc aacagaaaag cagcgagatg gaacacagag atattccccc tgattatcac    63120
ctttccgctg cactcccta cctcagtcc gctggggagc acagaaatgt tatccaaagg    63180
tggatgggaa agggtggaaa ggctgagacc caactgcagc ctggcctgag atggccacat    63240
catgttctgc ttcctgcctg gctgcccagg gagggcctgg atgggcagag ggccaagtca    63300
gtgtcaggct gggaacttta catgcttttc tcacttaaat attgtcatct cctttctcag    63360
aggaggaacc agagattcag agagactctg tagcctccaa gatcacgcag gcatcactag    63420
tagcagagaa gggatgtaga gcaagtgtga cggtccataa gacttactct cttcccacca    63480
caccacactc acccagcaag aactggaata aatgacaagg gagggaagag gggctcagac    63540
ttctctgtat attcacaagg atgtggaatg tgttcctgta agcgtaccca agttgggaat    63600
ttggtccttt aaagaaaaag gttgaagcag gaagacttcc agtttgctgg atgaaacata    63660
atgcagcaat caaacagccc gactcttttg agtgaatatc aataggaata ccactatacc    63720
attcacttgt tcttcaaagg aaaaaatgaa actaatgagt ccttgattcc atgacataga    63780
taaatgttct gagaaggaag aagttaatgg atcactggga aggcttcata gagccagaag    63840
attcaagtaa aagtcttgcc aaacaagaaa aggagaaagt tcattttgt cacagtctgg    63900 ttgcaacagt aaaaactagc ttttgtcatc atcacatttt ctaatatcga aaggacatat    63960
tttaggaaaa agcatcccaa atttataggt atgttgttat ttatagaact tcattttttt    64020
aaatcaaact cttcagtgaa ttaattttta ccacctcctc aggtacagga taaatgggac    64080
atttgcagcc agtttcctcc ttgcccatgt ttgctgcgag gtgggcgtg gatgtgggga    64140 acctctctgg gggaagagga tgggtgcagc agcccgacga ctggtcgtga ggccccacca    64200
caaaaagcct ccactaaaag ggcaatgctg agagccccac cacacctcat gatgggaat     64260 tcctctgtct agagatgtta tttattgtca ttcaagtcaa ggaactaaaa tcctaagaaa    64320
aagagcatac cccaaagcca aactaggcct cctaacagta gctctgtgct catcctgctt    64380
caacaaggag gcagagtaga gaggaaggag gtgaaagata tggaacccac tgagctccca    64440
```

```
ctttattcca ggcgtattat gcacctatct aagccaatgc tggtagatag ggatttcaat    64500
ttcattttca tagttgaggg cactgggtgt cagatagcaa caagtcaagc taacagcagg    64560
ctgaactgga attaaaagca ggactgaatg attgcatgct cgcctgtata gcacactacg    64620
tggatttgct tggcattgaa gaaataggtt ttagttccag ctctaccatt tactagctga    64680
gaggccttac attacccct cttccccatg gggaatccct tcctgcctca aatatattgtt    64740 tggattaaat aagccaatgt ttgtaaaaga gttttggaaa ttgtagacac cataacaaag    64800
taaagagtta tagtttttt taaacacatt ttcattcatt ctaatatgat ttctcatatg    64860
aattatctcc taaggatagt caatatttat ggagctccca ctatagggaa ggcatccttc    64920
ttgatgaaat aaggggcttt aacaatccct acaacttatg actttgactt aacaaaaacg    64980
aaatctagca tgtgttatat gaaagtagca ggtaacaagt ggtctagcaa agctgcagtg    65040
ctatatgctg agtgatagag gtatttgttg taacatccac tccaattcct caagaaaata    65100
gatggtggca aagaagatta agtgatattg ctcattaaat gatgagaatt tttacatact    65160
ggatattcag tgggagtttc attttgtccc aatctccgct gacactctaa gctcaggaga    65220
atggtagtaa tacaaaagaa ggggacaaaa ccagagattc acagtggagg gcaagcccct    65280
ctccagcaga cattggtaat gtctgagaca tttttactg tcacaaacag agtgagaatg    65340
ctactggtat ctagtgagta gaggccagaa gtgttactaa acatcctaca atgcacagga    65400
cagccccaca acaaagaatt atccagccca aaatgtcaat aatgcagagg ctgagaaacc    65460
ctggggtagt tggccatatt tctcaaagac ttgctaagag gtagacaaaa ctgatgactc    65520
caacctttgg ctcatgagct atatccaggc taattacagt aagagctttc ctggggactc    65580
taattttgca aagactttct ctgaaaagca ctgttgggat ttccctggaa acccctcct    65640 ctcccagtga ggaggtgatg aggtagctct tctacttcca caccaaatag gactctcagg    65700
tcctacatcc accatgggtc cagagcagag ccctgtgtgt gggtcatgga agtgttgggt    65760
ctgtgccgtg agcgtttggt ggccagataa accagtgagg actctcacct ggaaaagtgg    65820
acaggtggct tcaggtcata gcccacgtgg taacttggac caactctccc ctgaaatcag    65880
ttagataatc atgatgaaat aataatgg aaaagaatc tttctaaaag tttctaagag    65940
ttagcaagat aacaaggtga ataactttta ccctggcaaa tggactgatt atcatggtgt    66000
catacagcta tgggtaaagt tcccatgtga tcctgaccaa tcagcaacct cagaaatgac    66060
tgatctgggc gcagggccta aggacaccca ttttctctgt gaacactctt tgaggttccc    66120
cttcctcatc ctggtgcagc ttctcctgct ccaggttccc tatttcctca gccttgtctc    66180
aggcactcag cctgagcaga cgggacgtca cagctacaga tatgcacctg ttcttcactc    66240
tgggaatgtg aacttgttct cctacttctc agattggctg agggattttt ttgaaaatga    66300
atgtctcatt tcttgataac tttggtttca ttgaaaatgc tattttgttt ctaattgaaa    66360
ttgggtaaaa acaattgaag caagtaaaaa tctttatttc attagcagaa atgaagcata    66420
tattttcact gtagggtatt tagatagaac ttttcataca cactcaggta ctgaccaaca    66480
ccaaatcagg cttttgagga tttgatattt acttggaaaa aaaccctgtt ccaggtcaat    66540
tacaggcaaa gagctgcaac catatataaa attctgtata taaattctct atataaaatt    66600
ctgtctactt ccctttagtt cttaatataa aattcctaga aaaatagaaa gacatgatga    66660
cccaatataa tggcccccag gaaactagca tgacattgga gctgaggtaa tgggcacttg    66720
ccccattatc atgtctgcga ccacatcctt cccaatgtgg aagagcctcg tccagccctc    66780
tgccccagct aggcctcagc ctcagcttgc agcacttcct gtgttcctca gatgatgcct    66840
```

```
ctgtgatcac aggaaaccag aaagggagtc tgatgactat caatttcacc ccacaaatgc   66900
cagtacctat accccccaagt gtctgatttg acatcatttc ctattgactt aggttcctat   66960
ttagagacta tgtttgttga aactgcatga ttatttcaga gagaaagcaa ggtccattat   67020
atcatttctt agaaacttct agtcatggtg aattgctcag ggtgaagatg ccagcaagga   67080
acaagatgga attcatatcc actcagttcc cactggctgc cagaaaatgg gatagatgtt   67140
ctacatattc agaatttcag gtgattgtca taagaacctg gtaaataaac ttattcatga   67200
aagaaataac tgatgtttag acaggggcag ttatctgtcc aaacaaatag ttcatgctct   67260
ttcaagtgca ctattgggcc actttgaata cccttgggt ttattaactt aatggaaata   67320
gggccagggg cagtggctca ggcttataat tccagcgctt tcagaggctg aggcaggcag   67380
atcatttgtc ctcaggaatt caagaccagc ctgggcaaca tggtgaaact ccatctctac   67440
aaaaacacaa aaattaacca ggtgtggtgg agcttgcctg tagtctcagc tattccggaa   67500
gctgaggtgg gaggatcact tgagcccagg aggcagaggt tgcagagaga caagattgca   67560
gcactgcact ccagcctggg atacagagca agactctgtc tcaaaacaa acaaacaaaa   67620 ctttatagga atgaactgtg gcatttgtgg gtaattatgc gctggcccgg acttactgcc   67680
tagtcctgca gagctaggtc aagacagaat gggcagtgac tcaagacaga atgggcagtg   67740
actcaagaag ccatggctaa agggtcatgc tgaacacaca tttggaagag ttcccacccc   67800
ccaccccacc cccaccctgc tccccaccgg cattctgcct taggacccttc cttctcactg   67860 gagggggaaaa ggctaagaaa acagaaaacc ctctctgttc ttgtgaactt gctttagcag   67920
ataatatcat gggtgggata cctggagagg gatcaaaacc tcacagccca gacttaagta   67980
aatgatcaaa atgtgtaatg aggatcatgt tttggaaatg tggccaacat attttttattc   68040 tctaaaataa atcatgtcac cttttgtcct ttctttattg tagctaatcc atgatattta   68100
ctacccatag aaagagatgg tagttgccca gaacaaactc actttttttt tttttttttt   68160 tttttttga gatgaagtgt tactctgtcg cccaggctag agtgcagcgc acaggcgccc   68220
gccaccacgc ctggctaatt ttttttgtt tgtttgtttt tagcagagac ggggtttcac   68280
cgtgttagcc aggatggtct caatctcctg acctcgtgat acgcccgcct cagcctccta   68340
aagtgctggg attacaggcg taagccacca cagcctgcca caaactcact ttttgaatta   68400
attgtgagat gttgggcttg aaaatcaggt tcaattttt tttaaagagt tttctatagt   68460
tgtgattctc tcattcatag gtcaaaaggc cacactggca agtaacaac acagaatttt   68520 attacagctg ctagatatga agactcagca tatgatatcg gtgacgttaa taccttccca   68580
gggagaagcg ctgttccttc tggctgggaa gtgcgagccg gtgggggag agagaggagt   68640 agagcattat gtgaggtac ttcccggttc ccttgcgtct gagggtctta tgccagaggg   68700
gatagaaagc ccaacagaaa ctcaagatag aagaaggaga atctgcgagt gtctgtctcc   68760
tgtcaagctt ccctaataca gccctggtag aacttcatca acagtggaag gcatttgcaa   68820
aggtgagccc aaaccagcac cccttttccac acaggctgtc catgtagaag gcccagatgc   68880
ttctcagggt ctctgagagg atacaaagct actgaggggg ccagagggca cagcacctgg   68940
gatttggatg agaagctgca ggaagggaac tttgcacccc aagggcatgg tgtggagtca   69000
atagtggcaa gttcagtctg gttttttaca tcagccggtt cagaggaaga gtgaaatccc   69060
caagatcagc agggcaaaat gctggaagtt gtcgaggatg cagagagtag caggaagaca   69120
cctctgagaa ctcactcaca caccctgccc ctgtgtagag atgtcatcct ggggatgaga   69180
aggaggaaga cagagaaacg cagaaaagcc taagcaggca ccacaaagag accgagcccg   69240
```

```
tctgaaagag gctgctctaa cctggtggaa actattttaa gttggtaagt ttagtgcctc   69300
cccacaatat cagaacgagc aagagacgac aggtataggt tgtgtacatt tccsctctgc   69360
gttgaatgat agcgtgtgcg tgttccacca ctgtgccctg ctcaaagtta gctgggtggc   69420
tgtgccctgc tcaaagtcac ttgggtgagg ggcgcccgtg ggagccaaaa atcccatctt   69480
acacccaccc cctgcacact ctggagttgg gctgtgacat gctggagaaa ggtgtctttg   69540
tctaattatt ctgcctaagg gcatgccttt tgttaattag taaaaggaag ccttatttgt   69600
gctctgcaga gtgggggtgc tgtttaggag gtaattcgtg atagaaccac acagacaaga   69660
tagattcaat ttaaataaat tgaatctatg aagcttccta accccatgga aacacaaaat   69720
tagtttacac aaaaataatc attaaagaac taatgaaaat aatgtttgaa ttcagccacc   69780
agacattaca ttccagagcc ttgagaaaaa ctgatgaaaa aaaagtcatg aaaaaaagtc   69840
attcgcacaa gtgacaccat ggtgtgaagt caaggagcac agactctgga gtcagagggc   69900
ttgagtcaac ctgagcatct tcagcttgga ctgtgaagac acagctttga ctctctgtgt   69960
tgcagagatg gtagtgccca ctccagtgac gcttgtgagg attagttgag ataataaata   70020
caaaatgctg agcatcaaac ctagagtaga gaaaggtctc aagtaagtac tcattaccag   70080
tatttgttat ttaatttcac ttttgtctac attcccttgt gtgaaatggt ttggataatt   70140
aattaaggaa aactttccct cagggacatt gctgatattg caatcttcac tagatacact   70200
tatctctacc tccgcctcca cctccacctt cacctccatc tcttctctgt ctctatctct   70260
atcttcctgt tgtttatcta tctaattatt tataaatgaa ctggtgggtt tgttgttgtt   70320
gcagcctggc taatgttatc cagacatatc tgaaacctca tgagtggcat ggaatggcag   70380
tccctgcttg aaccatttac ctccctttcct aacaccaaca atcacacaca cctgacactg   70440
acctgaagcc tctggcctgt cctcggaggc aaagactggg tagacaagat gcctggttac   70500
cagcaatctt ctgcaatttc ctctgagcta ttgagattgc ttttctcttt gctcaaatta   70560
tgtgagaaac ttttaaaaaa gaatttaatg tgctcttttg atatttcagg tgttcattca   70620
aaagcctatg ttattctctg tctctctgtc tcttttccta gttgggtaat caaaatggca   70680
caatcagaaa tatttatatc tgcaacagaa aagaagaata aatttattca tgcacaagta   70740
cattatgtac atatatatgt ttgtgtatac atatatctgt ataattgata tatttgggag   70800
aaataaaagg tttcattaag cacacaagtt ctagagttag accctctgtc gcaaattact   70860
gtcctgtcac ttaactcctg ccagaacaaa gtgcatactt gaacaaaatg cctgctctgt   70920
aaaaatgcct tgatcttgaa taaaatgcct gctaggtcaa agcttctatt ttcccaccta   70980
gaaaatggga acaataataa gaatcctcac ttaatagata atggaaaaag ttgcttgcag   71040
cacagagcct gctacagaca atgccttcaa ttaatgcaaa ctattaatat tatgaaaagt   71100
gagtatctgt tttctgacaa tgttttcaat aatataaatt ctgcctttgt tcactttatt   71160
tgtttgaaaa aacaaataaa aaaccaaaca aaaaagtgtc ttaaaagtgt ccatttgtct   71220
ttcttcttga ctcctagtaa cgctttcctg tgtttaggga attttcacct catgggtttt   71280
ggtgagtgaa tgaattcatc tccctctaca gaaaagaaga atgcctgatg catttttctca   71340 gcctttattc caggtagtca ggtagactat ggactccagc aattagatac actcctcaca   71400 accccctccat tacacacaca cacacacaca cacacacaca cacacacacg   71460
gctgctggag ttgcagggtc tggaaggaac tgtctggcag ggatggagtg tgcagggtgc   71520
ctagtgagtt ccagcgtggc cgtggctgcc ctggctgtgg cagcaccagg gctctaagcc   71580
gggccctgca gactggctca atctgcagca tgggcgctct ctcttacttc ccattcccag   71640
```

```
gacacatcct gtgcagggga agagtgagtc cttctagttg tagccacagg cccattggtc   71700
tgctgacctc cacctcctca atattcgact ccccagcatt gagtgtctca aaaacagtat   71760
ttttcagaaa agagggtgaa cagggcaact gctttaggag gagccatccg agccagctgc   71820
ttcctctcct gtctcctagg gaggacccaa gctgtcggag ttcatacctg tcccacaaaa   71880
cacgagccag agctggacaa aagtgacagg acaaccact gtccaaggtt aagtgagccc    71940
tgaggcacca gaagatctcc aagaaagcca catggaaatc ataaaatgga gctgaatgga   72000
ggaaaagaga agttctgtaa tgtggaaaaa tgaagtacta acaatatttg actgttttcc   72060
cttgatttag ccaggttact acttcaaaac agtcagcaaa gcattttaac aatgaaagct   72120
gttggggaaa ttaaatggct ggaagtggag ggaaactgtg cattgtggtg catgcctgtt   72180
gtcctagcta ctcaagaggc tgaggcagga gggtggcttg agcccaggaa ttcaaggctg   72240
cagtgagcca tgatcacacc actgcactcc agcctggcca acatagcaag accctatctc   72300
tacaaaaata aaataagaa gtggagggga gataaaaatg tagtggtagg agtagtagta    72360
ataatatcta ataattactg aaaatttact atatgtcagg aactatacta ggtgtactta   72420
gctatttagt ctgcataaaa ttttaatacc agtgttatta ttgtatccat tttcagatga   72480
gagatttgag gcacaaagag attaagaagt ttgcacaggg tcagacagcc cctatgtgat   72540
aaagatgaac agttagacat taaaacatgt tttggttggg tgcagtggct cacgcctgta   72600
atcccagcac tttgggaagc tgaggtgggt ggactgcttg agctcagaag tcggaggcca   72660
gcctgggcaa catggtgaaa ccccgtctct acaaaaaata caaaattagc caggcatggt   72720
ggtgtgcacc tgtattccca gttactcaag aggctgggga tgaaaggatt gcttgagcct   72780
cagaggttga ggctgcagtg agccatgagt gtgccactgc actccagggt gggtgacaga   72840
acaagatctt gtctcaaaaa atatatgtaa agaaaaaatt ctccaatgac atgggaagtt   72900
gctcagaata taagctgaac tgaaagaata cagaacacta tacatgtaaa tatatctata   72960
gtccataaaa tcatattaat attcatgtat ccaaaatgaa aatatctaca agtgagcata   73020
tgataatgtg aatagtagtg ggcctttgtg atatgaccgt agatgttttt attgttatct   73080
ttccccattg ctctgagttt cttcaatgag cactgttacc agcatgttct acctatcagc   73140
tgtgtgactt ctgtggagtt gatgactctg tgcctcattc cctcatccaa aaaatgaaaa   73200
ttccaagtac ccatattaag tgatcattgt gaagattaga aggtgaaaaa cgtttagaaa   73260
aaaaaaaggc tagcaaatag aaaatgctca ataagtattt gctattataa aagttaatgt   73320
ttattaaata tgcaacaatt taaaatatta tgctgaggaa aagtgttcac gaacaactcc   73380
taggcaatta gaaatccttc tcatttccac agaaattaag caaccccat ggcccctca    73440 cattcgtgca gagaacacca tcgagattgc tagcctgatt tgagataagc agggtgagca   73500
ggaggggggc tcagtgctga gcctgcagga ggcactgaag ggcccaaaaa accatttct   73560 ttctctcccc agttcaggcc acaccctcca gaacctgacc agagtcgtct agccaccagg   73620
tccgcacttt cctgccttct ccttgggtac accgccccga agacaggatg tcactgctgg   73680
aagcatttgc cttctcctcc tgggctcctg agttgctgtc cgaacatttc agtctagctg   73740
cgtgaccaaa atcattcttc aatgtttccc tcttctactg tcagatgttc attggaaatt   73800
ctcctctttt acttacagtt ggacttggat tatcaaaagt ggagcagttc cagctatcca   73860
tttccacgga agtcaagaaa agtattgaca taccttgcaa gatatcgagc acaaggtttg   73920
aaacagatgt cattcactgg taccggcaga accaaatca ggctttggag cacctgatct    73980
atattgtctc aacaaaatcc gcagctcgac gcagcatggg taagacaagc aacaaagtgg   74040
```

-continued

```
aggcaagaaa gaattctcaa actctcactt caatccttac catcaagtcc gtagagaaag   74100
aagacatggc cgtttactac tgtgctgcgt gggattacac catactagaa ctgttgaaac   74160
aacatgcaca aaatcccctc ccagggtctg tgcccaccac atccttccca acaggggcaa   74220
ccacagccag tccccagctg ggctcccaga ctcaggctcg ccttctctga ggctcttccg   74280 gggcttttcca ggaagctgtt atgggttata ccttcgttcc cacctgatcc caggacttgt   74340
gctccagaat ctttatttga cactgtttct taatgcatta aagacttgtc tggggactga   74400
gagaacatag gtcgtgccac tgtccatcat atcaccacct agagacttcc agtaagtagc   74460
aaggtgcagt tgagacaggg atccttatta cgtacagtca agacaacccc cctgcaatat   74520
aactatcact ggcccagttt acaatgaaag aaatgaaagc ttagagaact gaggttgcat   74580
gatctgccag acaagtcatg tctttgagct ggtctatgag accacaccga acagtttaag   74640
gattgcaatt ctctaagtaa atgctaggat atctgggata aattcgggaa ggagtaagtg   74700 ccctttttttc tgggaggggt agggaggaga atttgcctgc atgagatcgt cagaatagag   74760
ctccaagtca tcccaggggc cattggatga gacccttcat gttggaataa cctttggtct   74820
tacctgtaaa ggaagagaga attgtatcgt gtgtgtgtgt gtgtgtgtgt gtgtgtgtgt   74880
gtaagttctc tacagtgttc tcaattcttt gcatatatta gctcctttaa cccacactac   74940
ctatagtgtc tgctctgttg ttctcatcaa acatatctaa ctcctgaaat aagtggagta   75000
ttagttcatg cacttgtcca aatcacagag ctgataggtg gcaggacagc ctagggaggg   75060
acccaggtaa tctggttcct cttgaatatg acactaaact gcttctgaat cacaggagta   75120
taaaagaaaa gacacattgt tcctgtcccc atggaggaga cagaactgac catcatggaa   75180
cagtaactga cacacattac taccgtgtgc tgaaacttgt gcccagggtt ccagtgatta   75240
ggtgtattca gagaacaagt aaaatgccaa taaagtacca aatgactttt ctttcttttt   75300 ttttttttt gagactgagt ctcgctctgt cgcccaggct ggagtgcagt ggcgccatct   75360
ccactcactg caagctccgc ctcccgggtt gaccccattc tcctgcctca gcctcccgag   75420
tagctgggac tactggcgcc cgccaccacg cccagctaat ttttttgtatt tttagtagag   75480 acggggtttc actgtgttag ccaggattgt ctcgatctct tgacttcgtg atccgccagc   75540
cttggcctcc caaagtgctg ggattacagg cgtgagccac tgcacccggc caccgattga   75600
cttttcaata taaaaacata agaaatttgg gttttccata tctaggtacg tgacaggtac   75660
tgttatctat acttcatgtt cattatcatt attatgtgat catgtaaatt tcttaagtct   75720
ctggaagcca tttaggcact tatagatgta gaactgagac ctaaagatttt caaataactc   75780 agctgatgtt agatagggta agtagtctag aagggtgcat attgtcatag gtcattaata   75840
gtaatattca gatgagcttt tgaaggacct gatatatttt taaatataaa attaaaagat   75900
cagaatataa aactgtaaat gtaaaaccca ttaaaaaacg tttaatcatg gctgggtgca   75960
gtggttcacg cctgaaatcc cagcacttgg ggaggccagg gtgggcggat cacgaggtaa   76020
ggagtttgaa accagcctgg ccaatatagt aaaacacgtt tctactaaaa atacaaaaat   76080
tagccgggtg tggtggtgca cgcctgtggt cccagctact caggaggctg aggcaggaga   76140
attgcttgaa tccgggaagt ggaggttgct gtgagccgag atcgtgccac tgtactccag   76200
tctgggtgac agagcaagac tctgtctaaa agaaaaaaaa aatttaatcc tgtgatcctg   76260
tgtaatgatc caaacaaata tattactatc tacaaatgtg tagagaacat gcttaaaagt   76320
aaattctgat tgctcttatt ttctttattt taattaacta attaatgttc tactagagtc   76380
ttctcaaaat attttcatca ttttgcaaca tttggtcagg ttttcttcag tgaggattgg   76440
```

```
gtagttatcc aagctcccat gtttaccaac tttgtgatct gggacgtcat gcgtgccaca   76500
ctgttcttgt ctatcagaga gagataataa taccactgcc tctcaacgct ggtgagaagt   76560
gtgaaggaag taatggaaga aaacgtttag aacaatgtta gcaagtctac aatagatgtt   76620
tgatataacg ttaattttaa aggcttatga ttacacataa aaatgaactt tatttaaaaa   76680 caccectctc tgtgacatag tgttcatgag atagttctga agtccaaggt gagttcccac   76740
agactgccct gtcggtccct ccagcaattt caatcaagtt tcctcttgag gtgcaccctc   76800
tttataagtg aaattggatt tctctgagtt ataatctgca ttgtgacatc ccaattaatt   76860
ataaaccaaa tactttactg tatttcaaac agaaatgact atagcttttt aaatgaggta   76920
tgaataatgc tagtgtaaaa tttcagtttg ccttttttaa aattgtaaaa tactgtccat   76980
gttttatact cctgagtcct gcatccccaa aacattaaca gagggatcaa ttttacgtg    77040 aggtaaagaa agttatatgc ttatatatct ggaaaaatat tgtacagtct gaaaatcaag   77100
gagagaacag ctaagtttga agcagaatta gttcaactcc agagctgctc ccatcccttt   77160
ccacagacac attcttgtca ggtaatgcac cctacacccc gtcagtggtc agtgtaatgc   77220
tcctgggaac tgctcagctc ttcagtaggc catgaagtcc ccagagggca cctgacccac   77280 cacattttc tctctcacca agtcatgcca tgctgtctcc ccactgactg gggccagcca   77340
gcaaccaggg tccttctcct ggggatatgg ctcagcagac agcaggatgt ccctgctgag   77400
aatattcata ttttctccc tctgcagcgg tgagttgctc ctcaattatt tcaacataga    77460
tgagagatga aagtgattct ttttttcttt tattttaaga cagtctcgtt ctttcaccca   77520
ggctggagtg cagtggtgtg atctcagctc acttcaacct ctgcctcctg ggttcaagca   77580
attctctctt gtgcttcagc ctccaaagta gctaagatta caggcatgcg ccactgtgcc   77640
tagcttattt ttttattttt agtagaggca gggttttgcc atgttggtca ggctggtctc   77700
gatctcctgg cctcatgtga tctgccctcc ttggcctccc aaagtactgt gattacagtc   77760
atgagccacc acacctggcc agatgaaagt gtttcattat catttcctct ttctatgtcc   77820
caggttcatg gggatttctc ttttttgttt gcagttgaac ttggtaagtt aaatttaaag   77880
caataaaaaa tgtcaactac attttgtca acagagcaac agataaaagt gtctaggtat    77940
cttgtgtggt gtccactgaa gactttgtaa atatagttat acactggtac cagcagaaac   78000
tgaatctaaa ttatgagcca tctgacaaat atcacttcaa taacaagccc cagttcgagt   78060
ttgcttaggt gagaaaaaca agaaacttga ggcaagaaca aattttcaaa tgtctacttc   78120
agtctttacc ataaacttca taggaaagga agatgaggcc atttactact gcactgctta   78180
ggacccacag catcagtgcc acactgtccc acacaacaac ctctgttggg tctctgccca   78240
accacatcct tcccatggga gcaaactcta tggactccta gctgggctcc caccctcagc   78300
cttgccttct ctgcggcact tctggatctt tctgggaagc catcttgggt taatgcttta   78360
agcaggaagc atgcctgatc atgacgttcc cagatattca ttgaacacta cttcctaatg   78420
aattaaggtt tggcctggga atgagtggac acaggctaag gtcccattcc tgtcagcatc   78480
cagataattc tattaactgc aaacggctta ggccaaggga gagaatcgtt gtgtatagga   78540
atcccatata taattatttc aacacctctg caacagaact attatttgcc cattttaata   78600
aagaaattaa agcttacaag ttcaaaatga ctggtcgaag ttgagaagtg catgtttttt   78660
gttttttaaa actggatcat gaggccacct tgaatatcta aaagtcacag ttgtacaaca   78720
gactctttga ggtgactttg gggtggagca agtgtctttt ttctgtagag aagaagatgg   78780
ttcctcactt cacactaagg ggtgtgacag tgtgatatca tcagaaaaga gccccaggca   78840
```

```
tcggactgtt aaatgagcca tactttgcat ttattaactc ctttaacctc tggcaacctc    78900
tgaggtctgt tctgttatga acagaagtgc attttactca ggtaagtgag atctatttgt    78960
cctagccact catccaggtc acacagctgg ttcatggcag tgtaggattg gacccagcta    79020
gtctggctcc agagtctgta ctcctcagtc acagaagggt aaagagaagt acattgttcc    79080
tactcccatg gagaagacaa tactgacaac ttctgtaaaa catttactgg cacaattatt    79140
attttgaact gaatcaggtg accagaattt gagcaattag gaatccttgt tgaataagtg    79200
aaataccaat aaattatcca tttttttcaaa atataaagtg atacaaattc gattatttta    79260
tgatgccatc tctaaaataa ttgagaaaga aatgaagaat acctttaatc catgtacttt    79320
tcctatagca gtacatacta ggcaccccca tggaaaaata tagataccac cttgcattcg    79380
tgccacgtgt tgtcttactt attcgataat ttccaaggtc aggacaacat attcatcctc    79440
atcatcccct tttccaagga gccaggaagg ctactgaagg aaataaaggg ggttccagga    79500
aaggctgacc tggggctgga atcagacaat ccgtcatcct ttatcctccc accccgatgc    79560
actcagcctt ttgtgatcca catcctgtct gtgtaattcc tgaccatcat attccctcag    79620
ggtgggccac acttggtttc ttgaacctat atgggccttt acttgttaac tttaatatta    79680
gctaaagtag acagtaagat ctgaggaaaa acacagcgaa tctgagagga taagctgttt    79740
tcagacaggg atgcatagac aggcttgcgg aaatacttgt gtcaccctct tctcgtggtt    79800
gtctcatcta ctactcaaaa cagcctcaga gagcagcaat gaggtatcca ctgccagatc    79860
cctgtgtcca gatcatagag cagagctctc ctgcagcctt tcaggcatca gactaaatgg    79920
tgagaaacag agaaagagat actagattca tagtgcattc aaatgacaga atactatgca    79980
gcctgtgaaa atgatattgt atgcatttat taataaaatt caaacatctt cacaatacaa    80040
tgtaaagaaa agttcttgaa gtgtacaaaa cctcttaaaa atataaatgt ctgtgttgat    80100
agaataattt tttaaaaaca gaaagaaatt atccaaaatt ttagaataat tattcccgag    80160
ggataaatta tttaaattat tctatgtact tttactaatt tttatatatt ttcttaagtg    80220
agatactaag gctttgttgt aagatatact taacaaagta attttctctt gtttggtagt    80280
aatactaaga cacgataacg tcattaagga ctcatgctgt gccaggtact gatatctgag    80340
tattttatgc attaccattg tgtaacacga taatataagc cccttagtac ctctagaaga    80400
tatatatgta ggcaaggtac acatgtagaa actgaggccc aagagcttaa ataactcagc    80460
ccacattcta tagggttaag tggtatagga gtgtttaatt gtattcggtc actaaaaata    80520
atgtgcacat agactcaaga cctgcagtat tgctcatgat aataaagtaa ccaaaataag    80580
agagtataaa gccaaatatg taaatcccac cgaaatatat acatatatca tatgtataaa    80640
taataccaag ccattctatt tcttttttaa aaattttaa cttttaagtt ctgaggtaca    80700
tgtgcaggat gtgcatgttt gttacatagg taaacgtgtg ctgtgtggtt tgttgcacct    80760
atcaacccat cacctaggta ctgagcccag catgcattag ctattttttcc taatgctatc    80820
cttccccaca ccctgcccgc caataggccc cagtgtgtgt tgtttctctc cctgtgtcca    80880
tgtgttctca tcattaagct cccacttata aatgcggaca tgcagtgttt ggctttctgt    80940
tcctgcatta gtttgctgag gataatggct ttcagctcat ccgttttcct gtgaaggaca    81000
tgatctcctt ccattttatg gctgcatagt actccatggt atatatgtac cataatttct    81060
ttatccaatc tatcattgat gggcatttgg gttaatacca tgtctttgct accgtgaata    81120
gtgctgcaat gaacaatacc aagctattct atttccaacc ataaatatgt tgagaaaaat    81180
tcaaaggaaa agtaaatgat gggtgccttt tgttgtcaat tttatatct cattttactc    81240
```

```
agattttcct taacggatga ctgctactca cctgagttct tatgtttacc agctctgtgt   81300
ttttgaatga gtcactcaaa ctctgtttgc cgttgtcctc atttgacaca tggagataat   81360
cataaaactt actgcacagg actgttgaga ggatcaagta aaataatata agaaaacatc   81420
tagacaagta gcaagttgta aatggatatt agatgcttgt caagtttctt actgcagttc   81480
tgaattaaca gctaattaca gaaagatagt cattgggaca gaacactgca ggtttatctt   81540
cacattttca aagccatatt tctgcaatat ggtactgctg gggaatggga gagtgggcaa   81600
gagaacatcc ctgccccacc cctagaggta cacattcata ctaggtattt ctttccagat   81660
agttaaccca cttacccgat ctgcccagca ctcatgggat gcaggaaacc ctggaactgc   81720
tcataactgt agcagctcat gaagaaccct aaggaaccac ctcatctagt acttctgaga   81780
gacctcaaca gccccgcctt ctgccactga cttgagacct ccagtgaaca gggttacctt   81840
ctccctgggg aaccagactg gcagaaagca tgccactggt agtagctgtt atcttcttct   81900
ccctctgggt ttgtgagttg cccctaatc atttcagtct acagaagaga ttgaagtcat   81960
tctgtattat tacctcttca cgtatcgttg gcttatggga atttctcttc acttgcaatt   82020
gcacttgggc agttggaaca acctgaaata tctatttcca gaccagcaaa taagagtgcc   82080
cacatatctt ggaaggcatc catccaaggc tttagcagta aaatcataca ctggtactgg   82140
cagaaaccaa acaaaggctt agaatattta ttacatgtct tcttgacaat ctctgctcaa   82200
gattgctcag gtgggaagac taagaaactt gaggtaagta aaaatgctca cacttccact   82260
tccactttga aaataaagtt cttagagaaa gaagatgagg tggtgtacca ctgtgcctgc   82320
tggattaggc accacagtgt tagagttgtc aagataacct acacagaaac tatctccgag   82380
tctgtgcctg tccacatcct tctccatgtg ggcaaccaca gcggtttgct cagctgggtg   82440
cccagccgga gcctgccctc cctgcagctc ttctggaatg ttgcaggaag acatcttaga   82500
ttctgctccc ttggtgtgca gaatcacatt ggtgattcat ggtgtccaaa cgggaaaagt   82560
tttcttgttc cctctcaggg cgtgcgataa ggatgtggct cccttcttgg tgcccctctc   82620
ctcaaacctc taggggagc atgcacacgt gcaggttgtg gggctccgac cccacagcag   82680
tgtctagggg tgaatgctta taactcctga ggccccagtg ggcctgtgtt acaaggtgtc   82740
cttttagttt ggctgtccat aggtgacttg ctttagccag ctcaattaga ccccctgcct   82800
tattgcaagg acgagggct ttctgtatcc ctgggtttct tgccttggtg tactgaaaga   82860
attggataac atgtgggctt ggagaatgag tgcaagtttt ttattttgt ttttgttttg   82920 agacggagtc tcgctttgtc gcctgggctg gagtgcagtg gcgcaatctc ggctcacgca   82980
agctccgcct cccgggttca cgccattctc ctgggcagtc tcccgagtag ctgggactac   83040
aggcgccccc caccatgcct ggctaatttt ttgtattttt agtagagacg gggtttcacc   83100
gtgttagcca ggattgtctc gaactcctga cctcgtgatc tgcccacctc ggcctcccaa   83160
agtgctggga ttacaggtgt gagccaccgc gcctggccga gtgcaaggtt ttattgagtg   83220
gaagtagctc ttagcagatg ggggagccag acgggagatg gagtgggaag gtggttttcc   83280
cctggagttg actgctcagc ggccaggctt tcctccaacc accccgccaa actctgcttt   83340
gttctgccag tcgatggcct gcagcccgcc agtctcgcca aactctgctt tgttctgcca   83400
gtcgatggcc tgcagcccgc cagtctctgt aggtgtgctt ttccacatta gtgttcctct   83460
cgatgtccag ccacttgtgt gtgtgcccac tagggtctca ggggttttat aggcacaaga   83520
tggaggcgtg gcgggccagg gtggtcttgg gaaatgcaac atttgggcgt ggaggcagga   83580
gtgcctgtcc tcacctaggt ccgtgggcac aggcctggga gtggggccct cgacagggac   83640
```

```
cacgtccttc ctttccctgc acttccctcc cccaatccca tatcagtgtc agcaattagg   83700
atccaaatta gggacatttt gacactattt cctacaacat taggatatct gggaactctg   83760
aaaatacaga gtgggtggct tagagcaaaa ttcatctgtc tagtaattcg ctacgtagag   83820
atttctagta actggttcag aatgaaagta ggaagcagta tatattttac atagatattc   83880
cctgctgtta tcattatttt cccatttggt tcatgagcat tggaggtttt caaagttaga   83940
gtgatctgtc aaacatagta actgtgtgct ttttattcgc acctgaggcc atcctgaaga   84000
aatctaggga caagtaagta gatctgtaag taaacaatca cctgtttggg gtatatgaga   84060
gatgaaagta taaatcctgt gtcctagagg aagagcatgc agctcacttc acactcaggg   84120
ctcagtgctg ggacaaaaca agcactgtgc agtggaaccc agctcctagg cacagtgggg   84180
gatctcagga tgggggctat gctttggaga tcttgtcttt cagggttctg caaagaaaac   84240
taaaaatcct gagtaaaata ggattagata gttaagaaga aagataatac atgcttcctg   84300
catcggtaaa ggaaataacc ataataatac ccctcagaaa ttaataaata agaaataatg   84360
attgacaatt attttatgtt tattccatga ttaatcattg ggtggttggg aactttcaaa   84420
aaataatgaa acaaaatata aaactgtaaa actgtaaaag tcctctctca cttctttgaa   84480
actttcaaac aacaaattaa tgatgaaaaa tccggagttt caaagatttt ctcctattta   84540
tacctttagt actatggata tctgacagca tattgccata catgcagtct acttacagtc   84600
cttgaagtaa ttgcaacgta ttttttctcc attctcccct ctgagaatca gcttgtacca   84660
tcctgatagg ataagaggag aaatgctatt gaaagcccaa tgagggaata ccaggagcct   84720
ccatggcagg tcagcccctt tccaggtgca gactcagaat ctggagtccc gcatcctgtc   84780
cgccatgatt cctgaccatg gtggtccaca gggagaatga cctgagcgcc tgagtgagtc   84840
ctcaacagac ctcacctctc acctgatgca tacataaaag caaagggaag aagattgtta   84900
aggaaataca gagcctgaga acatgaactt ttcaagaaat aggtgaatga aaagatggaa   84960
ttcagctttt cacaatgtca gtgttaagta ttttacatgg attattttat ttaatcctca   85020
aaagagcagt gtagagtgac tgtagtggcc acacaaggtc aggtcttaga agatgcagtc   85080
actttgactt tttaagagac tcctgggaga tttatgggga agaaaactta gagacacact   85140
agagtgagga agaggaagga aagagacacc gtatctgtgt gaatttaaag taatgaaata   85200
ctatgtagca attaagcagt gttttttgaag aactataagt aaaattgaaa atattcacca   85260
tgtatttagc aggaggatat tgaacacaga actgatttaa atagtaagct ctcatgtaca   85320
tacatgtata tattgaagaa cgagcaaaag gaaaaaaatt ctccaaagtt taaagagtgg   85380
gtgtctctga aaggatgggt gattttaaca tcttcttggt acttgcacag attttacaca   85440
ttgtaacaaa aagctgctac tactttttaaa gatgtatgcc ataatggctt caatatttta   85500
ttgattcatg catttaataa tgaaactgtt tatataacaa cataaaatat aactatatat   85560
ggcacactta aaattatttt tatgttttttc cacttaatca tatcactact ctatagctct   85620
cagaaaaaaa aaaacaaaaa taccaacctt catgttaata ctggttacta ttgagcagaa   85680
ggtcagcaaa ctatgtctat gaccagcagt ctccagtttt gtaaataaag ttttattgaa   85740
atacaaccat gcctatttat ttatatattg tttatggctg cttttgctag ctgcttttgc   85800
acttgaatgg tagagtacat tcagtcagtc ttcactatct gtgcattaaa tacctgcgaa   85860
ttcaaccaac agtggatcaa aaatatttga aaaaataaa aaattacaat acagcaataa   85920
aaataataca aataaaaaca atataatata gcaactacat acatagtatt tacattgtat   85980
taggtattat acataattag agatgatttg aagtgtagag gaggatgtgc atttgttata   86040
```

```
tgcaggtact atgccatttt atatcaggga cttgagcata catggatttt ggtatctgtc   86100 gggatcctg gaacaaatcc cctgaagatt ctgagagatg actgtagcta taacagagac   86160
ccacaaagcc caaatatttt attatttggg tctttacaga aaatgatttt cagtcactgt   86220
cctagagtga tagactcatg agtgacattt attcatattt agtgtttccc aatttctcaa   86280
tttttcttta atgacccttt gttacacatc caccctcccc atattagctg tgtgacttca   86340
gataaattag ttagcatata tttgattcat tttcctaatt gtaaaatgga gaacataata   86400
atgattactc aaataaactg ttgagaaaag taacttaaat aatacaaata aagttcttgc   86460
aagtgcttgg ggcatgccta atgctcaaca aattgaagca ctacattaat catatgagtt   86520
attattgcat attagaaaat aaaattattt agactaatac tctaagtcct tggtactcaa   86580
agtttgattt gtgaaccagc agcattggct tcacttagga gcttctttta aatccagtca   86640
gtcaagcctc agcccaggcc tactgcgtca gaagctcttt tcagaaggtc cctcctacat   86700
actatggtgt ggggagtggg agtctaaggg ccaaactgtt caagatataa gctccacagt   86760
ctggtacaag tgcaagccaa tcccatttcc ataggatggt tgtgtctagt gtcctctcta   86820
atttctggag agcaatattg aactgatatt tggcctctct ggggctgaaa tagatggcat   86880
cctcccaatt aattaaacaa atatactcaa ttgtccacgt atatgtactt ttatttttcat   86940 ttataaaatt tgttataaaa tcagcacaaa ttttcagtat tttatatagt gagaaataca   87000
ggtgttttat aaccttgagt tttagatcca cattcaaccc acaggaagag taattttgc    87060 tttgagtaca aaatacatat cactgtatcc tcatatccac atatcacata tcctcatatc   87120
actagggcta ctgaaaaacg aaataggagg caacagggaa ggggagagaa attgaagtta   87180
attgccactg tcaccactca cccacacctc acccttcata ggaagagttc tcctctaacc   87240
atcaccatat tgccagatct cctgggcact ggagtattta gagggccagc catttcagat   87300
ctgacaacgc tgcactctac agaaagggtt gtcaggaat cactgtgacc cactacttct    87360
ttccctgaca cctgctcaga ccaagctacc cttgccacac actaaacatt ctaggcacag   87420
gcatcctcac tttcctgctt cttcttggga acacagcctg gcagaccaga gcatgtcagc   87480
accaggagca tgtagggatt caccttgggg tttgctccag tcatttcact ttgtatatca   87540
ggtgaagaaa ttctttatca cttcatcttt acatatcagg tgttcatgag aattaatttt   87600 cttttgcttac agttattctc agggcgttaa agttggcaca aatttaaaat acccagggca   87660
aaagataagg atgctttat accttgtaaa atatccagcc aagactaaaa atgaagtcaa   87720
atactggtgt cagctgaaac ctaagtcggc attggatgtg tgttgacaat cgcacctgct   87780
cagggtccat taggtgttgt ggcttacaat gatgctcatc cttccacttc aaccttgaaa   87840
gtaaatttca caaacatgaa gatgaggtca tttactgctg tgattattga gcccactggg   87900
catcaagcac acacttccct gccttctcct tgggacacag caggatgtcg ttgctggaag   87960
catcatcttt tcctctctct ggactcttac gggttcccca tcattttgac tcttgaggag   88020
agagcaagta aattatttaa tggtgcatct ttatacctca ggtcttcata tggatttctc   88080
ttctttgctt acagcttgtt ttggatacaa gaaattggag caacctgaaa tattaatttc   88140
cagagaaaaa tattaaaagt ccaaatacta tctggggtgg tatctagccg cttatactgg   88200
ctgagacata acttgatgca ttttcctcaa caacatgacc ctctcaattc acttaggggc   88260
tgtagctgaa aatgatgttc ctagatctgt tttgacctac aagataaatt ctcaggaaaa   88320
aggaaatgga gatagttatg tgcttgctgg aatcacagat gagagatgtc aggacacccg   88380
cacagaatcc ctctttaggt ctgtgtgtac cagccccctt ccaacaggag cataggctta   88440
```

```
gcagggttgt cagggttgga ctgcacctcc caggacttcc ccttcaacct ctggaaactt    88500
gattatgttc acacattagg acatacagaa atcagtgtac tctgtgctca aggtccaggg    88560
attacctgaa agtttatatg atccagactc aaagagggaa tcactgagtg gcaggaaacg    88620
tgctgggtat cttacacatc ttatataacc attgcaatac tttcgcaatg tcatcttcat    88680
ttttttccac tttaatatga ataatttgaa agataaaat accttcttaa accccaaatg     88740
cccatgtttc ctcagctgtg tcctgtgacc ttgaagaagt tagcattcat ttgctccact    88800
catgttgggg gtgagtgtga aatgaagctc ctgccctctc ctcaggctca ttccactctg    88860
agggatcctc ctacagtcca gccagcacac ttcctttgca caggtctcag atcctcctag    88920
ggaagggagg gggcattaga tgatccaccg acaaggtgga tccccaccag gatggatcct    88980
cttcccggct tctgcctgtg attgcagcag ccgtttattc agggtactct gctccctctt    89040
gggcactgct ctaaatcctt tacatgtaac tcatctcatc cttgggacat cttttcacat    89100
tggtctgttg tgattctcat cttacggggg aggaaacaga ggcagagcga tgtgatttac    89160
tttgtggtca gagttcttaa ctgggggggg ggaggggctg gggttctggc ttcagcgtct    89220
gtcctcgtaa ccacgctgtg tcctgactct gagagaggag gtaaaaatag catctaatat    89280
gtggtctcta cggctagaaa gaaaactgat aggaaattaa actagacatt ttagtgaaat    89340
tataaaggct gaatgcagac tagtgggaga gtgtgagccg ctgggggcca aaattttagg    89400
gaatttccca ccatcttta gacttttct ccaggaaccc tatgcaggct cttgcaggga     89460
agagcatgga gaatccagag aaagctcccc tttttggtac tggcttagaa ggggaacagt    89520
agccactgtc taaattcacc cagacctacc ccacctcttc tccactgtag aaggacttaa    89580
tctgcaagag aaggtttcta tggaatttca tttagttga gggagggaaa aggaagccac      89640
catcaactct gcccaatact ttatccctat ctccacagag taatgagttt taatgtgcag    89700
aagggtgggt gtcaaaatca tagcccaagg acactggtgg gtgcctccta tgactggaaa    89760
tgtgccacct ctggaataag agcagcaaca gttgtgaagt tacattctca agtcccggtt    89820
tgaccctgcc tgtttaagac agaagctgaa tgaaaatagc agagaatggc tcccttcctc    89880
acctcaccac catactacct tgagcaaaag caacagtaga atgcagtgaa gagagcttca    89940
aaagacagac tgtctctggg gagcagaaca aagggatggc tcaaagccaa gaacaaggga    90000
tgattagaga aatctaaagt ctctaatgtc ctatgaagaa caaactccaa tccagacaac    90060
ttagtagcaa caacaaactt ctaacccagt ctaactccta actagattaa cacaaactcc    90120
cacactaaag gtctggcaga aagaaagatg caggcatttt ttttttcttt tttcttttt     90180 cttttttttt ttttttttga ggcggagtct tgctctgtca cccaggctag agtgcagtgg    90240
ctgatctcag ctcactgcaa cctctacctc ccgggttcga gtgatttacc tgcctcagcc    90300
tcccgagtag ctgggactat aggcatgcgt caccatgcct ggctaatctt tctatttta     90360 gtagagacgg ggttttacc atattggcca ggatggtctc aatctcttga cctcgtgatc      90420
tgcccacctt ggcctcccaa agtgctggga ttacaggcat gaaccagcgt gcctggccaa    90480
tgtaggcatt tttaagcatc aaatatagtt atctcagtat ctactgtgtt atacaacatc    90540
gtcccctttc aataaaaaaa tctaagtacc ttaccccaaa acaagaagga acacagtctt    90600
gaagccacaa agcaatcata cgcatcggac tctgatatga ctcagatgtt tgagctgtca    90660
ggcagggagt ttaaaataac tgatgagtat gttaaaggct ctaatggaaa aggtagacaa    90720
catgcaaggt cagacagaga atttcagcaa agagacagca attacataaa aaaattcaaa    90780
tgaaaatgca agacataaaa aaaaaacaca gtaacagaaa tcaagaatgc ctttgaaggg    90840
```

```
ctcaccagta gaccctatgg agataaggaa agatttggtt aacataaaga taggccacta   90900
gatatgaccc aaactgcaat gcaaggagat gagaaagaaa gaacaggaga gaaagcatat   90960
cttcatggaa gaacagaact gtggacaata tcatattttc aaacatattt gtaactagaa   91020
tccctgaaac aaaagagaca aagagcagaa caaatatttg aaaaaataat ggctgagagt   91080
attccaaatg tagtgataga taccaaacca cagaacaaaa aagctaggaa aacaccaacc   91140
aggataaata ttaaaaacag aacaaaatac ctagacatat tagatttaaa ctgttgaaaa   91200
ccaaaaataa agagaaactc ttgaaggtag ctagagggaa aaaagcagat tttccatctg   91260
aaaccacgca agcaagaaga cattggagtg aaatctacaa agtgttaaat gaaaaaactg   91320
tcacttggca taaagacagc ttcagacaaa ataaaaactg agagaattca ttgccagcag   91380
ttgcacttca caagaaatgt ctgaagttat tcaggcaaaa aaaaaaaaaa tgatatgggt   91440
caaaaacttg aattcacaca aggaaatgat aagaactgga aataaaataa atgaaggtaa   91500
aacatagtcc tttaaacctt aattgctcta aaacaggagt tggcaaacta tttttgcaaa   91560
ggacccaata gtaaatatat tctacgttgg tggacaacat agtctctgtt gtaactacac   91620
aaatgggcta ttgcaacaca aaagtccttg ctactcttaa gtctggaggg acatggaact   91680
gttataacaa ccgggagggt atctgtattg aaagggacac agccaaccgg tcttagtttg   91740
agttcccccca ggaagtgagc ctcaggcttt gaggacagct agtttgtttg ggagacacag   91800
gaagactagt aggagagtga ggagatgatg ttaagaaaag gaaggcagat aattaaatta   91860
ctttcattaa ttagatacta aatgagcaac aggaacctca tagaagttca aaacctaaca   91920
gatcaattaa atcataattt cttgtttttc tgttccttta attcgtggga ctggccatgt   91980
aaaataaata aaatctgcag accctatgt gatctgatgg ttagtgtggt agtgaaccag   92040
ggaatcttgc taagtgtcag aacgtgataa gaaagtaacc acagagcaga aaaatattcc   92100
tggtgttacc ttaagttata aagacagagc ttaaaatcga gcacacatat tatatctatg   92160
tgaagcaaat gaaaaagatg agcagatatt agcctgtaag ggaatacacc aaactgttaa   92220
tagtagttgt ctctggttgg tggggacaaa aagtgactgt tttctctgca tttctttctg   92280
acccatctac ccatgttgtc ttcccatagc tatttactgc cctttgtttc tacagcttcc   92340
taactgttct gaaatccctt actaatcaga gcagtttccc tggtatgccc atcacacata   92400
tgggcatgtg ggacatagag attagctttt tttctgacta gattagtaaa ttcttataat   92460
agaaggacct gctgaaccaa ggctggaatt tcctactctt cactctgaaa gctggaacca   92520
atcccaaggg gctggccaca cacttggttc aaattgggta gtcctggcct gctttctgcc   92580
ttcttagagt gacctaggac ttgttcatgt ccaaggcctt accagccaca cctagaaaat   92640
agcaagaaca atagtagcaa ccatatctat accattacat ttagctcagt acctctcttt   92700
ttggatgtct gacaagtagc caaaaaaatt attgattcca attccactcc cttcccccaa   92760
tctccaagca tgtattattt tcctccccag actttcctat tgcagtaaat ggcaacagta   92820
tattgtatca tctgatggaa tggcaagggt gttttctcaa gcagatagtg ttttgttgac   92880
ttctgtgttt tttgttctc ctagtaatga gagaagagtg cagagaccca actattactg   92940
agtttcctgt gatatgagat ctgaagggag tttacaggag ctcttgaagc tatggtttca   93000
cctgcgagaa agacacccac aaaccaggcc caaccctgtg tggtccaatc tgagactgga   93060
gtaggctgtc tcaacagagc ccctgaccga aacactacag acccaatgca gggaagaccc   93120
agtcttctct ctaacttact gcaggtttag aaactctttg tgttccccct gacatgtgca   93180
gggcaatagg ccagccatga cggcaatgat tgtcattctg aagtgcatgg cccaaatggc   93240
```

```
cccatggatg tataatctcc tggtgtcact gaaagacaaa taaaaagaaa gtaaattgtg   93300
agatataatt tgatattcag attcaactag ccccgctcct cacagattat tttgctaggt   93360
gttgtcactg actactcaat gcttttagga atatgcaaat caaccatttc atctgctttt   93420
tatttcgttt aatatgttct gtgattccta gaaagcaata cccagcatcc tctatatggc   93480
catttgagat acagattctc tatattatac agacctagac tatacttggg aactgcgttc   93540
cttccacaca tatctctcca actgtgaagt aattgatgaa cagggtttgg gatctggaaa   93600
acttgaactg aaatcctggc tcagtttgaa ctccctaatt ctgtttcctc acatgacttt   93660
taatggtaat aaccatttat agggtaaagc agaaagagat aaatgcatag ttagtgcctg   93720
actcatggta gacactatat ttatgagttt tcttctcttt cactatcaga aagcacaggc   93780
ccatggattg tcatcctgca gcaggggggaa ggtaagtgaa aaggagattt ggggcttaga   93840
gtagcatatc aatttctcaa gacatttttc cagacacgag tctttatgc aaacatttct   93900 tgtttgccaa aaagaaacaa gtgtttcacc aggcatgttt gcctgtggga gcagtatcag   93960
ttgaaaagta tctataaatc tacaatatgc atagtggcat gttaagtacc ccaagtgcaa   94020
aagaaaccct aaaagactaa atcttcaggt taagaatgaa gacaggtggc acaattgcta   94080
aaagggagaa tctgattgaa agtgcagtga cccggcctct cccaaacact gccctggtgt   94140
ttttagaaac aagtgaagat ccactggact atattgtaac atatctgata ttatctaagt   94200
gatgacatat gtgaaatcaa attatgctaa tttatgaaag ttagtggtcc acagattgtc   94260
agtatgtgat tttttttatct cttgtacatg tcagataatg tgttttttttt tgcttcagag   94320 ggtggtctct ctcagaagtg tcttaactta ctgctgtacc tgatttaatt aagatccact   94380
acaatttctg aaagataaac caatgtgaaa aaaatgtgca aattattatt ttggttcatg   94440
ttggcaacca aaccctgaaa tgaaatgtga gatatatttt cgtatctttt gatggtctaa   94500
caaatttggt tgaagctgtt ctctatgaaa attattatca tcagacttga aaaagtgatg   94560
caaaacttca agcaatgcag tatcaacttg tgctttacct cacttgactt acttgttatt   94620
tatatatttg ttcattcata acccatcttc ttggaagcag gatttaagtt gcctcagttt   94680
gttaactcaa gacatgacaa atgtggcggg gaggatgtat gtgttccaaa acacagggtt   94740
agaggcgaaa ctgcttatct ttatacacat tcatttgggt ttcattttac gcctttagta   94800
aaactgaaca tcatggtctt cacatagttc tttttttttg taaacttaat aaaatatgtt   94860
ataattcatt acttactttt tacattgtat tacttaaatc tttcatggct gttgaaatgt   94920
agacagcttc taagacttct gatacttccc cacatggttc tggaataagg aaaagcagag   94980
gacaaagagg gattgaatgg gcatcatccc atctatgaca ggtgcaaagg gtaattgaca   95040
gtacgaagta acaataactt attattttca gataaaaaga cacagaaata agatcttttcc   95100 attctacctt atgaagtgaa gtctctctgt ctgaattatt acataaatga taagagaaaa   95160
ttaaacagtt tttagcccct actgtgtccc atgctcgatt ataaatatcg tacaaaagtc   95220
ctgggaaata ggtctaattc tctccattta aaagatgagg aaacccaggc tctgagaagt   95280
gtgtgtgccc aagggcacat caccaggagt ggaagaactg gaatctgaac ctgggttttc   95340
caattttaaa gtgtctttttt cttcattccc aacttcctga gataataatt tatttcataa   95400 gaatcccttta aaagctcgag taaacttgtt aatgtttatt gctgcagcca ctctgtccat   95460
ctccaccatc actgcaacaa ttcaggtcct ggttgcctct tattggatta tggcgaccac   95520
ctataaaacc atctgcttca gccaaattgc tgtcctgggg agcgccccttt cctttctgct   95580 tgcacatcta tctttctcca gtgcaaatgt gatcatgtca ctttcctctc taaatttttt   95640
```

```
agcaagtcct cattgtctat tctttcaaaa acatttattt gaaaatacta taaaaataga   95700
aaattttcca catgcttact tcctaaaaat taatgtgtta agtttctcct accccatttc   95760
catcccatgc cccttactc aatggataca ataaatctcc aatatgttcc ttctggccac    95820
gtgttgcttt gtaattttaa ttttaatcta tttggaccct gtgttatctg ggatgaggta   95880
gagtggtatt tttatttct aaggtaatta ttttcctaat gcccgtttcc aaacaatcca    95940
tcatttcctt tcaatttaaa aatgctgcag cgtgttttaa atatgcacac atatttgaca   96000
cattttctgg agaatttctg ttttatttgt ctgtttcatt attcttacat cattatcata   96060
ttatctcagt agctttgtga taaaaattaa gatctactat gccaaatgtc tattcactgt   96120
accatttttc agaaaatctt tttcaatcat ctcatattta ttcactcctg tagaatttaa   96180
aatcaactta tctagcccaa cattaaacct cacagcctag aacaacaaca acatgtcgta   96240
gtaattctga ctggaattgc tggaaattta tagatgaatt taggatgtat tggcctcttt   96300
atgataggag cttttattc atcaatgtat gtttctccat ttatttaggt tttattttat    96360
gcccttagga aaactaaaca ctgtgttctt catatcattc ttgtattttt ttggtaaatt   96420
taataaaaga ttttataatt cattactttt ccacatttta ttagttaaat ccttcatggc   96480
tcttgaaata ttgacagctg ctaagacttc tgatgcttcg cctcatggtc ctgaaataag   96540
gaaggccaga ggacaagaag agattgagcg ggcgtcattc catctatcac aggtgtaaag   96600
ggtcattgac agcgccacat aataattttg aattttctat taagaagaaa cccttttccaa  96660 acataatttt cacccagccc cattgtcctc tccattgaat tgggggctgt gagctgctgt   96720
gtatggacag gtaccctctg tgacctcatt catatcttcc tgaatgagga ctcaggggac   96780
ttaggctgga gcagggtgga tctggagtgg acatggaggt tgtcaaggct tgtcctcctc   96840
agcccttgca agtgaacacc tcatctgtac tcaggagatc acacagctga ccccggctta   96900
agatggcaga ttttcaaca tattagataa ctggatttgt tttttttggt catgcctcag    96960
tataattaaa gaatgtatta tttcatggga gatagaattc tacaaatttc ttctattatt   97020
ccaggagaaa taataagtca ttgcagaaca cattttttca tttggcattg ccttggtaaa   97080
gcatcatgtt gccaaatgat aaaagtggct ttttgaaagt ggagaccgtt gttcaaattt   97140
ctcaagtata tctgcattga cacatttgca ttttcagtta ctaaagagct tcctcctttc   97200
agaagtatct tcccaaattg ctagcagaga ggctctggtg tttgtgggaa cagaagggct   97260
tttcctttga tgtaatctca aagcagtttc aacacaattg aacccctgga aaaaaaaag    97320 acaattctct gaatactttt cctggtaatt tagaaaagca gtgggttgac ccattaaacc   97380
tgctgttttc tcttcctgct ttttttttc catttcccctt ttctgttggt gcttttcaag   97440
aattactgcc ttagaagaaa acaggcaatt tatgaggaaa aattacaaac tatcacatgt   97500
cacaaaacct atattcaagg acttccaaaa aagccagaag atgaaattgc tagttcaaag   97560
ttgttggatt gctagtcgtg tcccgaggat cagaaggctg agattttgt agaagcttag    97620 accggtgtga taccactggt tggttcaaga tatttgctga agggactaag ctcatagtaa   97680
cttcacctgg taagtaactt ttctttctgt ttttattcca gtaatgaaaa actgatagat   97740
gatttttaga aaaaaatgat caaccttatc tgaatatgtc acattcctgg cctcagtata   97800
cgaacagcaa ttttgcagat tagctgaata tggaaacaaa acgattttgt acatgatatc   97860
ttcccttccc tgtctgtaag cggattaaaa ttctacttta agaatacaca cacacacaca   97920
cacacacaca cacacacaaa agatagactc tggcaagaaa ttaaaatgtt ttgaggccca   97980
tgtctataca ccattagtgt aagtccttgg tccaagttac ttttttgttg gtctttaag    98040
```

```
tgagagacat aaaaatggag ttttattaat tacttcttct ctgtattttg agatataaca   98100
tagtgctccc ttcttctgct agcctgccaa acccatgtta ttgattttga tctcatcctg   98160
agaaatagta tagaaaaaaa ttacttctta tagtaaatta ctatagaagg tcaatacatc   98220
ccacttatta gtgttctagt ttctttgagg gaggctgaag tcagtcaaaa tttatgcaat   98280
tgggactctt gttatatcac ctggaaatgg cccggtttaa tagaatttgt aagttcaacc   98340
agccatgtca gctccaaggt caatgaaaag agtcttcatc attttacatc ttcatttgtt   98400
cattcatcct ctcagcaaat atttatcaaa acagttttt gttctggatg ctagagataa    98460
aagggcaaag aagacacagt ctcaacactc aaaagctgcc agtctggcag ataagtattc   98520
tagattctgg cttggttggg ccctgtccac gttctttggc ctgtggctgc cggagaagca   98580
gaaggtcttg ggttcatgag ctcattttct ttcttaattt gtgtagcagt tattgcttat   98640
aagatctatg tattgcgttt ggtgggagga tttgataaaa tgacccaata ttgtcctttt   98700
aaggagaaaa ttaatattag caaagtttat tgagagccag acaccatgct aaatagtttc   98760
aatgctttat ctccttcctc atcagaccta tgcaggagat cctcttagtc ccatttcaca   98820
gatgaggaaa ctgaggccta gagaagctca gttactttct taaagtcaca tgactagtca   98880
ctgtggaaaa gtctgggatc tatctaagct tgtctactcc aaagtgcctg gtctggaccc   98940
ttatgtgata tttagaaata ttaagtcata ttttatact ttgaatatttt cttcttctgt   99000 agcttgaccc tatgaatgga ctctttagtt gactattttt ctagtaacaa ctcccaattt   99060
gtattactat ttgtgtatta atacaattct tctacttcta attatggcac tgaaatgacc   99120
tctctcctcc aaaaagtcat atgggatata cattattaa atactcaaaa tataattttt    99180
agggtatttc tgtagaatga gtcattttga cgtcattcca ctcagctgtc tttctgtatt   99240
ggcatcaaat ttgctagata tgttgaaact gatgtaggag ctatcgcagc tatgctatat   99300
tgcagtgcta agtcgcataa ctcagagctg cctcagattc tctgttgagt agcacacgat   99360
ttaatttgat gaaactgtat agatatttc aagtcaaaag tagcagtctt tcagcaatga    99420
atcatcatta agaattcata ttttctaaca actcatcagt attctatcag tgagaactgg   99480
attctaaaaa gaacttactt tattttatt ttttatttttt tgagatggag tctcactctg    99540
tcgcccagct ggaatgcagt ggcatcatct ctgctcactg caacctccgc ttcccagttt   99600
caagagattc ttctgcttcg gcctcctgag tagctaggat tacaggctcc tgccactacg   99660
cccaactaat gttttgggtt ttttttgtat ttttagtaga gatggggttt caccatgttg   99720
accaggctgg ttttcaactc ctgagctcaa gtgatccgct tgcctcagcc tcccaaagtg   99780
ctaggattac agggatgagc cactgtgcct ggccaaaaag aagttatttt agaatcaatc   99840
tagataccca tccctccata catatgaatc ccaaaatacc tataaatcat attgaatatc   99900
tatttattaa atgtcaaaca taggaatcct attattgtct ctctttgaaa attaaggaaa   99960
tattaactct aaattacact taagacaaag tgtatacaag aaaactttt agggaagatt    100020 tagaagattc aggcaaaatc atgagaaaag gtaaaatcag actctctaat gtatgggata   100080
caaggagaga atgtacatag cccaaagtgc ccagggcaag gtgaggtcag ttcttaaatt   100140
cctgattaca ttcagatcca gtgtgatttt gtttgacctt tgtcttgact taacgtcagc   100200
agggccaatt tttatgtatt tatgtaaata ttgaaaaaaa tgttggcaca atttaagac    100260 aaacacaaag ggagattctt ataaaggctt ctcaggtggt gggcaagagt tgggcaaaaa   100320
aatcaaggta tttggtcccg gaacaaagct tatcattaca ggtaagtttt ctttaaattt   100380
tgcaatgtaa agaagggatg ggaggctggc aggcaggagc tggctcagaa ttctaggatt   100440
```

```
ccctccttgg tcactaatca tggtgaaatc tccagagagg tcaggtgact tggttcatgc   100500
cttaggagtc agaactttc ctgccctagc atgggagaca ttactaagga gcttagacca    100560
actgcaaatc tctaaaggat ggaggcctta tgttgttcca ttggtatctc tctgttgaaa   100620
gttttgtgaa caagtttagt tttgagattt tatttcttca gttctaaaaa taaccaatgg   100680
aaaaaattaa aaaaaaaaaa agtaaaatca gctaccctcc ttatttggtc accaaaagat   100740
gaaatatttg ataatttgac caagaatgg ttaatatcaa atgttaaaat atttctcggt    100800
gtgaccatat ttagaagtaa cataagctgc atttattgtt atttaaattg gtccaatgag   100860
tttgtttatt atttgttagc ttaagtttaa agatgtaatt ttgcctggat gagagaaaac   100920
atctcataaa gatactctta gtctgttaga tccactgaaa tgaaagtttt cagagaattt   100980
tcacaaagtt gataaagcat cggaaaaaat gaaagcagtt ttacattttt aattccttag   101040
tggttgagat cttatgataa aatgaactta taagttaaaa agtgaccttc cgattctctt   101100
ttatccaatt gacttaatga gaattgtagc aatcaaattc ataatttgta attttctgag   101160
aagtgatttt tcaggaaagt gcggtgcaag aaaaggtatg gactttgttt ctcgactcct   101220
ggagctagca cttctatgt aactcccttt taggaagtgt attttgattt accagttgtt   101280
caaattataa aaatgctggt tcattataga aaaattggaa aacacaaaaa taaacaaaaa   101340
attataattt gatattgacc ctcatcacat tatcattttg ttatatttt attaaacat    101400 ttttctctgc tttttgtttg tttgttttac aaagttggaa tcatactaga tacacaataa   101460
tagatctggc ttttcactt cacactgctt cataaacatt cttttcaaat gtccttaata   101520
tttttcaata ccagaacaaa gttgaaactt ctgttttcac gttgatctgt acaagaaga   101580 taatggagat tatttatcta aagtggatgt tataaagatt aaatgaaatt aaatatggaa   101640
attacctacc agaatgcctg gcacttggta ggtgatagaa atattatttc ctcttctaga   101700
attcaagtta ctacccacga aaggtcttta tacactcagg aatacagata aatgtatcga   101760
ctcccatcta ttcagcagct cacttcagaa caaatatcac tatttgtaaa atgctttcta   101820
tgtctaaaag actaattgta cctgcttcta aaagtaatta gaatgtttta cgtattatct   101880
caaatatgat ctacctgaat acaaggtgat ttttcatttt caagagaaaa tttatgttta   101940
agaaaatatg tatttteccc tcccccaact cgaatatgta aatttatagg gctacaggta   102000
aaacagtcaa atgtctacct ataacattta atttcttacc tggttcatac tttcaaagtt   102060
aaaaattata tcaatatcaa tatcagttga gaaatattgc ctttttgcc cttatatttc    102120 attaaaactt ttgttttgat gcttcacatg catgtaaagc atctatctca gaacagcttt   102180
ctaaggcatc tcaggtcaaa gcgtccactt tggaatcctc ttatgatggt gtctctgaat   102240
attttattct aagacacaat tattcactca caaaataaaa ggatatattt ttttccaatt   102300
tattctgtta ttctacagtt gtatgaagta aaaactacag agacattacc ccaagtaata   102360
atgaccaaat ccgtgataaa tttctttgcc tttttttttc cttttaccag tgctattccc   102420
caaactagca tcattgagtt catttcatgt cgatatctcc tccagttagt ccttctggat   102480
caaagcagag tattagaaga acatttttta atatgagaag ttacacaaag actgtaccat   102540
acataaggca cctccccatg ttgtgagaga aaattttggg gaaaaaaagc ttcattttaa   102600
gttctggcac tttctatcta aatttagtat gtaggtgtcc ctatcacaga gctaggattt   102660
gcaaacatag tctccattcc ttgtgtctta tttgagcttg accttacaaa accatcaact   102720
cctggggcaa aaggagaaac atgctaaatg cacaaactct ttgttatta tttaagctat    102780 ctctttccaa aatctatttg agaagaccta aattaaaata tacaagcaca gtcagaccat   102840
```

```
taaatatata cagatgatct aaagccctaa ggaaaggaga aggaaaaagg cctgtgatta    102900
cctagtgagg agcacagttt aaaattttat gctcaaaaga aggagaaaaa ggtaggggaa    102960
tacatacatc ttactaattg ataaaaagaa gcacaccaaa ttttcaaata tcatattttt    103020
ttctattact agattggaaa aagacttcaa tgcatgagtc ctttagaagg aaatggaaga    103080
gtgggcagtg ccttcaactt ccatttggaa aaatgaaagg aatggtcatg aaaaacccac    103140
tgcatattac cactgcatca gtgctatggg catcctgaca tttaatgaaa tgcgcagatg    103200
gtgatgctca gcagacatgg tcaggcagat aacatgtagt gatctaaagt gacaacagag    103260
agatggattt gaggaccagg cctcttgcct tttctctacc cattctgcct tgaagggtaa    103320
agccaggtgt ttcaagctgg actttggcat gaactagaca gaagtcagtt tcaggctgaa    103380
gtttctggtg aaacttggaa ggcaaataag ttgtgctgct gattagaaaa aggctcactt    103440
gttttgaaaa acacaagtga agaattccca tacactgact gcatatatta gactttagcc    103500
aatgttccct ttgactttct aacacggta ggtaaggcaa aggataacct attaaagatt    103560
gggcgtgtga aagccatgtt tcttgtgatg atggggacga tggctttgag aatcccagag    103620
caaagtggaa tgcaaacaga ggaactgaga aattattcct cctgcttaat tgctatggat    103680
ttaactgcca ctccaaaatg ctgaattttt tttagtaagg gcaatgcttg gtcctatagg    103740
gttaaaatgt catgtcaagg cacacaatca tagcaaacag attgctaatc ataacaatga    103800
catcatcatc atcataatct cttatatttc catagcattt attttgagg cagggtcttc    103860 ccctgttgcc caggcaggag tgcagtggtg tgatcaattc tcactgcagc ctcgaactcc    103920
taggctcaag tgaccctcct gcctcagctt ctcgagtagc tgggcctaca gtcgtgcaca    103980
tcatgctcag ctaatgcttt ttgtatttt agtgaatatg gggtctcact gtgttgccca    104040
ggctggcctc aaaattctga gctcaagcaa tcctcccacc tcagcctccc aaagtgctgg    104100
aattataggc acaaaccact gcactgggac ctataacatt ttaatcaaat tgctttttta    104160
tatcttgttt cattttggtc tcacttcagt gctggtagcg atgttgaact gattttgaaa    104220
catcactgtt tttagacaaa taaaacacca aaagctttaa gttatttgat ttgtggagca    104280
acagaacttg ttatgagcaa aatgaaccag gactggaacc ctggtctttt gagaatccca    104340
gaccaccaga atttgaagaa ctcagggaaa ctgaattaga gttttgata tggactgaat    104400 cactgtggaa ttattataag aaactctttg gcagtggaac aacacttgtt gtcacaggta    104460
agtatcggaa gaatacaaca tttccaaggt aatagaggga aagcaggaaa ttattaaact    104520
ggaataatgt aataatgttt agaaaaaga ggaattggat ggggatttga tgtagaaaac    104580
ttaggagaga cttaaaaca aacgctcata ctaaaagaga acatagataa cattgcacag    104640
atatcataat aagatttggc tttgtgcata tacggacttc cataaagggc tcatatgtaa    104700
tgtatgaaat gatctcatta aaatgtctgg ccctgagacc aaatgtatta tgacaggtaa    104760
gtttgtgata gactctacag agtggacaca tattcatctc tgatggtcaa agacatgttt    104820
actcttgttg tgaaggagcc cgggtgttgg agtcaggtcc acctggaact ctggctccac    104880
cactcactgc ttagtgaaat tgagtgatta ttctctggcc tcagttttct aatccataaa    104940
atgggataac agtatgaatt cagcagggtt gtataagaat tgcacaacat agtgtgaatt    105000
aagtacttgg cacattgtcc aacccaaaat aggtgcccaa caaatgtttt ctggattcac    105060
atgtaaagag acaatgggat ctactatgga gagttgctct cagtccatct aatttacaga    105120
gcagcaattc tccagaggat tcagctgtac ttctaactgc tcaaatggaa ggttatcaac    105180
atcagctcac acacgcaaaa attgaactta tggattcgtt tcttgttagc aggctttta    105240
```

```
atcacgtggc aaaaacattg tattaagatg tctgttttt attttgttg ttctatgtgc    105300 tttacttaat cctttatctt aattgatatc atttctaaca ccaacatatt ggtcctaaga    105360
tttatagcca attagtttag ggttctgttc atatgtctca ggaaaaaaag gttaaaatct    105420
taccaaaaat ggtcaagata tcaaatcaat taaatccagt tggaaacatc ataaatctga    105480
aatacatatt taaacataaa atggctataa ctatttagct aatgaaaaaa taagaaatag    105540
agaacactta aataaatatc catatgtaga tttaatatat cataccgtct ctaaaaactg    105600
tagttgatat ttggtaaatt tacaatgctg catttaata aactacaaac aacttaggca    105660
atttaactca aatatactat ttgattttgc aaataaatgt acataaatga atccaacaat    105720
aaaataaatt ttatttatta ttttaaataa aatatgtaaa ttctatttgt tattgaagta    105780
agtaaaaatg taccatactt ggccataaaa aactcttaat atgtacattt taaaagtagt    105840 atttaaaaa tcatgtgaga ggatgatcca caatatcggc ccttaccatg tgtaatcaag    105900
tatgctattt aatgattcgt taactactac gttgagaaag ttttggaagt tccagattca    105960
ttttgtcctg aaaagaatga aacttaaaga atctagctaa agaaggggga caagaggcaa    106020
tgaatgctgt ggtaccgtac agaaaatgtc caagtttatc atttgatttt taatttcttt    106080
agtacaatga attagaagta tttcaatgaa gagacactag ttcttaggat gaaaattaga    106140
ttggaaaata tattgactag agactacaat tatataaata taatgtacaa ttgaaaaatt    106200
actcatattt tataacatgc ttttaaaatt agaagcaaac tatatggtgg agaaatatac    106260
actgtctcac aagtataaca agtaaaatac tatttgcact aaaagcaaag agtatgaaat    106320
taagatgagc acattatgcc taattaaatt tatagcatgc tcacaaatta atatttctgt    106380
atatgtttac taattttgta tgaaaatcag aagctttgct acacagacag aaattatcaa    106440
gactgttttc ttttcttctg aaatgagaaa tttaattctt attttcttag aaattgttca    106500
attattaaat tcacttcaaa ccagccaaag cattggagtt tcaattggaa atcaaaatag    106560
aaagaattgt aacatttata atttcagtta ttagattaaa aatacgtgta taacccatta    106620
acattccaga ttcaagtgat atgccttttgt aaacatatga tgctttgtta tgtatcttga    106680
ccctatccct ataagaagct ctgaaatcat gacttttaat agagcaatta tatgtacatt    106740
ttattcagca ggctaagatg aagagaataa tggagcttta aaacagttaa gcagcatata    106800
ggacagatac aaattctggg agagacataa agagtcaaaa tatagataca ctgatttaca    106860
cagaccttct cattaatggg gtaaatttat ataaaccca gtataaaaaa tacaccctg    106920 gtgcattctt agtcattctt aaacttcaaa tgaaattcca aaataaaatg tgcttttggt    106980
gaatattttc tgaagcaaaa tgaaattttg ataagtgcgt tactgcagaa gattaacaca    107040
agagtatttc tgaaaataat caagaaaaaa tttaaataag agttttggaa agttgccatt    107100
ttgtttctaa attcaggaga tggtgaataa tctggaggta cagctgtaaa tactgctgca    107160
tcccaaaact tggagggtgc agatgtgaaa ttgagatgtt atataaagtt agatattaac    107220
tagggggact gctcatggta tacacattga agctacatgg tcaacttgat agacagtatg    107280
tacatgcgga agtagattct ctttaaaaca agtgactgtg tatgttaaaa ataaaagtga    107340
acaaaatggc taggcatggt ggctcacacc tataatccca ggatttggga ggctgaggca    107400
ggcagatcac ttgagcgcag gagttttaaa ccagcctggt caatatggtg aaacatgttc    107460
ctagaaaaaa aatattagcc aggcatggtg atgcatacct gtagtcccag ctacttggga    107520
ggctgaggtg ggaggatcac ttgagcctgg gaagtcgaga ctgcagtgag ctatgatctt    107580
gccgctgcat tccaacctgg acgacagagc aagccccagt ctcaacaaca acaaaaattt    107640
```

```
tgacattgat tcatatggga aataagataa ataataagat aaatatggtg catcgcagaa    107700
tcagttaaat gaagagtggg agtacacgaa attgcagaac atgagaatgt gtcatatttg    107760
gccaaagaac ataagttaca aaggatggaa aagggaagtg ggaaaaggac caaagagtct    107820
catctgtaga gagatcatta aggttttctg accttccact ttcccctgcc atccaccttg    107880
aaaacctgct tcactatgat gaaacaaaag agattaaaaa ataaaataaa tatgctcatg    107940
aactttggaa gccctggtag gaggcagtta aaaatcacac tcatcacagc atgtgcaaa    108000 taaacaaagg ccaggttttc gtccagcatc tgacatttga gagctgtgac ttttggcaag    108060
ttatttaatg tcttgattct cttttcaaca tctgtaaaat aagcacaata ataagtactg    108120
tgcagcctat cctggatgaa aggccgcagt ggacaccagc tcaatggcat cttctctttt    108180
tatggttatg tactaggcca ctccaaactg tgcaatgtgt gtgtttctct aatgattctt    108240
ttaaactcat atttcatttc tccccataga taaacaactt gatgcagatg tttcccccaa    108300
gcccactatt ttcttccttt caattgctga aacaaagctc cagaaggctg aacataacct    108360
ttgtcttctt gagaaatttt tccctgatgt tattaagata cattggcaag aaaagaagag    108420
caacacgatt ctgggatccc aggaggggaa caccatgaag actaacgaca catacatgaa    108480
atttagctgg ttaacggtgc cagaaaagtc actggacaaa gaacacagat gtatcgtcag    108540
acatgagaat aataaaaacg gagttgatca agaaattatc tttcctccaa taaagacagg    108600
tatgtgttta cgcatatcat ctgtcagaac acttctttga aagtgaatgc tgcattttt    108660 cctttcagta ttaatgaaaa acaaacataa atctttctta aatattgtta catttaatgg    108720
tagcataaat gccctgctac ttttctatag aattaaaatg gtataggttt tggagaaaac    108780
aaaattgaaa aagttactga aggtttgtca gcctcagctc cattatccaa aataagaaag    108840
tcacgtgctg gttttaggg ttgttagatg gattaaagaa acaacataca cagaagcatc    108900
tagcaacgtg acacgtggta aacgctcaaa aagtgttctc ccttcttttg atgactttac    108960
ttgatcagga aataacatat atatgtcttt caggaatgtt ctgcccaagc aggagagtca    109020
ctcacctcaa tcttgctacc cacaaagttt aacctaaaaa caacgggttc attgttgaca    109080
aaatgatgtt tatctgttgt tgacagaatg atgtttatct aaaaacagtt ccaatttct    109140 atttcctttg ctgagacaca aaggggaggc aaatgtgcaa agcttgaggg tagtcttacc    109200
actgtgctta agtgttctga tttttctagt gatcagggca aaataaaaag tatagtaagt    109260
tccaaggcag tgaatattat acaggagaga agttacagtt ttataatgtg ttttccttta    109320
cactaaattc taaaagtaaa aagtcttttt ttttttttga cagagtttca ctcttgttgc    109380
ccaagcaggt gtgctatggt atgatctcag ctcactgcaa cctccacctc ccgggttcaa    109440
gtgattctct tacttcagcc tcccgacagg ctgggattgc aggcgcctgc caccacacct    109500
ggctaatttt tgtgttttta gtagagatgg ggtttcacca tgttggccag gctggtctca    109560
aattcctgac ctcaagtgat ccatccacct cggcctccaa gtgctgggat tatgggcgtc    109620
agccactgtg cccagcctaa aagtaaaatg tctttcatga gcttcccaag gcagctacgt    109680
taaggaggac acttctctta atgtcattct acagtagatt tctaatgctc tttcttgaa    109740 gtttgttttt ctgagaaaag ctaaaaatat aacatggaag tgatcatatt ataatcaa     109800 tgaagtgctt ttcaaggaga taaaactaat ctggtccaca cttgcaacca accttgattg    109860
agagagagag agaactcagg atacacttga agattttatt atggggaaca gttactttat    109920 tcttttacc tcaatcaatg catggaaata agtgatagtc attttcattt atcttttaat    109980
aaatgaagtc accatgagga aaataaaaag acattgaaaa cccattaaag tcagcccta    110040
```

```
aagatatttg gacatgcaga cttgataact aacgtttgca ttcttgagac ttacccaaaa   110100
cccatacctc aagtccaagt ttttagaatt catgaaataa agatctcagt gagtgcataa   110160
aattgcgcac cagaatcata tccgtataga caagaacaca tctactagaa aaataataaa   110220
ccaacacacc aatgcaactg tgttttcttc tgttttaaag tatgttgtct ttgtatgcat   110280
gtttgcttct tccttttttt ttttaacatc acagataaat tcaactctca cctcaggttt   110340
tattgagaga actgtcaatg tgacttggcc tctgtctttc tagtcccaga aagaattgca   110400
ctgaaatctg agctcctgta ataaaaacaa ccatttgctg agagtaatta acatactgaa   110460
agagattttc ttagagtaca caatggtgac attatattgc ctctttataa ataactttct   110520
atctatttct gtggattatt cctacaaagt acttttcata tgtccaattt ctttcttcc    110580 cctacaacta ctgtctgaat actggctctg ctatttgctg atatgattct cggcaagttg   110640
cctgcacttt ttaaacttta tttcctcatt cagaacatgg ggccatacat aatacaactc   110700
acttcagtgt tattggggaa ttaaacaaaa aatgcatggg aagcatttaa catagtgcct   110760
gacacaataa tgagtactca gtagatgtta gcttttatta atattgttgt tgttatgtcc   110820
agaaacacta tacctccaga aaatcatggg tacttgctgg ggacattggg gatatgcatg   110880
atttggaaaa gaatgactgc ttttttttgct tagatgagaa attttttctaa gccagactcc   110940 ttcaaatatg taagattctg ttgtggattc aaggactgaa agaattcttg gccgagtgtg   111000
gtggcttatc cctgtaatcc cagcattttg tgaggacaag gcaggaagat tgcttgagtc   111060
caggagtttg aaaccagcct gcgcaacatg gcgaaaccct gtctctacaa aaaatacaaa   111120
cattagctcg gagtgagtgc tgacatgtgc ctgtactccc agctactcag aaggctgaga   111180
tgggaggatc tcatgagcct ggggagtttg aggcttcagt gagccgtgat gacaccgtac   111240
tatactccac tccagcctgg gtgacagtga gaccctgcct caaaaaacaa acaaacaaac   111300
aaacaaaaca aaattaatct ttttgctgat gtcatgtcag cagtgtgtgt tgaaggctgt   111360
aaagcagcca tttgttcagt ttattttttcc attgaacaag tatttatcaa aaacatactt   111420
tgtggcagtc actatgctag gagctatgaa tacagaagga aaagtaaatg ctcttggata   111480
ctacactcca gttgtgataa aaagaaaaa atgtattctt caccaacttc aacatcttga    111540
tgtgcaaaaa cataatacat gaattagatc tacctaatta cacagaatta gaccaattgt   111600
ttctggaatt gtgggctcat atttttaata actgtcctcc tgcctctctg tcgacaggtt   111660
ttataaatat tcatttaatt acacacacac acacgaacaa ttgactagta cttgctctca   111720
ttcttctaga tgtcatcaca atggatccca aagacaattg ttcaaaagat gcaaatggta   111780
agcttttgtg tttttccctt cctcctgatc attttgtttt gaacttctct ggcttgaaaa   111840
atcagggaat ggattttgct aggttggatg ctgcagaatg gacctagtga tattttaaat   111900
tagtccctca ttttctagga gttgtattaa caaacctaac tactgctttg gggtatgaga   111960
tgactgtaaa ttagagaggg tacagtggta tagtgatatg cttttaatta tttcaaaaaa   112020 aagatttttat tcattcatgt gtcttttttc tttttctttt cttttttttt tttttttgga   112080
cagagtcttg ctctgtcacc caggctggag tgcggtggca gtatctcagc tcaccacaac   112140
ctccgcctcc cggcttcaag tgattctcct gcctcagctt ctcgagtagc tgggactaca   112200
ggcgcgtgcc accatgcccg gctaattttt gtattttttag tagagttggg gtttcaccat   112260
gttggccagg atggcctcga atttgtgacc tcgtgatctg ccccctcgcc ctcccgaact   112320
gttgggatta caggcgtgag tcactgtgcc cggcctcctg tcctgtcttt tgtttaatga   112380
ctgggaaaaa catgatacca tgttgcttct cgagttgttt tgttttagtc tttggtcttt   112440
```

```
gctagtagct aataacacga actagtgttt atcaagtgct ttttacacag aagggcttgg    112500
gctgtgttct gcattttctt gtttaaccct cttaaaactc ctataaaatg gtacatattt    112560
ttctcccaat ttacagtccc tttaaagcaa ataattataa aaatccctat acatgtcaca    112620
cagctagatc tgggatttca aatcaggcca tcaaacaaag agtttatgta cttagtaagt    112680
tttctgttct ttttctacaa tagagtcaga tagcaagaaa ttaccaagcc aggaacctga    112740
aacaaaacgg acatcatgtg gggctggggtg ggtgcatggg cttttgcagac tggacttttca    112800 ctccagctct tttaatgatt aggtgtaagt gacctacatt ttgtgagcaa cagttttctc    112860
atcagccaac aaagaataat tacaccagat tcacagttat tgaagagata aaggcatgaa    112920
tgtgagatgt ctggcatagg gcatctcatt tagcagacac agaatgagta cttgtttctg    112980 gcttttctc tctacatatg cacaaagaat gcgactagaa gcatgggctc tagccctgct     113040
caactttcct ctatttccaa taccaagggg ctctgactta ggctgccaca ccaggcaagg    113100
agggcagtac cacctcactt gaccaagggc agggagtcac ggacacatca cttcttgaga    113160
tccttttcca caccaaggac tgatgtttct ggaattctca ctttatgaag acaaaacata    113220
taaatggaaa ttttctcagg tagagactca ctcttgtagc tcattgagta ggcactagtg    113280
gtccaccccc actgtcttta cttattcctt gacatcacat atctcttgca aaacctcaaa    113340
taatattaaa tgcaatcacc caataatagc atagccataa ttagaggcat ttaggaaaga    113400
caggtgagtg tgccacaact acctaacaca tcagcaaatc tggattaacc actttctttg    113460
attttccaca atgcaacctt acttttaat agttgggaat gttctaagtg aatttagcag    113520
aggttgttaa tcaacttgaa agctgaattc tgacttgtct gactcttggt ggtgctggta    113580
gcagtagatg tttactttta ggttttggtg gtggtggaat atcacttcaa cgtaaatcat    113640
cagaaataag tatttgtgaa cccctctcgc attaatgtat cttattctgt aaaaagaaca    113700
tgtgcaattt ctcttagata cactactgct gcagctcaca aacacctctg catattcat     113760 gtacctcctc ctgctcctca agagtgtggt ctattttgcc atcatcacct gctgtctgct    113820
tagaagaacg gctttctgct gcaatggaga gaaatcataa cagacggtgg cacaaggagg    113880
ccatcttttc ctcatcggtt attgtcccta gaagcgtctt ctgaggatct agttgggctt    113940
tctttctggg tttgggccat ttcagttctc atgtgtgtac tattctatca ttattgtata    114000
acggttttca aaccagtggg cacacagaga acctcactct gtaataacaa tgaggaatag    114060
ccacggcgat ctccagcacc aatctctcca tgttttccac agctcctcca gccaacccaa    114120
atagcgcctg ctatagtgta gacatcctgc ggcttctagc cttgtccctc tcttagtgtt    114180
ctttaatcag ataactgcct ggaagccttt cattttacac gccctgaagc agtcttcttt    114240
gctagttgaa ttatgtggtg tgttttccg taataagcaa aataaattta aaaaaatgaa     114300
aagttgactt ttgtccatgg tatttttaatt ggatgacatc aaattgaaca tccaaggtaa    114360
gaaacagcat ggcaatttggg ctgtggaatt ctgtattggt tgtaagaatg gtccaacacc    114420
ccatttctaa ttcttttccct gagatcgtgg ttatcacacc ttctaagaag aactacaacc    114480
aaatgaagga gctcatgtga cttctgttttg aaaggtcacc agagtcagat tcattcggtt    114540
taggacattc cagtggctat aggacactat ctactgtgac gcgtaccgtg tgagctcagc    114600
tctagagtgt ttcacagaca ctgtgttttcc tgatcctcac gataccccca tgagagctgc    114660
cctaaaagca gagaggcagc gtgatggaga ggttcagcac atgctctctg atcccaggaa    114720
tcctgggtat ggtgtttcgt atctgtgtga cctcaggtga gttccaggaa ctctatgtgc    114780
cataatctcc tcatgtaaaa tgaagttata atgccccgtt tcctggagtt atgtggatta    114840
```

```
gatgagttaa tgacacctgg cacatgcaag tcctccacag tgtcggcacg cactgttggt    114900
agctctactc tagagacagt aataaaccaa aaagtatctg acacaggcct caatcaactt    114960
agaagtttat tttgcctatg ttaagggcat gcccaacttc ctgagataat aatttatttc    115020
ataagaatat tttaaaaact cgagtaaact tgttaatgtt tattgctgca gccactctgt    115080
ccatctccac catcactgca acaacgcagg tccttgttgc ctcttattgg cttatggtga    115140
ccacctataa aaccatctgc ttcacccaaa ttgctgtcct ggggagtgcc ccttcctttc    115200
tgcttgcaca tttatcttcc tcaagtgcaa atgtgatcat gtgactttcc tccctaaatc    115260
ttttagcaag tcctcattgt ctattcttct ttcaaaaaca tttatttgaa aatactatta    115320
aaatagaaaa ttttccacat tcttacttct taaaaattaa tgtgttttaa gtttctccta    115380
ctccatttcc atcccatgcc tctttactca atggatgcaa ttattcttct acatgttcct    115440
tctggccatg tgtagctttg tcattttaat tttaatctat ttggaccctg tgttatctgg    115500
gatgaggtag agtgatattt ttattttctc aggtaattat ttgcctaatg cctgtttcca    115560
aataatccac catttcctta caatttaaaa atgctccagc atgttttaa tagctacaca    115620 tatttgacac attttctgga gaatttctgt tttatttgtc tatttcatta ttcttgtatc    115680
attatcatat tatctcagta gctttgtggc aagtattaag atctactatg ccaaatgtct    115740
attcactgta ccatttttca gaaaattctt tttcaatcat ctcatatta ttcactcctg    115800 tagaatttaa aatcaactta tctagcctaa cattaaacct cacacctag aacaacaaca    115860 tgtcgtagta attctgacta aaattgctgg aaatttatag atgaatttag ggtgtattgg    115920
cctctttatg atagaagctt tttattcatc aatgtatgtt tctccattta tttaggtttt    115980
attttatgcc cttaggaaaa ctaaatactg tgttcttcat atcattcttg tattttttg     116040 gtaaatttaa taaagattt tataattcat tacttcttca cattttatta gttaaatcct    116100
tcatggctct tgaaatattg acagctgcta agacttctga tgcttcccct catggtcctg    116160
aaataaggaa ggccagagga caaaaagaga ttgagtgggc gtcattccat ctatcacagg    116220
tgtaaagggt cattgacagc gccacataat aatttgaat tttctattaa gaagaaaccc    116280
tttccaaaca taattttcac ccagcccat tgtcttctcc attgttgtgg gggctgtggc    116340
ctgccgtgta tggataggtg ccctctgtga cctcactcat accttcctga atgaagactc    116400
aggagactta ggctggagca gggtggatct ggagtggaca tggaggttgt caaggcttgt    116460
cctcctcagt ccttgcaact gaacacctca tctgtacaca ggagatcaca cagccgacac    116520
cagcttaaga tggcagattt ttcaacatat cagataacta aatttttttt tttggttatg    116580
ccatagttta aataaagaat gtattacttc atgggacata gaattctaca aatttcttct    116640
gctattccag gaaaatgat aagtcattgt ggaaaacatt tcctcatttg gcattgcctt    116700
ggtaaagcat cgtgttgcca aatgatacaa gtggcttttt gaaagtggag acctttgttc    116760
aaatttctca agtatatctg tgttgacaca tttgcatttt cagttactaa agagcttcct    116820
cctttcagaa gtatcttccc aaattactaa caggccctgg tgtttgtggg aacagaaggg    116880
cttttccttt gatgtaatct caaagcagtt tcaacacaat tgaacccctg gaaattaaaa    116940
aagaaaaaaa acgacaattc tctgaatact tttcctggta atttagaaaa gtagtgcatt    117000
gacccactga gcctgctctt ttttctctct atcgcccagg ctggagtgca atggcacgat    117060
ctcggctcac tgcaacctct gcctccctgg ttcaagcaat tctcctgcct cagcctcccg    117120
agtagctgtg actacaggca cacgccacca cgcccggata atattttttt gtatgttagt    117180
agagacgggg tttcactgtg ttgccaaagc tggtcttgaa ctcctgagtt caggcaatcc    117240
```

```
acctgactca gcctctgaaa gtgctaggat tacaggcgtg acccactgcg cccggccttt    117300
cttttttgt  tgttgttggt tttttatctt aacatttctt ttttctgttg atgcttttca   117360
agaattactg ccttagaaga aagcaggcaa tttatgagga aaaattacaa actatcacat   117420
gtcacaaaac ctatattcaa ggacttccaa aaaagccaga agatgaaatt gctagttcaa   117480
agttgttgga ttgctagtca tgtcatgagg atcagaaggt tgagattttt gtagaagctt   117540
agaccagtgt gatagtagtg attggatcaa gacgtttgca aaagggacta ggctcatagt   117600
aacttcgcct ggtaagtaat ttttttttctg tttttattcc agtaatgaaa aactgataga  117660
tgtttttag aaaaaaatga tcaaccttac ctgaatatgt cacattcctg gcctcagtat    117720
acgaacagca attttttcagg gtagctgaat gcctggcact tggtaggtga tagaaatatt  117780
attttcctctt ccagaattca agttactacc caagagaggc ttttatacac tcaggaatac 117840
agataaatgt atcaatcccc atctattcaa cagctcactt cagaagaaat gtcactattc   117900
ataaaatgct ttttatttct aaaagcctaa ttgtacctgc ttctaaaagc aattagaatg   117960
ttttacgtat tatctcaaat atgatctgcc tgaatacaag gtgattttttc attttccaga  118020
gaaaatttat acaagtttaa gaaaatatgt atttttcccct cccccaactt gaatatgtaa  118080
atttataggg atacaagtaa aaaagtgaaa tgtctaatta taacattcaa tttcttaact   118140
ggatcatacc tcaaagttaa agattatatc aataccaata tcagttgaga aatattgcct   118200
tttttgccct tatatttcat taaaatttttt gttttatgct tcacatgcat gtaaagcatc  118260
tatctcagag caacttttcta aggcatctca ggtctcagtg tccatttttgg attcctcaaa 118320
tgatgatgtc cctgaatatt ttactctaag aaacaatgat ccactcacaa aataaaagga   118380
aattattttt tccgatttat tctgttattc tacacttgta tgaagtaagt aagaactaca   118440
gggactttag ctccaagtaa taatgaccaa atccatgata aatttctttg cttttttttcc 118500
ttttaccagt gctatcccca aaactagcat tcattgagtt catttcatgt cggtatctcc   118560
tccagttagt ccttctggat caaagcagag tattagaaga acattttttta atatgagagt  118620
ttacacaaag actgtaccat acataaggca cctccccatg ttgtgagaga aaatttttgg   118680
aaaaaaagcc tcatttttagg ttctggcact ttctatctaa atttagtatg taggtgtccc  118740
tatcacagag ctaggatttg caaacatatt ctccattcct tgtgtcttat ttgagcttga   118800
ccttacaaaa ccatcaactc ctggggacaa aagagaaaca tgctaaatgc acaaactctt   118860
tgttatttat ttaagctatc tgtttctaaa atctatttga gaagacctaa attaaaatac   118920
acaagcacag tcagaccatt aaatatatac agatgatcta aagccctaag gaaggagaa    118980
ggaaaaaggc ctgtgattac ctagtgagga gcacagttta aaatttttatg ctcaaaagaa 119040
ggagaaaaag gtagggggaat acatacatct tactaattga taaaaagaag cacaccaaat 119100
tttcaaatat catattttttt ctattactaa attggaaaaa gacttcaatg catgagtcct  119160
ttagaaggaa atggaagagt gggcagtgcc ttcaacttcc attttggaaa atgaaaggaa   119220
tggtcatgaa aaacccactg catattacca ctgcatcagt gctatgggca tcctgacatt   119280
taatgaaatg cgcagatggt gatgctcagc agacatggtc aggcagataa catgtagtga   119340
tctaaagtga caacagagag atggatttga ggaccaggcc tcttgccttt tctctaccca   119400
ttctcccttg aagggtcaag ccaggtgttt cgagcgggac tttggcataa actagacaga   119460
agtcagtttg aggctgaagt ttctggtgaa acttggaagg caaataagtt gtgctgctga   119520
ttagaaaaag gctcacttgt tttgaaaaac acaagtgaag aatttccata cactgacact   119580
gactgcatat attagacttt agccaatatt cccttttgatt ttcttaacac ggcaggtaag  119640
```

```
gcaaaggata acctattaaa gattgggtgt gtggaaggca tgtttcttgt gatgatgggg   119700
acgatggctt tgagaatccc agagcaaagt ggaatgcaaa cagaggaact gagaaattat   119760
tcttcctgct taattgctat ggatttaact gccactccaa aatgctgaat ttttttttagt  119820 aagggcaatg cttggtccta tagggttaaa atgtcatgtc aaggcacaca atcatagcaa   119880
acagattgcc aatcataaca atgacaccat attcatcata atctcttata tttccacagc   119940
attttttttt gaggcagggt cttcccctgt tgcccagtcg ggagtgcagt ggtgtgatca   120000
aggctcactg cagcctcgaa ctcctaggct caagtgaccc tcctgcctca gcctctcgag   120060
tagctgggcg tacagtcgtg cacatcatgc tcagctaatg cttttttgtat ttttagtaaa  120120 tatggggtct cactagatac tgggttgccc aggctggctt caaaattctg agctcaagca   120180
atcctcccac ctcagcctcc caaagtgctg ggattatagg cacgagccac tgcactggga   120240
cctataacat tttaatcaaa ttgctttttt atatcttgtt tcattttggt ctcacttcag   120300
tgttggtagc gatgttgaac tgattttgaa acatcactgt ttttagacaa ataaaacacc   120360
aaaagcttta agttatttga tttgtggagc aacagaactt gttatgagca aaatgaacca   120420
ggactggaac cctggtcttt tgagaatccc agaccaccag aatttgaaga actcaggaa    120480 actgaattag agtttttgat atggactgaa tcactgtgga attattataa gaaactcttt   120540
ggcagtggaa caacacttgt tgtcacaggt aagtatcgga agaatacaac atttccaagg   120600
taatagaggg aaggcaggaa atgattaaac tggaataatg taataatgtt tagaaaaaag   120660
aggaattgga tggggatttg atgtagaaat cctaggagag actttaaaac aaatgctcat   120720
actaaaagag aacatagata acatggcaca gatatcataa taggatttgg ctttgtgcat   120780
atacggactt ccataaaggg ctcatatgta atgtatgaaa tgatctcatt aaaatgtctg   120840
gccctgagac caaatgtatt atgacaggtt agtttgtgat agactctata aagcggacac   120900
atgttcatct ctgatggtca aagagatgtt gactcttgtt gtgaaggagc ccgggtgttg   120960
gagtcaggtc cacctggaac tctggctcca ctactcactg cttagtgaaa ttgagtgatt   121020
attctctggc ctcagttttc taatccataa aatgggataa cagtatgaat tcagcagggt   121080
tgtataagaa ttgcacaaca tagtgtgaat taagtacttg gcacattgtc caacccaaaa   121140
taggtgccca acaaatgttt tctggattca catgtaaaga gacaatggga tctactatgg   121200
agagttgctc tcagtccatc taatttacag agcagcaatt ctccagagga ttcagctgta   121260
cttctaactg ctcaaatgga aggttatctt aacatcagct cacagacaaa aattgaactt   121320
atggattcgt ttcttgttag cagacttttt aatcacgtgg caaaaacatt gtattaagat   121380
gtctgttttt tattttgttt gttctatgtg ctttacttaa tcctttatct taattgatat   121440
catttctaac accaacatat tggtcctaag atttatagcc aattagttta gggttctgtt   121500
catatgtctc aggaaaaaaa ggttaaaatc ttaccaaaaa tagtcaagat atcaaatcaa   121560
ttaaatccag ttgaaacat cataaatctg aaatacatat ttaaacataa aatggctata    121620
actatttagc tagtgaaaaa ataagaaata gagaactctt aaataaatat ccacatgtag   121680
atttaatata tcataccgtc tataaaactg tagttgatac ttggtaaatt tacaacgctg   121740
cattttaata aactacaaac aacttaggca atttaactca aatatactat ttgattatgc   121800 aaatataatgt atataaatga atccaacagg tttatttaaa taaataaaat atatatattc  121860
tatttgttac tgaagtaagt aaaaatgtac catacttgac cataaaaaac actcttaata   121920
tgtacatttt aaaagtagta ttttaaaaat catgtgagag gatgatccag aatatcggcc   121980
cttaccatgt ataatcgagt atgctattta atgattcgtt aactattacc ttgagaaagt   122040
```

```
tatggaagtt ccagattcat tttgtcctga aaagaatgaa acttaaagaa tctagctaaa   122100
gaaaggggca agagacaatg aatgctgtgg taccgtacag aaaatgtcca agtttatcat   122160 ttgatttta atttctttag tacaatgaat tagaagtatt tcaatgaaga gacactagtt   122220
cttaggatga aaattagatt ggaaaataca ttgactagag actaaaatta tataaatata   122280
atgtacaatt gaaaaattac tcatatttta taacatgctt ttaaaattag aagcaaacta   122340
tatggtggag aaatatacac tgtctcacaa gtataacaag taaaatacta tttgcactaa   122400
aagcaaagag tatgaaatta agatgagcac attatgccta attaaattta tagcatgctc   122460
acaaattaat atttctgtat atgtttacta attttgtatg aaaatcagaa gctttgctac   122520
acagacagaa attatcaaga ttgttttctt ttcttctgaa atgagaaatt taattcttat   122580
tttcttaaga aattgttcaa ttattaaact cacttcaaac cagccaaagc attggagttt   122640
caatgggaaa tcaaaataga aagaattgta acatttataa tttcagttat tagattaaaa   122700
atacgtgtat aacccattaa catcccagat tcaagtgata tgccttgta aacatatgat   122760 gctttgttat gtatcttgac cctatcccta taagaagctc tgaaatcatg acttttaata   122820
gagcaattac atactcattt tattcagcag gctaagacaa agagaataat ggagatttaa   122880
aacagttaaa tagcatatta ggacagatac aaattctggg agagacataa agagtcaaaa   122940
tatagataca ctgatttaca tagaccttct cattaatggg gtaaatttat ataaaaacca   123000
gtataaaaat tacacccctg gtgcattctt agtcattctt aaacttcaaa tgaaattcca   123060
aaataaaatg tgcttttggt gaatattttc taaagcaaaa tgaaatttg ataagtgcat   123120 tactggagaa gattaacaca agagtatttc tgaaaataat caagaaaaaa tttaaataag   123180
aattttggaa atgttgccat tttgtttcta aagtcaagag atggtgaata atctggaggt   123240
acagctgtaa gtactgctgc atcccaaaac ttggagggtg cagatgtgaa attgagatgt   123300
tatataaagt tagatattaa ctaggggac tgctcatggt atacacattg aagctacatg   123360
gtcaacttga tagacagtat gtacatgcgg aagtagattc tctttaaaac aagtgactgt   123420
gtatgttaaa aataaaagtg aacaaaatgg ctaggcatgg tggctcacac ctataatccc   123480
aggatttggg aggctgaggc aggcagatca cttgagcgca ggagttttaa accagcctgg   123540
tcaatatggt gaaatatgtc tctagaaaaa acaaatatta gccaggcatg gtgatgcata   123600
cctgtagtcc cagctacttg ggaggctgag gtggaggat cacttgagcc tgggaagtcg   123660
agactgcagt gagctatgat cttgccgctg cattccaacc tggacgacag agcaagcccc   123720
agtctcaaca acaacaacaa aaattttgac attgattcat atgggaaata agataaataa   123780
caagataaat atggtgcatc gcagaatcag ttaaatgaag agtggaagta cacgaaattg   123840
cagaacatga gaatgtgtca tatttggcca aagaacataa gttacaaagg atggaaaagg   123900
gaagtgagaa aaggaccaaa gagtctcatc tgtagagaga tcattaaggt tttctgacct   123960
tccactttcc cctgccatcc accttgaaaa cctgcttcac tgtgatgaaa caaagagat   124020 ttaaaaataa aataaatatg ctcatgaact ttggaagccc tggtaggagg cagttaaaaa   124080
tcacactcat cacagcatgt gcagaataaa caaaggccag gttttcgtcc agcatctgac   124140
acttgagagc tgtgactttt ggcaagttat ttaatgtctt gattctcttt tcaacatctg   124200
taaaataagc acaataataa gtactgtgca gcctatcctg gatgaaaggc cgcggtggac   124260
accagctcaa tggcatcttc tcttttatg gttatgtact aggccactcc aaaccgtgca   124320
atgtgtgtgt ttctctaatg attcttttaa actcatattt catttctccc catagataaa   124380
caacttgatg cagatgtttc ccccaagccc actatttttc ttccttcgat tgctgaaaca   124440
```

```
aaactccaga aggctggaac atacctttgt cttcttgaga aattttttccc agatattatt   124500
aagatacatt ggcaagaaaa gaagagcaac acgattctgg gatcccagga ggggaacacc   124560
atgaagacta acgacacata catgaaattt agctggttaa cggtgccaga agagtcactg   124620
gacaaagaac acagatgtat cgtcagacat gagaataata aaaacggaat tgatcaagaa   124680
attatctttc ctccaataaa gacaggtatg tgtttacaca tatcatctgt cagaacactt   124740
cttttgaaagt gaatgctgca tttttttcctt tcagtattaa tgaaaaacat aaatcttttct   124800
taaaaattgt tacatttaat ggtagcgtaa atgccctgct acttttctat agaattaaaa   124860
tggtatagggt tttggagaaa acaaaattga aaaagttgct gaaggtttgt cagcctcagc   124920
tccattatcc aaaataagaa agtcacgtgc tggttttttag ggttgttaga tggattaaag   124980
aaacaacata cacagaagca tctagcaacg tgacacgtgg taaacgctca aaaagtgttc   125040
tcccttctttt tgatgacttt acttgatcag gaaataacat atatatgtct ttcaggaatg   125100
ttctgcccaa gcaggagagt cactcacctc aatcttgcta cccacaaagt ttaacctaaa   125160
aacaacgggt tcattgttga caaaataatg tttatctgaa gataactgta gatcatattt   125220
atctgtagat aatgtttatc tgtggagtgt ggctctacaa acatagaat agtcttggtc   125280
actgcagttt tatagaggcc ttgggttttt cagagtttca ttttatatat caccataaag   125340
taacatttca taattacagg ttggtaaggc ttacatgtac aaacattctt ccattttcca   125400
taataaatgc atttcctgcc attggtgaat gcagctcaat aaacatttat tgtacaatta   125460
tgacacgcca ggcttagtgg aaatgtggat gaacagacaa ggatgagtta ctgtcctaag   125520
gatgatgcat gacagtgcag agaatatact ctcttcctga tcactcaggg tcactcatga   125580
ttcatgcgcg aggtcccaaa acagtgcctt tgatgcagat tctgtacatc tctagacgat   125640
tggtccaagg gctgaatgtg ctctggccca gtggtccagt ctgtcactat atgtcaacat   125700
cctgaatatg aacataacag tccaacatct caagagtggg catgaaaagg actcattttg   125760
tgcttttttcc tgtggttaac aagtcctttt tagcctgggg gaacaagcat taacaaaatg   125820
tttgaagatc tttgccacgt accattccaa atttctaggg taagtcttta gcttttcaga   125880
tcctgagttt ctgcaatgat caaatgtgat ttggacagtt gcgttgactt tctcctgggg   125940
ctataatgga gtgcaaagga aacaatggca gggaaaatgc ttgctttcaa aatggtagca   126000
tggatgtgtt cattcgtgta gttactgtat taggtatagc ctttcctgaa actaactgaa   126060
gtggggttat aaaaacagtc ccaattttct atttcctttg ctgagacaca aagaggagac   126120
aaaagagcaa agcttgaggg tagttttacc actgtgctta agtgttctga tttttccagt   126180
gatcagggtg aaataaaaag catagtaagt tccagggcag tgaataccat acaggagaca   126240
agttacagtt ttataatgtg ttttactttaa cactaaattc taaaagtaaa atgtcttttt   126300
ttttttccga gacagagttt cactcttgta gcccaggcag gagtgctatg gtgtgatctc   126360
ggctcacagc aacctccacc tcccagtttc aagcgattct tctgcctcag cctcccgaga   126420
agttgaaatt acaggtgcct ggcaccatat ctcgctaatt attctatttt tagtagagat   126480
cgggtttttac catgttggcc aggctggtct cgaactcctg acttcaagtg atccaccccgc   126540
ctcagcctcc caaagtgctg ggattacagg tgtgagtcac tgtgccggac ctaacagtaa   126600
aatgtctttc atgtgcttct caaggcaact acattaagga ggacacatct cttaatgtca   126660
ttctacagta gatttctaat gctctttctt ggaagtttgt ttttctgaga agagctaaaa   126720
atataataac atgaaagtga tcatattata taatcaatga agtgctttca aaggagataa   126780
aactaacctg gtctgcattt gcaaccagcc ttgattgaga gagagagaac tcaggataca   126840
```

```
cttagagatt ttattatggg gaatagttac tttattcatt ttacctcaat caatgcatgg   126900
aaataagtga cagtcatttt catttatctt ttaataaata aagtcaccat gaggaaaatg   126960
aaaacccatt aaagtcagtc cttaaagata tttggacatg cagacatgat aactaacatt   127020
tccattcgtg agacttaccc aaaacctata cctcaagtcc atttcttaga atacatgaaa   127080
taaagatctc agtgagtgta taaaactgca caccagaatc atatccgtat agacaagaat   127140
acatctacta gaaaaatata aaccaaaaca ccaaggtgac tctgtttttt tctgttttaa   127200
aatatgttgt ctttgtatgc atgtttgctt cttcctttt ttttttaaac atcgcagata    127260
aattcaactc tcacctcagt tgagagagaa ctgtcaatgt gacttggcct ctctctttct   127320
agtcccagaa agaattgcac tgaaatgctg agctcctgta ataaaaatga ccatttgctg   127380
agagtaatta acatactgaa agagattttc ttagaatagt gcacaatggc ccaatggtga   127440
cattatattg tctctttata aattattttc tatctatttc tgtggattat ttctacaaag   127500
cacttttcat atgtccaatt cctttattc ccctacaagt actgactgac tactggctct     127560
gctgttcact gatatgactt tcggcaagtt gcctgcactt tttaaacgtt atttcctcat   127620
tcagaacatg gggccataca aaatacaact cacttcagtg ttattgggga attaaacaaa   127680
taaatgcatg ggaagcattt aacatagtgc ctgacacaat aatgagcact cagtagatgt   127740
tagcttttat taatattgtt gttgctatgt ccagaaacac tatacctcca gaaaatcatg   127800
ggtacttgct ggggacgttg gggatatgca tgattttgaa aggagtgact gctctttact   127860
gctcagatga gaatttttc taagccgac tccttcaaac atgtaagatt ctgttgtgga      127920
ttctaggact gaaagaattc ttggccgagt gtggtggctt atcctggtaa tctcatcatt   127980
tgggaggaca aggcaggaag attgcttgag cccaggagtt ggaaacaagc ctggacaaca   128040
tggcgaaacc ctgtctctac aaaaaatata aacattagct ggtcatggga gtgagtgcct   128100
gtactcccag ctactcagga ggctaagata ggaggatcac ctgagcctgg cagtttgag    128160 gtttcagtga gccgtgatga caccatacta tactccactc cagcctgggt gacagtgaca   128220
tcctgcctca aaaaaacccc caaaattatt cttttgctg atttcatgtc agcagtgtgt     128280
gctgaaggct gtaaagtagc cacttgttct gtttattttt ccattgaaca agtatttatc   128340
aaaaacgtac tttgtggaag gcactgtgct aggaactatg catacagaag gaaaaccaaa   128400
tgttcttgga tactacactc cagttgtgat aaaaaagaaa aaagtattct tcacaaactt   128460
caacattttg atgtgcaaaa acataatata tgaattagat ctacctaact acacagaatt   128520
agaccaatta tttctgggat tatgggctca tatttttaat aactgtcctc ctacctctct   128580
gttgacaggt tttataaata ttcatttaat tacacacagt cacagacaca ctcagacaca   128640
cacacataca cacacacaca caccttgaca aataatgggc atgaacaatt gactggtact   128700
tgctctcatt cttctagatg tcaccacagt ggatcccaaa tacaattatt caaaggatgc   128760
aaatggtaag ttttgtgtt ttttatttcc tcctgatcat tttaagtttt gaacttctct     128820
ggcttgaaaa atcagggaat ggattttgct aggttggatg ctgcagaatg gacctaatca   128880 tatttaaat tagtccctct ttttctagga gttgtattaa caaacctaac tactgcttca     128940
tgtaagagat gactgtaaat tgaagggtac agtgatatgc tttcagttat ttcaaaaaac   129000
agactttact catccatgtg tcttttttct tttcttttt ttcttttttg agacggagtc      129060
tcgctctgtt gaacaggctg gattgcagtg acgcgatctc acctcactac aacctccgcc   129120
tctggagttc aagcgattct ccagcctcag cttctcaagt agctgggact acaggcacat   129180
gccaccatgt ccgggtcatc tttgtatttt tagcagagac cgggtttcac tatgttggcc   129240
```

```
aggctggtct agaattcctg acttcgtgat ctgccccctc agccctccga agtgctggga    129300
ttacagacgt gagtcactgt gcccggccta acagtaaaat gtctttcatg cgcttctcaa    129360
ggcaactacg ttaaggagga cacttctctt aatgtcattc tacagtagat ttctaatgct    129420
ctttcttgga agtttgtttt tctgagaaaa gctaaaaata taacatggaa gtgatcatat    129480
tgtataatca atgaagtgct tttcaaggag ataaaactaa tctggtccac gtttgcaacc    129540
aaccttgatt gagagagaga gagaactcag gatacacttg gagattttat tatggggaat    129600
agttacttta ttcttttttc ctcaatcaat tcatggaaat aagtgatagt catattcatt    129660
tatcttttaa taaatgaagt caccatgagg aaaataaaaa gacattgaaa acccattaaa    129720
gttagccctt aaagatattt ggacatgcag acttgataac taacgtttgc attcttgaga    129780
cttacccaaa acccatacct caagtccatg tttttagaat tcatgaaata aagatctcag    129840
tgagtgcata aaattgcgca ccagaatcat atccgtatag acaagaacac atctactaga    129900
aaaataataa accaacacac caatgcaact gtgttttctt ctgttttaaa atatgttgtc    129960
tttgtatgca tgtttgcttc ttcctttttt tttttaaca tcacagataa attcaactct    130020
cacctcaggt tttattgaga gaactgtcaa tgtgacttgg cctctgtctt tctagtccca    130080
gaaagaatcg cactgaaatg ctgagctcct gtaataaaaa tgaccatttg ctgagagtaa    130140
ttaacatact gaaagagatt ttcttagagt acacaatggt gacattatat tgtctcttta    130200
taaataactt tctatctatt tctgtggatt attcctacaa agtactttc atatgtccag    130260 tttcttttct tcccctacaa ctaccgtctg aatactggct ctgctatttg ctgatatgat    130320
tctcggcaag ttgcctgcac ttttttaaact ttatttcctc attcagaaca tggggccatg    130380
taatactcat gtacgtgagt attacgtaat aatgctcact taagtgttac tggggaatta    130440
aacaaaaaaa tgcatggcaa gcatttaaca tagtgcctga cacaataatg agcactcagt    130500
agatgttaga ttttattaat attgttgttg ttatgtccgg aaacactata cctccagaaa    130560
atcatgggta cttgcttggg atgttgggga tatgcatgat ttggaaaggt atgactgctt    130620
ttttctgctt agatgagaaa ttttttctaag ccagactcct tcaaatatgt aagattctgt    130680
tgtggattct aggacggaaa gaattcttgg tcaggtgtgg tttcttatcc ctgtaatccc    130740
agaattttgg gaggacaagg caggaagatt gcttgagccc aggagtttga aaccagcctg    130800
ggcaacaaga cgaaaccctg tctctacaaa agtacataaa ttagcttggc ttggtggtgt    130860
gtgcctgtat taccagctat tcgggagact gagatgggag gatctcctga acctgtgaag    130920
tttgaggctt cagtgagccg tgatgacacc atactatact cgactccagc ctgtgcgaca    130980
gtgagactct gcgtcaaaaa aaaaacccca aaattattgt ttttgctgat ttcaggtcag    131040
cagtgtgtgc tgaagggtgt aaagtagcca cttgatcagt ttattttttcc actgaacaag    131100 tatttatcaa aaacatactt tgtggtctgt ttttgataaa taaaaaggca ctgtgctagg    131160
agccatgaat acagaaggaa aaccaaatgt tcttggatac tacactccag ttgtgataaa    131220
aaagaaaaat gtattcttca cgaacttcaa catttgata tgcaaaaaca tagtatataa    131280
attagatcta cctgattacg tagaatcaga ccaattattt ctggaattga gggctcatat    131340
ttttaataac tgtcctcctg cctctctgtt gacaggtttt ataaatattc atttaattac    131400
acacacacac acacacacct tgacaaataa tggacatgaa caattgacta gtacttgctc    131460
tcattcttct agatgtcatc acaatggatc ccaaagacaa ttggtcaaaa gatgcaaatg    131520
gtaagctttt tgtgtttttcc tttcctcctg atcatttaa gttttgaact tctctggctt    131580
gaaaaatcag ggaatgggcc gggtgcggtg gctcacgcct gtaatcccag cactttggga    131640
```

```
ggccgaggcg ggcggatcac gaggtcagga gatcgagacc atcccggcta aaacggtgaa   131700
accccgtctc tactaaaaat acaaaaaatt agccgggctt agtggcgggc gcctgtagtc   131760
ccagctactt gggaggctga ggcaggagaa tggcgtgaac ccgggaggcg agcttgcag    131820 tgagccgaga ttgcgccact gcactccact ccagcctggg cgacagagcg agactccgtc   131880
tcaaaaaaaa aaaaaaaaa aaaaaagaa aaatcaggga atggattttg ctaggttgga     131940
tgctgcagaa tggacctagt gatattttaa attagtccct cttttctag gagttgtatt    132000 aacaaaccta actactgctt cgggtatgag atgactgtaa attagagggt acagtgatat   132060
gctttcagtt atttcaaaaa acagacttta ttcatccgtc tgtcttttt ttttttttt      132120 ttttttttt ttgagacgga ggagtctcac tctatcaccc aggctggagt gcagtggcgc    132180
gatctcggct caccataacc tccgccttac tggttcaagc gattctccag cctcagcttc   132240
tcaagtagct gggactacag gtgcacacca ccatacctgg ctaattttg tattttaat     132300 agagatgggg tttcaccacg ctggccagga tggtcttgaa ttcttgacct cgtgatctgc   132360
cccctcgggc tcccaaactt ctgggattat aggcgtgagc cactgtgccc ggccttctgt   132420
cttttgttat aatgactggg gaaaacatga taccatgttg cttcttgagt tgttttgttt   132480
tagtctttgg tctttgctag tagctaataa cacgaactag tgtttatcaa gtgcttttta   132540
cacagaaggg cttgttctgc attttctagt ttaatcatct taatactcct ataaagtagt   132600
acaatatatt ttctcccatt ttacagtccc tttaaagtaa ataactataa aaatccctta   132660
tacatgtcac acagctaggt ctggcatttc aaatcaggac atcaaacaaa gaattcgtgc   132720
agttactaag tcctctattt tttctacaat agaaaaaata gcaagaatta cagatagcaa   132780
gacattacaa ggcaggaatc tgaaacgaaa gggacataat gtggggctgg gtgggtgcat   132840
gagctttgca gactagactt tcattccagc tcttttaatg attaggtgta agtgacctac   132900
attttgtgag taacagtttt ctcatcagcc aactaagaat aattcacca gattcacagt    132960 tattgaagag ataagggcat gaatgtgaga tgtctggcgt agggtatctc atttagcaga   133020
cacagaatga atacttgttt ctggcttttt ctctctacat atgcacaaag aatgtgacta   133080
gaagcattgg ctctagccct gctcaacttt cctctatttc caataccaag gggctctgac   133140
ttaggctgcc acaccaggca aggagggca gtaccacctc acttgaccaa gggcagggag    133200
tcacggacac atcacttcct gagatccttt tccacaccaa ggactgatgt ttctggaatt   133260
ctcactttat gaagacaaaa catataaatg gaaatttctg caggaagaga ctcactcttg   133320
tagctcattg agtaggcact agtggtccac ccccactgtc tttacttatt ccttgacatc   133380
acatatctct tgtaaaacct caaataatgt taaatgcaat cacccaataa tagcatagcc   133440
ataattagag gcatttagga aagacaggtg agtgtgccac aactacctaa cacatcagca   133500
aatctggatt aaccactttc tttgattttc cacaatgcaa ccttactttt taatagttgg   133560
gaatgttcta agtgaattta gcagaggttg ttaatcaact tgaaagctga attctgactt   133620
gtctgactct tggtggtgct ggtagcagta gatgtttact tttaggtttt ggtggtggtg   133680
gaatatcact tcaacgtaaa tcatcagaaa taagtatttg tgaaccccte tcgcattaat   133740 atatcttatt ctgtaaaaag aacatgtgca atttctctta gatacactac tgctgcagct   133800
cacaaacacc tctgcatatt acacgtacct cctcctgctc ctcaagagtg tggtctattt   133860
tgccatcatc acctgctgtc tgcttagaag aacggctttc tgctgcaatg gagagaaatc   133920
ataacagacg gtggcacaag gaggccatct tttcctcatc ggttattgtc cctagaagcg   133980
tcttctgagg atctagttgg gctttctttc tgggtttggg ccatttcagt tctcatgtgt   134040
```

```
gtactattct atcattattg tataatggtt ttcaaaccag tgggcacaca gagaacctca   134100
ctctgtaata acaatgagga atagccatgg cgatctccag caccaatctc tccatgtttt   134160
ccacagctcc tccagccaac ccaaatagcg cctgctatag tgtagacagc ctgcggcttc   134220
tagccttgtc cctctcttag tgttctttaa tcagataact gcctggaagc ctttcatttt   134280
acacgccctg aagcagtctt ctttgctagt tgaattatgt ggtgtgtttt tccgtaataa   134340 gcaaataaa tttaaaaaaa tgaaaagttg acttttgtcc atggtatttt aattggatga    134400
catcaaattg aacatccaag gtaagaaaca acatggcaat tgggctgtgg aattctgtat   134460
tggttgtaag aatggtccaa caccccattt ctaattcttt ccctgagatc gtggttatca   134520
caccttctaa gaggaactac aaccaaacga aggagcccat gtggcttctg tttgaaaggt   134580
caccagagtc agattcatct ggtttaggac attccagtgg ctataggaca ctatctactg   134640
tgacgcgtac cgtgtgagct cagctgtaga gtgtttcgca gacactgtgt tcctgatcc    134700 tcacgatacc cccgtgagag ctgccctaaa agcagagagg cagcgtgatg gagaggttca   134760
gcacatgctc tctgatccca ggaatcctgg gtatggtgtt tcgtatctgt gtgacctcag   134820
gtgagttcca ggaaatctat gtgccataat ctcctcatgt aaaatgaagt tataatgccc   134880
catttcctga agttatgtgg attagatgag ttaatgacac ctggcacatg caagtcctcc   134940
acagtatcgg cacgcactgt tggtgctcta gagacagtaa taaccaaaa agtgtctgac    135000 acaggcctca atcaacttag aagtttattt tgcctagtct aagggcatga tcagaagaaa   135060
ataacatgga atcacagaaa cagtctatgg tctacacctt tctccaaaga tgaaattgag   135120
ggcctcaatg tttaaaaaag gaaagtgggc tggaggggag agagggaggg tataattatc   135180
cacatgttgc aagagcaagg gagcaggtag gggaactgcc aattatgtat tcatgttgcg   135240
ctcaataaat cagcacttta cataagatat ggttaacata gagtagctac ctctggagct   135300
atttcacctt tcatctgtag ctctctgttt aggcacaaaa ggaaaggcag cttctcacat   135360
gacccagctt ttggcttatt tttttctaaa acatagcatg atgaattggg atccagagtt   135420
tttcttttcc tttcacatag tagattccac acatatgcaa aagcactaac agttatctct   135480
actctcacct ctccgcagag aggttaggtg gtgggaatag ggacccagtg agtgtctact   135540
atgcactagg catccgaaat ccttgatgag ccagttgagg tcagtacaat taaggctcac   135600
agttcacaga tgagaaagat taaattacct actcaaggtc actattttta aagtaatagt   135660
cgtaatttaa agctaggtcc ctctgaaccc agagcccata tatttaaaca cacacacaca   135720
cacacacaca catttatcca acatcacgac tttcctttca ccgactttca actggggaaa   135780
acaaaacaaa acatgcgttg tttctttact aaaggcatcc tcaccagagt caatgagaat   135840
tttcttaagg aaataatggt gcacctgtgt tttctcctta tctacactcc aggccactgg   135900
tttgtcacta atttcccatt tgtttttttct ctttgggtaa aattggccta ctctggaatt   135960
accattattg cttccttggc tgtaaagagt atagaaattc taccctgtg agtgtgtgtc     136020 ctagatctgc agctgctctt tttgggggtg ctaatggact gtaaatttca gacacagcag   136080
gacggttcat ggtgctctct gggtatgtat aacattctga cacccagct ccttccgag     136140 actaaacagg ctcagagctc tgcagaatca ccttggagga gattctggaa cacccacgtg   136200
catttctgag gtaggaggta gaagaaggtt atgcattgtt cttggtccag tacgtttcca   136260
ccatggcaca gctaccacat atcgggaggt cacatggtgt gggaggaata ctagtcacac   136320
ttcacagcta gttagagccc tggccacttg gtctggctct aacaagctgt accatttgtt   136380
cttttctttt ccttttttttg agaaggagtc tcattctgtt gcctaggccg gagtgcagtg   136440
```

```
acatgatctt ggctcactgc aatctccacc tccaggttca agtgattctc ctgcctcagc   136500
ttcccaagta gctgggatta taggtgccca ccaccacact cagctaacct cagtcctgcc   136560
ttcaggcgat ccgcccaact cggcctccca aagtgctggg attacaggct tcagccacca   136620
tgaccggcca caatttgttc ttaaccatcc cacattgcct aagttcatct gtctttagaa   136680
gaatgtgttt agattaaata atttcagatt tctacctaaa gttacaaatt cagtgattac   136740
caccctgagg aagtaatgat agcaatcaca aatacagtgc ccaccatgta cccggtcctg   136800
gcttaaggac gtgttcactc atttaattct cacaaaaatt ctatatgtac aattatctct   136860
gttctatgga tggggaaact gaggcagagg gggctaaaga actttcgcat aatcaaacag   136920
ctactaagaa acagggctgg aatttgaact caagcagcca ggctccagga cctccgctct   136980
taccttctat gttatttcct cttagagtga aaacaggtta cttgtagttt caattaacac   137040
atgaaaatgt ccttccttat taggctatga agtaggaagg aaattgcctc tttggctgtt   137100
cacatttccc ctccttgctc caatgctgtt cagataatta gagggttata agccaacctg   137160
ccaatttgtc aatgctggga agacttttat atgctgagct cccatccatc atataggact   137220
tctgtgatta aagaccgaag cacatggttg gacaaaataa gtaccagaac aggcagtgcc   137280
cacaggtgtg caatggaaaa attaggcaaa gatttataca gttctacaca aaaacacgta   137340
tctcaatagt cactacagag ttagcatact ccacacgctt gtcaaataaa aagaaaaaa    137400 actccaatat ggtgacaccc tgtctctact aaaaatacaa aaattagcca ggtgtagtgg   137460
cttgtgcctg taatcccagc tacttgggag gctgaggcag gagaaccact tgaacccggg   137520
aggcggaggt tgcagtgagc cgagatcgcg caactgcatt ccagcctagg cgacagagcg   137580
agactctgtc tcaaaaaaga aaagaaaga  aaaaaaaaa  ggaaaaacta tatataaaaa   137640
aactccatat atttctcaac tataaaaaag taaaacttca gttcaacagt tctcaaaata   137700
tttctaatta tttattcttt ctactgtttt ggaattcctt tcctcataga ttttattttt   137760
gaaggttttt ggtctttcaa gaaggtcacg attaatgttt tccccattat actaatcaaa   137820
gtcctatata actgccagtg agaaattctg agtaataaga gataaccaga gacactacac   137880
ccatataatt cagccaaaca gctagaaatt caagattttc attagccatg aaaagttatt   137940
tgagtagatg cgtagcttgc accatgattt gttaggttct ttttcattta tttgcttttt   138000
ctgttgtgtt tgaggaatag tgagtaccaa ccacttactg agcagcagaa atatggcttg   138060
gcagcttgcg tcctctctct ctaatgctct caactgcatc accttacagc cattatgctc   138120
atttcactga taagaaaacc agatctcgag gttaaaaaat atgcccaatt aaccactgag   138180
tgagtcccag agttcacatg attccaggac tgtctgactt aagacctgct gccttatcca   138240
tcctaccagg ggctctcctt atgggagcct ttatcacggg ccaggcatca ggaccttgga   138300
aaatcctctt ttcataattc taatatgcag ccagggtgga ggccagcaag tgactgaaat   138360
agtgcctgaa ctccagctgt gctccacaca agccgtaagg aaacatctca gagctcacta   138420
cacacgggtg gaacacacgc cacctggaag gtgttcttat catgggaccc atttatttcc   138480
caaggaaacg aaagggtgt  accaagattt atgtgcaagg atgttcattc acgatagtgt   138540
tatttcaaac agccccaaat taacccaggt gaacaatcag aaattcataa atagacaaat   138600
acgcatcttc caaaagtat  agattccttta acccatttcc catttagaaa aagtgcagc   138660 tcgctgtttt tacataaaca cactcttttg aggctgaagc aaatatgact gattttcaac   138720
gtgaatataa aatgtcaaat ctgttcctgg gctgggtgca gtggctcacg cctgtaatac   138780
tagcattttg ggaggctgag gcgggtggac tgcctgagct caggagttcg agaccagcct   138840
```

```
gggcaacacg gtgaaacccc gtctctatta aaatacaaaa aattagccgg gagtggcagc   138900
gtgcacctgt agtcccagct actcaggagg ctgagtcagg accatcactt gaacccggag   138960
gcggaacgga ggttgcagtg agctgagatc acgccactgc actccagcct gggcgacaca   139020
gtgagactct ctctctctta aaacaaaac aaaacaaaaa ctgttcttgg agttatttct    139080
aaacagaact tctctctaat cctaatgtaa catcatgtac atttctgttg cattaggatt   139140
agaaatgagt attcttgggg caaaaggaa atgggttaaa aactggaaaa taaatagata    139200
tggagttgaa aaataatatt catagcataa atcctattgt gagataaata catttgaaca   139260
cttacatggt tcgaaaacac tccaattttt atttagttaa atatgatgt acatatataa    139320
gtatccatgt acatgtatat atgttctcat ttcccctttt tacacaggga gtatatagca   139380
tatattaatc tgcacatctc tttccattta taaatcttaa agctctttt atgtttatat    139440
acagggcac ttcactacag gtattttttt tttcttttt ttgttttga gacagagtct      139500
tgctctgtgg cccaggctgg agtgcagtgg ctgatctcgg ctcactgcaa cctctgcctc   139560
ctgggttcaa acgattctcc tgcctcagct tcccgagtag ctgggattac aggctcccac   139620
caccatgccc aactaatttt tgtgttttta gtagagacag gtttcacca ggttggccag    139680
gctggtcccg aacttctgac ctcaagtgat tcgcccacct cagcctccca aagtgctggg   139740
attacaagtg tgagccactg tgcccagcta aatacagata ttttcactg gtgaacatac    139800
tttcaatcgg tgccttggtt tagtaccagt cttttgctat tataaaaat gctgaaatga    139860
atgatagtgt tttatgtcat ttgaacatat gcactggtaa ttttgatggg tactgccaaa   139920
ctgccctcca tagaaatggc cctaaccct tctcccacaa tgtgtgtgag tgctgacagc     139980
ctactgctta atgttgggtt ttgctaattt gacaggtaaa aatagtactg cattgtggtt   140040
ttaatttgct ttttttctta ctgtgagtga agataaacat ctttttatgt ttaaggtcta   140100
ttttatatta ttctgtgcca tatttgttca tgtcctttgg ccattttttc tactgagtaa   140160
taacacaaat aggcatgcca ttcatttata tgtgtgtctg tgtatttctg cagacaaaga   140220
taaaacaatg ttcattgttg gtatgtgggt gaaaaataa gtgattgtgt gttttctgtt    140280
ttctccggtg aatcctttta aagtaaacat ttttatatat tagaattaaa acaatgtgtt   140340
actgaacatt gggaaggttt tctggttttgc ctacaatcag cttgtttctg tgaaacatgt   140400
tcttttggaa accaagtaga gaatcctact tgtaaacaaa gcaagaccaa ccagacttaa   140460
gaaagatcaa atttaattta gatctactcc ttgattctca tgaattgatt gaatctcttt   140520
agggcaaata cctggcctct atagagaaat ctggaatgat ttctgcactg ggagaggaaa   140580
cttttcagatc actaagggct ttgtggggct gatatcacca gccgaggtac tgggcaatgt   140640
ctcctgtggt ttcacacttc ttagcgattt ccttccccaa cgcaagctgg gctgccccga   140700
acttcagcaa tgtagagaga gaatgcag                                     140728
```

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagggttgtg ttggaatcag g                                            21

<210> SEQ ID NO 3
<211> LENGTH: 24

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgttccactg ccaaagagtt tctt                                          24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcttccaact tggaagggag a                                             21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tctgcaacat ctgtatattg gtatc                                         25

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctggtaccgg cagaaaccaa a                                             21

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taaacattat tacattattc cagtt                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctatcagtt tttcattact ggaat                                         25

<210> SEQ ID NO 9
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 9
ctcccatccc ttctttacat tgca                                              24

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaaggcccca cagcgtcttc                                                   20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaggaatctg gcattccgtc ag                                                22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgtctcaaca aaatccgcag ct                                                22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaagactaa gaaacttgag gt                                                22

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcttccgata cttacctgtg acaac                                             25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 15
gaagttacta tgagcctagt ccctt                                          25

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagctttgtt ccgggaccaa atac                                           24

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
caacacaacc ttggagttgt a                                              21

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
acatcccttg cggtggaga                                                 19

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
acaacgctgg aggtgta                                                   17

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
acacatcctt tgagttggag a                                              21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
```

-continued

<400> SEQUENCE: 21
accctggagt agtaggggt                                              19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
aacacaaccc tggagttgta                                             20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gtcctgtttc tctacattgt g                                           21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cttgatggta aggattgaag t                                           21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
gaagtggaag tgtgagcatt t                                           21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gttgttccac tgccaaagag tt                                          22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

```
gcaaatatct tgaaccaacc agt                                              23
```

\<210\> SEQ ID NO 28
\<211\> LENGTH: 24
\<212\> TYPE: DNA
\<213\> ORGANISM: Artificial Sequence
\<220\> FEATURE:
\<223\> OTHER INFORMATION: Description of Artificial Sequence: Synthetic
      probe

\<400\> SEQUENCE: 28

```
cttgatttttt ttgcccaact cttg                                             24
```

\<210\> SEQ ID NO 29
\<211\> LENGTH: 23
\<212\> TYPE: DNA
\<213\> ORGANISM: Artificial Sequence
\<220\> FEATURE:
\<223\> OTHER INFORMATION: Description of Artificial Sequence: Synthetic
      probe

\<400\> SEQUENCE: 29

```
tgcaaacgtc ttgatccaat cac                                              23
```

\<210\> SEQ ID NO 30
\<211\> LENGTH: 19
\<212\> TYPE: DNA
\<213\> ORGANISM: Artificial Sequence
\<220\> FEATURE:
\<223\> OTHER INFORMATION: Description of Artificial Sequence: Synthetic
      primer

\<400\> SEQUENCE: 30

```
acctgaggag acggtgacc                                                   19
```

\<210\> SEQ ID NO 31
\<211\> LENGTH: 20
\<212\> TYPE: DNA
\<213\> ORGANISM: Artificial Sequence
\<220\> FEATURE:
\<223\> OTHER INFORMATION: Description of Artificial Sequence: Synthetic
      probe

\<400\> SEQUENCE: 31

```
atgactgaat ataaacttgt                                                  20
```

\<210\> SEQ ID NO 32
\<211\> LENGTH: 23
\<212\> TYPE: DNA
\<213\> ORGANISM: Artificial Sequence
\<220\> FEATURE:
\<223\> OTHER INFORMATION: Description of Artificial Sequence: Synthetic
      probe

\<400\> SEQUENCE: 32

```
tggtagttgg agctggtggc gta                                              23
```

\<210\> SEQ ID NO 33
\<211\> LENGTH: 21
\<212\> TYPE: DNA
\<213\> ORGANISM: Artificial Sequence
\<220\> FEATURE:
\<223\> OTHER INFORMATION: Description of Artificial Sequence: Synthetic
      primer

\<400\> SEQUENCE: 33

```
gcctgctgaa aatgactgaa t                                                21
```

-continued

```
<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggtcctgcac cagtaatatg c                                              21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acctgaggag acggtgacc                                                 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(17)
<223> OTHER INFORMATION: a, c, t, g, unknown or other

<400> SEQUENCE: 36
tggrtccgmc aggcycngg                                                 19

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtcgacacg gcystgtatt actg                                           24

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acacggccgt gtattactg                                                 19

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(12)
```

```
<223> OTHER INFORMATION: a, c, t, g, unknown or other

<400> SEQUENCE: 39
gtgaccaggg tnccttggcc ccag                                        24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggataaagg cgaggagcat aa                                          22

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
actgcatatt cggttagact gtgattagct tt                               32

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acctgaggag acggtgacc                                              19

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttagagagtt gctttacgtg gcc                                         23

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cctggcttcc ttccctctgt                                             20

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 45
caggagggct ctgggtgggt ctgt                                              24

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tgtccttcct ttccactcct ccccaga                                           27
```